United States Patent
O'Malley et al.

(10) Patent No.: US 12,187,706 B2
(45) Date of Patent: Jan. 7, 2025

(54) NLRP3 MODULATORS

(71) Applicant: INNATE TUMOR IMMUNITY, INC., Princeton, NJ (US)

(72) Inventors: Daniel O'Malley, New Hope, PA (US); Ashvinikumar V. Gavai, Princeton Junction, NJ (US); Derek J. Norris, Pennington, NJ (US); Hua Gong, King of Prussia, PA (US); Yong Zhang, West Windsor, NJ (US); Patrice Gill, Levittown, PA (US); Christine M. Tarby, Lawrenceville, NJ (US); Matthias Broekema, New Hope, PA (US); Scott Hunter Watterson, Pennington, NJ (US)

(73) Assignee: Innate Tumor Immunity, Inc., Princeton, NJ (US)

( * ) Notice: Subject to any disclaimer, the term of this patent is extended or adjusted under 35 U.S.C. 154(b) by 709 days.

(21) Appl. No.: 17/422,283

(22) PCT Filed: Jan. 13, 2020

(86) PCT No.: PCT/US2020/013262
§ 371 (c)(1),
(2) Date: Jul. 12, 2021

(87) PCT Pub. No.: WO2020/150113
PCT Pub. Date: Jul. 23, 2020

(65) Prior Publication Data
US 2022/0089571 A1    Mar. 24, 2022

Related U.S. Application Data

(60) Provisional application No. 62/791,913, filed on Jan. 14, 2019.

(51) Int. Cl.
| | | |
|---|---|---|
| *C07D 403/04* | (2006.01) | |
| *A61K 45/06* | (2006.01) | |
| *C07D 401/14* | (2006.01) | |
| *C07D 403/14* | (2006.01) | |
| *C07D 405/14* | (2006.01) | |
| *C07D 409/14* | (2006.01) | |
| *C07D 413/14* | (2006.01) | |
| *C07D 417/14* | (2006.01) | |
| *C07D 471/04* | (2006.01) | |
| *C07D 498/04* | (2006.01) | |

(52) U.S. Cl.
CPC ............ *C07D 403/04* (2013.01); *A61K 45/06* (2013.01); *C07D 401/14* (2013.01); *C07D 403/14* (2013.01); *C07D 405/14* (2013.01); *C07D 409/14* (2013.01); *C07D 413/14* (2013.01); *C07D 417/14* (2013.01); *C07D 471/04* (2013.01); *C07D 498/04* (2013.01)

(58) Field of Classification Search
CPC .. C07D 403/04; C07D 401/14; C07D 403/14; C07D 405/14; C07D 409/14; C07D 413/14; C07D 417/14; C07D 471/04; C07D 498/04; A61K 45/06; A61K 31/517; A61P 35/00
See application file for complete search history.

(56) References Cited

U.S. PATENT DOCUMENTS

| | | | | |
|---|---|---|---|---|
| 2006/0211715 A1* | 9/2006 | Berthel | ................ | C07D 405/12 |
| | | | | 514/266.4 |
| 2010/0143299 A1* | 6/2010 | Gao | .................... | C07D 403/04 |
| | | | | 514/266.3 |

FOREIGN PATENT DOCUMENTS

WO    WO-2019166532 A1 *  9/2019  ........... A61K 31/517

* cited by examiner

*Primary Examiner* — Valerie Rodriguez-Garcia
*Assistant Examiner* — Kyle Nottingham
(74) *Attorney, Agent, or Firm* — Jing G. Sun

(57) ABSTRACT

The present invention provides compounds of Formula (I): Formula (I) wherein all of the variables are as defined herein. These compounds are modulators of NLRP3, which may be used as medicaments for the treatment of proliferative disorders, such as cancer in a subject (e.g., a human).

(I)

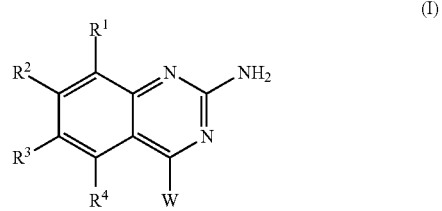

18 Claims, No Drawings

NLRP3 MODULATORS

CROSS-REFERENCE TO RELATED APPLICATIONS

This application is a 371 of International Application No. PCT/US2020/013262 filed on Jan. 13, 2020, which claims the priority benefit of U.S. Provisional Application No. 62/791,913, filed Jan. 14, 2019; the content of which is herein incorporated by reference in their entirety.

TECHNICAL FIELD

This disclosure features chemical entities (e.g., a compound or a pharmaceutically acceptable salt, and/or hydrate, and/or cocrystal, and/or drug combination of the compound) that modulate (e.g., agonizes or partially agonizes) NLRP3 that are useful, e.g., for treating a condition, disease or disorder in which an increase in NLRP3 signaling may correct a deficiency in innate immune activity that contributes to the pathology and/or symptoms and/or progression and/or treatment refractory state of the condition, disease or disorder (e.g., cancers with low T-cell infiltration) in a subject (e.g., a human). This disclosure also features compositions as well as other methods of using and making the same.

BACKGROUND

Nucleotide-binding oligomerization domain-like receptors ("NLRs") include a family of intracellular receptors that detect pathogen-associated molecular patterns ("PAMPs") and endogenous molecules (see, e.g., Ting, J. P. Y. et al., "The NLR gene family: a standard nomenclature," *Immunity*, 28(3):285-287, (2008)).

NLRPs represent a subfamily of NLRs that include a Pyrin domain and are constituted by proteins such as NLRP1, NLRP3, NLRP4, NLRP6, NLRP7, and NLRP12. NLRPs are believed to be involved with the formation of multiprotein complexes termed inflammasomes (see, e.g., Chaput, C. et al., "NOD-like receptors in lung diseases," *Frontiers in Immunology*, 4: article 393, (2013)). These complexes typically include one or two NLR proteins, the adapter molecule apoptosis associated speck-like containing a CARD domain (ASC) and pro-caspase-1 F (see, e.g., Bauernfeind, F and Hornung, V. "Of inflammasomes and pathogens—sensing of microbes by the inflammasome," *EMBO Molecular Medicine*, 5(6):814-826, (2013)).

One such inflammasome is formed by the NLRP3 scaffold, the ASC adaptor and pro-caspase-1 (see, e.g., Hirota, J. A., et al., "The airway epithelium nucleotide-binding domain and leucine-rich repeat protein 3 inflammasome is activated by urban particulate matter," *Journal of Allergy and Clinical Immunology*, 129(4):1116.e6-1125.e6, (2012)), and its expression is believed to be induced by inflammatory cytokines and TLR agonists in myeloid cells and human bronchial epithelial cells (Id). The NLRP3 inflammasome is believed to mediate the caspase-1-dependent conversion of pro-IL-1β and pro-IL-18 to IL-1β and IL-18. Further, IL-1β and IL-18 have potential in the treatment of various types of cancer (see, e.g., Chen, L-C. et al., *EMBO Mol Med.*, 4(12):1276-1293 (2012) and Tse, B. W-C. et al., *PLoS One*, 6(9):e24241 (2011)). IL-18 has been shown to override resistance to checkpoint inhibitors in colon cancer animal tumor models (see e.g., Ma, Z. et al., *Clin. Cancer Res.* January 11. (2016) DOI: 10.1158/1078-0432.CCR-15-1655).

SUMMARY

The invention is directed to compounds of Formula (I):

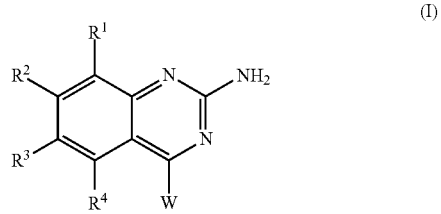

wherein all of the variables are as defined herein below.

Also within the scope of the invention are pharmaceutically acceptable salts, stereoisomers, tautomers, and solvates of the compounds of Formula (I).

The invention is also directed to pharmaceutical compositions comprising one or more compounds of the invention. The invention is also directed to methods of treating cancer using one or more compounds of the invention.

The invention also provides processes and intermediates for making the compounds of Formula (I) or pharmaceutically acceptable salts, stereoisomers, tautomers, and solvates thereof.

The compounds of the invention may be used in therapy.

The compounds of the invention may be used for the manufacture of a medicament for the treatment of cancer.

The compounds of the invention can be used alone, in combination with other compounds of the present invention, or in combination with one or more other agent(s).

Other features and advantages of the invention will be apparent from the following detailed description and claims.

DETAILED DESCRIPTION

Compounds of Invention

In a first aspect, the present invention provides, inter alia, a compound of Formula (I):

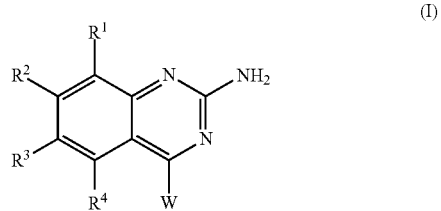

or a stereoisomer, a tautomer, or a pharmaceutically acceptable salt thereof, wherein:

W is independently selected from: —Y—$R^6$, -Q-Y—$R^6$, -Q-$R^{6a}$, and $R^{6b}$;

Q is independently selected from: $NR^5$, $CHR^5$, O, and S;

Y is independently selected from: $C_{1-10}$ alkylene, $C_{2-10}$ alkenylene, and $C_{2-10}$ alkynylene, each of which is substituted with 0 to 4 $R^e$ and/or each of which is optionally interrupted by one of the following:

(i) O;
(ii) N($R^f$);
(iii) $C_{3-6}$ cycloalkylene substituted with 0 to 4 $R^g$;
(iv) phenylene substituted with 0 to 4 $R^d$;
(v) heteroarylene including from 5 to 10 ring atoms, wherein from 1 to 4 ring atoms are each independently selected from N, N($R^f$), O, and S, and which is substituted with 0 to 4 $R^d$; or (vi) heterocycloalkylene including from 3 to 10 ring atoms, wherein from 1 to 3 ring atoms are each independently selected from N, N($R^f$), O and $S(O)_{1-2}$, and which is substituted with 0 to 4 $R^g$;

$R^1$ and $R^3$ are, at each occurrence, independently selected from: H, halogen, cyano, $C_{1-4}$ alkyl, $C_{1-4}$ haloalkyl, $C_{1-4}$ alkoxy, and $C_{1-4}$ haloalkoxy;

$R^2$ is independently a heteroaryl including 5 ring atoms, wherein from 1 to 4 ring atoms are each independently selected from N, NH, O, and S, wherein the heteroaryl is substituted with 0 to 3 $R^d$;

provided that when $R^2$ is optionally substituted thienyl or optionally substituted isoxazolyl; W is not $NH_2$, $NHCH_3$ or $N(CH_3)_2$;

$R^4$ is independently selected from: H, halogen, cyano, $C_{1-4}$ alkyl, $C_{1-4}$ haloalkyl, $C_{1-4}$ alkoxy, $C_{1-4}$ haloalkoxy, $N(C_{1-4}$ alkyl$)_2$, and —$(C_{0-3}$ alkylene)-heteroaryl including 5 ring atoms, wherein from 1 to 4 ring atoms are each independently selected from N, NH, $N(C_{1-4}$ alkyl), O, and S, wherein the heteroaryl is substituted with 0 to 3 $R^d$;

$R^5$ is independently H or $C_{1-4}$ alkyl;

$R^6$ is independently selected from: H, —OR, $C_{1-4}$ haloalkoxy, —C(O)$R^a$, —$CO_2R^a$, —$NR^bR^c$, —$SO_{1-2}$($R^h$), —$CONR^iR^j$, cyano and $R^{6a}$;

$R^{6a}$ is independently selected from: phenyl substituted with 0 to 4 $R^d$; heteroaryl including from 5 to 10 ring atoms, wherein from 1 to 4 ring atoms are each independently selected from N, N($R^f$), O, and S, wherein the heteroaryl is substituted with 0 to 4 $R^d$; $C_{3-10}$ cycloalkyl substituted with 0 to 4 $R^g$; and heterocyclyl including from 3 to 10 ring atoms, wherein from 1 to 3 ring atoms are each independently selected from N, N($R^f$), O and $S(O)_{1-2}$, wherein the heterocyclyl is substituted with 0 to 4 $R^g$;

$R^{6b}$ is independently selected from: $C_{1-6}$ alkoxy, $C_{1-4}$ haloalkoxy, —C(O)$R^a$, —$CO_2R^a$, —$NR^bR^c$, —$SO_{1-2}$($R^h$), —$CONR^iR^j$, cyano, phenyl substituted with 0 to 4 $R^d$; heteroaryl including from 5 to 10 ring atoms, wherein from 1 to 4 ring atoms are each independently selected from N, N($R^f$), O, and S, wherein the heteroaryl is substituted with 0 to 4 $R^d$; $C_{3-10}$ cycloalkyl substituted with 0 to 4 $R^g$; and heterocyclyl selected from

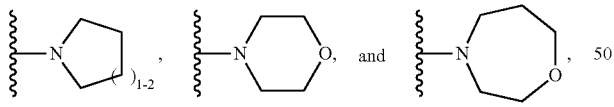

wherein the heterocyclyl is substituted with 0 to 2 $R^g$;

$R^a$ is independently selected from: H; $C_{1-8}$ alkyl substituted with 0 to 2 $R^e$; —$(C_{0-3}$ alkylene)-$C_{3-10}$ cycloalkyl, wherein the cycloalkyl is substituted with 0 to 4 $R^g$; —$(C_{0-3}$ alkylene)-heterocyclyl including from 3 to 10 ring atoms, wherein from 1 to 3 ring atoms are each independently selected from N($R^f$), O, and S, wherein the heterocyclyl is substituted with 0 to 4 $R^g$; —$(C_{0-3}$ alkylene)-$(C_{6-10}$ aryl), wherein the aryl is substituted with 0 to 4 $R^d$; and —$(C_{0-3}$ alkylene)-heteroaryl including from 5 to 10 ring atoms, wherein from 1 to 4 ring atoms are each independently selected from N, N($R^f$), O, and S, wherein the heteroaryl is substituted with 0 to 4 $R^d$;

$R^b$ and $R^c$ are, at each occurrence, independently $R^a$ or —C(O)$R^a$;

$R^d$ is independently selected from: halogen, OH, cyano, $C_{1-4}$ alkoxy, $C_{1-4}$ alkoxy, $C_{1-4}$ haloalkyl, $C_{1-4}$ haloalkoxy, —C(O)O($C_{1-4}$ alkyl), $NH_2$, $N(C_{1-4}$ alkyl$)_2$, —$C(O)NH_2$, —$C(O)N(C_{1-4}$ alkyl$)_2$, $C_{2-6}$ alkenyl, $C_{2-6}$ alkynyl, and $C_{1-6}$ alkyl substituted with 0 to 2 $R^e$;

$R^e$ is independently selected from: F, OH, cyano, $C_{1-4}$ alkoxy, $C_{1-4}$ haloalkyl, $C_{1-4}$ haloalkoxy, and $C_{1-4}$ alkyl substituted with 0 to 1 $R^n$;

$R^f$ is independently selected from: H, $C_{1-4}$ alkyl substituted with 0 to 1 OH, —C(O)($C_{1-4}$ alkyl), and —C(O)O($C_{1-4}$ alkyl);

$R^g$ is independently oxo or $R^d$;

$R^h$ is independently selected from: $C_{1-6}$ alkyl, $C_{1-4}$ haloalkyl, —$(C_{0-3}$ alkylene)-phenyl, and —$(C_{0-3}$ alkylene)-heteroaryl including from 5 to 6 ring atoms, wherein from 1-4 ring atoms are each independently selected from N, N($R^f$), O, and S;

$R^i$ and $R^j$ are, at each occurrence, independently H or $R^h$; or $R^i$ and $R^j$ together with the nitrogen atom to which each is attached forms a ring including from 5 to 6 ring atoms, wherein the ring includes: (a) from 3 to 5 ring carbon atoms, each of which is substituted with from 1 to 2 substituents independently selected from H and $R^m$; and (b) from 0 to 2 ring heteroatoms (in addition to the nitrogen atom attached to $R^i$ and $R^j$), which are each independently selected from N($R^f$), O, and S;

$R^m$ is independently oxo or RV; and $R^n$ is independently selected from: OH, $CONH_2$ and $C_{1-4}$ alkoxy.

In a second aspect, within the scope of the first aspect, wherein:

Q is independently selected from: NH, N($C_{1-4}$ alkyl), $CH_2$, and O;

Y is independently selected from: $C_{1-10}$ alkylene, $C_{2-6}$ alkenylene, and $C_{2-6}$ alkynylene, each of which is substituted with 0 to 4 $R^e$ and/or each of which is optionally interrupted by one of the following:

(i) O;

(ii) N($R^f$);

(iii) $C_{3-6}$ cycloalkylene substituted with 0 to 4 $R^g$;

(iv) phenylene substituted with 0 to 4 $R^d$;

(v) heteroarylene including from 5 to 6 ring atoms, wherein from 1 to 4 ring atoms are each independently selected from N, N($R^f$), O, and S, and which is substituted with 0 to 4 $R^d$; or (vi) heterocycloalkylene including from 3 to 7 ring atoms, wherein from 1 to 3 ring atoms are each independently selected from N, N($R^f$), O and $S(O)_{1-2}$, and which is substituted with 0 to 4 $R^g$;

$R^2$ is independently 5-membered heteroaryl including from 1 to 2 ring atoms are each independently selected from N, NH, O, and S;

provided that when $R^2$ is optionally substituted thienyl or optionally substituted isoxazolyl; W is not $NH_2$, $NHCH_3$ or $N(CH_3)_2$;

$R^4$ is independently selected from: H, halogen, cyano, $C_{1-4}$ alkyl, $C_{1-4}$ haloalkyl, $C_{1-4}$ alkoxy, $C_{1-4}$ haloalkoxy, $N(C_{1-4}$ alkyl$)_2$, and 5-membered heteroaryl including from 1 to 2 ring atoms are each independently selected from N, NH, O, and S;

$R^a$ is independently selected from: H, $C_{1-6}$ alkyl substituted with 0 to 2 $R^e$, and benzyl;

$R^h$ is independently $C_{1-6}$ alkyl or benzyl; and $R^i$ and $R^j$ are, at each occurrence, independently H or $R^h$.

In another aspect, within the scope of the first or second aspect, wherein:

$R^2$ is independently pyrazolyl or isothiazolyl; and $R^4$ is independently selected from: H, halogen, cyano, $C_{1-4}$ alkyl, $C_{1-4}$ haloalkyl, $C_{1-4}$ alkoxy, $C_{1-4}$ haloalkoxy, $N(C_{1-4}$ alkyl$)_2$, and heteroaryl selected from pyrazolyl, thienyl and isothiazolyl.

In a third aspect, within the scope of the first or second aspect, the invention provides a compound of Formula (II):

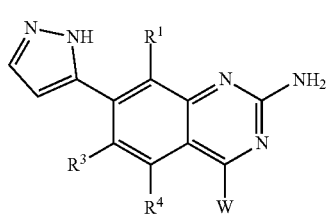

(II)

or a stereoisomer, a tautomer, or a pharmaceutically acceptable salt thereof, wherein:

W is independently selected from: —Y—$R^6$, —O—$R^{6a}$, —NH—$R^{6a}$, —O—Y—$R^6$, —NH—Y—$R^6$, and $R^{6b}$;

Y is independently $C_{1-8}$ alkylene or $C_{2-6}$ alkynylene, each of which is substituted with 0 to 4 $R^e$; wherein $C_{1-8}$ alkylene is optionally interrupted by one O;

$R^1$ and $R^3$ are, at each occurrence, independently selected from: H, halogen and $C_{1-4}$ alkyl;

$R^4$ is independently selected from: H, halogen, $C_{1-4}$ alkyl, $C_{1-4}$ alkoxy, $N(C_{1-4}$ alkyl$)_2$, and 5-membered heteroaryl including from 1 to 2 ring atoms are each independently selected from N, NH, O, and S;

$R^6$ is independently selected from: H, OH, $C_{1-6}$ alkoxy, $N(C_{1-4}$ alkyl$)_2$, $C_{1-6}$ haloalkyl, cyano, and $R^{6a}$;

$R^{6a}$ is independently selected from: phenyl substituted with 0 to 3 $R^d$; heteroaryl including from 5 to 10 ring atoms, wherein from 1 to 4 ring atoms are each independently selected from N, N($R^f$), O, and S, wherein the heteroaryl is substituted with 0 to 3 $R^d$; $C_{3-6}$ cycloalkyl substituted with 0 to 3 $R^g$; heterocyclyl including from 3 to 8 ring atoms, wherein from 1 to 3 ring atoms are each independently selected from N, N($R^f$), O and S(O)$_{1-2}$, wherein the heterocyclyl is substituted with 0 to 3 $R^g$; and;

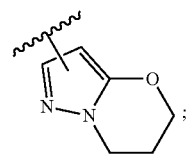

$R^{6b}$ is independently selected from: $C_{1-6}$ haloalkyl, cyano, phenyl substituted with 0 to 4 $R^d$; heteroaryl including from 5 to 10 ring atoms, wherein from 1 to 4 ring atoms are each independently selected from N, N($R^f$), O, and S, wherein the heteroaryl is substituted with 0 to 4 $R^d$; $C_{3-10}$ cycloalkyl substituted with 0 to 4 $R^g$; and heterocyclyl selected from

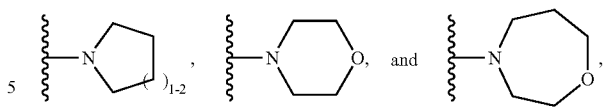

wherein the heterocyclyl is substituted with 0 to 2 $R^g$;

$R^d$ is independently selected from: halogen, cyano, OH, —(CH$_2$)$_{1-4}$OH, $C_{1-4}$ alkoxy, $C_{1-4}$ haloalkyl, N($C_{1-4}$ alkyl)$_2$, and $C_{1-4}$ alkyl substituted with 0 to 2 $C_{1-4}$ alkoxy;

$R^e$ is independently selected from: F, OH, —(CH$_2$)$_{1-4}$OH, —CH$_2$CONH$_2$ and $C_{1-4}$ alkyl substituted with 0 to 1 $C_{1-4}$ alkoxy;

$R^f$ is independently H or $C_{1-4}$ alkyl; and $R^g$ is independently oxo or $R^d$.

In a fourth aspect, within the scope of any of the first to third aspects, wherein:

W is independently selected from: —Y—$R^6$, —O—$R^{6a}$, —NH—$R^{6a}$, —O—Y—$R^6$, —NH—Y—$R^6$, $R^{6b}$, and;

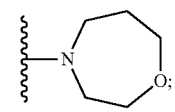

Y is independently $C_{1-8}$ alkylene or $C_{2-6}$ alkynylene, each of which is substituted with 0 to 3 $R^e$; wherein $C_{1-8}$ alkylene is optionally interrupted by one O;

$R^1$ is H;

$R^3$ is independently selected from: H, F and Cl;

$R^4$ is independently selected from: H, F, Cl, CH$_3$, OCH$_3$, N(CH$_3$)$_2$, and pyrazolyl;

$R^6$ is independently selected from: H, OH, $C_{1-6}$ alkoxy, CN, N($C_{1-4}$ alkyl)$_2$, $C_{1-6}$ haloalkyl, and $R^{6a}$;

$R^{6a}$ is independently selected from: phenyl substituted with 0 to 3 $R^d$; heteroaryl selected from oxazolyl, isoxazolyl, thiazolyl, imidazolyl, N—$C_{1-4}$ alkyl-imidazolyl, pyrazolyl, N—$C_{1-4}$ alkyl-pyrazolyl, N—CH$_2$CH$_2$OH-pyrazolyl, oxadiazolyl, triazolyl, N—$C_{1-4}$ alkyl-triazolyl, pyridyl, pyrimidinyl, pyrazinyl, and pyridazinyl, wherein the heteroaryl is substituted with 0 to 3 $R^d$; $C_{3-6}$ cycloalkyl substituted with 0 to 3 $R^g$; heterocyclyl selected from

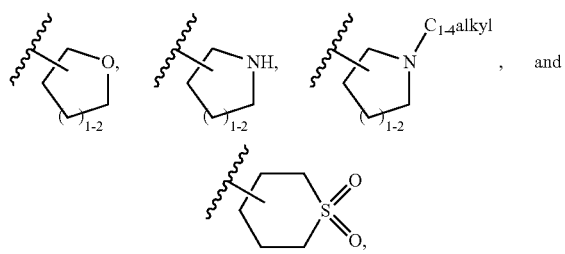

wherein the heterocyclyl is substituted with 0 to 3 $R^g$; and

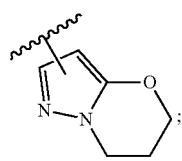

and $R^{6b}$ is independently selected from: $C_{1-6}$ alkoxy, $C_{1-4}$ haloalkoxy, $N(C_{1-4}$ alkyl$)_2$, $C_{1-4}$ haloalkyl, cyano, phenyl substituted with 0 to 4 $R^d$; heteroaryl including from 5 to 10 ring atoms, wherein from 1 to 4 ring atoms are each independently selected from N, N($R^f$), O, and S, wherein the heteroaryl is substituted with 0 to 4 $R^d$; $C_{3-10}$ cycloalkyl substituted with 0 to 4 $R^g$.

In a fifth aspect, within the scope of any of the first to fourth aspects, wherein:

W is independently selected from: —Y—$R^6$, —NH—$R^{6a}$, —NH—Y—$R^6$, $R^{6b}$, and

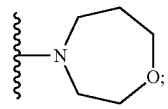

Y is independently $C_{1-6}$ alkylene or $C_{2-4}$ alkynylene, each of which is substituted with 0 to 3 $R^e$; wherein $C_{1-6}$ alkylene is optionally interrupted by one O;

$R^4$ is independently selected from: H, F, Cl, $CH_3$ and $OCH_3$;

$R^{6a}$ is independently selected from: phenyl substituted with 0 to 3 $R^d$; heteroaryl selected from oxazolyl, isoxazolyl, thiazolyl, imidazolyl, pyrazolyl, oxadiazolyl, triazolyl, pyridyl, pyrimidinyl, pyrazinyl, and pyridazinyl, wherein the heteroaryl is substituted with 0 to 3 $R^d$; $C_{3-6}$ cycloalkyl substituted with 0 to 3 $R^g$; heterocyclyl selected from

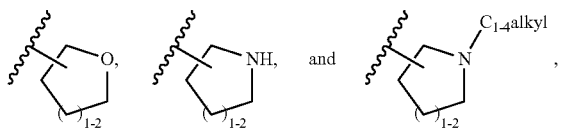

wherein the heterocyclyl is substituted with 0 to 3 $R^g$; and $R^e$ is independently selected from: F, OH and $C_{1-4}$ alkyl.

In a sixth aspect, within the scope of the fifth aspect, wherein:

W is independently —NH—$R^{6a}$ or —NH—Y—$R^6$;

Y is independently $C_{1-4}$ alkylene substituted with 0 to 3 $R^e$;

$R^1$ is H;

$R^3$ is H;

$R^4$ is H;

$R^{6a}$ is independently selected from: heteroaryl selected from oxazolyl, isoxazolyl, thiazolyl, imidazolyl, pyrazolyl, pyridyl, pyrimidinyl, pyrazinyl, and pyridazinyl; $C_{3-6}$ cycloalkyl substituted with 1 OH; and

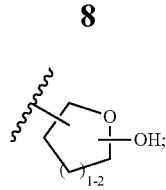

$R^6$ is OH; and $R^e$ is independently OH or $C_{1-4}$ alkyl.

In a seventh aspect, within the scope of the sixth aspect, wherein:

W is independently selected from: —NH(CH$_2$)$_{2-4}$OH, —NHCH$_2$CH(CH$_3$)OH, —NHCH$_2$CH(CH$_2$CH$_3$)OH, —NHCH$_2$C(CH$_3$)$_2$OH, —NH(CH$_2$)$_2$C(CH$_3$)$_2$OH, —NHCH$_2$C(CH$_3$)$_2$CH$_2$OH,

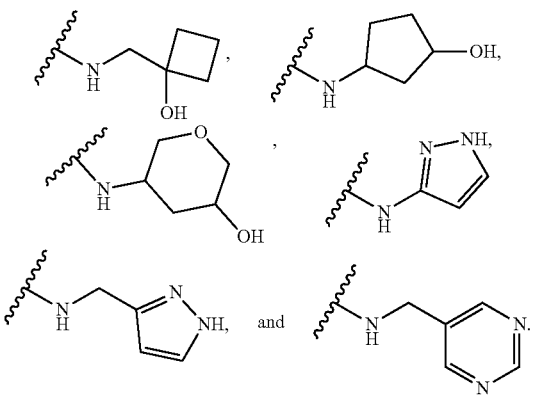

In another aspect, the invention provides a compound selected from the exemplified Examples 1 to 204 or a stereoisomer, a tautomer, or a pharmaceutically acceptable salt thereof.

In another aspect, the present invention provides a compound selected from any subset list of compounds or a single compound from the exemplified examples within the scope of any of the above aspects.

In some embodiments, $R^2$ is independently pyrazolyl, thienyl or isothiazolyl. In other embodiments, $R^2$ is pyrazolyl. In other embodiments, $R^2$ is thienyl. In other embodiments, $R^2$ is isothiazolyl.

The skilled artisan will recognize that some chemical structures described herein may be represented on paper by one or more other resonance forms; or may exist in one or more other tautomeric forms, even when kinetically, the artisan recognizes that such tautomeric forms represent only a very small portion of a sample of such compound(s).

Such compounds are clearly contemplated within the scope of this disclosure, though such resonance forms or tautomers are not explicitly represented herein.

OTHER ASPECTS AND EMBODIMENTS OF THE INVENTION

In one aspect, methods for modulating (e.g., agonizing, partially agonizing, antagonizing) NLRP3 activity are featured that include contacting NLRP3 with a chemical entity described herein (e.g., a compound described generically or specifically herein or a pharmaceutically acceptable salt thereof or compositions containing the same). In preferred embodiments, methods for modulating NLRP3 activity are agonizing and partially agonizing. In certain embodiments, methods for modulating NLRP3 activity are agonizing. In certain embodiments, methods for modulating NLRP3 activity are partially agonizing. Methods include in vitro methods, e.g., contacting a sample that includes one or more cells comprising NLRP3 (e.g., THP-1 cells) with the chemical entity. Methods can also include in vivo methods; e.g., administering the chemical entity to a subject (e.g., a human) having a disease in which an increase in NLRP3 signaling may correct a deficiency in innate immune activity that contributes to the pathology and/or symptoms and/or progression of the disease (e.g., cancer; e.g., a refractory cancer).

In some embodiments, compounds of the invention are useful for treating a condition, disease or disorder in which a decrease in NLRP3 activity (e.g., a condition, disease or disorder associated with repressed or impaired NLRP3 signaling) contributes to the pathology and/or symptoms and/or progression of the condition, disease or disorder (e.g., cancer) in a subject (e.g., a human).

A cancer is said to be refractory when it does not respond to (or is resistant to) cancer treatment. Refractory cancer is also known as resistant cancer.

In another aspect, methods of treating cancer are featured that include administering to a subject in need of such treatment an effective amount of a chemical entity described herein (e.g., a compound described generically or specifically herein or a pharmaceutically acceptable salt thereof or compositions containing the same). In some embodiments, the cancer may be a refractory cancer.

In a further aspect, methods of treatment of a disease in which an increase in NLRP3 signaling may correct a deficiency in innate immune activity that contributes to the pathology and/or symptoms and/or progression of the disease are featured that include administering to a subject in need of such treatment an effective amount of a chemical entity described herein (e.g., a compound described generically or specifically herein or a pharmaceutically acceptable salt thereof or compositions containing the same).

In another aspect, methods of treatment are featured that include administering to a subject having a disease in which an increase in NLRP3 signaling may correct a deficiency in innate immune activity that contributes to the pathology and/or symptoms and/or progression of the disease an effective amount of a chemical entity described herein (e.g., a compound described generically or specifically herein or a pharmaceutically acceptable salt thereof or compositions containing the same).

In a further aspect, methods of treatment are featured that include administering to a subject a chemical entity described herein (e.g., a compound described generically or specifically herein or a pharmaceutically acceptable salt thereof or compositions containing the same), wherein the chemical entity is administered in an amount effective to treat a disease in which an increase in NLRP3 signaling may correct a deficiency in innate immune activity that contributes to the pathology and/or symptoms and/or progression of the disease, thereby treating the disease.

Embodiments can include one or more of the following features.

The chemical entity can be administered in combination with one or more additional cancer therapies (e.g., surgery, radiotherapy, chemotherapy, toxin therapy, immunotherapy, cryotherapy or gene therapy, or a combination thereof, e.g., cancer therapies that include administering one or more (e.g., two, three, four, five, six, or more) additional anticancer agents. Non-limiting examples of additional anticancer agents (chemotherapeutic agents) are selected from an alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a vinca alkaloid and/or a taxane; e.g., Vincristine, Vinblastine, Vinorelbine and/or Vindesine, Taxol, Paclitaxel and/or Docetaxel); a topoisomerase (e.g., a type I topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a lutenizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from CTLA-4, PD-1, PD-L1, PD-1-PD-L1, PD-1-PD-L2, T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, Phosphatidylserine, TIM3, Phosphatidylserine-TIM3, SIRPA-CD47, VEGF, Neuropilin, CD160, CD30, and CD155 (e.g., CTLA-4 or PD1 or PD-L1) and other immunomodulatory agents, such as interleukin-2 (IL-2), indoleamine 2,3-dioxygenase (IDO), IL-10, transforming growth factor-β (TGFβ), CD39, CD73 Adenosine-CD39-CD73, and CXCR4-CXCL12.

The subject can have cancer; e.g., the subject has undergone and/or is undergoing and/or will undergo one or more cancer therapies.

Non-limiting examples of cancer include acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

In other embodiments, the mammal has been identified as having a cancer or an infectious disease. Representative infectious diseases include, without limitation, Acinobacter infection, actinomycosis, African sleeping sickness, acquired immunodeficiency syndrome, amebiasis, anaplasmosis, anthrax, *Arcanobacterium haemolyticum* infection, Argentine hemorrhagic fever, ascariasis, aspergillosis, astrovirus infection, babesiosis, *Bacillus cereus* infection, bacterial pneumonia, bacterial vaginosis, *Bacteroides* infection, balantidiasis, *Baylisascaris* infection, BK virus infection, black piedra, *Blastocystic hominis* infection, blastomycosis, Bolivian hemorrhagic fever, botulism, Brazilian hemorrhagic fever, brucellosis, bubonic plaque, Burkholderi infection, Buruli ulcer, Calicivirus infection, camptobacteriosis, candidiasis, cat-scratch disease, cellulitis, Chagas disease, chancroid, chickenpox, chikungunya, chlamydia, *Chlamydophila pneumoniae* infection, cholera, chromoblastomycosis, clonorchiasis, *Clostridium difficile* infection, coccidioidomycosis, Colorado tick fever, common cold, Creutzfeldt-Jakob disease, Crimean-Congo hemorrhagic fever, crytococcosis, cryptosporidiosis, cutaneous larva migrans, cyclosporiasis, cysticercosis, cytomegalovirus infection, dengue fever, Desmodesmus infection, deintamoebiasis, diphtheria, diphyllobothriasis, dracunculiasis, ebola hemorrhagic fever, echinococcosis, ehrlichiosis, enterobiasis, *Enterococcus* infection, Enterovirus infection, epidemic typhus, erythema infection, exanthema subitum, fasciolopsiasis, fasciolosis, fatal familial insomnia, filariasis, food poisoning by *Clostridium myonecrosis*, free-living amebic infection, *Fusobacterium* infection, gas gangrene, geotrichosis, Gerstmann-Sträussler-Scheinker syndrome, giardiasis, glanders, gnathostomiasis, gonorrhea, granuloma inguinale, Group A streptococcal infection, Group B streptococcal infection, *Haemophilus influenzae* infection, hand foot and mouth disease, hantavirus pulmonary syndrome, Heartland virus disease, *Heliobacter pylori* infection, hemolytic-uremic syndrome, hemorrhagic fever with renal syndrome, hepatitis A, hepatitis B, hepatitis C, hepatitis D, hepatitis E, herpes simplex, histoplasmosis, hookworm infection, human bocavirus infection, human ewingii ehrlichiosis, human granulocyte anaplasmosis, human metapneuomovirus infection, human monocytic ehrlichiosis, human papillomavirus infection, human parainfluenza virus infection, hymenolepiasis, Epstein-Barr virus infectious mononucleosis, influenza, isosporiasis, Kawasaki disease, keratitis, *Kingella kingae* infection, kuru, lassa fever, Legionnaires' disease, Pontiac fever, leishmaniasis, leprosy, leptospirosis, listeriosis, lyme disease, lymphatic filariasis, lymphocytic choriomeningitis, malaria, Marburg hemorrhagic fever, measles, Middle East respiratory syndrome, melioidosis, meningitis, meningococcal disease, metagonimiasis, microsporidiosis, molluscum contagiosum, monkeypox, mumps, murine typhus, mycoplasma pneumonia, mycetoma, myiasis, neonatal conjunctivitis, variant Creutzfeldt-Jakob disease, nocardiosis, onchocerciasis, paracoccidioidomycosis, paragonimiasis, pasteurellosis, pediculosis capitis, pediculosis corporis, pediculosis pubis, pelvic inflammatory disease, pertussis, plague, pneumonia, poliomyelitis, *Prevotella* infection, primary amoebic meningoencephalitis, progressive multifocal leukoencephalopathy, psittacosis, Q fever, rabies, relapsing fever, respiratory syncytial virus infection, rhinosporidiosis, rhinovirus infection, rickettsial infection, rickettsialpox, Rift Valley Fever, Rocky Mountain spotted fever, rotavirus infection, rubella, salmonellosis, severe acute respiratory syndrome, scabies, schistosomiasis, sepsis, shigellosis, shingles, smallpox, sporothrichosis, staphylococcal food poisoning, staphylococcal infection, strongyloidiasis, subacute sclerosing panencephalitis, syphilis, taeniasis, tetanus, tinea barbae, tinea capitis, tinea corporis, tinea cruris, tinea manum, tinea nigra, tinea pedis, tinea unguium, tinea *versicolor*, toxocariasis, trachoma, toxoplasmosis, trichinosis, trichomoniasis, trichuriasis, tuberculosis, tularemia, typhoid fever, *Ureaplasma urealyticum* infection, valley fever, Venezuelan hemorrhagic fever, viral pneumonia, West Nile fever, white piedra, *Yersinia psuedotuberculosis* infection, yersiniosis, yellow fever, and zygomycosis.

The chemical entity can be administered intratumorally.

The chemical entity can be administered systemically (including but not limited to orally, subcutaneously, intramuscular, intravenously).

The methods can further include identifying the subject.

Other embodiments include those described in the Detailed Description and/or in the claims.

DEFINITIONS

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

For purposes of clarity and in accordance with standard convention in the art, the symbol  is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —OCH$_3$ is attached through the oxygen atom.

As used herein, the term "NLRP3" is meant to include, without limitation, nucleic acids, polynucleotides, oligonucleotides, sense and antisense polynucleotide strands, complementary sequences, peptides, polypeptides, proteins, homologous and/or orthologous NLRP3 molecules, isoforms, precursors, mutants, variants, derivatives, splice variants, alleles, different species, and active fragments thereof.

An "agonist" of NLRP3 includes compounds that, at the protein level, directly bind or modify NLRP3 such that an activity of NLRP3 is increased, e.g., by activation, stabilization, altered distribution, or otherwise.

Certain compounds described herein that agonize NLRP3 to a lesser extent than a NLRP3 full agonist can function in assays as antagonists as well as agonists. These compounds antagonize activation of NLRP3 by a NLRP3 full agonist because they prevent the full effect of NLRP3 interaction. However, the compounds also, on their own, activate some NLRP3 activity, typically less than a corresponding amount of the NLRP3 full agonist. Such compounds may be referred to as "partial agonists of NLRP3".

In some embodiments, the compounds described herein are agonists (e.g. full agonists) of NLRP3. In other embodiments, the compounds described herein are partial agonists of NLRP3.

Generally, a receptor exists in an active (Ra) and an inactive (Ri) conformation. Certain compounds that affect the receptor can alter the ratio of Ra to Ri (Ra/Ri). For example, a full agonist increases the ratio of Ra/Ri and can cause a "maximal", saturating effect. A partial agonist, when bound to the receptor, gives a response that is lower than that elicited by a full agonist (e.g., an endogenous agonist). Thus, the Ra/Ri for a partial agonist is less than for a full agonist. However, the potency of a partial agonist may be greater or less than that of the full agonist.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity (e.g., a compound exhibiting activity as a mitochondrial uncoupling agent or a pharmaceutically acceptable salt and/or hydrate and/or cocrystal thereof, e.g., a compound, such as niclosamide or a pharmaceutically acceptable salt and/or hydrate and/or cocrystal thereof, e.g., a compound, such as a niclosamide analog, or a pharmaceutically acceptable salt and/or hydrate and/or cocrystal thereof) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy,* 22nd Edition, Pharmaceutical Press, London, U K (2012); *Handbook of Pharmaceutical Excipients,* 6th ed.; Rowe et al., Eds.; The Pharmaceutical Press and the American Pharmaceutical Association: (2009); *Handbook of Pharmaceutical Additives,* 3rd ed.; Ash and Ash Eds.; Gower Publishing Company: (2007); *Pharmaceutical Preformulation and Formulation, 2nd ed.;* Gibson Ed.; CRC Press LLC: Boca Raton, FL, (2009).

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt is not specifically limited as far as it can be used in medicaments. Examples of a salt that the compounds described herein form with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. The "treatment of cancer", refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii)

reducing tumor size, (iii) slowing the growth of a tumor, (iv) reducing, slowing or preventing invasion and/or (8) relief, to some extent, of the severity or number of one or more symptoms associated with the disorder.

The term "halo" or "halogen" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "alkylene" refers to a branched or unbranched divalent alkyl (e.g., —CH$_2$—).

The term "haloalkyl" refers to an alkyl, in which one or more hydrogen atoms is/are replaced with an independently selected halo.

The term "alkoxy" refers to an —O-alkyl radical (e.g., —OCH$_3$).

The term "haloalkoxy" refers to an —O-haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy.

The term "alkenyl" refers to a hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it.

The term "aromatic" refers generally to a ring that includes a cyclic array of resonance-stabilized 4n+2 pi electrons, wherein n is an integer (e.g., 1 or 2). Aromatic moieties include aryl and heteroaryl groups. The term "nonaromatic" describes any moiety that does not fall within the definition of "aromatic".

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic e.g. tetrahydronaphthyl. Examples of aryl groups also include phenyl, naphthyl and the like.

The term "cycloalkyl" as used herein includes saturated cyclic hydrocarbon groups having 3 to 10 carbons, preferably 3 to 8 carbons, and more preferably 3 to 6 carbons, wherein the cycloalkyl group may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl. The term "cycloalkylene" as used herein refers to divalent cycloalkyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic (but does not have to be a ring which contains a heteroatom, e.g. tetrahydroisoquinolinyl. Examples of heteroaryl groups also include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like. The term "heterocycloalkylene" refers to divalent heterocyclyl.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The details of one or more embodiments of the invention are set forth in the accompanying drawings and the description below. Other features and advantages of the invention will be apparent from the description and drawings, and from the claims.

This disclosure features chemical entities (e.g., a compound or a pharmaceutically acceptable salt, and/or hydrate, and/or cocrystal, and/or drug combination of the compound) that modulate (e.g., agonizes or partially agonizes) NLRP3 that are useful, e.g., for treating a condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) in a subject (e.g., a human). This disclosure also features compositions as well as other methods of using and making the same.

Pharmaceutical Compositions and Administration

In some embodiments, a chemical entity (e.g., a compound that modulates (e.g., agonizes or partially agonizes) NLRP3, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, a pharmaceutical composition comprising a compound of the present invention or a salt thereof, and one or more pharmaceutically acceptable excipients. In certain embodiments, a pharmaceutical composition comprising a compound of the present invention or a pharmaceutically acceptable salt thereof, and one or more pharmaceutically acceptable excipients. In certain embodiments, a pharmaceutical composition comprising a therapeutically effective amount of a compound of the present invention or a pharmaceutically acceptable salt thereof, and one or more pharmaceutically acceptable excipients.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see Remington: *The Science and Practice of Pharmacy*, $22^{nd}$ Edition (Pharmaceutical Press, London, U K. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral). In certain embodiments, a preferred route of administration is systemic.

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "*Effect of Intratumoral Injection on the Biodistribution and the Therapeutic Potential of HPMA Copolymer-Based Drug Delivery Systems*" Neoplasia. 10:788-795 (2006).

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEGs, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry*, 2013, 13, 776-802.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 1 mg/kg; from about 0.1 mg/kg to about 0.5 mg/kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) are provided.

Indications

In any of the methods described herein, the subject can have a cancer. In some examples of any of the methods described herein, the mammal has been identified as having a cancer, or has been diagnosed as having a cancer.

Non-limiting examples of cancer include: acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

In certain embodiments, non-limiting examples of cancer include: breast cancer, colon cancer, rectal cancer, colorectal cancer, pancreatic cancer, and prostate cancer.

Methods for diagnosing a subject as having a cancer or identifying a mammal as having a cancer are well known in the art. For example, a medical professional (e.g., a physician, a physician's assistant, or a technician) can diagnose cancer in a mammal by observing one or more symptoms of cancer in a mammal. Non-limiting examples of symptoms of cancer include: fatigue, lump or area of thickening felt under the skin, weight change, jaundice, darkening or redness of the skin, sores that won't heal, changes to existing moles, changes in bowel or bladder habits, persistent cough or trouble breathing, difficulty swallowing, hoarseness, persistent indigestion or discomfort after eating, persistent, unexplained muscle or joint pain, persistent, unexplained fevers or night sweats, and unexplained bleeding or bruising. Methods of diagnosing a subject as having a cancer or identifying a subject as having a cancer can further include performing one or more diagnostic tests (e.g., performing one or more diagnostic tests on a biopsy or a blood sample).

In some examples of any of the methods described herein, a subject can be a subject having a cancer, a subject diagnosed as having a cancer, or a subject identified as having a cancer that has been unresponsive to a previously administered treatment for cancer. Diagnostic tests for diagnosing a subject as having a cancer or identifying a mammal as having a cancer are known in the art.

In some embodiments, methods for treating a subject having condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) are provided.

In some embodiments, the present invention provides a method of treating cancer, wherein the cancer can be any cancer that does not elicit an optimal innate immune system response.

Innate immune system refers to a part of the immune system consisting of cells that react to threats for the organism like infections or cancer in an antigen-non-specific way and stimulate the adaptive, antigen-specific immune system. In general, complete removal of the threat and long-lasting protection (=immunity) requires activity of the adaptive, antigen-specific immune system that in turn depends on stimulation by the innate immune system.

In some embodiments, the present invention provides a method of treating case, the cancer is selected based on resistance to T-cell checkpoint inhibition, either independent of cancer type and based on failure to respond to previous T-cell checkpoint inhibitor therapy or based on cancer type that is generally resistant to T-cell checkpoint inhibitor therapy such as hormone receptor positive breast cancer, microsatellite stable colon or rectal cancer, pancreatic cancer and prostate cancer.

In certain other embodiments, the present invention provides a method of treating cancer comprising an NLPR3 agonist of the present invention to treat non-inflamed tumors with low CD8+ T-cell infiltration to enhance tumor immunogenicity and promote inflammatory responses. For example, the combination may be used to treat a solid tumor based on results of a biopsy that demonstrated low CD8+ T-cell infiltration or low expression of genes produced by CD8+ T-cells.

Resistance to T-cell checkpoint inhibition refers to cancer progression on therapy or lack of response within 6 months of therapy according to consensus response criteria for the respective cancer, such as RECIST1.1 for most solid tumors.

T-cell infiltration refers to percent of T-cells of all nucleated cells by immunohistochemistry of tumor biopsy specimens.

CD8+ T-cell infiltration refers to percent of CD8+ cells of all nucleated cells by immunohistochemistry of tumor biopsy specimens.

In addition to immunohistochemistry for quantifying CD8+ T-cells in biopsy specimens, expression of genes produced by CD8+ T-cells like interferon-γ can be measured by quantifying mRNA using for example next generation sequencing and inform about CD8+ T-cell infiltration. Thresholds for low and high CD8+ T-cell infiltration by immunohistochemistry of mRNA quantifying techniques are being developed by various groups and take the spectrum of CD8+ T-cell infiltration across cancers as well as for specific cancers into account.

In any of the methods described herein, the subject can have an infectious disease. In some examples of any of the methods described herein, the subject has been identified as having an infectious disease, or has been diagnosed as having an infectious disease.

For example, an infectious disease can be caused by a bacterium, virus, fungus, parasite, or a *mycobacterium.*

Non-limiting examples of infectious disease include: Acinobacter infection, actinomycosis, African sleeping sickness, acquired immunodeficiency syndrome, amebiasis, anaplasmosis, anthrax, *Arcanobacterium haemolyticum* infection, Argentine hemorrhagic fever, ascariasis, aspergillosis, astrovirus infection, babesiosis, *Bacillus cereus* infection, bacterial pneumonia, bacterial vaginosis, *Bacteroides* infection, balantidiasis, *Baylisascaris* infection, BK virus infection, black piedra, *Blastocystic hominis* infection, blastomycosis, Bolivian hemorrhagic fever, botulism, Brazilian hemorrhagic fever, brucellosis, bubonic plaque, Burkholderi infection, Buruli ulcer, Calicivirus infection, camptobacteriosis, candidiasis, cat-scratch disease, cellulitis, Chagas disease, chancroid, chickenpox, chikungunya, chlamydia, *Chlamydophila pneumoniae* infection, cholera, chromoblastomycosis, clonorchiasis, *Clostridium difficile* infection, coccidioidomycosis, Colorado tick fever, common cold, Creutzfeldt-Jakob disease, Crimean-Congo hemorrhagic fever, crytococcosis, cryptosporidiosis, cutaneous larva migrans, cyclosporiasis, cysticercosis, cytomegalovirus infection, dengue fever, Desmodesmus infection, deintamoebiasis, diphtheria, diphyllobothriasis, dracunculiasis, ebola hemorrhagic fever, echinococcosis, ehrlichiosis, enterobiasis, *Enterococcus* infection, Enterovirus infection, epidemic typhus, erythema infection, exanthema subitum, fasciolopsiasis, fasciolosis, fatal familial insomnia, filariasis, food poisoning by *Clostridium myonecrosis*, free-living amebic infection, *Fusobacterium* infection, gas gangrene, geotrichosis, Gerstmann-Sträussler-Scheinker syndrome, giardiasis, glanders, gnathostomiasis, gonorrhea, granuloma inguinale, Group A streptococcal infection, Group B streptococcal infection, *Haemophilus influenzae* infection, hand foot and mouth disease, hantavirus pulmonary syndrome, Heartland virus disease, *Heliobacter pylori* infection, hemolytic-uremic syndrome, hemorrhagic fever with renal syndrome, hepatitis A, hepatitis B, hepatitis C, hepatitis D, hepatitis E, herpes simplex, histoplasmosis, hookworm infection, human bocavirus infection, human *ewingii* ehrlichiosis, human granulocyte anaplasmosis, human metapneuomovirus infection, human monocytic ehrlichiosis, human papillomavirus infection, human parainfluenza virus infection, hymenolepiasis, Epstein-Barr virus infectious mononucleosis, influenza, isosporiasis, Kawasaki disease, keratitis, *Kingella kingae* infection, kuru, lassa fever, Legionnaires' disease, Pontiac fever, leishmaniasis, leprosy, leptospirosis, listeriosis, lyme disease, lymphatic filariasis, lymphocytic choriomeningitis, malaria, Marburg hemorrhagic fever, measles, Middle East respiratory syndrome, melioidosis, meningitis, meningococcal disease, metagonimiasis, microsporidiosis, molluscum contagiosum, monkeypox, mumps, murine typhus, mycoplasma pneumonia, mycetoma, myiasis, neonatal conjunctivitis, variant Creutzfeldt-Jakob disease, nocardiosis, onchocerciasis, paracoccidioidomycosis, paragonimiasis, pasteurellosis, pediculosis capitis, pediculosis corporis, pediculosis pubis, pelvic inflammatory disease, pertussis, plague, pneumonia, poliomyelitis, *Prevotella* infection, primary amoebic meningoencephalitis, progressive multifocal leukoencephalopathy, psittacosis, Q fever, rabies, relapsing fever, respiratory syncytial virus infection, rhinosporidiosis, rhinovirus infection, rickettsial infection, rickettsialpox, Rift Valley Fever, Rocky Mountain spotted fever, rotavirus infection, rubella, salmonellosis, severe acute respiratory syndrome, scabies, schistosomiasis, sepsis, shigellosis, shingles, smallpox, sporothrichosis, staphylococcal food poisoning, staphylococcal infection, strongyloidiasis, subacute sclerosing panencephalitis, syphilis, taeniasis, tetanus, tinea barabe, tinea capitis, tinea corporis, tinea cruris, tinea manum, tinea nigra, tinea pedis, tinea unguium, tinea versicolor, toxocariasis, trachoma, toxoplasmosis, trichinosis, trichomoniasis, trichuriasis, tuberculosis, tularemia, typhoid fever, *Ureaplasma urealyticum* infection, valley fever, Venezuelan hemorrhagic fever, viral pneumonia, West Nile fever, white piedra, *Yersinia psuedotuberculosis* infection, yersiniosis, yellow fever, and zygomycosis.

Methods for diagnosing a subject as having an infectious disease, or identifying a subject as having an infectious disease are well known in the art. For example, a medical professional (e.g., a physician, a physician's assistant, or a technician) can diagnose infectious disease in a subject by observing one or more symptoms of infectious disease in a subject. Non-limiting examples of symptoms of infectious disease include: fever, diarrhea, fatigue, and muscle aches. Methods of diagnosing a mammal as having an infectious disease or identifying a subject as having an infectious disease can further include performing one or more diagnostic tests (e.g., performing one or more diagnostic tests on a biopsy or a blood sample). Diagnostic tests for diagnosing a subject as having an infectious disease or identifying a subject as having an infectious disease are known in the art.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the methods described herein can further include administering one or more additional cancer therapies.

The one or more additional cancer therapies can include, without limitation, surgery, radiotherapy, chemotherapy, toxin therapy, immunotherapy, cryotherapy, cancer vaccines (e.g., HPV vaccine, hepatitis B vaccine, Oncophage, Provenge) and gene therapy, as well as combinations thereof. Immunotherapy, including, without limitation, adoptive cell therapy, the derivation of stem cells and/or dendritic cells, blood transfusions, lavages, and/or other treatments, including, without limitation, freezing a tumor.

In some embodiments, the one or more additional cancer therapies is chemotherapy, which can include administering one or more additional chemotherapeutic agents.

In certain embodiments, the additional cancer therapy comprises (chemotherapeutic agent) an immunomodulatory moiety, e.g., an immune checkpoint inhibitor. In certain of these embodiments, the immune checkpoint inhibitor targets an immune checkpoint receptor selected from CTLA-4, PD-1, PD-L1, PD-1-PD-L1, PD-1-PD-L2, T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, Phosphatidylserine, TIM3, Phosphatidylserine-TIM3, SIRPA-CD47, VEGF, Neuropilin, CD160, CD30, and CD155 (e.g., CTLA-4 or PD1 or PD-L1) and other immunomodulatory agents, such as interleukin-2 (IL-2), indoleamine 2,3-dioxygenase (IDO), IL-10, transforming growth factor-β (TGFβ), CD39, CD73 Adenosine-CD39-CD73, and CXCR4-CXCL12. See, e.g., Postow, M. J. Clin. Oncol. 33, 1 (2015).

In certain embodiments, the immune checkpoint inhibitor targets an immune checkpoint receptor selected from CTLA-4, PD-1, PD-L1, PD-1-PD-L1, and PD-1-PD-L2.

In certain embodiments, the immune checkpoint inhibitor is selected from: nivolumab (also known as "OPDIVO"; formerly designated 5C4, BMS-936558, MDX-1106, or ONO-4538), pembrolizumab (also known as "KEYTRUDA", lambrolizumab, and MK-3475. See WO 2008/156712), PDR001 (Novartis; see WO 2015/112900), MEDI-0680 (AstraZeneca; AMP-514; see WO 2012/145493), cemiplimab (REGN-2810) (Regeneron; see WO 2015/112800), JS001 (TAIZHOU JUNSHI PHARMA; see Si-Yang Liu et al., J. Hematol. Oncol. 10:136 (2017)), BGB-A317 (Beigene; see WO 2015/35606 and US 2015/0079109), INCSHR1210 (SHR-1210; Jiangsu Hengrui Medicine; see WO 2015/085847; Si-Yang Liu et al., J. Hematol. Oncol. 10:136 (2017)), TSR-042 (ANB011; Tesaro Biopharmaceutical; see WO2014/179664), GLS-010 (WBP3055; Wuxi/Harbin Gloria Pharmaceuticals; see Si-Yang Liu et al., J. Hematol. Oncol. 10:136 (2017)), AM-0001 (Armo), STI-1110 (Sorrento Therapeutics; see WO 2014/194302), AGEN2034 (Agenus; see WO 2017/040790), MGD013 (Macrogenics); IBI308 (Innovent; see WO 2017/024465, WO 2017/025016, WO 2017/132825, WO2017/133540); BMS-936559 (formerly 12A4 or MDX-1105; see, e.g., U.S. Pat. No. 7,943,743 and WO 2013/173223), MPDL3280A (also known as RG7446, atezolizumab, and TECENTRIQ; U.S. Pat. No. 8,217,149; see, also, Herbst et al. (2013) J Clin Oncol 31(suppl):3000), durvalumab (IMFINZI; MEDI-4736; AstraZeneca; see WO 2011/066389), avelumab (Pfizer; MSB-0010718C; BAVENCIO; see WO 2013/079174), STI-1014 (Sorrento; see WO2013/181634), CX-072 (Cytomx; see WO2016/149201), KN035 (3D Med/Alphamab; see Zhang et al., Cell Discov. 7:3 (March 2017), LY3300054 (Eli Lilly Co.; see, e.g, WO 2017/034916), CK-301 (Checkpoint Therapeutics; see Gorelik et al., AACR:Abstract 4606 (April 2016)); urelumab, PF-05082566, MEDI6469, TRX518, varlilumab, CP-870893, BMS-986016, MGA271, lirilumab, IPH2201, emactuzumab, INCB024360, galunisertib, ulocuplumab, BKT140, Bavituximab, CC-90002, bevacizumab, MNRP1685A, ipilimumab (YERVOY; U.S. Pat. No. 6,984,720), MK-1308 (Merck), AGEN-1884 (Agenus Inc.; WO 2016/196237), and tremelimumab (formerly ticilimumab, CP-675,206; AstraZeneca; see, e.g., WO 2000/037504 and Ribas, Update Cancer Ther. 2(3): 133-39 (2007)).

In certain embodiments, the immune checkpoint inhibitor is selected from: nivolumab, pembrolizumab, JS001, BGB-A317, INCSHR1210, TSR-042, GLS-010, STI-1110, MGD013, IBI308, BMS-936559, atezolizumab, durvalumab, avelumab, STI-1014, CX-072, KN035, LY3300054, CK-301, urelumab, PF-05082566, MEDI6469, TRX518, varlilumab, BMS-986016, ipilimumab, AGEN-1884, and tremelimumab.

In certain of these embodiments, the immune checkpoint inhibitor is selected from: Urelumab, PF-05082566, MEDI6469, TRX518, Varlilumab, CP-870893, Pembrolizumab (PD1), Nivolumab (PD1), Atezolizumab (formerly MPDL3280A) (PDL1), MEDI4736 (PD-L1), Avelumab (PD-L1), PDR001 (PD1), BMS-986016, MGA271, Lirilumab, IPH2201, Emactuzumab, INCB024360, Galunisertib, Ulocuplumab, BKT140, Bavituximab, CC-90002, bevacizumab, and MNRP1685A.

In certain embodiments, the immune checkpoint inhibitor is selected from: nivolumab, ipilimumab, pembrolizumab, atezolizumab, durvalumab and avelumab.

In certain embodiments, the immune checkpoint inhibitor is selected from: nivolumab and ipilimumab.

In certain embodiments, the additional anti-cancer agent (chemotherapeutic agent) is a STING agonist. For example, the STING agonist can include cyclic di-nucleotides, such as cAMP, cGMP, and cGAMP as well as modified cyclic di-nucleotides that include one or more of the following modification features (2'-O/3'-O linkage, phosphorothioate linkage, adenine and/or guanine analogue, 2'-OH modification (e.g., —OCH$_3$ or replacement, e.g., —F or N$_3$). See, e.g., WO 2014/189805.

In certain embodiments, the additional chemotherapeutic agent is an alkylating agent. Alkylating agents are so named because of their ability to alkylate many nucleophilic functional groups under conditions present in cells, including, but not limited to cancer cells. In a further embodiment, an alkylating agent includes, but is not limited to, Cisplatin, carboplatin, mechlorethamine, cyclophosphamide, chlorambucil, ifosfamide and/or oxaliplatin. In an embodiment, alkylating agents can function by impairing cell function by forming covalent bonds with the amino, carboxyl, sulfhydryl, and phosphate groups in biologically important molecules or they can work by modifying a cell's DNA. In a further embodiment an alkylating agent is a synthetic, semisynthetic or derivative.

In certain embodiments, the additional chemotherapeutic agent is an anti-metabolite. Anti-metabolites masquerade as purines or pyrimidines, the building-blocks of DNA and in general, prevent these substances from becoming incorporated in to DNA during the "S" phase (of the cell cycle), stopping normal development and division. Anti-metabolites can also affect RNA synthesis. In an embodiment, an antimetabolite includes, but is not limited to azathioprine and/or mercaptopurine. In a further embodiment an antimetabolite is a synthetic, semisynthetic or derivative.

In certain embodiments, the additional chemotherapeutic agent is a plant alkaloid and/or terpenoid. These alkaloids are derived from plants and block cell division by, in general, preventing microtubule function. In an embodiment, a plant alkaloid and/or terpenoid is a *vinca* alkaloid, a podophyllotoxin and/or a taxane. *Vinca* alkaloids, in general, bind to specific sites on tubulin, inhibiting the assembly of tubulin into microtubules, generally during the M phase of the cell cycle. In an embodiment, a *vinca* alkaloid is derived, without limitation, from the Madagascar periwinkle, Catharanthus *roseus* (formerly known as *Vinca rosea*). In an embodiment, a *vinca* alkaloid includes, without limitation, Vincristine, Vinblastine, Vinorelbine and/or Vindesine. In an embodiment, a taxane includes, but is not limited to, Taxol, Paclitaxel and/or Docetaxel. In a further embodiment a plant alkaloid or terpernoid is a synthetic, semisynthetic or derivative. In a further embodiment, a podophyllotoxin is, without limitation, an etoposide and/or teniposide. In an embodiment, a taxane is, without limitation, docetaxel and/or ortataxel. In an embodiment, a cancer therapeutic is a topoisomerase. Topoisomerases are essential enzymes that maintain the topology of DNA. Inhibition of type I or type II topoisomerases interferes with both transcription and replication of DNA by upsetting proper DNA supercoiling. In a further embodiment, a topoisomerase is, without limitation, a type I topoisomerase inhibitor or a type II topoisomerase inhibitor. In an embodiment a type I topoisomerase inhibitor is, without limitation, a camptothecin. In another embodiment, a camptothecin is, without limitation, exatecan, irinotecan, lurtotecan, topotecan, BNP 1350, CKD 602, DB 67 (AR67) and/or ST 1481. In an embodiment, a type II topoisomerase inhibitor is, without limitation, epipodophyllotoxin. In a further embodiment an epipodophyllotoxin is, without limitation, an amsacrine, etoposid, etoposide phosphate and/or teniposide. In a further embodiment a topoisomerase is a synthetic, semisynthetic or derivative, including those found in nature such as, without limitation, epipodophyllotoxins, substances naturally occurring in the root of American Mayapple (*Podophyllum peltatum*).

In certain embodiments, the additional chemotherapeutic agent is a stilbenoid. In a further embodiment, a stilbenoid includes, but is not limited to, Resveratrol, Piceatannol, Pinosylvin, Pterostilbene, Alpha-Viniferin, Ampelopsin A, Ampelopsin E, Diptoindonesin C, Diptoindonesin F, Epsilon-Vinferin, Flexuosol A, Gnetin H, Hemsleyanol D, Hopeaphenol, Trans-Diptoindonesin B, Astringin, Piceid and Diptoindonesin A. In a further embodiment a stilbenoid is a synthetic, semisynthetic or derivative.

In certain embodiments, the additional chemotherapeutic agent is a cytotoxic antibiotic. In an embodiment, a cytotoxic antibiotic is, without limitation, an actinomycin, an anthracenedione, an anthracycline, thalidomide, dichloroacetic acid, nicotinic acid, 2-deoxyglucose and/or chlofazimine. In an embodiment, an actinomycin is, without limitation, actinomycin D, bacitracin, colistin (polymyxin E) and/or polymyxin B. In another embodiment, an antracenedione is, without limitation, mitoxantrone and/or pixantrone. In a further embodiment, an anthracycline is, without limitation, bleomycin, doxorubicin (Adriamycin), daunorubicin (daunomycin), epirubicin, idarubicin, mitomycin, plicamycin and/or valrubicin. In a further embodiment a cytotoxic antibiotic is a synthetic, semisynthetic or derivative.

In certain embodiments, the additional chemotherapeutic agent is selected from endostatin, angiogenin, angiostatin, chemokines, angioarrestin, angiostatin (plasminogen fragment), basement-membrane collagen-derived anti-angiogenic factors (tumstatin, canstatin, or arrestin), anti-angiogenic antithrombin III, signal transduction inhibitors, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment) and the like.

In certain embodiments, the additional chemotherapeutic agent is selected from abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

In certain embodiments, the additional chemotherapeutic agent is platinum, cisplatin, carboplatin, oxaliplatin, mechlorethamine, cyclophosphamide, chlorambucil, azathioprine, mercaptopurine, vincristine, vinblastine, vinorelbine, vindesine, etoposide and teniposide, paclitaxel, docetaxel, irinotecan, topotecan, amsacrine, etoposide, etoposide phosphate, teniposide, 5-fluorouracil, leucovorin, methotrexate, gemcitabine, taxane, leucovorin, mitomycin C, tegafur-uracil, idarubicin, fludarabine, mitoxantrone, ifosfamide and doxorubicin. Additional agents include inhibitors of mTOR (mammalian target of rapamycin), including but not limited to rapamycin, everolimus, temsirolimus and deforolimus.

In still other embodiments, the additional chemotherapeutic agent can be selected from those delineated in U.S. Pat. No. 7,927,613.

In yet another embodiment, the methods can further include administering one or both of: (i) one or more anti-fungal agents (e.g., selected from the group of bifonazole, butoconazole, clotrimazole, econazole, ketoconazole, luliconazole, miconazole, omoconazole, oxiconazole, sertaconazole, sulconazole, tioconazole, albaconazole, efinaconazole, epoziconazole, fluconazole, isavuconazole, itraconazole, posaconazole, propiconazole, ravusconazole, terconazole, voriconazole, abafungin, amorolfin, butenafine, naftifine, terbinafine, anidulafungin, caspofungin, micafungin, benzoic acid, ciclopirox, flucytosine, 5-fluorocytosine, griseofulvin, haloprogin, tolnaflate, undecylenic acid, and balsam of peru) and (ii) one or more antibiotics (e.g., selected from the group of amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin, amoxicillin, calvulanate, ampicillin, subbactam, piperacillin, tazobactam, ticarcillin, clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethoxazole, sulfanilimide, sulfasalazine, sulfisoxazole, trimethoprim-sulfamethoxazole, sulfonamideochrysoidine, demeclocycline, minocycline, oytetracycline, tetracycline, clofazimine, dapsone, dapreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalopristin, thiamphenicol, tigecycyline, tinidazole, trimethoprim, and teixobactin).

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of such treatment (e.g., by way of biopsy, endoscopy, or other conventional method known in the art). In certain embodiments, the NLRP3 protein can serve as a biomarker for certain types of cancer.

In some embodiments, the chemical entities, methods, and compositions described herein can be administered to certain treatment-resistant patient populations (e.g., patients resistant to checkpoint inhibitors).

In some embodiments, the compounds of the present invention may be used in therapy. In certain embodiments, the present invention provides a combined preparation of a compound of the present invention, or a pharmaceutically acceptable salt thereof, and additional therapeutic agent(s) for simultaneous, separate or sequential use in therapy.

In some embodiments, a compound of the present invention, or a pharmaceutically acceptable salt thereof, or a pharmaceutical composition containing the same, may be used as a medicament. In certain embodiments, the compounds of the invention may be used for the manufacture of a medicament for the treatment of cancer. In certain embodiments, the compounds of the invention may be used for the manufacture of a medicament for modulating NLRP3 activity. In certain embodiments, the modulating comprises agonizing NLRP3.

Methods of Preparation

As can be appreciated by the skilled artisan, methods of synthesizing the compounds of the formulae herein will be evident to those of ordinary skill in the art. For example, the compounds described herein can be synthesized, e.g., using one or more of the methods described herein and/or using methods described in, e.g., US 2015/0056224. Synthetic chemistry transformations and protecting group methodologies (protection and deprotection) useful in synthesizing the compounds described herein are known in the art and include, for example, those such as described in Larock, R. C., *Comprehensive Organic Transformations,* $2^{nd}$ Edition, Wiley-VCH, New York, NY (1999); Wuts, P. G. M., *Greene's Protective Groups in Organic Synthesis,* 5th Edition, Wiley (2014); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof. The starting materials used in preparing the compounds of the invention are known, made by known methods, or are commercially available. The skilled artisan will also recognize that conditions and reagents described herein that can be interchanged with alternative art-recognized equivalents. For example, in many reactions, triethylamine can be interchanged with other bases, such as non-nucleophilic bases (e.g. diisopropylamine, 1,8-diazabicycloundec-7-ene, 2,6-di-tert-butylpyridine, or tetrabutylphosphazene).

The skilled artisan will recognize a variety of analytical methods that can be used to characterize the compounds described herein, including, for example, $^1$H NMR, heteronuclear NMR, mass spectrometry, liquid chromatography, and infrared spectroscopy. The foregoing list is a subset of characterization methods available to a skilled artisan and is not intended to be limiting.

The following abbreviations have the indicated meanings:
ACN=acetonitrile
AcOH=acetic acid
BOP=(Benzotriazol-1-yloxy)tris(dimethylamino)phosphonium hexafluorophosphate
$CDCl_3$=chloroform-d
$CD_3OD$=methanol-$d_4$
$CH_2Cl_2$=dichloromethane
$CH_3ReO_3$=methyltrioxorhenium
$Cs_2CO_3$=cesium carbonate
CuI=copper (I) iodide
d=doublet
DCM=dichloromethane
DIEA=N,N-diisopropylethylamine
DMF=N,N-dimethylformamide
DMSO=dimethylsulfoxide
ES=electrospray ionization
$Et_2O$=diethyl ether
EtOAc=ethyl acetate
EtOH=ethanol
equiv=equivalents
g=gram(s)
h=hour(s)
HCl=hydrogen chloride (usually as a solution)
$H_2O$=water
$H_2O_2$=hydrogen peroxide
HATU=1-[Bis(dimethylamino)methylene]-1H-1,2,3-triazolo[4,5-b]pyridinium 3-oxide hexafluorophosphate
HPLC=high-performance liquid chromatography
$I_2$=iodine
$K_2CO_3$=potassium carbonate
$K_2HPO_4$=potassium phosphate, dibasic
KI=potassium iodide
kg=kilogram(s)
LC/MS=liquid chromatography mass spectrometer
$LiBH_4$=lithium borohydride
m=multiplet
m/z=mass to charge ratio
M=molar
m-CPBA=meta-chloroperoxybenzoic acid
mg=milligram(s)
MeOH=methanol
MHz=megahertz
mL=milliliter(s)
mmol=millimole(s)
min=minute(s)
$NaHCO_3$=sodium hydrogen carbonate
$Na_2CO_3$=sodium carbonate
NaOH=sodium hydroxide
$Na_2SO_4$=sodium sulfate
$NEt_3$ and TEA=triethylamine
$NH_4OH$ or $NH_3H_2O$=ammonium hydroxide
$NH_4HCO_3$=ammonium hydrogen carbonate
nm=nanometer
$PdCl_2(PPh_3)_2$=bis(triphenylphosphine)palladium (II) dichloride
$Pd(dppf)Cl_2$=[1,1'-Bis(diphenylphosphino)ferrocene]dichloropalladium(II)
$Pd(dppf)Cl_2DCM$=[1,1'-Bis(diphenylphosphino)ferrocene]dichloropalladium(II) dichloromethane complex
$Pd(OH)_2$=palladium hydroxide
PMB=para-methoxybenzyl
$POCl_3$=phosphorous oxychloride
ppm=parts per million
Pt=platinum
Pt/C=platinum on carbon
s=singlet
t=triplet
TFA=trifluoroacetic acid
TLC=thin layer chromatography
TsCl=para-toluenesulfonyl chloride
° C.=degrees Celsius
µmol=micromole(s)

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention.

The compounds of this invention may be prepared using the reactions and techniques described in this section (e.g., Scheme 1).

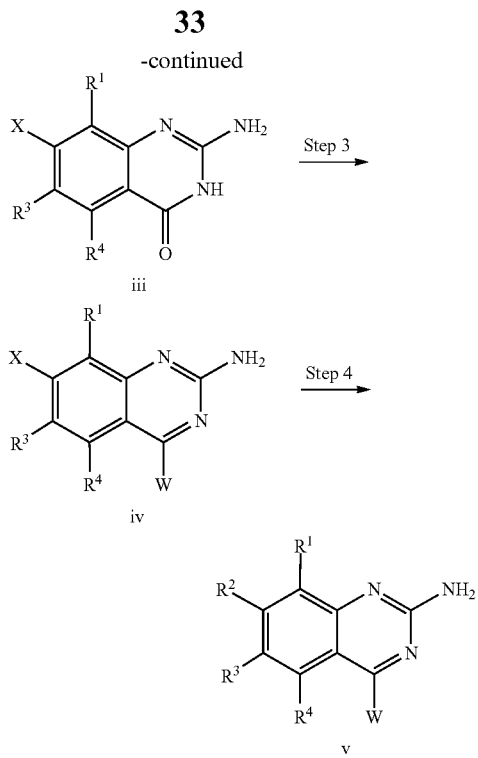

Step 1: The first step of begins with a suitably functionalized aminobenzoate (i). If desired, the group Z may be the group $R^2$ found in the final product. Alternatively, the group Z may be a group that can be transformed into the group $R^2$ found in the final product, such as bromo. This aminobenzoate may be available commercially or synthesized by methods known to one skilled in the art. In step 1, aminobenzoate (i) is reacted with a reagent or combination of reagents to transform it into aminoquinazolinone (ii), such as cyanamide and hydrochloric acid, in a suitable solvent, such as dioxane.

Step 2: In this optional step, the group Z present in (ii) may be transformed into a different group X. This group X may be the group $R^2$ present in the final product, if desired. Alternatively, group X may be a group that can be transformed into group $R^2$ at a later stage. One skilled in the art will recognize that the conditions selected for step 2 will depend on the identities of the groups X and Z. For example, if group Z is bromo, and the group X is a heteroaryl ring, this transformation may be effected by reaction with a suitable boronic acid or boronic ester in the presence of a catalyst such as $PdCl_2(dppf)$, and base such as cesium carbonate in a solvent mixture such as dioxane and water.

Step 3: In step 3, the quinazolone (iii) is reacted with an appropriate set of reagents to install the group W found in the final molecule. For example, if the desired group W is an amine, this transformation may be effected by reacting (iii) with the desired amine, a reagent such as BOP, and a base such as DBU. Depending on the identity of the desired group W, additional reactions may be performed at this point. For example, if the installed group contains an alkene and the desired group W contains a diol, this transformation may be accomplished by reaction with a reagent such as osmium tetroxide and an oxidant such as NMO.

Step 4: In this optional step, if the group X in (iv) is not the desired group $R^2$ in the final molecule (v), it may be transformed into $R^2$ under suitable conditions. For example, if the desired group $R^2$ is 3-pyrazoyl and the group X is a pyrazole protected by a tetrohydropyran group, the protecting group may be removed by a suitable combination of acid and solvent, such as HCl and methanol, or TFA and DCM.

Evaluation of Biological Activity

Measurement of IL-1β Production in PMA-Differentiated THP-1 Cells

THP-1 cells were purchased from the American Type Culture Collection and sub-cultured according to instructions from the supplier. Prior to experiments, cells were cultured in RPMI 1640 containing 10% heat inactivated FBS, penicillin (100 units/ml) and streptomycin (100 μg/ml), and maintained in log phase prior to experimental setup. Prior to the experiment THP-1 were treated with PMA (Phorbol 12-myristate 13-acetate) (10 μg/ml) for 24 hours. The day of the experiment the media was removed and attaching cells were treated with trypsin for 2 minutes, cells were then collected, washed with PBS (phosphate buffer saline), spin down, resuspended in 2% heat inactivated FBS with RPMI at a concentration of 1×10⁶ cells/ml, and 100 μl was plated in a 96 well plate. Compounds were dissolved in dimethyl sulfoxide (DMSO) and added to the culture medium to achieve desired concentration (e.g. 100, 30, 10, 3, 1, 0.3 or 0.1 μM). Cells were incubated with compounds for 4 hours. Cell free supernatant was collected and the production of IL-1β was evaluated by ELISA. A vehicle only control was run concurrently with each experiment. Final DMSO concentration was 1%. Compounds exhibit a dose-related increase of IL-1β production in PMA-differentiated THP-1 cells.

Measurement of IL-1β Production in PMA-Differentiated THP-1 Cells (Alternative Procedure)

THP-1 cells were purchased from the American Type Culture Collection and sub-cultured according to instructions from the supplier. Prior to experiments, cells were cultured in RPMI 1640 containing 10% heat inactivated FBS, penicillin (100 units/ml), streptomycin (100 μg/ml), HEPES (10 mM) and sodium pyruvate (1 mM) and maintained in log phase prior to experimental setup. Prior to the experiment, THP-1 cells were treated with PMA (Phorbol 12-myristate 13-acetate) (20 μg/ml) overnight. The day of the experiment, the media was removed and attached cells were treated with trypsin for 2 minutes, cells were then collected, washed with PBS (phosphate buffer saline), pelleted by centrifugation and resuspended in 2% heat inactivated FBS with RPMI at a concentration of 50,000 cells/well in a 384 well plate. Cell free supernatant was collected and the production of IL-1β was evaluated by ELISA. Compounds were dissolved in dimethyl sulfoxide (DMSO) and added to the culture medium to achieve desired concentration (e.g. 100, 30, 10, 3, 1, 0.3 or 0.1 μM). Cells were incubated with compounds for 2 hours. A vehicle only control was run concurrently with each experiment. Final DMSO concentration was 1%. Compounds exhibit a dose-related increase of IL-1β production in PMA-differentiated THP-1 cells.

Measurement of IL-1β Production—hTRF Protocol (Second Alternative Procedure)

Serial dilutions of compounds in DMSO were added to low volume 384 well plates at 100 nl/well using an ECHO 550 acoustic dispenser (Labcyte) to achieve final starting concentration of 10 μM in assay.

THP-1 cells in RPMI (Gibco, 11875) media with 10% FBS at a density of 1×10⁶ cell/ml in a T175 flask were treated with a final concentration of phorbol 12-myristate 13-acetate (PMA) (Sigma, P1585) of 50 ng/ml overnight at 37° C. at 5% $CO_2$ for differentiation. Cells were harvested the next day after rinsing well with dPBS using 0.5% trypsin. A cell solution was prepared of 1×10⁶ cells/ml for 50,000 cells in 50 μl/well in RPMI media with 2% FBS. Cells were plated using a multichannel pipette onto the compound dilutions in Greiner, 384 well, black clear bottom tissue culture treated plates (781090). The plates were incubated in 37° C. incubator at 5% $CO_2$ for 2 hours.

After the 2 hour incubation, the cell plates were spun in the centrifuge for 5 minutes at 1200 rpm. Using the Felix (CyBio), 8 μl of the supernatant was transferred to 384 well, low volume, white proxy plates. (Perkin Elmer, 6008230). A human IL1beta hTRF kit was used to analyze the supernatant (CISBIO, 62HIL1BPEG). The kit instructions were followed for preparing the IL1Beta standard curve and then the antibodies from the kit were diluted 1:40 rather than 1:20 as kit instructed. Once combined, the antibodies were added across the plates, 5 μl/well. The plates were sealed and incubated at 4° C. overnight. The plates were then read on the Perkin Elmer EnVision at 665/615 nm using the hTRF laser. Compounds exhibited a dose-related increase of IL-1β production.

Measurement of IL-1β Production—Human Whole Blood Assay

Serial dilutions of compounds in DMSO were added to low volume 384 well plates at 100 nl/well using an ECHO 550 acoustic dispenser (Labcyte) to achieve final starting concentration of 10 uM in assay.

Human venous whole blood obtained from healthy donors was pre-treated with LPS (Invivogen, Cat #tlrl-eblps) at 1 ng/ml for four hours at 37° C. in a humidified 95% air/5% CO2 incubator. Primed blood was added to the compound plate and incubated for additional 4 hours at 37° C. IL-1beta in the supernatants was measured using AlphLISA kit (Cat #AL220) according to manufacturer's instructions. Compounds exhibited a dose-related increase of IL-1β production. EC50 was determined using primed but untreated blood as baseline.

Measurement of IL-1β Production—Mouse hTRF Protocol

Immortalized mouse macrophages derived from C57BL/6 mice were obtained from Ericke Latz, University of Bonn/ University of Massachusetts Worchester, MA The cells were harvested using 0.05% Trypsin and washed with PBS. Cell were plated at 30,000 cells per well in 25 ul in DMEM (Gibco, 11965) supplemented with 2% FBS and incubated for 10 minutes at 37° C. at 5% $CO_2$. LPS-EB (Invivogen, tlr-eblps) was added to a final concentration of 200 ng/ml at 5 ul/well and cells were incubated for 2 hours at 37° C. at 5% $CO_2$.

Serial dilutions of compounds in DMSO were added to cells in low volume 384 well plates at 60 nl/well using an ECHO 550 acoustic dispenser (Labcyte) to achieve final starting concentration of 50 uM in assay and incubated with compounds for additional 2 hours at 37° C. at 5% $CO_2$.

After the 2 hour incubation, the cell plates were spun in the centrifuge for 5 minutes at 1200 rpm. Using the Felix (CyBio), 5 ul of the supernatant was transferred to 384 well, low volume, white proxy plates. (Perkin Elmer, 6008230). A human IL1beta hTRF kit was used to analyze the supernatant (CISBIO, 62MIL1BPEH). The kit instructions were followed for preparing the ILiBeta standard curve (the antibodies from the kit were diluted 1:40 rather than 1:20 as kit instructed). Once combined, the antibodies were added across the plates at 5 ul/well. The plates were sealed and incubated at 4° C. overnight. The plates were read on the Perkin Elmer EnVision at 665/615 nm using the hTRF laser. Data was then converted to pg/ml of Il1Beta. Compounds exhibited a dose-related increase of IL-1β production.

In Vitro Human TLR7 and TLR8 Binding Reporter Assays

Logarithmically-growing human HEK-Blue cells co-expressing a TLR7 or TLR8 gene and a NF-kB/AP1-inducible SEAP (secreted embryonic alkaline phosphatase; Invivogen, San Diego, CA) reporter gene are added to individual wells of a 384-well plate (15,000 cells per 20 μL per well) and maintained for 24 h at 37° C., 5% $CO_2$. Test compounds or DMSO are distributed to separate wells the next day using acoustic liquid handling technology (100 nL per well) and cells are subsequently incubated for 18 h at 37° C., 5% $CO_2$. Cellular SEAP production is measured using an Envision plate reader instrument thirty minutes after adding freshly-made Quanti-Blue reagent (prepared by following manufacturer instructions; Invivogen, San Diego, CA) to the HEK-Blue TLR Nf-kB-SEAP cell reactions. All $EC_{50}$ values (half-maximal effective concentration) are determined using proprietary data analysis software. Normalized $EC_{50}$ value=absolute value determined by setting 100% Ymax using a reference standard RLU (relative light unit) values from cells treated with 50 μM of the reference standard.

EXAMPLES

To further illustrate the foregoing, the following non-limiting, exemplary synthetic schemes are included. Variations of these examples within the scope of the claims are within the purview of one skilled in the art and are considered to fall within the scope of the invention as described, and claimed herein. The reader will recognize that the skilled artisan, provided with the present disclosure, and skill in the art is able to prepare and use the invention without exhaustive examples.

HPLC/MS and Preparatory/Analytical HPLC Methods Employed in Characterization or Purification of Examples Analytical HPLC/MS was performed using the following methods:

Method A. Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min;

Method B. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV 220 nm;

Method C. Column: Acquity BEH C18, 2.1 mm×50 mm, 1.7 μm particles; Mobile Phase A: water with 5 mM ammonium bicarbonate; Mobile Phase B: acetonitrile; Gradient: 2% B to 98% B over 1 min, then a 0.5 min hold at 98% B; Flow: 0.8 mL/min; Detection: MS and UV.

Method D. Column: Chiral AS, 100 mm×4.6 mm, 5-μm particles; Mobile Phase: 75% $CO_2$: 25% with 0.1% DEA; Flow Rate: 2 mL/min.

Method E. Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm).

Nuclear Magnetic Resonance (NMR) Spectroscopy

Chemical shifts are reported in parts per million (ppm) downfield from internal tetramethylsilane (TMS) or from the position of TMS inferred by the deuterated NMR solvent.

Apparent multiplicities are reported as: singlet-s, doublet-d, triplet-t, quartet-q, or multiplet-m. Peaks which exhibit broadening are further denoted as br. Integrations are approximate. It should be noted that integration intensities, peak shapes, chemical shifts and coupling constants can be dependent on solvent, concentration, temperature, pH, and other factors. Further, peaks which overlap with or exchange with water or solvent peaks in the NMR spectrum may not provide reliable integration intensities. In some cases, NMR spectra are obtained using water peak suppression, which may result in overlapping peaks not being visible or having altered shape and/or integration.

Example 1. (R)-1-((2-amino-7-(1H-pyrazol-5-yl)quinazolin-4-yl)amino)propan-2-ol

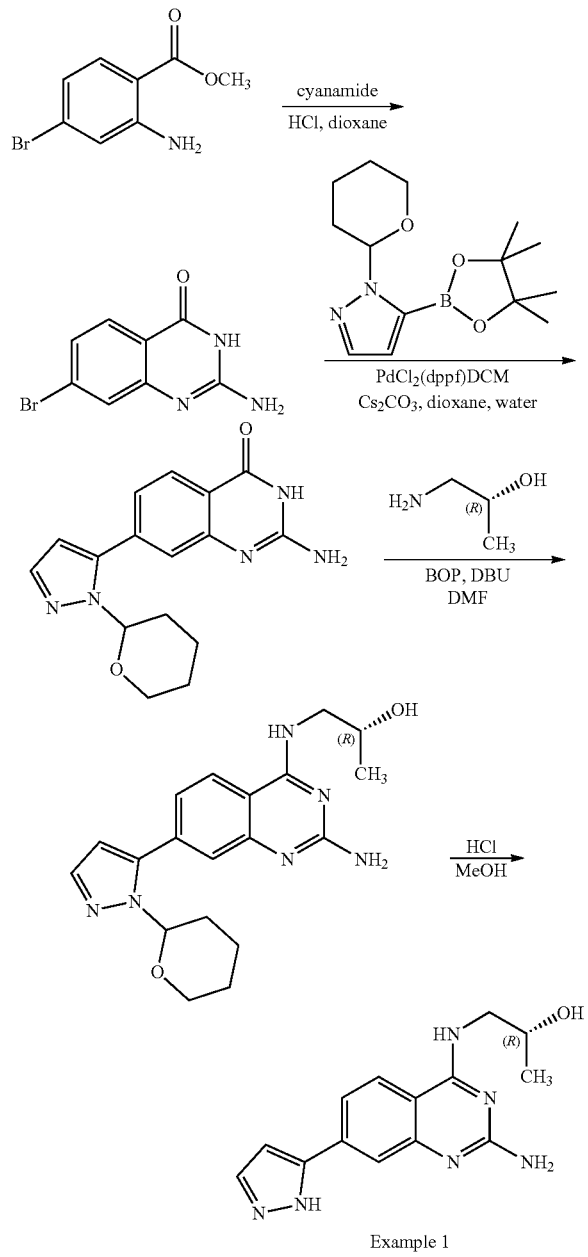

Example 1

1A. 2-amino-7-bromoquinazolin-4(3H)-one

To a mixture of methyl 2-amino-4-bromobenzoate (485 mg, 2.1 mmol) and cyanamide (106 mg, 2.5 mmol) in dioxane (5 mL) was added 4M HCl in dioxane (0.69 mL, 2.7 mmol). The reaction mixture was heated at 70° C. for 2 hours then heated to 100° C. for 1 hour. The reaction mixture was cooled to room temperature and diluted with Et$_2$O. The white precipitate was collected by filtration and rinsed with Et$_2$O followed by small EtOH rinse and water rinses. The solid was dried under vacuum to give 2-amino-7-bromoquinazolin-4(3H)-one (429 mg, 85% yield). HPLC RT: 0.605 min (Method A). LC-MS: (ES, m/z): [M+H]$^+$=240. $^1$HNMR (400 MHz, DMSO) δ 8.33-8.04 (m, 2H), 7.88 (d, J=8.4 Hz, 1H), 7.64 (d, J=1.6 Hz, 1H), 7.51 (dd, J=8.4, 1.7 Hz, 1H).

1B. 2-amino-7-(1-(tetrahydro-2Hpyran-2-yl)-1Hpyrazol-5-yl)quinazolin-4(3H)-one

To a mixture of 2-amino-7-bromoquinazolin-4(3H)-one (2.86 g, 11.9 mmol), 1-(tetrahydro-2H-pyran-2-yl)-5-(4,4,5,5-tetramethyl-1,3,2-dioxaborolan-2-yl)-1Hpyrazole (3.97 g, 14.3 mmol) and Cs$_2$CO$_3$ (11.6 g, 35.7 mmol) in Dioxane (120 mL) and water (30 mL) was added PdCl$_2$(dppf)-DCM Adduct (0.97 g, 1.2 mmol) under N$_2$. The reaction mixture was heated with reflux condensor on 110° C. heating block. When complete, the reaction was cooled to room temperature and concentrated. To the residue was added 1M NaOH (120 mL) and stirred for 20 minutes. The mixture was filtered through celite with 1M NaOH rinses. The basic aqueous mother liquor was slowly acidified with 1M aqueous citric acid to pH 4 and the resulting light tan precipitate was collected by filtration with water rinses. The solid was dried under vacuum to give 2-amino-7-(1-(tetrahydro-2Hpyran-2-yl)-1Hpyrazol-5-yl)quinazolin-4(3H)-one (2.28 g, 61.5% yield). HPLC RT: 1.138 min (Method A). LC-MS: (ES, m/z): [M+H]$^+$=312. $^1$HNMR (400 MHz, DMSO) δ 11.35-10.75 (m, 1H), 7.96 (br d, J=8.1 Hz, 1H), 7.59 (s, 1H), 7.35 (s, 1H), 7.23 (br d, J=8.0 Hz, 1H), 6.66-6.36 (m, 3H), 5.26 (br d, J=9.3 Hz, 1H), 4.01 (br d, J=10.9 Hz, 1H), 3.57 (br t, J=8.8 Hz, 1H), 2.45-2.32 (m, 1H), 1.93 (br s, 1H), 1.78 (br d, J=12.5 Hz, 1H), 1.65-1.48 (m, 3H).

1C. (2R)-1-((2-amino-7-(1-(tetrahydro-2H-pyran-2-yl)-1H-pyrazol-5-yl)quinazolin-4-yl)amino)propan-2-ol To a mixture of 2-amino-7-(1-(tetrahydro-2Hpyran-2-yl)-1Hpyrazol-5-yl)quinazolin-4(3H)-one (50 mg, 0.16 mmol) and BOP (92 mg, 0.21 mmol) in DMF (0.6 mL) was added DBU (73 µL, 0.48 mmol) and the dark red solution was stirred at room temperature for 5 min then (R)-1-aminopropan-2-ol (0.019 mL, 0.241 mmol) was added. When complete the reaction mixture was diluted with water and 10% LiCl aq and extracted 3× with EtOAc. The organic layer was dried over MgSO$_4$, filtered and concentrated to give the crude material which was used directly without purification. HPLC RT: 1.340 min (Method A). LC-MS: (ES, m/z): [M+H]$^+$=369.

Example 1

To a solution of (2R)-1-((2-amino-7-(1-(tetrahydro-2H-pyran-2-yl)-1H-pyrazol-5-yl)quinazolin-4-yl)amino)propan-2-ol (58.9 mg, 0.16 mmol) in EtOH (2 mL) was added 4M HCl in dioxane (241 uL, 0.96 mmol) and the reaction was stirred at room temperature. When complete the white precipitate that formed was collected by filtration with EtOH rinses and dried under vacuum to give (R)-1-((2-amino-7-(1H-pyrazol-5-yl)quinazolin-4-yl)amino)propan-2-ol, HCl (34.1 mg, 65.5% yield).

Example 2. N4-(1H-pyrazol-3-yl)-7-(1H-pyrazol-5-yl)quinazoline-2,4-diamine

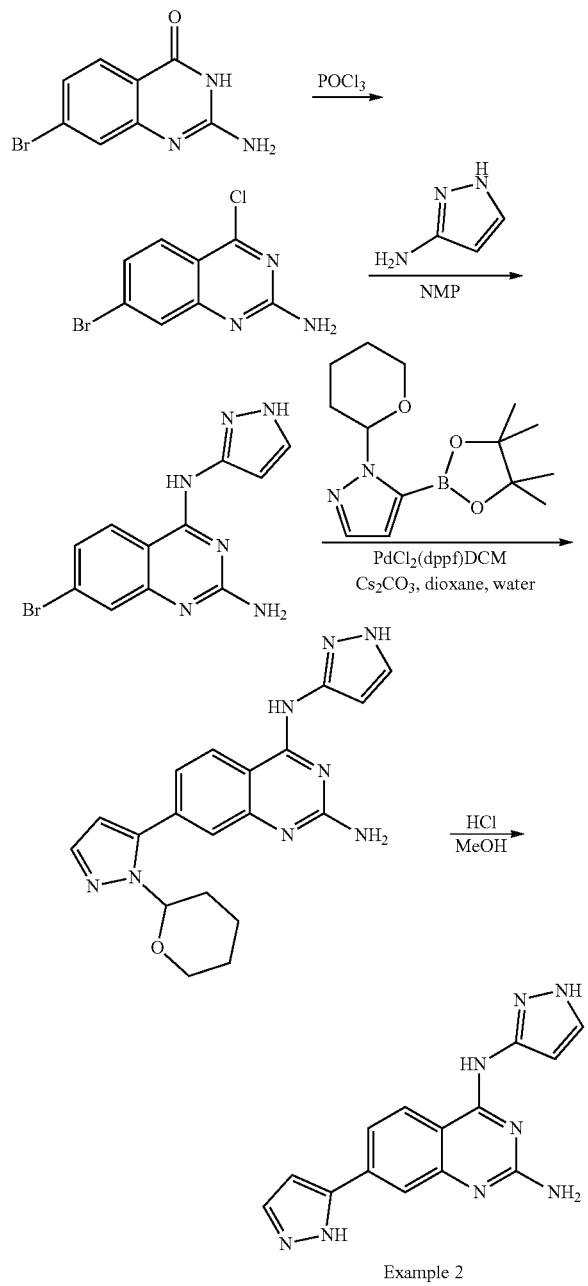

Example 2

2A. 7-bromo-4-chloroquinazolin-2-amine

A mixture of 2-amino-7-bromoquinazolin-4(3H)-one (600 mg, 2.5 mmol) in POCl$_3$ (6 mL, 64 mmol) was heated in a sealed 40 mL vial under N$_2$ on a 100° C. heating block for 48 hours. The reaction mixture was concentrated then ice and water were added and the reaction mixture slowly neutralized with saturated aqueous NaHCO$_3$. The yellow solid formed was collected by filtration with water rinses and dried under vacuum to give 7-bromo-4-chloroquinazolin-2-amine (629 mg, 97%). HPLC RT: 1.097 min (Method A). LC-MS: (ES, m/z): [M+H]$^+$=258.

2B. 7-bromo-N4-(1H-pyrazol-3-yl)quinazoline-2,4-diamine

A mixture of 7-bromo-4-chloroquinazolin-2-amine (60 mg, 0.23 mmol) and 1H-pyrazol-3-amine (77 mg, 0.92 mmol) in NMP (0.6 mL) was heated on a 80° C. heating block for 18 hours. The reaction mixture was cooled to room temperature and diluted with water and saturated aqueous NaHCO$_3$. The pale yellow solid formed was collected by filtration with water rinses and dried under vacuum to give 7-bromo-N4-(1H-pyrazol-3-yl)quinazoline-2,4-diamine (56.9 mg, 80%). HPLC RT: 1.078 min (Method A). LC-MS: (ES, m/z): [M+H]$^+$=305.

2C. N4-(1H-pyrazol-3-yl)-7-(1-(tetrahydro-2H-pyran-2-yl)-1H-pyrazol-5-yl)quinazoline-2,4-diamine To a mixture of 7-bromo-N4-(1H-pyrazol-3-yl)quinazoline-2,4-diamine (56.9 mg, 0.13 mmol), 1-(tetrahydro-2H-pyran-2-yl)-5-(4,4,5,5-tetramethyl-1,3,2-dioxaborolan-2-yl)-1Hpyrazole (56.6 mg, 0.20 mmol) and Cs$_2$CO$_3$ (133 mg, 0.40 mmol) in dioxane (1 mL) and water (0.2 mL) was added PdCl$_2$(dppf)-CH$_2$Cl$_2$Adduct (11 mg, 0.014 mmol) under N$_2$. The reaction mixture was heated on an 80° C. heating block for 1 hour. The reaction was cooled to room temperature and concentrated. The residue was diluted with water and the resulting precipitate was collected by filtration with water rinses. The solid was dried under vacuum to give N4-(1H-pyrazol-3-yl)-7-(1-(tetrahydro-2H-pyran-2-yl)-1H-pyrazol-5-yl)quinazoline-2,4-diamine which was used directly without purification. HPLC RT: 1.483 min (Method A). LC-MS: (ES, m/z): [M+H]$^+$=377.

Example 2

To a solution of N4-(1H-pyrazol-3-yl)-7-(1-(tetrahydro-2H-pyran-2-yl)-1H-pyrazol-5-yl)quinazoline-2,4-diamine (51 mg, 0.13 mmol) in EtOH (1 mL) was added 4M HCl in dioxane (68 μL, 0.27 mmol) and the reaction was stirred at room temperature. When complete the white precipitate that formed was collected by filtration with EtOH rinses and dried under vacuum. The solid was purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 5-minute hold at 0% B, 0-20% B over 25 minutes, then a 5-minute hold at 100% B; Flow Rate: 20 mL/min; Column Temperature: 25 C. Fraction collection was triggered by MS signals. Fractions containing the desired product were combined and dried via centrifugal evaporation to give N4-(1H-pyrazol-3-yl)-7-(1H-pyrazol-5-yl)quinazoline-2,4-diamine (16.6 mg, 29% yield) as a TFA salt.

Example 3. 3-((2-amino-6-chloro-7-(1H-pyrazol-5-yl)quinazolin-4-yl)amino)propan-1-ol

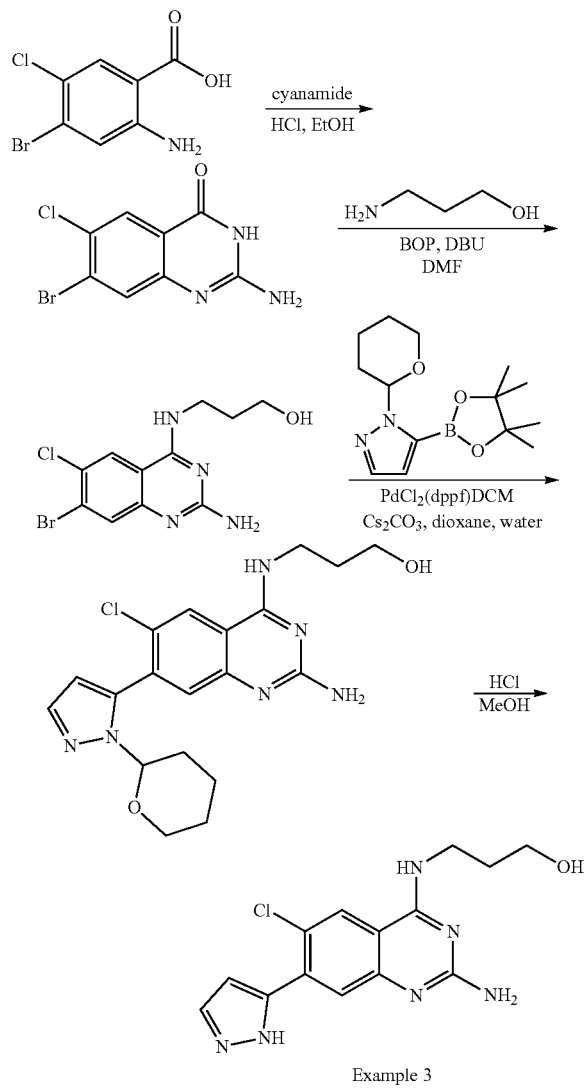

Example 3

3A. 2-amino-7-bromo-6-chloroquinazolin-4(3H)-one

To a mixture of 2-amino-4-bromo-5-chlorobenzoic acid (500 mg, 1.99 mmol) and cyanamide (504 mg, 11.9 mmol) in EtOH (5 mL) was added concentrated aqueous HCl (0.49 mL, 5.9 mmol). The reaction mixture was stirred at room temperature for 1 hour, then cyanamide (504 mg, 11.9 mmol) and concentrated aqueous HCl (0.49 mL, 5.9 mmol) were added, and the reaction heated on a 50° C. heating block for 1 hour. The reaction mixture was then heated at 90° C. for 2 hours. The reaction mixture was cooled to room temperature and the yellow precipitate was collected by filtration and rinsed with EtOH. The solid was dried under vacuum to give 2-amino-7-bromo-6-chloroquinazolin-4 (3H)-one (356.1 mg, 65% yield). HPLC RT: 0.953 min (Method A).

3B. 3-((2-amino-7-bromo-6-chloroquinazolin-4-yl)amino)propan-1-ol

To a mixture of 2-amino-7-bromo-6-chloroquinazolin-4 (3H)-one (50 mg, 0.18 mmol) and BOP (105 mg, 0.23 mmol) in DMF (0.6 mL) was added DBU (41p L, 0.27 mmol) and the dark red solution was stirred at room temperature for 5 min then 3-amino-1-propanol (42 uL, 0.54 mmol) was added. When complete the reaction mixture was diluted with water and 10% aqueous LiCl and extracted with EtOAc. The organic layer was washed with 10% aqueous LiCl and then dried over MgSO$_4$, filtered and concentrated to give the 3-((2-amino-7-bromo-6-chloroquinazolin-4-yl) amino)propan-1-ol (46.2 mg, 76% yield). HPLC RT: 1.257 min (Method A). LC-MS: (ES, m/z): [M+H]$^+$=331.

3C. 3-((2-amino-6-chloro-7-(1-(tetrahydro-2H-pyran-2-yl)-1H-pyrazol-5-yl)quinazolin-4-yl)amino) propan-1-ol To a mixture of 3-((2-amino-7-bromo-6-chloroquinazolin-4-yl)amino)propan-1-ol (46 mg, 0.13 mmol), 1-(tetrahydro-2H-pyran-2-yl)-5-(4,4,5,5-tetramethyl-1,3,2-dioxaborolan-2-yl)-1Hpyrazole (46 mg, 0.16 mmol) and Cs$_2$CO$_3$ (136 mg, 0.41 mmol) in dioxane (2 mL) and water (0.5 mL) was added PdCl$_2$(dppf)-CH$_2$Cl$_2$Adduct (11 mg, 0.014 mmol) under N$_2$. The reaction mixture was heated on an 110° C. heating block for 1 hour. The reaction was cooled to room temperature and concentrated. The residue was diluted with water and the resulting precipitate was collected by filtration with water rinses. The solid was dried under vacuum to give 3-((2-amino-6-chloro-7-(1-(tetrahydro-2H-pyran-2-yl)-1H-pyrazol-5-yl)quinazolin-4-yl)amino)propan-1-ol (35 mg, 62% yield) which was used directly without purification. HPLC RT: 1.472 min (Method A). LC-MS: (ES, m/z): [M+H]$^+$=403.

Example 3

To a solution of 3-((2-amino-6-chloro-7-(1-(tetrahydro-2H-pyran-2-yl)-1H-pyrazol-5-yl)quinazolin-4-yl)amino) propan-1-ol (35 mg, 0.087 mmol) in MOH (1 mL) was added 4M HCl in dioxane (109 µL, 0.43 mmol) and the reaction was stirred at room temperature. When complete the reaction mixture was purified via preparative LC/MS with the following conditions: Column: XBridge C18, 200 mm×19 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 0% B, 0-40% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to give 3-((2-amino-6-chloro-7-(1H-pyrazol-5-yl)quinazolin-4-yl)amino)propan-1-ol (11.2 mg, 29% yield) as a TFA salt.

Example 4. 2-((2-amino-7-(1H-pyrazol-3-yl)quinazolin-4-yl)oxy)ethan-1-ol

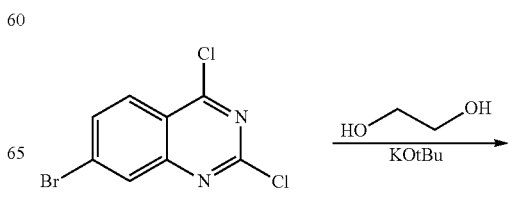

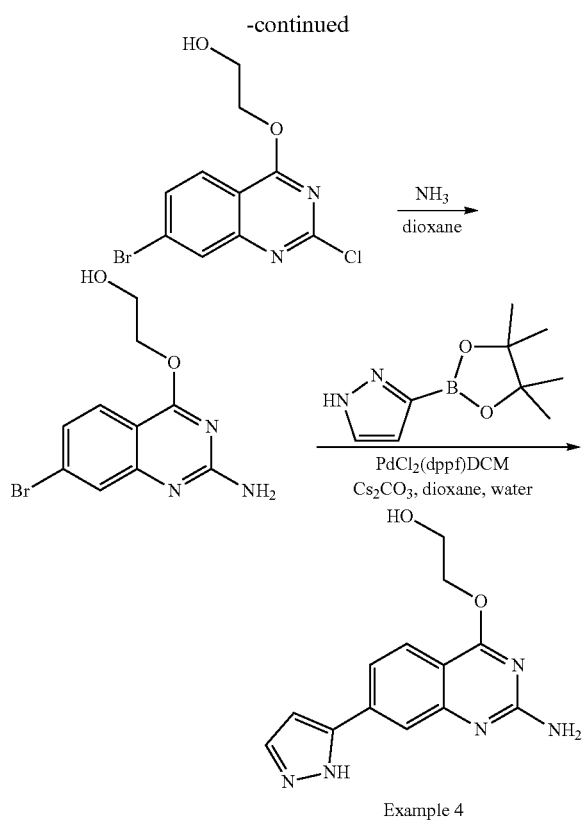

Example 4

4A. 2-((7-bromo-2-chloroquinazolin-4-yl)oxy)ethan-1-ol

To a mixture of 7-bromo-2,4-dichloroquinazoline (100 mg, 0.36 mmol) in NMP (2 mL) cooled in an ice/MeOH bath was added a solution of KOtBu (44 mg, 0.39 mmol) in ethylene glycol (0.2 mL). The reaction mixture was removed from the ice/MeOH bath and stirred at room temperature for 3 hours then water and saturated aqueous $NaHCO_3$ was added to give a white precipitate. The white precipitate was collected by filtration and rinsed with water then dried under vacuum to give 2-((7-bromo-2-chloroquinazolin-4-yl)oxy) ethan-1-ol (77 mg, 70% yield). HPLC RT: 1.763 min (A). LC-MS: (ES, m/z): $[M+H]^+$=303. $^1$H NMR (500 MHz, DMSO-$d_6$) δ 8.16 (dd, J=8.7, 0.4 Hz, 1H), 8.13 (dd, J=1.9, 0.4 Hz, 1H), 7.88 (dd, J=8.7, 1.9 Hz, 1H), 5.05 (t, J=5.8 Hz, 1H), 4.59-4.55 (m, 2H), 3.86-3.81 (m, 2H).

4B. 2-((2-amino-7-bromoquinazolin-4-yl)oxy)ethan-1-ol

A mixture of 2-((7-bromo-2-chloroquinazolin-4-yl)oxy) ethan-1-ol (67 mg, 0.22 mmol) in 0.5M ammonia in dioxane (4.4 mL, 2.2 mmol) was heated to 120° C. in a 20 mL thick walled pressure tube for 24 hours. The reaction mixture was cooled to room temperature and concentrated then purified by silica gel column (24 g, ISCO) eluting with a gradient from 100% $CH_2Cl_2$ to 10% $MeOH/CH_2Cl_2$. The tubes with product were collected and concentrated then dried under vacuum to give 2-((2-amino-7-bromoquinazolin-4-yl)oxy) ethan-1-ol (16.9 mg, 26% yield). HPLC RT: 0.798 min (Method A). LC-MS: (ES, m/z): $[M+H]^+$=284.

Example 4

To a mixture of 2-((2-amino-7-bromoquinazolin-4-yl) oxy)ethan-1-ol (16.9 g, 0.059 mmol), 3-(4,4,5,5-tetramethyl-1,3,2-dioxaborolan-2-yl)-1H-pyrazole (23 g, 0.11 mmol) and $Cs_2CO_3$ (58 mg, 0.17 mmol) in dioxane (0.4 mL) and water (0.04 mL) was added $PdCl_2(dppf)$-$CH_2Cl_2$Adduct (4.8 mg, 0.0059 mmol) under $N_2$. The reaction mixture was heated in a sealed 1 dram vial and heated on a 100° C. heating block for 18 hours. The reaction mixture was cooled to room temperature and diluted with MeOH then purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 2-minute hold at 0% B, 0-40% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to give 2-((2-amino-7-(1H-pyrazol-3-yl)quinazolin-4-yl)oxy)ethan-1-ol (7.1 g, 42% yield).

Example 5 and Example 6: Enantiomer A and Enantiomer B of 5-(((2-amino-7-(1H-pyrazol-5-yl)quinazolin-4-yl)amino)methyl)pyrrolidin-2-one The chiral separation of racemic 5-(((2-amino-7-(1H-pyrazol-5-yl)quinazolin-4-yl)amino)methyl)pyrrolidin-2-one (18 mg, 0.05 mmol) was performed with the following conditions: Column: Chiral AS, 250 mm×30 mm, 5-μm particles; Mobile Phase: 75% $CO_2$: 25% with 0.1% DEA; Flow Rate: 100 mL/min. Fractions containing Enantiomer A were combined and dried via centrifugal evaporation to give 5.9 mg, 36.5% yield. Fractions containing Enantiomer B were combined and dried via centrifugal evaporation to give 5.6 mg, 34.6% yield. Analytical Chiral SFC conditions Column: Chiral AS, 100 mm×4.6 mm, 5-μm particles; Mobile Phase: 75% CO2: 25% with 0.1% DEA; Flow Rate: 2 mL/min. Example 5 RT: 3.8 min. Example 6 RT: 6.2 min.

Example 7. 4-((1-methyl-1H-1,2,4-triazol-5-yl)methoxy)-7-(1H-pyrazol-5-yl)quinazolin-2-amine

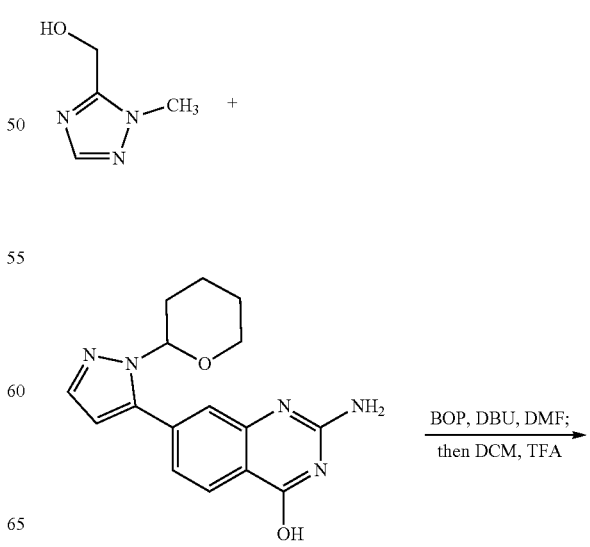

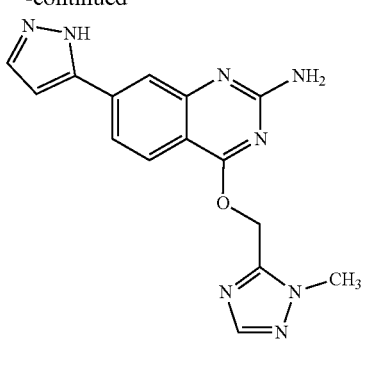

To a suspension of 2-amino-7-(1-(tetrahydro-2H-pyran-2-yl)-1H-pyrazol-5-yl)quinazolin-4-ol (25 mg, 0.080 mmol) and (1-methyl-1H-1,2,4-triazol-5-yl)methanol, HCl (36.0 mg, 0.241 mmol) in DMF (0.5 mL) was added DBU (0.054 mL, 0.361 mmol) and BOP (46.2 mg, 0.104 mmol). The reaction was stirred overnight at room temperature, then diluted with water and extracted three times with EtOAc. The organic layers were concentrated. The residue was dissolved in 0.5 mL DCM and 0.5 mL TFA. After ca. 45 minutes, the reaction was concentrated, azeotroped with DCM, dissolved in DMF, and filtered through a syringe filter. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-40% B over 25 minutes, then a 4-minute hold at 100% B; Flow Rate: 20 mL/min; Column Temperature: 25° C. Fraction collection was triggered by UV signals. Fractions containing the desired product were combined and dried via centrifugal evaporation to give 4-((1-methyl-1H-1,2,4-triazol-5-yl)methoxy)-7-(1H-pyrazol-5-yl)quinazolin-2-amine (6.9 mg, 27%).

Example 8. rac-1-((2-amino-7-(1H-pyrazol-5-yl)quinazolin-4-yl)amino)-3-methylbutane-2,3-diol, TFA and Example 9 and Example 10. 1-((2-amino-7-(1H-pyrazol-5-yl)quinazolin-4-yl)amino)-3-methylbutane-2,3-diol as Single Unidentified Enantiomers

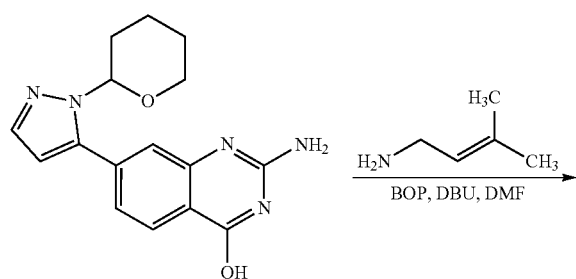

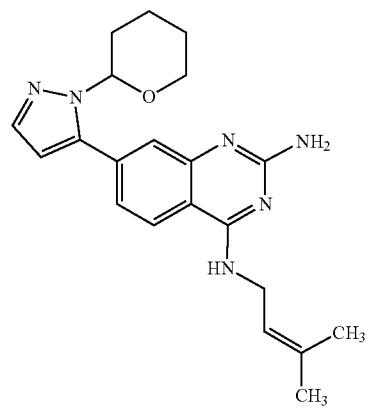

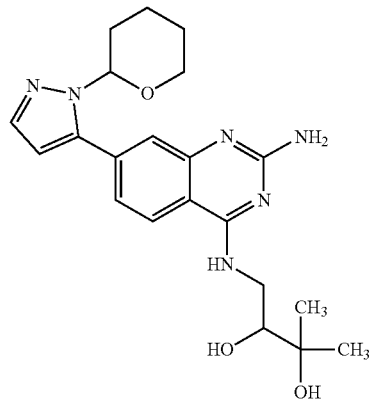

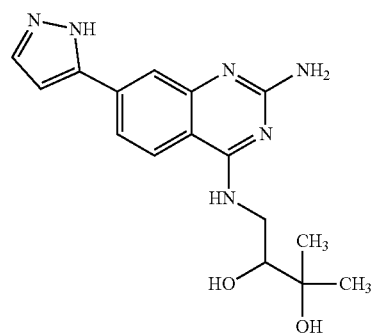

racemate
Example 8

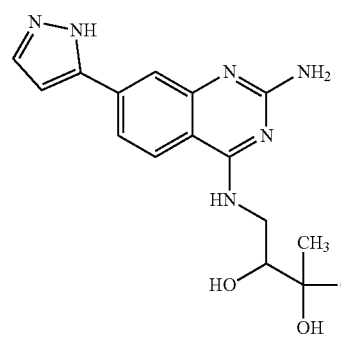

First eluting enantiomer
Example 9

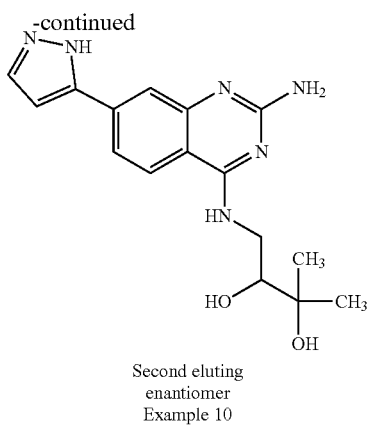

Second eluting
enantiomer
Example 10

8A. N4-(3-methylbut-2-en-1-yl)-7-(1-(tetrahydro-2H-pyran-2-yl)-1H-pyrazol-5-yl)quinazoline-2,4-diamine To a suspension of 2-amino-7-(1-(tetrahydro-2H-pyran-2-yl)-1H-pyrazol-5-yl)quinazolin-4-ol (50 mg, 0.161 mmol) and 3-methylbut-2-en-1-amine, HCl (78 mg, 0.642 mmol) in DMF (1 mL) was added DBU (0.145 mL, 0.964 mmol) and BOP (142 mg, 0.321 mmol). After 3 hours, the reaction was combined with an identical reaction run on 25 mg of 2-amino-7-(1-(tetrahydro-2H-pyran-2-yl)-1H-pyrazol-5-yl)quinazolin-4-ol. The reaction was diluted with water and extracted three times with EtOAc. The organic layers were concentrated. The residue was purified via ISCO (24 g column; DCM/MeOH; 0 to 10% gradient) to give N4-(3-methylbut-2-en-1-yl)-7-(1-(tetrahydro-2H-pyran-2-yl)-1H-pyrazol-5-yl)quinazoline-2,4-diamine, which was taken on directly to the next reaction. M/Z=379.4 (M+H).

8B. 1-((2-amino-7-(1-(tetrahydro-2H-pyran-2-yl)-1H-pyrazol-5-yl)quinazolin-4-yl)amino)-3-methylbutane-2,3-diol To a solution of N4-(3-methylbut-2-en-1-yl)-7-(1-(tetrahydro-2H-pyran-2-yl)-1H-pyrazol-5-yl)quinazoline-2,4-diamine (77 mg, 0.102 mmol) (purity estimated at 50%) and NMO (23.83 mg, 0.203 mmol) in water (100 µL) and tBuOH (500 µL) was added osmium tetroxide (2.5% in tBuOH) (25.5 µL, 2.034 µmol). After 5 hours, the reaction was diluted with EtOAc and quenched with solid sodium bisulfite and stirred overnight. The reaction was combined with an identical reaction run on the same scale. The residue was purified via ISCO (24 g column; DCM/MeOH; 0 to 15% gradient) to give 1-((2-amino-7-(1-(tetrahydro-2H-pyran-2-yl)-1H-pyrazol-5-yl)quinazolin-4-yl)amino)-3-methylbutane-2,3-diol (68 mg, 81% over two steps). $^1$H NMR (400 MHz, DMSO-d6) δ 8.35 (br d, J=8.3 Hz, 1H), 7.65 (d, J=1.8 Hz, 1H), 7.59-7.45 (m, 2H), 6.63 (d, J=1.7 Hz, 1H), 5.30 (br d, J=9.7 Hz, 1H), 4.96 (d, J=5.3 Hz, 1H), 4.44 (d, J=1.9 Hz, 1H), 4.06-3.98 (m, 1H), 3.90-3.81 (m, 1H), 3.71-3.45 (m, 4H), 2.44-2.35 (m, 1H), 2.02-1.94 (m, 1H), 1.83 (br d, J=12.9 Hz, 1H), 1.66-1.51 (m, 3H), 1.19 (s, 3H), 1.14 (s, 3H).

Example 8

To a solution of 1-((2-amino-7-(1-(tetrahydro-2H-pyran-2-yl)-1H-pyrazol-5-yl)quinazolin-4-yl)amino)-3-methylbutane-2,3-diol (68 mg, 0.165 mmol) in Methanol (2 mL) was added concentrated aqueous HCl (80 µL, 0.974 mmol). After 45 minutes, the reaction was concentrated and azeotroped with MeOH, then dissolved in MeOH, and filtered through a syringe filter. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 5-minute hold at 0% B, 0-25% B over 25 minutes, then a 8-minute hold at 100% B; Flow Rate: 20 mL/min; Column Temperature: 25° C. Fraction collection was triggered by MS signals. Fractions containing the desired product were combined and dried via centrifugal evaporation to give rac-(1-((2-amino-7-(1H-pyrazol-5-yl)quinazolin-4-yl)amino)-3-methylbutane-2,3-diol (31.2 mg, 42%, Example 8 (racemate)). The racemic material was purified via preparative SFC with the following conditions: Instrument: Waters 100 Prep SFC; Column: Chiral IC 250 mm×21 mm, 5-µm particles; Mobile Phase: 70% CO$_2$/30% MeOH w 0.1% diethylamine; Flow Rate: 60 mL/min. Peak 1 RT: 11.37 min. Peak 2 RT: 13.85 min.

Example 9 and Example 10 (Single Unidentified Enantiomers)

Analytical Chiral SFC conditions: Instrument: Shimadzu Nexera UC SFC; Column: Chiral IC, 150 mm×4.6 mm, 5-µm particles; Mobile Phase: 70% CO$_2$/30% MeOH w 0.1% diethylamine; Flow Rate: 2 mL/min. Example 9 (First eluting isomer): Yield 9.2 mg. Peak 1 Chiral SFC RT: 7.5 min. Example 10 (Second eluting isomer): Yield 9.6 mg. Peak 2 Chiral SFC RT: 9.1 min.

Example 11. rac-3-((2-amino-7-(1H-pyrazol-5-yl)quinazolin-4-yl)amino)-2-methylpropane-1,2-diol

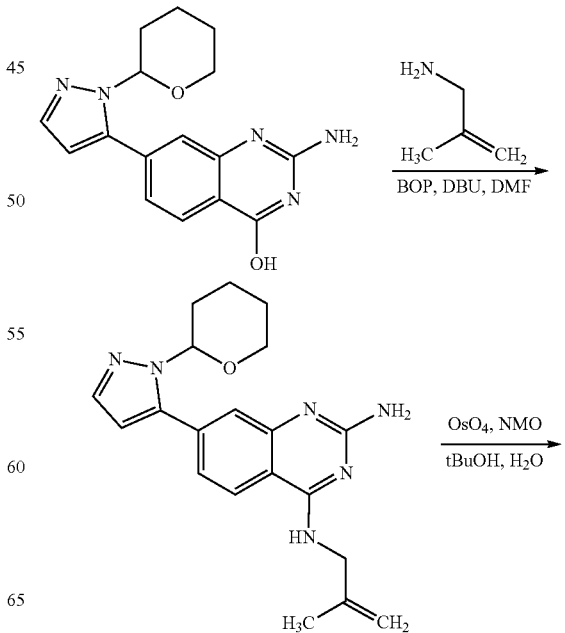

-continued

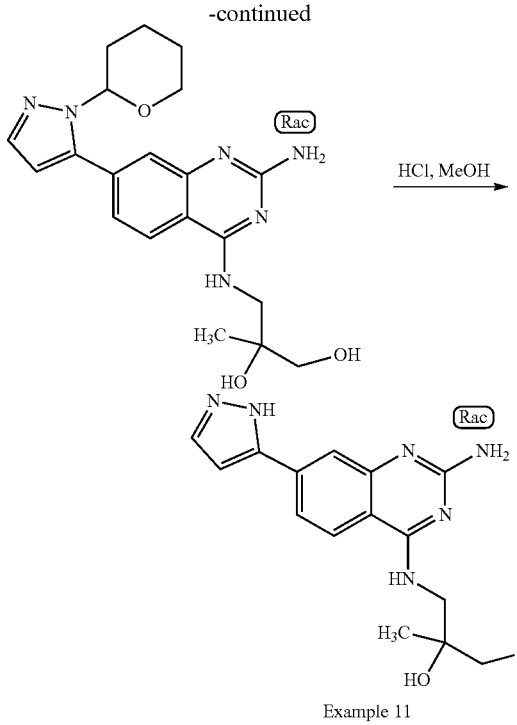

Example 11

11A. N4-(2-methylallyl)-7-(1-(tetrahydro-2H-pyran-2-yl)-1H-pyrazol-5-yl)quinazoline-2,4-diamine To a suspension of 2-amino-7-(1-(tetrahydro-2H-pyran-2-yl)-1H-pyrazol-5-yl)quinazolin-4-ol (75 mg, 0.241 mmol) and 2-methylprop-2-en-1-amine (68.5 mg, 0.964 mmol) in DMF (1 mL) was added DBU (0.218 mL, 1.445 mmol) and BOP (213 mg, 0.482 mmol). The reaction was stirred overnight, then diluted with water and extracted three times with EtOAc. The organic layers were concentrated. The residue was purified via ISCO (24 g column; DCM/MeOH; 0 to 10% gradient) to give N4-(2-methylallyl)-7-(1-(tetrahydro-2H-pyran-2-yl)-1H-pyrazol-5-yl)quinazoline-2,4-diamine (168 mg, purity estimated at 50%), which was taken on directly to the next step. M/Z=399.3 (M+H).

11B. rac-3-((2-amino-7-(1-(tetrahydro-2H-pyran-2-yl)-1H-pyrazol-5-yl)quinazolin-4-yl)amino)-2-methylpropane-1,2-diol To a solution of N4-(2-methylallyl)-7-(1-(tetrahydro-2H-pyran-2-yl)-1H-pyrazol-5-yl)quinazoline-2,4-diamine (88 mg, 0.241 mmol) in tBuOH (1339 μL) and water (268 μL) was added osmium tetroxide (2.5% in tBuOH) (60.5 μL, 4.82 μmol) and NMO (56.5 mg, 0.482 mmol). The reaction was stirred overnight, then 110 mg NMO and 0.12 mL osmium tetroxide (2.5% in tBuOH) were added. After six hours, NMO (56.5 mg, 0.482 mmol) and osmium tetroxide (2.5% in tBuOH) (60.5 μl, 4.82 μmol) were added. After a further three hours, the reaction was diluted with EtOAc and quenched with sodium hydrogen sulfite, then stirred over the weekend. The material was absorbed onto silica gel. The residue was purified via ISCO (24 g column; DCM/MeOH; 0 to 15% gradient) to give 3-((2-amino-7-(1-(tetrahydro-2H-pyran-2-yl)-1H-pyrazol-5-yl)quinazolin-4-yl)amino)-2-methylpropane-1,2-diol (100 mg, 0.251 mmol, 104% yield). M/Z=365.3 (M+H).

Example 11

3-((2-amino-7-(1-(tetrahydro-2H-pyran-2-yl)-1H-pyrazol-5-yl)quinazolin-4-yl)amino)-2-methylpropane-1,2-diol (100 mg, 0.251 mmol) was dissolved in MeOH (2.5 mL) and 100 uL concentrated HCl was added. After 1 hour, the reaction was concentrated and azeoptroped with MeOH. The residue was dissolved in MeOH, filtered through a syringe filter, and the crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-40% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to give rac-3-((2-amino-7-(1H-pyrazol-5-yl)quinazolin-4-yl)amino)-2-methylpropane-1,2-diol (15.8 mg, 20%).

Example 12. cis-(3R,5S)-5-((2-amino-7-(1H-pyrazol-5-yl)quinazolin-4-yl)amino)tetrahydro-2H-pyran-3-ol (First Eluting Enantiomer) and

Example 13. cis-(3R,5S)-5-((2-amino-7-(1H-pyrazol-5-yl)quinazolin-4-yl)amino)tetrahydro-2H-pyran-3-ol (second eluting enantiomer) as Single Unassigned Enantiomers

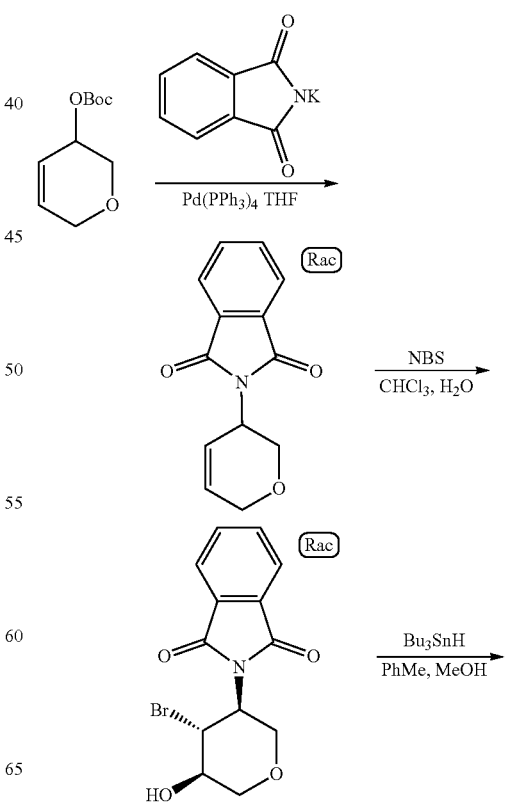

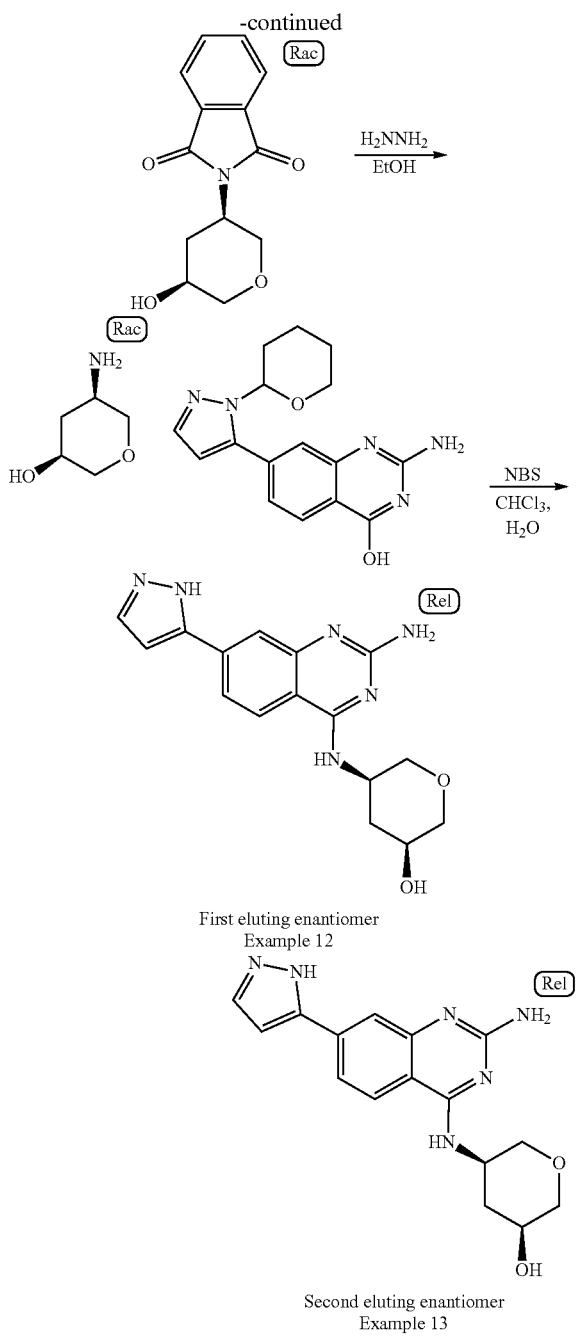

First eluting enantiomer
Example 12

Second eluting enantiomer
Example 13

12A. rac-2-(3,6-dihydro-2H-pyran-3-yl)isoindoline-1,3-dione

Tert-butyl (3,6-dihydro-2H-pyran-3-yl) carbonate (1 g, 4.99 mmol), 1,3-dioxoisoindolin-2-ide, K+ (1.110 g, 5.99 mmol), and tert-butyl (3,6-dihydro-2H-pyran-3-yl) carbonate (1 g, 4.99 mmol) were placed in a pressure vial. The vial was placed under vacuum and backfilled with nitrogen three times. THF (24.97 mL) was added and the reaction was wrapped in aluminum foil and stirred at room temperature for four days. The reaction was diluted with water and extracted three times with EtOAc. The organic layers were concentrated. The residue was purified via ISCO (24 g column; Hex/EtOAc; 0 to 50% gradient) to give 2-(3,6-dihydro-2H-pyran-3-yl)isoindoline-1,3-dione (0.848 g, 3.70 mmol, 74.1% yield). $^1$H NMR (400 MHz, CHLOROFORM-d) δ 7.85 (br dd, J=4.3, 3.1 Hz, 2H), 7.80-7.62 (m, 2H), 6.03 (br d, J=10.4 Hz, 1H), 5.82 (br d, J=10.3 Hz, 1H), 5.03 (br d, J=2.6 Hz, 1H), 4.39-4.27 (m, 1H), 4.27-4.15 (m, 1H), 4.08-3.89 (m, 2H).

12B. rac-2-((3R,4S,5S)-4-bromo-5-hydroxytetrahydro-2H-pyran-3-yl)isoindoline-1,3-dione To a solution of 2-(3,6-dihydro-2H-pyran-3-yl)isoindoline-1,3-dione (400 mg, 1.745 mmol) in chloroform (11.633 mL) and water was added NBS (932 mg, 5.23 mmol). The vial was covered with foil and stirred overnight in a darkened fume hood. NBS (932 mg, 5.23 mmol) was added and the reaction was stirred for a further 6 hours. The reaction was quenched with saturated sodium thiosulfate solution and extracted three times with DCM. The organic layers were concentrated. The residue was absorbed onto silica gel and purified via ISCO (40 g column; Hex/EtOAc; 0 to 50% gradient) to give rac-2-((3R,4S,5S)-4-bromo-5-hydroxytetrahydro-2H-pyran-3-yl)isoindoline-1,3-dione (486 mg, 1.490 mmol, 85% yield). $^1$H NMR (400 MHz, CHLOROFORM-d) δ 7.91-7.81 (m, 2H), 7.79-7.70 (m, 2H), 4.90 (dd, J=11.3, 9.7 Hz, 1H), 4.57 (td, J=11.1, 5.2 Hz, 1H), 4.18-4.12 (m, 1H), 4.01-3.90 (m, 2H), 3.90-3.82 (m, 1H), 3.37 (dd, J=11.1, 10.4 Hz, 1H), 2.98 (d, J=3.9 Hz, 1H).

12C. rac-2-((3R,5S)-5-hydroxytetrahydro-2H-pyran-3-yl)isoindoline-1,3-dione

To a solution of rac-2-((3R,4S,5S)-4-bromo-5-hydroxytetrahydro-2H-pyran-3-yl)isoindoline-1,3-dione (240 mg, 0.736 mmol) and AIBN (5 mg, 0.030 mmol) in MeOH (669 μl) and toluene (6690 μl) was added tributylstannane (397 μL, 1.472 mmol). The reaction was heated to 100° C. overnight. Tributylstannane (397 μL, 1.472 mmol) and AIBN (5 mg, 0.030 mmol) were added. After 5 hours, the reaction was cooled and concentrated. The residue was purified via ISCO (40 g column; Hex/EtOAc; 0 to 100% gradient) to give rac-2-((3R,5S)-5-hydroxytetrahydro-2H-pyran-3-yl)isoindoline-1,3-dione (111 mg, 0.449 mmol, 61.0% yield). $^1$H NMR (400 MHz, CHLOROFORM-d) δ 7.90-7.82 (m, 2H), 7.78-7.69 (m, 2H), 4.47-4.37 (m, 1H), 4.05 (ddd, J=10.7, 5.0, 1.9 Hz, 1H), 3.97 (t, J=10.8 Hz, 1H), 3.93-3.85 (m, 1H), 3.83-3.74 (m, 1H), 3.22 (t, J=10.4 Hz, 1H), 2.44 (q, J=11.8 Hz, 1H), 2.32-2.19 (m, 1H), 0.91-0.76 (m, 2H).

12D. rac-(3R,5S)-5-aminotetrahydro-2H-pyran-3-ol

To a suspension of rac-2-((3R,5S)-5-hydroxytetrahydro-2H-pyran-3-yl)isoindoline-1,3-dione (75 mg, 0.303 mmol) in ethanol (1.5 mL) was added hydrazine (0.025 mL, 0.334 mmol). The reaction was heated to 75° C. Suspended material dissolved as the reaction was heated. After 2.5 hours, the reaction was cooled, filtered, and the solid was washed with EtOH. The filtrate was concentrated to give rac-(3R,5S)-5-aminotetrahydro-2H-pyran-3-ol (29 mg, 0.248 mmol, 82% yield), containing ca. 0.15 equivalents of phthalazidinone. The material was taken forward without further purification. $^1$H NMR (400 MHz, METHANOL-d$_4$) δ 3.83-3.73 (m, 2H), 3.71-3.62 (m, 1H), 3.12 (ddd, J=14.7, 11.0, 8.5 Hz, 2H), 2.93-2.80 (m, 1H), 2.26-2.14 (m, 1H), 1.35 (dt, J=12.5, 9.3 Hz, 1H).

Example 12 and Example 13 as Single Unidentified Enantiomers

To a suspension of 2-amino-7-(1-(tetrahydro-2H-pyran-2-yl)-1H-pyrazol-5-yl)quinazolin-4-ol (45 mg, 0.145 mmol) and rac-(3R,5S)-5-aminotetrahydro-2H-pyran-3-ol (35.5 mg, 0.303 mmol) in DMF (0.5 mL) was added DBU (0.044 mL, 0.289 mmol) and BOP (128 mg, 0.289 mmol). After four hours, BOP (128 mg, 0.289 mmol) was added and the reaction was stirred overnight. The reaction was diluted with water and extracted three times with EtOAc. The organic layers were concentrated. The residue was dissolved in 1 mL MeOH and 0.05 mL conc. HCl. After 2 hours, the reaction was concentrated, azeotroped with DCM, dissolved in DMF, and filtered through a syringe filter. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-40% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation. The material was further purified by SCP using SFC-chiral chromatography with the following conditions: Instrument: Waters 100 Prep SFC; Column: Chiral IC 250 mm×21 mm, 5-µm particles; Mobile Phase: 60% $CO_2$/40% MeOH w 0.1% diethylamine; Flow Rate: 60 mL/min. Peak 1 RT: 6.98 min. Peak 2 RT: 12.69 min.

Example 12 (first eluting enantiomer): Yield: 4.3 mg (8.6%). Chiral SFC conditions: Instrument: Shimadzu Nexera UC SFC; Column: Chiral IC, 150 mm×4.6 mm, 5-µm particles; Mobile Phase: 60% $CO_2$/4% MeOH w 0.1% diethylamine; Flow Rate: 2 mL/min. Chiral SFC RT: 4.2 min. Example 13 (second eluting enantiomer): Yield: 4.1 mg (8.3%). Chiral SFC RT: 7.4 min.

Example 14. 3-((2-amino-7-(1H-pyrazol-3-yl)quinazolin-4-yl)amino)propan-1-ol

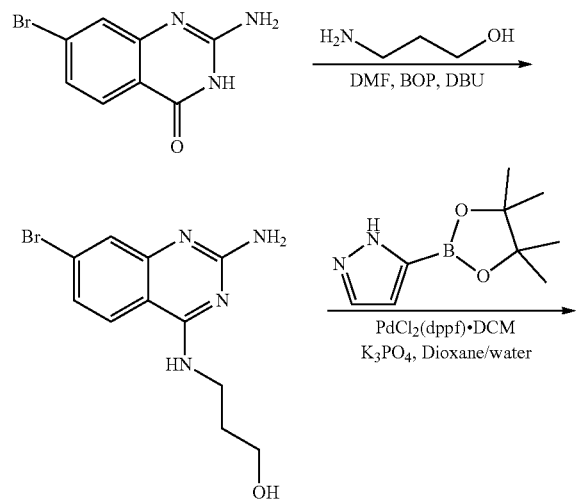

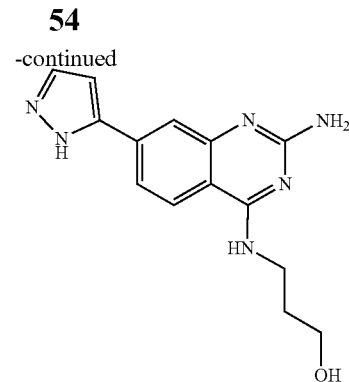

Example 14

14A. 3-((2-amino-7-bromoquinazolin-4-yl)amino)propan-1-ol

To a mixture of 2-amino-7-bromoquinazolin-4(3H)-one (30 mg, 0.13 mmol), 3-aminopropan-1-ol (29 µL, 0.38 mmol) and BOP (71.9 mg, 0.162 mmol) in DMF (625 µL) was added DBU (28 µL, 0.19 mmol) and the solution was stirred at room temperature. When complete the reaction mixture was diluted with water and extracted with EtOAc. The organic layer was concentrated in vacuo to give the crude material which was used directly without purification. HPLC RT (Method A): 0.51 min. LCMS $(M+H)^+$: 297.0.

Example 14

To a mixture of 3-((2-amino-7-bromoquinazolin-4-yl)amino)propan-1-ol (37.1 mg, 0.125 mmol), 3-(4,4,5,5-tetramethyl-1,3,2-dioxaborolan-2-yl)-1H-pyrazole (36.3 mg, 0.187 mmol) and $K_3PO_4$ (2M aqueous) (187 µL, 0.375 mmol) in Dioxane (1.2 mL) was added $PdCl_2(dppf)$-$CH_2Cl_2$ adduct (10.2 mg, 0.012 mmol) under $N_2$. The reaction was heated at 90° C. for 1 hour. The reaction was concentrated, the residue was dissolved in DMF, filtered through a syringe filter, and the crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to give 3-((2-amino-7-(1H-pyrazol-3-yl)quinazolin-4-yl)amino)propan-1-ol (14.4 mg, 0.050 mmol, 40% yield).

Example 15. 3-((2-amino-5-fluoro-7-(1H-pyrazol-3-yl)quinazolin-4-yl)amino)propan-1-ol

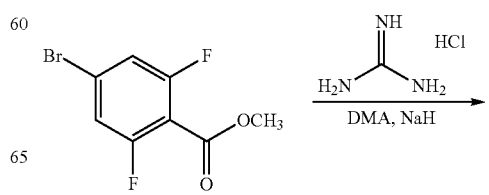

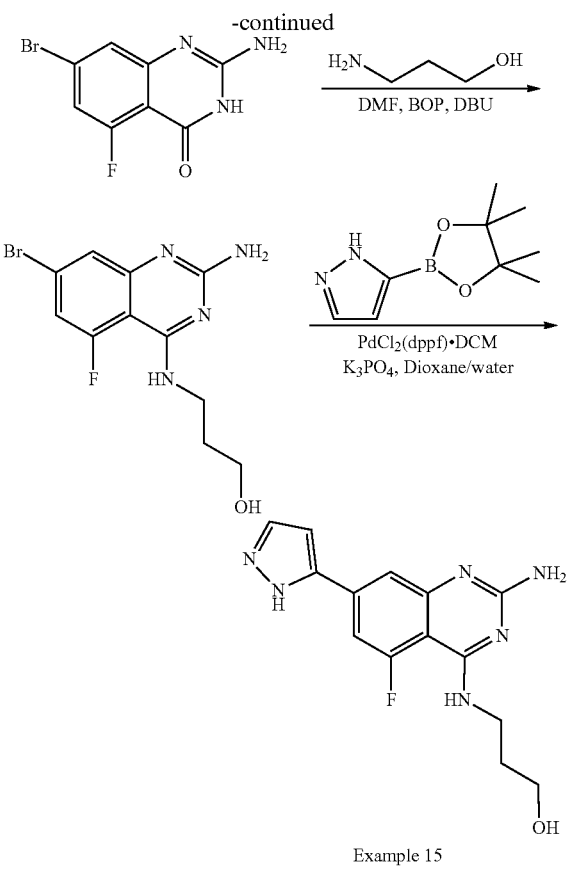

Example 15

15A.
2-amino-7-bromo-5-fluoroquinazolin-4(3H)-one

To a solution of guanidine hydrochloride (571 mg, 5.98 mmol) in DMA (10.0 mL) was added NaH (263 mg, 6.57 mmol) portion wise. The reaction was stirred for 30 minutes at room temperature and methyl 4-bromo-2,6-difluorobenzoate (500 mg, 1.99 mmol) was added. The reaction was stirred at room temperature for 30 min and heated at 80° C. for 3 hours. The reaction was quenched with water and diluted with EtOAc. To this mixture was added 1M NaOH (4 mL) and the mixture was washed with water. The basic water layer was acidified with 5% aqueous citric acid to pH 4 and the resulting white precipitate was collected by filtration with water rinses. The solid was dried under vacuum to give 2-amino-7-bromo-5-fluoroquinazolin-4 (3H)-one (256 mg, 0.994 mmol, 50% yield). HPLC RT (Method A): 0.53 min. LCMS (M+H)$^+$: 257.9. $^1$H NMR (400 MHz, DMSO-d$_6$) δ 11.07 (br s, 1H), 7.19-7.13 (m, 1H), 7.06 (dd, J=10.5, 1.6 Hz, 1H), 6.73-6.54 (m, 2H).

15B. 3-((2-amino-7-bromo-5-fluoroquinazolin-4-yl)amino)propan-1-ol

To a mixture of 2-amino-7-bromo-5-fluoroquinazolin-4 (3H)-one (30 mg, 0.12 mmol), 3-aminopropan-1-ol (27 μL, 0.35 mmol) and BOP (66.8 mg, 0.151 mmol) in DMF (581 μL) was added DBU (26 μL, 0.17 mmol) and the solution was stirred at room temperature. When complete the reaction was mixture diluted with water and extracted 3× with EtOAc. The combined organic layers were concentrated in vacuo to give the crude material which was used directly without purification. HPLC RT (Method A): 0.52 min. LCMS (M+H)$^+$: 315.0.

Example 15

To a mixture of 3-((2-amino-7-bromo-5-fluoroquinazolin-4-yl)amino)propan-1-ol (36.6 mg, 0.116 mmol), 3-(4,4,5,5-tetramethyl-1,3,2-dioxaborolan-2-yl)-1H-pyrazole (33.8 mg, 0.174 mmol) and K$_3$PO$_4$ (2M aqueous) (174 μL, 0.348 mmol) in Dioxane (1.2 mL) was added PdCl$_2$(dppf)-CH$_2$Cl$_2$ adduct (9.5 mg, 0.012 mmol) under N$_2$. The reaction was heated at 90° C. for 1 hour. The reaction was concentrated, the residue was dissolved in DMF, filtered through a syringe filter, and the crude material was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 5-minute hold at 0% B, 0-23% B over 30 minutes, then a 5-minute hold at 100% B; Flow Rate: 20 mL/min; Column Temperature: 25° C. Fraction collection was triggered by MS signals. Fractions containing the desired product were combined and dried via centrifugal evaporation to give 3-((2-amino-5-fluoro-7-(1H-pyrazol-3-yl)quinazolin-4-yl)amino)propan-1-ol (5.4 mg, 0.017 mmol, 15% yield).

Example 16. cis-3-((2-amino-5-fluoro-7-(1H-pyrazol-3-yl)quinazolin-4-yl)amino)cyclohexan-1-ol and
Example 17 trans-3-((2-amino-5-fluoro-7-(1H-pyrazol-3-yl)quinazolin-4-yl)amino)cyclohexan-1-ol

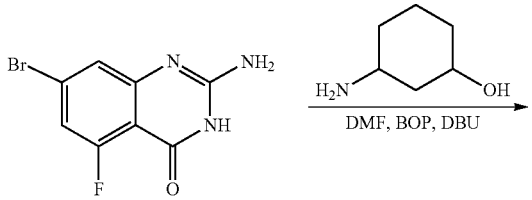

Racemic mixture of cis/trans isomers

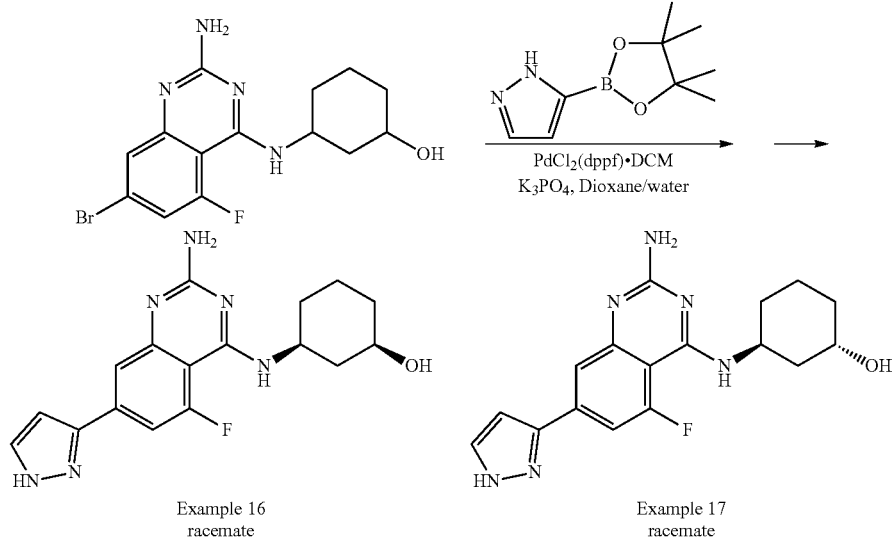

Example 16
racemate

Example 17
racemate 16A. 3-((2-amino-7-bromo-5-fluoroquinazolin-4-yl) amino)cyclohexan-1-ol (Mixture of cis- and trans-isomers)

To a mixture of 2-amino-7-bromo-5-fluoroquinazolin-4 (3H)-one (30 mg, 0.12 mmol), 3-aminocyclohexan-1-ol (40.2 mg, 0.349 mmol, racemic mixture of cis- and trans-isomers) and BOP (66.8 mg, 0.151 mmol) in DMF (581 µL) was added DBU (26 µL, 0.17 mmol) and the solution was stirred at room temperature. When complete the reaction was mixture diluted with water and extracted 3× with EtOAc. The combined organic layers were concentrated in vacuo to give the crude material which was used directly without purification. HPLC RT (Method A): 0.59 min. LCMS (M+H)$^+$: 355.0.

Example 16 and Example 17 (cis- and trans-isomer Pairs Isolated Separately as Enantiomeric Mixtures)

To a mixture of 3-((2-amino-7-bromo-5-fluoroquinazolin-4-yl)amino)cyclohexan-1-ol (41.3 mg, 0.116 mmol) (mixture of cis- and trans-isomers), 3-(4,4,5,5-tetramethyl-1,3,2-dioxaborolan-2-yl)-1H-pyrazole (33.8 mg, 0.174 mmol) and $K_3PO_4$ (2M aqueous) (174 µL, 0.348 mmol) in Dioxane (1.2 mL) was added PdCl$_2$(dppf)-CH$_2$Cl$_2$ adduct (9.5 mg, 0.012 mmol) under $N_2$. The reaction was heated at 90° C. for 3 hours. The reaction was concentrated, the residue was dissolved in DMF, filtered through a syringe filter, and the crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 5% B, 5-45% B over 28 minutes, then a 4-minute hold at 100% B; Flow Rate: 20 mL/min; Column Temperature: 25° C. Fraction collection was triggered by MS signals. The cis- and trans-geometric isomer pairs were separated and isolated as two different peaks. One isomer pair eluting first and the other isomer pair eluting second. Fractions containing the first eluting product were combined and dried via centrifugal evaporation to give the racemic cis isomer Example 16 (13.6 mg, 0.0397 mmol, 32% yield). Fractions containing the second eluting product were combined and dried via centrifugal evaporation to give the racemic trans isomer Example 17 (5.8 mg, 0.0169 mmol, 32% yield).

Example 18. 3-((2-amino-5-chloro-7-(1H-pyrazol-3-yl)quinazolin-4-yl)amino)propan-1-ol and Example 19. 3-((2-amino-5,7-di(1H-pyrazol-3-yl) quinazolin-4-yl)amino)propan-1-ol

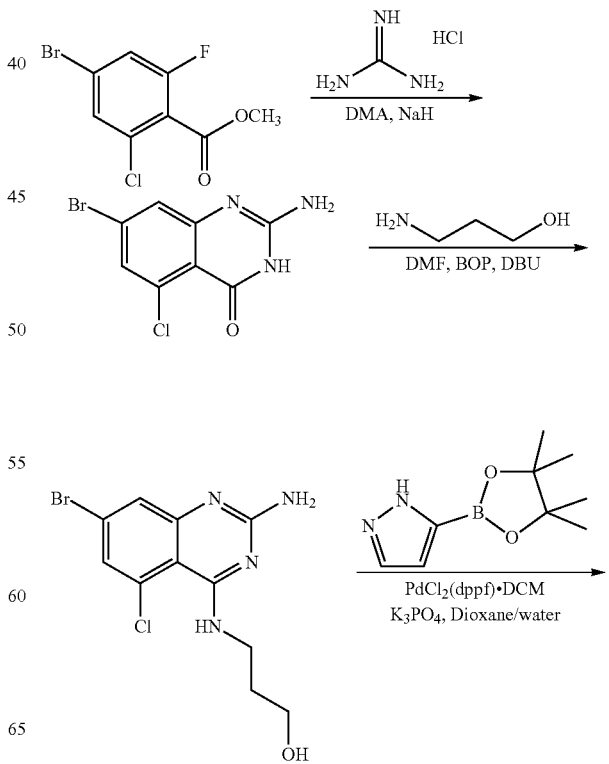

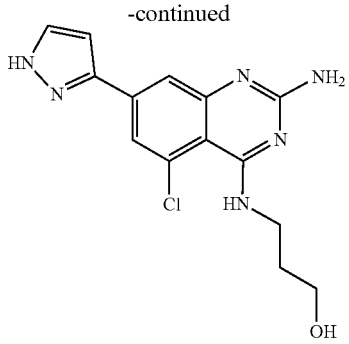

Example 18

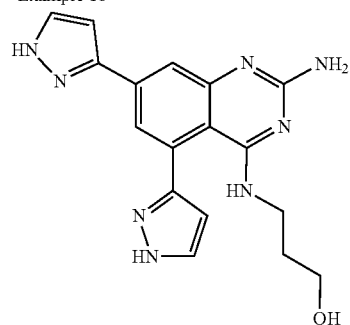

Example 19

18A. 2-amino-7-bromo-5-chloroquinazolin-4(3H)-one

To a solution of guanidine hydrochloride (321 mg, 3.36 mmol) in DMA (5.6 mL) was added NaH (148 mg, 3.70 mmol) portion wise. The reaction was stirred for 15 minutes at room temperature and methyl 4-bromo-2-chloro-6-fluorobenzoate (300 mg, 1.12 mmol) was added. The reaction was stirred at 80° C. for 1 hour. The reaction was quenched with water and diluted with EtOAc. To this mixture was added 1M NaOH (4 mL) and the mixture was washed with water. The basic water layer was acidified with 5% aqueous citric acid to pH 4 and the resulting white precipitate was collected by filtration with water rinses. The solid was dried under vacuum to give 2-amino-7-bromo-5-chloroquinazolin-4(3H)-one (195.1 mg, 0.711 mmol, 63% yield). HPLC RT (Method A): 0.58 min. LCMS (M+H)$^+$: 273.9. $^1$H NMR (400 MHz, DMSO-d$_6$) δ 11.14-11.04 (m, 1H), 7.30-7.28 (m, 1H), 7.27-7.24 (m, 1H), 6.71-6.55 (m, 2H).

18B. 3-((2-amino-7-bromo-5-chloroquinazolin-4-yl)amino)propan-1-ol

To a mixture of 2-amino-7-bromo-5-chloroquinazolin-4(3H)-one (30 mg, 0.11 mmol), 3-aminopropan-1-ol (25 µL, 0.33 mmol) and BOP (62.8 mg, 0.142 mmol) in DMF (546 µL) was added DBU (25 µL, 0.16 mmol) and the solution was stirred at room temperature. When complete the reaction was mixture diluted with water and extracted with EtOAc. The organic layer was concentrated in vacuo to give the crude material which was used directly without purification. HPLC RT (Method A): 0.55 min. LCMS (M+H)$^+$: 331.0.

Example 18 and Example 19

To a mixture of 3-((2-amino-7-bromo-5-chloroquinazolin-4-yl)amino)propan-1-ol (36.2 mg, 0.109 mmol), 3-(4,4, 5,5-tetramethyl-1,3,2-dioxaborolan-2-yl)-1H-pyrazole (31.8 mg, 0.164 mmol) and K$_3$PO$_4$ (2M aqueous) (164 µL, 0.328 mmol) in Dioxane (1.1 mL) was added PdCl$_2$(dppf)-CH$_2$Cl$_2$ adduct (8.9 mg, 0.011 mmol) under N$_2$. The reaction was heated at 90° C. for 1 hour. The reaction was concentrated, the residue was dissolved in DMF, filtered through a syringe filter, and the 2 major products in the crude material were purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 5% B, 5-45% B over 25 minutes, then a 4-minute hold at 100% B; Flow Rate: 20 mL/min; Column Temperature: 25° C. Fraction collection was triggered by MS signals. Fractions containing each of the desired product were combined and dried via centrifugal evaporation to give 3-((2-amino-5-chloro-7-(1H-pyrazol-3-yl)quinazolin-4-yl)amino)propan-1-ol (2.5 mg, 7.5 µmol, 7% yield) and 3-((2-amino-5,7-di(1H-pyrazol-3-yl)quinazolin-4-yl)amino)propan-1-ol (4.9 mg, 0.014 mmol, 13% yield).

Example 20. 2-((2-amino-5-methoxy-7-(1H-pyrazol-3-yl)quinazolin-4-yl)amino)ethan-1-ol

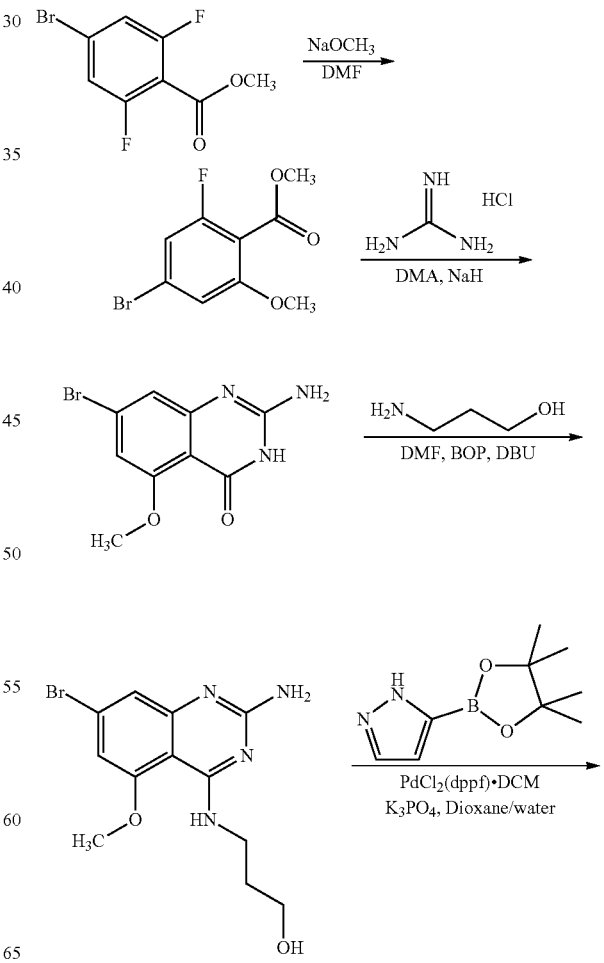

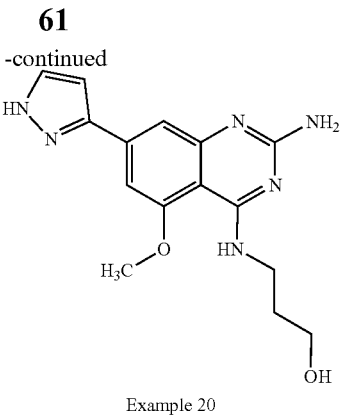

Example 20

20A. methyl 4-bromo-2-fluoro-6-methoxybenzoate

To a mixture of methyl 4-bromo-2,6-difluorobenzoate (322.5 mg, 1.285 mmol) in DMF (7.8 mL) was added sodium methoxide (69.4 mg, 1.29 mmol), the reaction was stirred at room temperature for 30 minutes. The reaction mixture was diluted with water and extracted with EtOAc. The organic layer was washed with a saturated NaHCO$_3$ solution, a saturated NaCl solution, dried over Na$_2$SO$_4$, filtered and concentrated to give the crude material which was used directly without purification. HPLC RT (Method A): 0.90 min. LCMS (M+H)$^+$: 263.0.

20B. 2-amino-7-bromo-5-methoxyquinazolin-4(3H)-one

To a solution of guanidine hydrochloride (542 mg, 5.67 mmol) in DMA (9.5 mL) was added NaH (249 mg, 6.24 mmol) portion wise. The reaction was stirred for 30 minutes at room temperature and a solution of methyl 4-bromo-2-fluoro-6-methoxybenzoate (497.2 mg, 1.890 mmol) in DMA (1 mL) was added. The reaction was stirred at 80° C. for 8 hours, at 120° C. for 30 minutes and 110° C. for 5 hours. The reaction was quenched with water and diluted with EtOAc. To this mixture was added 1M NaOH (4 mL) and the mixture was washed with water. The basic water layer was acidified with 5% aqueous citric acid to pH 4 and the resulting white precipitate was collected by filtration with water rinses. The solid was dried under vacuum to give 2-amino-7-bromo-5-methoxyquinazolin-4(3H)-one (205.8 mg, 0.762 mmol, 40% yield). HPLC RT (Method A): 0.49 min. LCMS (M+H)$^+$: 270.1. $^1$H NMR (400 MHz, DMSO-d$_6$) δ 10.73 (br s, 1H), 6.92-6.86 (m, 1H), 6.73 (d, J=1.8 Hz, 1H), 6.42 (br s, 2H), 3.81 (s, 3H).

20C. 3-((2-amino-7-bromo-5-methoxyquinazolin-4-yl)amino)propan-1-ol

To a mixture of 2-amino-7-bromo-5-methoxyquinazolin-4(3H)-one (30 mg, 0.11 mmol), 3-aminopropan-1-ol (26 µL, 0.33 mmol) and BOP (63.9 mg, 0.144 mmol) in DMF (555 µL) was added DBU (25 µL, 0.17 mmol) and the solution was stirred at room temperature. When complete the reaction was mixture diluted with water and extracted 3× with EtOAc. The combined organic layers were concentrated in vacuo to give the crude material which was used directly without purification. HPLC RT (Method A): 0.55 min. LCMS (M+H)$^+$: 327.2.

Example 20

To a mixture of 2-((2-amino-7-bromo-5-methoxyquinazolin-4-yl)amino)ethan-1-ol (35.0 mg, 0.112 mmol), 3-(4,4,5,5-tetramethyl-1,3,2-dioxaborolan-2-yl)-1H-pyrazole (32.5 mg, 0.168 mmol) and K$_3$PO$_4$ (2M aqueous) (168 µL, 0.335 mmol) in Dioxane (1.1 mL) was added PdCl$_2$(dppf)-CH$_2$Cl$_2$ adduct (9.1 mg, 0.011 mmol) under N$_2$. The reaction was heated at 90° C. for 90 minutes. The reaction was concentrated, the residue was dissolved in DMF, filtered through a syringe filter, and the crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 5-minute hold at 0% B, 0-20% B over 25 minutes, then a 5-minute hold at 100% B; Flow Rate: 20 mL/min; Column Temperature: 25° C. Fraction collection was triggered by MS signals. Fractions containing the desired product were combined and dried via centrifugal evaporation to give 2-((2-amino-5-methoxy-7-(1H-pyrazol-3-yl)quinazolin-4-yl)amino)ethan-1-ol (19 mg, 0.060 mmol, 52% yield).

Example 21. 3-((2-amino-5-methyl-7-(1H-pyrazol-3-yl)quinazolin-4-yl)amino)propan-1-ol

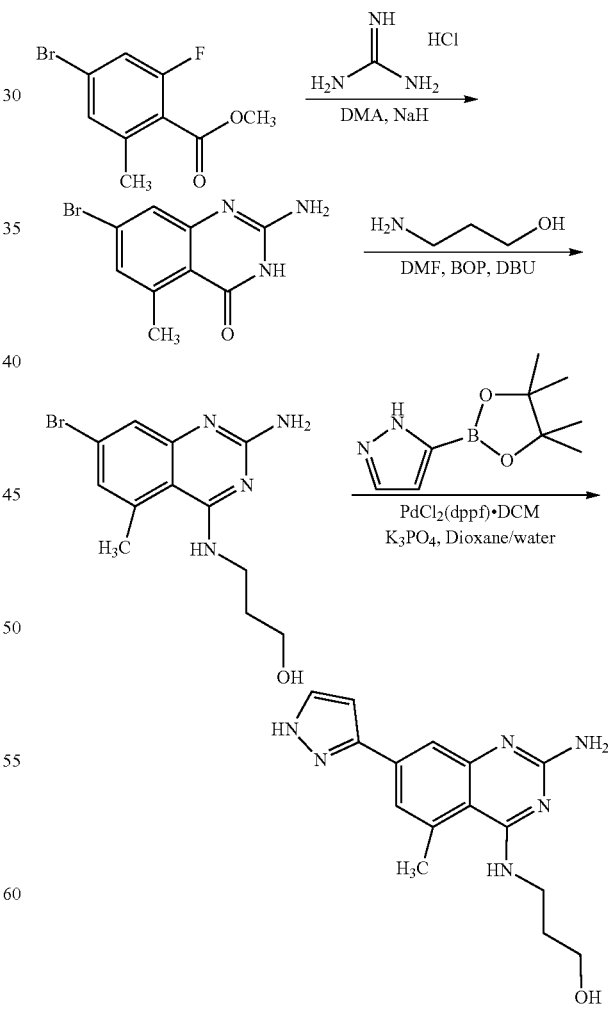

Example 21

21A.
2-amino-7-bromo-5-methylquinazolin-4(3H)-one

To a solution of guanidine hydrochloride (290 mg, 3.04 mmol) in DMA (5.1 mL) was added NaH (134 mg, 3.34 mmol) portion wise. The reaction was stirred for 30 minutes at room temperature and methyl 4-bromo-2-fluoro-6-methylbenzoate (250 mg, 1.01 mmol) was added. The reaction was stirred at 85° C. for 3 hours and at 110° C. for 7 hours. The reaction was quenched with water and diluted with EtOAc. To this mixture was added 1M NaOH (4 mL) and the mixture was washed with water. The basic water layer was acidified with 5% aqueous citric acid to pH 4 and the resulting white precipitate was collected by filtration with water rinses. The solid was dried under vacuum to 2-amino-7-bromo-5-methylquinazolin-4(3H)-one (62 mg, 0.244 mmol, 24% yield). HPLC RT (Method A): 0.57 min. LCMS (M+H)$^+$: 254.1. 1H NMR (400 MHz, DMSO-d$_6$) δ 10.92-10.78 (m, 1H), 7.16 (d, J=1.6 Hz, 1H), 7.00 (s, 1H), 6.42 (br s, 2H), 2.63 (s, 3H).

21B. 3-((2-amino-7-bromo-5-methylquinazolin-4-yl)amino)propan-1-ol

To a mixture of 2-amino-7-bromo-5-methylquinazolin-4(3H)-one (20 mg, 0.079 mmol), 3-aminopropan-1-ol (18 µL, 0.24 mmol) and BOP (45.3 mg, 0.102 mmol) in DMF (394 µL) was added DBU (18 µL, 0.12 mmol) and the solution was stirred at room temperature for 16 hours and stirred at 50° C. for 3 hours. The reaction mixture was diluted with water and extracted with EtOAc. The organic layer was concentrated in vacuo to give the crude material which was used directly without purification. HPLC RT (Method A): 0.56 min. LCMS (M+H)$^+$: 311.2.

Example 21

To a mixture of 3-((2-amino-7-bromo-5-methylquinazolin-4-yl)amino)propan-1-ol (25 mg, 0.080 mmol), 3-(4,4,5,5-tetramethyl-1,3,2-dioxaborolan-2-yl)-1H-pyrazole (23.4 mg, 0.12 mmol) and K$_3$PO$_4$ (2M aqueous) (121 µL, 0.241 mmol) in dioxane (803 µL) was added PdCl$_2$(dppf)-CH$_2$Cl$_2$ adduct (6.6 mg, 0.080 mmol) under N$_2$. The reaction was heated at 95° C. for 3 hours. The reaction was concentrated, the residue was dissolved in DMF, filtered through a syringe filter, and the crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 5-minute hold at 0% B, 0-20% B over 25 minutes, then a 5-minute hold at 100% B; Flow Rate: 20 mL/min; Column Temperature: 25° C. Fraction collection was triggered by MS signals. Fractions containing the desired product were combined and dried via centrifugal evaporation to give 3-((2-amino-5-methyl-7-(1H-pyrazol-3-yl)quinazolin-4-yl)amino)propan-1-ol (4.2 mg, 0.014 mmol, 17% yield).

Example 22. 3-((2-amino-5-(dimethylamino)-7-(1H-pyrazol-3-yl)quinazolin-4-yl)amino)propan-1-ol

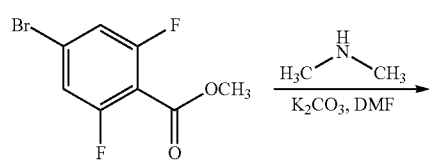

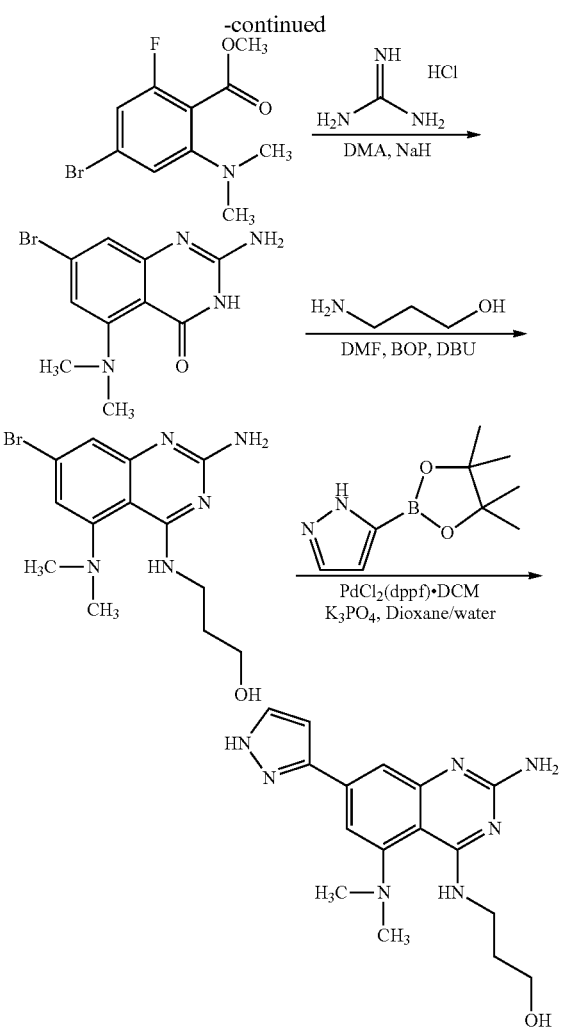

Example 22

22A. methyl 4-bromo-2-(dimethylamino)-6-fluorobenzoate

To a mixture of methyl 4-bromo-2,6-difluorobenzoate (500 mg, 1.99 mmol) and K$_2$CO$_3$ (826 mg, 5.98 mmol) in DMF (2.8 mL) was added dimethylamine (201 µl, 2.19 mmol), the reaction was stirred at 100° C. for 2 hours. The reaction mixture was concentrated and the residue dissolved in EtOAc, washed with a saturated NaHCO$_3$ solution and water. Organic layer was dried with Na$_2$SO$_4$, filtered and concentrated to give methyl 4-bromo-2-(dimethylamino)-6-fluorobenzoate (545.3 mg, 1.975 mmol, 99% yield). HPLC RT (Method A): 0.96 min. LCMS (M+H)$^+$: 276.1. $^1$H NMR (400 MHz, CHLOROFORM-d) δ 6.78 (t, J=1.4 Hz, 1H), 6.75-6.70 (m, 1H), 3.93 (s, 3H), 2.87 (s, 6H).

22B. 2-amino-7-bromo-5-(dimethylamino)quinazolin-4(3H)-one

To a solution of guanidine hydrochloride (566 mg, 5.92 mmol) in DMA (9.9 mL) was added NaH (261 mg, 6.51 mmol) portion wise. The reaction was stirred for 30 minutes at room temperature and methyl 4-bromo-2-(dimethylamino)-6-fluorobenzoate (545 mg, 1.97 mmol) was added.

The reaction was stirred at 80° C. for 2 hours, at 110° C. for 2 hours and at 130° C. for 12 hours. The reaction was quenched with water and diluted with EtOAc. To this mixture was added 1M NaOH (4 mL) and the mixture was washed with water. The basic water layer was acidified with 5% aqueous citric acid to pH 4 and concentrated, the residue was purified by preparative HPLC. Column: 2-Phen Axia C18 30×100 mm 5-μm particles; Mobile Phase A: 10:90 acetonitrile:water with 0.1% trifluoroacetic acid; Mobile Phase B: 90:10 acetonitrile:water with 0.1% trifluoroacetic acid; Gradient: 0-40% B over 10 minutes; Flow Rate: 40 mL/min. Fractions containing the desired product were combined and concentrated to give 2-amino-7-bromo-5-(dimethylamino)quinazolin-4(3H)-one, TFA (155 mg, 0.391 mmol, 20% yield). HPLC RT (Method A): 0.44 min. LCMS (M+H)$^+$: 283.1. $^1$H NMR (400 MHz, DMSO-d$_6$) δ 8.25-8.05 (m, 2H), 7.16-7.09 (m, 1H), 7.00 (br s, 1H), 2.92 (s, 6H).

22C. 3-((2-amino-7-bromo-5-(dimethylamino)quinazolin-4-yl)amino)propan-1-ol

To a mixture of 2-amino-7-bromo-5-(dimethylamino)quinazolin-4(3H)-one, TFA (45.6 mg, 0.115 mmol)), 3-aminopropan-1-ol (26 μL, 0.34 mmol) and BOP (66.0 mg, 0.149 mmol) in DMF (574 μL) was added DBU (87 μL, 0.57 mmol) and the solution was stirred at room temperature for 3 hours. The reaction mixture was diluted with water and extracted with EtOAc. The organic layer was concentrated in vacuo to give the crude material which was used directly without purification. HPLC RT (Method A): 0.60 min. LCMS (M+H)$^+$: 340.0.

Example 22

To a mixture of 3-((2-amino-7-bromo-5-(dimethylamino)quinazolin-4-yl)amino)propan-1-ol (39.1 mg, 0.115 mmol), 3-(4,4,5,5-tetramethyl-1,3,2-dioxaborolan-2-yl)-1H-pyrazole (33.4 mg, 0.172 mmol) and K$_3$PO$_4$ (2M aqueous) (172 μL, 0.345 mmol) in dioxane (1.2 mL) was added PdCl$_2$(dppf)-CH$_2$Cl$_2$ adduct (9.4 mg, 0.011 mmol) under N$_2$. The reaction was heated at 95° C. for 2 hours. The reaction was concentrated, the residue was dissolved in DMF, filtered through a syringe filter, and the crude material was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 3-minute hold at 0% B, 0-30% B over 25 minutes, then a 5-minute hold at 100% B; Flow Rate: 20 mL/min; Column Temperature: 25° C. Fraction collection was triggered by MS signals. Fractions containing the desired product were combined and dried via centrifugal evaporation to give 3-((2-amino-5-(dimethylamino)-7-(1H-pyrazol-3-yl)quinazolin-4-yl)amino)propan-1-ol (8.6 mg, 0.025 mmol, 22% yield).

Example 23. (S)-7-(1H-pyrazol-5-yl)-N4-(tetrahydrofuran-3-yl)quinazoline-2,4-diamine

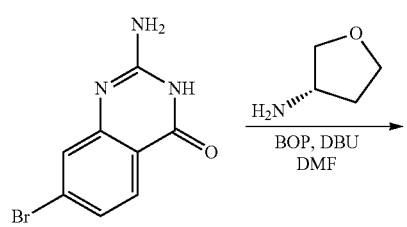

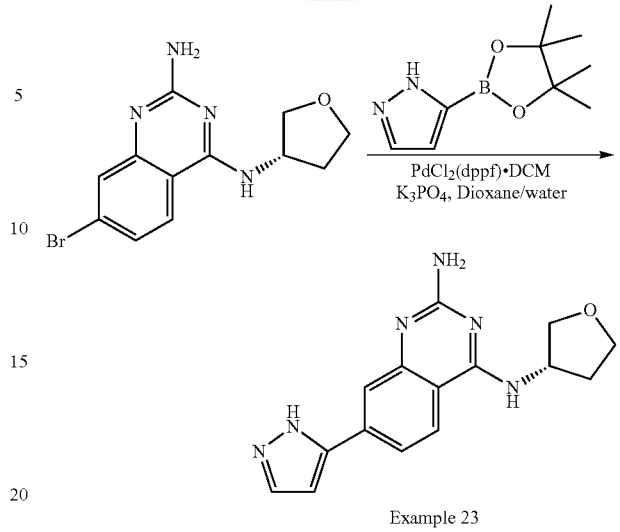

Example 23

23A. (S)-7-bromo-N4-(tetrahydrofuran-3-yl)quinazoline-2,4-diamine

In a 2 dram vial was added 2-amino-7-bromoquinazolin-4(3H)-one (30 mg, 0.125 mmol), (S)-tetrahydrofuran-3-amine (32.7 mg, 0.375 mmol), and BOP (71.9 mg, 0.162 mmol) in DMF (0.5 mL) to give a white suspension. DBU (0.028 mL, 0.187 mmol) was added. Solid dissolving to give a light yellow solution. The resulting mixture was heated to 50° C. stirred at that temperature for 30 min. LC-MS showed completion of the reaction, the reaction mixture was proceeded to next step without purification. LC-MS m/z (M+H)$^+$ 242.0.

Example 23

To above reaction mixture was added 5-(4,4,5,5-tetramethyl-1,3,2-dioxaborolan-2-yl)-1H-pyrazole (22.59 mg, 0.116 mmol), PdCl$_2$(dppf)-CH$_2$Cl$_2$ adduct (7.92 mg, 9.70 μmol) and potassium phosphate, dibasic (0.146 mL, 0.291 mmol) (2 M) in 1,4-Dioxane (20 mL) and Water (5 mL) to give a orange suspension. The reaction mixture was heated on a 110° C. heating block under nitrogen for 2 h. During the reaction, solid dissolved to give a dark solution. LC-MS showed completion of the reaction, the reaction was filtered through a microfilter to remove catalysts. The reaction mixture was purified by prep-HPLC to yield the desired product 18.7 mg (64% yield).

Example 24. 3-((2-amino-6-fluoro-7-(1H-pyrazol-5-yl)quinazolin-4-yl)amino)propan-1-ol

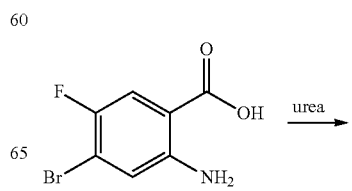

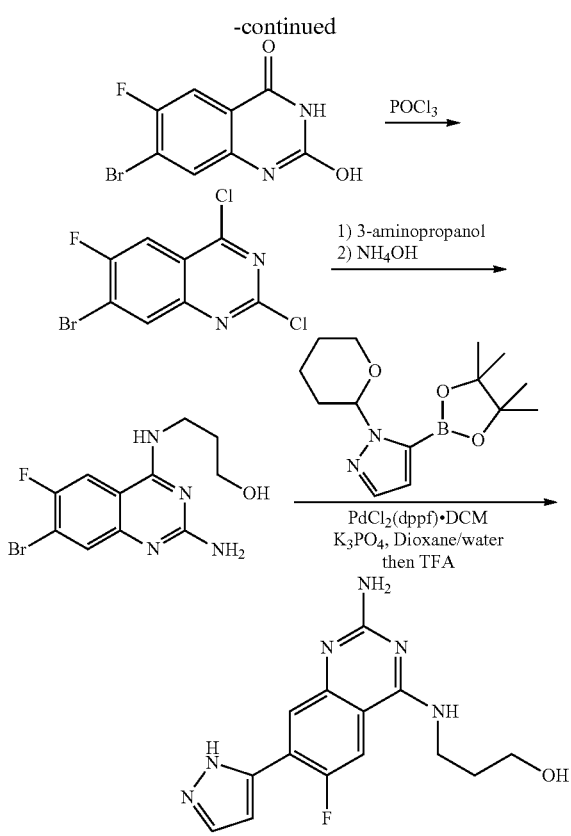

Example 24

24A. 7-bromo-6-fluoroquinazoline-2,4-diol

A suspension of 2-amino-4-bromo-5-fluorobenzoic acid (5 g, 21.37 mmol) and urea (12.83 g, 214 mmol) was heated to 200° C. for one hour. After cooling to room temperature the reaction is diluted with water and the solid filtered and dried to yield 7-bromo-6-fluoroquinazoline-2,4-diol (2.62 g, 47%). HPLC RT (method C): 0.61 min, LCMS (M+H)$^+$: 260, $^1$H NMR (400 MHz, DMSO-$d_6$) δ 7.74-7.65 (m, 1H), 7.45 (d, J=5.7 Hz, 1H)

24B. 7-bromo-2,4-dichloro-6-fluoroquinazoline

A solution of 7-bromo-6-fluoroquinazoline-2,4-diol (1 g, 3.86 mmol), DIPEA (2 ml, 11.45 mmol), and POCl$_3$ (13.9 ml, 149 mmol) is heated to 110° C. for 16 hours. Once cooled to room temperature the reaction is evaporated under reduced pressure. The residue is partitioned between DCM and saturated sodium carbonate, dried and evaporated. The residue was purified via ISCO (40 g column; Hexanes/Ethyl acetate; 0 to 100% gradient) to give 7-bromo-2,4-dichloro-6-fluoroquinazoline (392 mg, 3.1 mmol, 34%). HPLC RT (Method C): 1.00 min, LCMS (M+H)$^+$: 295.

24C. 3-((2-amino-7-bromo-6-fluoroquinazolin-4-yl)amino)propan-1-ol

A solution of 7-bromo-2,4-dichloro-6-fluoroquinazoline (85 mg, 0.287 mmol), 3-amino-1-propanol (0.044 mL, 0.574 mmol) and DIPEA (0.100 mL, 0.574 mmol) in NMP (1 mL) is heated to 120° C. for 20 minutes. The reaction is cooled to room temperature, diluted with water (5 ml) filtered and dried. The solid is dissolved in dioxane (0.5 mL) and ammonium hydroxide (0.5 mL, 12.84 mmol) was added. The reaction is heated to 120° C. for 16 hours and ammonium hydroxide (0.5 mL, 12.84 mmol) was added. After continued heating to 120° C. for 40 hours the reaction is evaporated and dried under high vacuum. The residue was purified via ISCO (24 g column; DCM/MeOH; 0 to 30% gradient) to give 3-((2-amino-7-bromo-6-fluoroquinazolin-4-yl)amino)propan-1-ol (60 mg, 66%). HPLC RT: 0.53 min (Method C), LCMS (M+H)$^+$: 315.

Example 24

To a mixture of 3-((2-amino-7-bromo-6-fluoroquinazolin-4-yl)amino)propan-1-ol (80 mg, 0.254 mmol), 1-(tetrahydro-2H-pyran-2-yl)-5-(4,4,5,5-tetramethyl-1,3,2-dioxaborolan-2-yl)-1Hpyrazole (106 mg, 0.381 mmol) and tripotassium phosphate (2M aqueous) (0.381 mL, 0.762 mmol) in dioxane (5 mL) was added PdCl$_2$(dppf)-CH$_2$Cl$_2$Adduct (20.7 mg, 0.025 mmol) under N$_2$. The mixture is heated to 110° C. during 16 hours. The reaction was partitioned between DCM (50 mL) and brine (25 mL). The organic layer was dried with Na$_2$SO$_4$, filtered and concentrated. The reaction mixture was diluted with DCM (10 mL) and TFA (0.5 mL, 6.49 mmol) was added. The reaction is evaporated under reduced pressure after 20 minutes at room temperature. The residue was diluted with DMF (1 ml), filtered through a syringe filter, and the crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-28% B over 28 minutes, then a 8-minute hold at 100% B; Flow Rate: 20 mL/min; Column Temperature: 25° C. Fraction collection was triggered by MS signals. Fractions containing the desired product were combined and dried via centrifugal evaporation to give 3-((2-amino-6-fluoro-7-(1H-pyrazol-5-yl)quinazolin-4-yl)amino)propan-1-ol (1.3 mg, 1.6%).

Example 25. Racemic trans-4-((2-amino-7-(1H-pyrazol-5-yl)quinazolin-4-yl)amino)tetrahydrofuran-3-ol

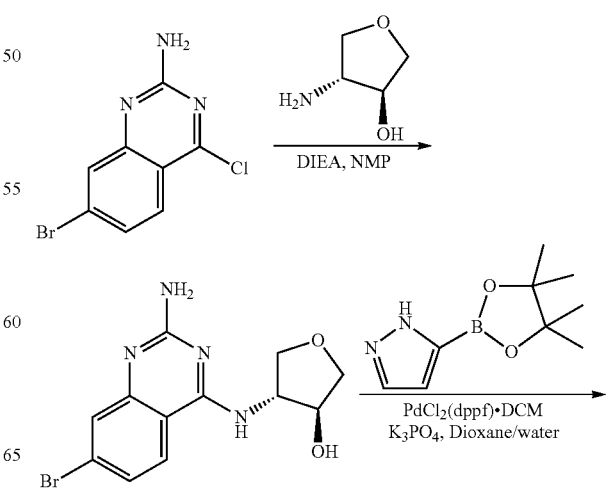

-continued

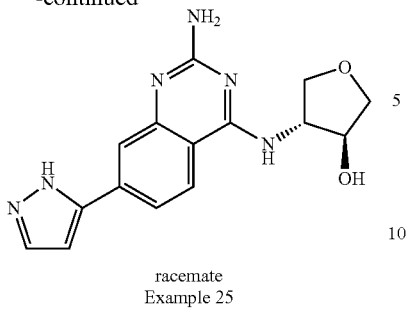

racemate
Example 25

25A. trans-4-((2-amino-7-bromoquinazolin-4-yl)amino)tetrahydrofuran-3-ol

In a 2 dram vial was added 7-bromo-4-chloroquinazolin-2-amine (30 mg, 0.116 mmol), (3S,4R)-4-aminotetrahydrofuran-3-ol (35.9 mg, 0.348 mmol), and DIEA (0.101 mL, 0.580 mmol) in NMP (0.5 mL) to give a white suspension. The resulting mixture was heated to 120° C. stirred at that temperature for 12 h. LC-MS showed completion of the reaction, the reaction mixture was used in the next step without purification. LC-MS m/z (M+H)$^+$ 325.1.

Example 25

To above reaction mixture was added 5-(4,4,5,5-tetramethyl-1,3,2-dioxaborolan-2-yl)-1H-pyrazole (21.48 mg, 0.111 mmol), PdCl$_2$(dppf)-CH$_2$Cl$_2$ adduct (7.53 mg, 9.23 µmol) and potassium phosphate, tribasic (0.138 mL, 0.277 mmol) in 1,4-dioxane (2 mL) to give a orange suspension. The reaction mixture was heated on a 110° C. heating block under nitrogen for 2 h. During the reaction, solid dissolved to give a dark solution. LC-MS showed completion of the reaction, the reaction was filtered through a microfilter to remove catalysts. The reaction mixture was purified by prep-HPLC to yield the desired product 13 mg (41% yield).

Example 141: rac-(1R,2R,4S)-4-((2-amino-7-(1H-pyrazol-5-yl)quinazolin-4-yl)amino)-2-methoxycyclopentan-1-ol

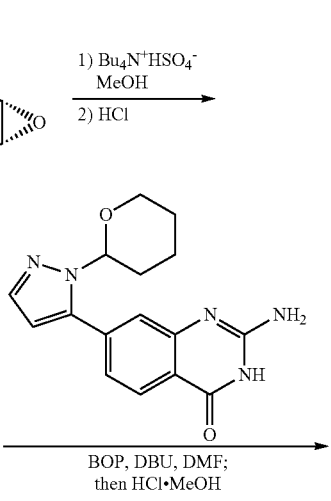

-continued

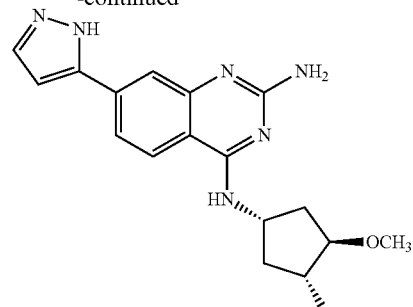

racemate
Example 141

141A. (1R,2R,4R)-4-amino-2-methoxycyclopentan-1-ol and (1S,2S,4S)-4-amino-2-methoxycyclopentan-1-ol racemic mixture A solution of racemic tert-butyl ((1R,3S,5S)-6-oxabicyclo[3.1.0]hexan-3-yl)carbamate (200 mg, 1.004 mmol) and tetrabutylammonium hydrogen sulfate (136 mg, 0.402 mmol) in methanol (10 mL) was heated to 50° C. for 48 hours. To the reaction was added concentrated hydrochloric acid (0.1 ml). After 16 hours, the reaction was evaporated under reduced pressure and dried under high vacuum to give a 1 to 1 mixture of (1R,2R,4R)-4-amino-2-methoxycyclopentan-1-ol and (1S,2S,4S)-4-amino-2-methoxycyclopentan-1-ol hydrochloride (0.151 g, 0.90 mmol, 90% yield), which was used as is without further purification. HPLC RT (Method C): 0.23 min. [M+H]$^+$=132.0.

Example 141

Example 141 was prepared from (1R,2R,4R)-4-amino-2-methoxycyclopentan-1-ol and (1S,2S,4S)-4-amino-2-methoxycyclopentan-1-ol racemic mixture following the procedure given for Example 1.

Examples 96 to 98: rac-3-((2-amino-7-(1H-pyrazol-5-yl)quinazolin-4-yl)amino)hexan-1-ol and its Separation into Single Unassigned Enantiomers Example 96 was prepared from the appropriate starting materials using the procedure described in Example 1. Example 96 was purified via preparative chiral SFC with the following conditions to separate the enantiomers: Instrument: Waters 100 Prep SFC; Column: Chiral IC 250 mm×21 mm, 5-µm particles; Mobile Phase: 65% CO$_2$/35% MeOH w 0.1% diethylamine; Flow Rate: 60 mL/min. Peak 1 RT: 6.52 min. Peak 2 RT: 9.39 min.

Example 97 and Example 98. 3-((2-amino-7-(1H-pyrazol-5-yl)quinazolin-4-yl)amino)hexan-1-ol as Single Unassigned Enantiomers Analytical Chiral SFC conditions: Instrument: Shimadzu Nexera UC SFC; Column: Chiral IC, 150 mm×4.6 mm, 5-µm particles; Mobile Phase: 65% CO$_2$/35% MeOH w 0.1% diethylamine; Flow Rate: 2 mL/min. Example 97 (First eluting isomer): Peak 1 Chiral SFC RT: 4.5 min. Example 98 (Second eluting isomer): Peak 2 Chiral SFC RT: 6.2 min.

Examples 99 to 101: rac-3-((2-amino-7-(1H-pyrazol-5-yl)quinazolin-4-yl)amino)heptan-1-ol and its Separation into Single Unassigned Enantiomers Example 99 was purified via preparative chiral SFC with the following conditions to separate the enantiomers: Instrument: Waters 100 Prep SFC; Column: Chiral IC 250 mm×21 mm, 5-μm particles; Mobile Phase: 60% $CO_2$/40% MeOH w 0.1% diethylamine; Flow Rate: 60 mL/min. Peak 1 RT: 6.46 min. Peak 2 RT: 9.39 min.

Example 100 was prepared from the appropriate starting materials following the procedure described in Example 1. Example 100 and 101. 3-((2-amino-7-(1H-pyrazol-5-yl)quinazolin-4-yl)amino)heptan-1-ol as single unassigned enantiomers Analytical Chiral SFC conditions: Instrument: Shimadzu Nexera UC SFC; Column: Chiral IC, 150 mm×4.6 mm, 5-μm particles; Mobile Phase: 60% $CO_2$/40% MeOH w 0.1% diethylamine; Flow Rate: 2 mL/min. Example 100 (First eluting isomer): Peak 1 Chiral SFC RT: 3.2 min. Example 101 (Second eluting isomer): Peak 2 Chiral SFC RT: 4.3 min.

Examples 149 and 150: rac-2-((2-amino-7-(1H-pyrazol-5-yl)quinazolin-4-yl)amino)-1-(1-methyl-1H-imidazol-2-yl)ethan-1-ol and its Separation into Single, Unassigned Enantiomers rac-2-((2-Amino-7-(1H-pyrazol-5-yl)quinazolin-4-yl)amino)-1-(1-methyl-1H-imidazol-2-yl)ethan-1-ol was prepared from 2-amino-7-(1-(tetrahydro-2H-pyran-2-yl)-1H-pyrazol-5-yl)quinazolin-4-ol and 2-amino-1-(1-methyl-1H-imidazol-2-yl)ethan-1-ol (bis hydrochloride salt) as described in Example 1. This material was purified via preparative chiral SFC with the following conditions to separate the enantiomers: Instrument: Waters 100 Prep SFC; Column: Chiral OD 250 mm×30 mm, 5-μm particles; Mobile Phase: 80% $CO_2$/20% MeOH w 0.1% diethylamine; Flow Rate: 100 mL/min. Peak 1 RT: 20.15 min. Peak 2 RT: 24.99 min. Analytical Chiral SFC conditions: Instrument: Shimadzu Nexera UC SFC; Column: Chiral OD, 100 mm×4.6 mm, 5-μm particles; Mobile Phase: 80% $CO_2$/20% MeOH w 0.1% diethylamine; Flow Rate: 2 mL/min. Example 149 (First eluting isomer): Peak 1 Chiral SFC RT: 6.8 min. Example 150 (Second eluting isomer): Peak 2 Chiral SFC RT: 8.3 min.

Examples 162 and 163: rac-7-(1H-pyrazol-5-yl)-N4-((trans)-2-(pyridin-3-yl)cyclopropyl)quinazoline-2,4-diamine and its Separation into Single, Unassigned Enantiomers rac-7-(1H-Pyrazol-5-yl)-N4-((1R,2S)-2-(pyridin-3-yl)cyclopropyl)quinazoline-2,4-diamine and its separation into single, unassigned enantiomers was prepared from rac-(trans)-2-(pyridin-3-yl)cyclopropan-1-amine (2 HCl salt) and 2-amino-7-(1-(tetrahydro-2H-pyran-2-yl)-1H-pyrazol-5-yl)quinazolin-4-ol as described in Example 1. This material was purified via preparative chiral SFC with the following conditions to separate the enantiomers: Instrument: Waters 100 Prep SFC; Column: Chiral OJ 250 mm×30 mm, 5-μm particles; Mobile Phase: 75% $CO_2$/25% MeOH w 0.1% diethylamine; Flow Rate: 100 mL/min. Peak 1 RT: 3.61 min. Peak 2 RT: 8.55 min. Analytical Chiral SFC conditions: Instrument: Shimadzu Nexera UC SFC; Column: Chiral OJ, 100 mm×4.6 mm, 5-μm particles; Mobile Phase: 75% $CO_2$/25% MeOH w 0.1% diethylamine; Flow Rate: 2 mL/min. Example 162 (First eluting isomer): Peak 1 Chiral SFC RT: 1.9 min. Example 163 (Second eluting isomer): Peak 2 Chiral SFC RT: 3.8 min.

Example 164: N4-((6-(dimethylamino)pyridazin-3-yl)methyl)-7-(1H-pyrazol-5-yl)quinazoline-2,4-diamine, 2 TFA

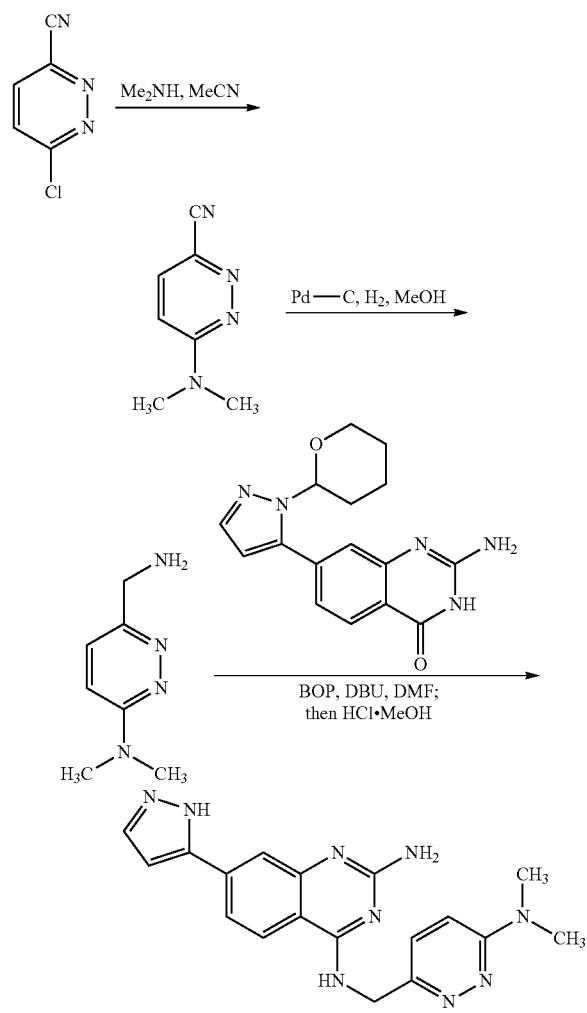

Example 164

164 A: 6-(dimethylamino)pyridazine-3-carbonitrile

6-Chloropyridazine-3-carbonitrile (300 mg, 2.150 mmol) was dissolved in acetonitrile (8.6 mL). dimethylamine (2M in THF) (2687 μl, 5.37 mmol) was added and the reaction was heated to 60° C. After ca. 2 hours, the reaction was concentrated. The solid was suspended in water, filtered, and dried to give 6-(dimethylamino)pyridazine-3-carbonitrile (244 mg, 1.647 mmol, 77% yield). $^1$H NMR (400 MHz, DMSO-$d_6$) δ 8.72-8.60 (m, 2H), 7.83 (d, J=9.7 Hz, 1H), 7.15 (d, J=9.7 Hz, 1H), 3.22-3.16 (m, 6H).

164 B: 6-(aminomethyl)-N,N-dimethylpyridazin-3-amine, 2 HCl 6-(dimethylamino)pyridazine-3-carbonitrile (122 mg, 0.823 mmol) was dissolved in methanol (8.2 mL). HCl (715

μl, 8.23 mmol) and Pd—C(10% on carbon, 50% wet) (12 mg, 5.64 μmol) were added, and the atmosphere was exchanged for hydrogen three times. The reaction was stirred under a hydrogen balloon. After 8 hours, the reaction was filtered and concentrated to give 6-(aminomethyl)-N,N-dimethylpyridazin-3-amine, 2 HCl (196 mg, 0.871 mmol, 106% yield). $^1$H NMR (400 MHz, METHANOL-$d_4$) δ 7.99-7.92 (m, 1H), 7.90-7.83 (m, 1H), 4.38 (s, 2H), 3.41-3.36 (m, 6H).

Example 164

N4-((6-(Dimethylamino)pyridazin-3-yl)methyl)-7-(1H-pyrazol-5-yl)quinazoline-2,4-diamine, 2 TFA was prepared from 6-(aminomethyl)-N,N-dimethylpyridazin-3-amine, 2 HCl and 2-amino-7-(1-(tetrahydro-2H-pyran-2-yl)-1H-pyrazol-5-yl)quinazolin-4-ol as described in Example 1.

Example 178 and 179: racemic-(cis)-3-((2-amino-7-(1H-pyrazol-5-yl)quinazolin-4-yl)amino)cyclohexan-1-ol and its separation into single, unassigned enantiomers Racemic-(cis)-3-((2-amino-7-(1H-pyrazol-5-yl)quinazolin-4-yl)amino)cyclohexan-1-ol was prepared from 2-amino-7-(1-(tetrahydro-2H-pyran-2-yl)-1H-pyrazol-5-yl)quinazolin-4-ol and (cis)-3-aminocyclohexan-1-ol, HCl (58.4 mg, 0.385 mmol) following the procedure given in Example 1.

This material was purified via preparative chiral SFC with the following conditions to separate the enantiomers: Instrument: Waters 100 Prep SFC; Column: Chiral IC 250 mm×21 mm, 5-μm particles; Mobile Phase: 65% $CO_{2/35}$% MeOH w 0.1% diethylamine; Flow Rate: 60 mL/min. Peak 1 RT: 10.07 min. Peak 2 RT: 15.91 min.

Analytical Chiral SFC conditions: Instrument: Shimadzu Nexera UC SFC; Column: Chiral IC, 150 mm×4.6 mm, 5-μm particles; Mobile Phase: 65% $CO_{2/35}$% MeOH w 0.1% diethylamine; Flow Rate: 2 mL/min. Example 178 (First eluting isomer): Peak 1 Chiral SFC RT: 7.7 min. Example 179 (Second eluting isomer): Peak 2 Chiral SFC RT: 11.5 min.

Example 184 and 185: racemic (trans)-3-((2-amino-7-(1H-pyrazol-5-yl)quinazolin-4-yl)amino)cyclopentane-1-carbonitrile and its Separation into Single, Unassigned Enantiomers Racemic (trans)-3-((2-amino-7-(1H-pyrazol-5-yl)quinazolin-4-yl)amino)cyclopentane-1-carbonitrile was prepared as described for Example 1 was purified via preparative chiral SFC with the following conditions to separate the enantiomers: Instrument: Waters 100 Prep SFC; Column: Chiral OJ 30×250 mm, 5-μm particles; Mobile Phase: 85% $CO_{2/15}$% MeOH w 0.1% diethylamine; Flow Rate: 100 mL/min. Peak 1 Example 184 RT: 17.6 min. Peak 2 Example 185 RT: 26.2 min.

Analytical SFC conditions: Column: Chiral OJ, 100 mm×4.6 mm, 5-μm particles; Mobile Phase: 85% $CO_2$: 15% with 0.1% DEA; Flow Rate: 2 mL/min. Example 178 (Peak 1) RT: 8.4 min. Example 179 (Peak 2) RT: 12.1 min.

Example 191: (cis)-3-((2-amino-7-(1H-pyrazol-5-yl)quinazolin-4-yl)amino)-1-methylcyclobutan-1-ol

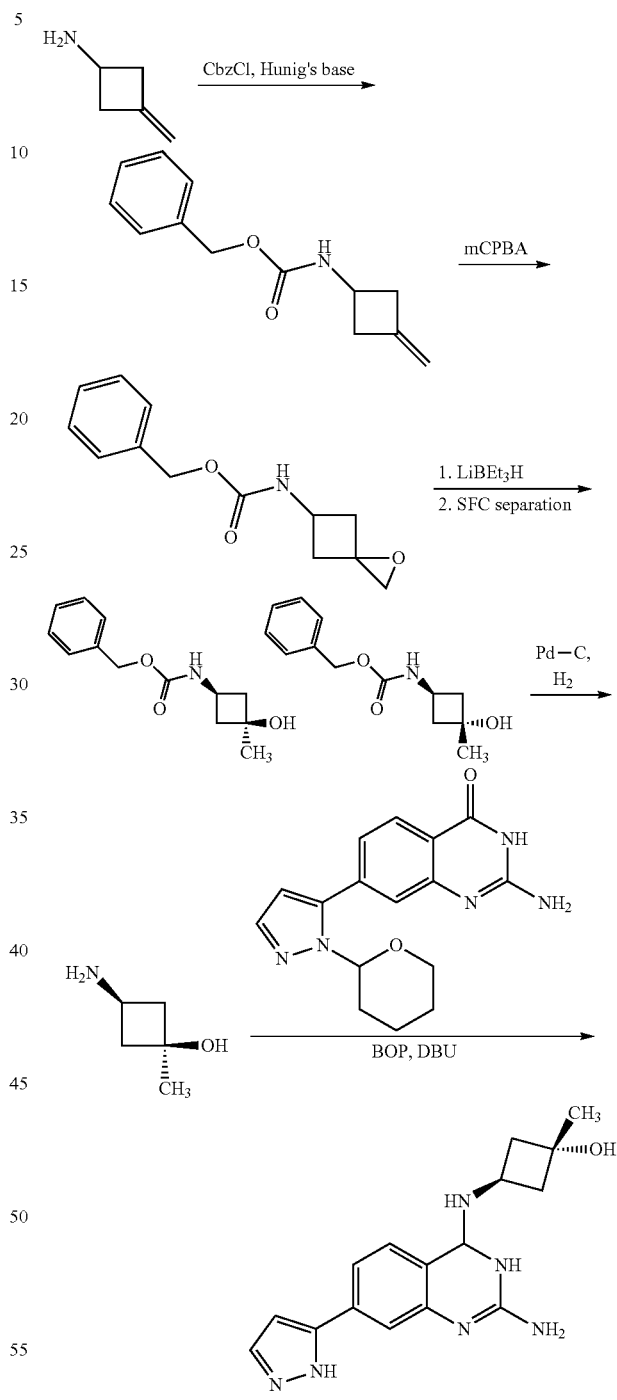

Example 191

191A: Benzyl (3-methylenecyclobutyl)carbamate

3-Methylenecyclobutan-1-amine, HCl (300 mg, 2.508 mmol) was suspended in DCM (12.542 mL). Hunig's base (1.314 mL, 7.53 mmol) was added; the suspended material dissolved. The reaction was cooled in an ice bath and Cbz-Cl (0.537 mL, 3.76 mmol) was added dropwise. After 5 minutes, the ice bath was removed. The reaction was stirred overnight, then diluted with water and extracted twice with DCM. The organic layers were dried with sodium sulfate and concentrated. The residue was purified via ISCO (40 g column; Hex/EtOAc; 0 to 30% gradient) to give benzyl (3-methylenecyclobutyl)carbamate (546 mg, 2.51 mmol, 100% yield). $^1$H NMR (400 MHz, CHLOROFORM-d) δ 7.40-7.31 (m, 4H), 5.10 (s, 2H), 5.02-4.91 (m, 1H), 4.85 (dt, J=4.9, 2.3 Hz, 2H), 4.30-4.14 (m, 1H), 3.14-2.96 (m, 2H), 2.62 (ddt, J=14.0, 6.9, 3.5 Hz, 2H).

191B: Benzyl (1-oxaspiro[2.3]hexan-5-yl)carbamate (Cis/Trans Mixture)

A solution of benzyl (3-methylenecyclobutyl)carbamate (546 mg, 2.51 mmol) in DCM (5026 µl) was cooled in an ice bath. m-CPBA (954 mg, 2.76 mmol) was added. After 30 minutes, the ice bath was removed. The reaction was stirred for 4 hours, then quenched with saturated sodium bicarbonate solution and extracted three times with DCM. The organic layers were washed with brine, dried with sodium sulfate, and concentrated. The residue was purified via ISCO (40 g column; Hex/EtOAc; 0 to 50% gradient) to give benzyl (1-oxaspiro[2.3]hexan-5-yl)carbamate as a mixture of cis and trans isomers (356 mg, 1.526 mmol, 60.7% yield). $^1$H NMR (400 MHz, CHLOROFORM-d) δ 7.43-7.30 (m, 5H), 5.11 (br s, 2H), 5.04-4.90 (m, 1H), 4.39-4.08 (m, 1H), 2.86-2.69 (m, 4H), 2.53-2.35 (m, 2H).

191C: benzyl ((cis)-3-hydroxy-3-methylcyclobutyl) carbamate and benzyl ((trans)-3-hydroxy-3-methylcyclobutyl)carbamate A solution of benzyl (1-oxaspiro[2.3]hexan-5-yl)carbamate (178 mg, 0.763 mmol) in THF (7631 µl) was cooled in an ice bath. Lithium triethylborohydride (1M in THF) (992 µl, 0.992 mmol) was added. After 10 minutes, the ice bath was removed. After 1.75 hours, the reaction was quenched with water and extracted three times with EtOAc. Brine was added to break the emulsion. The organic layers were dried with sodium sulfate and concentrated. The material was combined with the material from an identical reaction and absorbed onto silica gel. The residue was purified via ISCO (40 g column; Hex/EtOAc; 0 to 100% gradient) to give a mixture of cis and trans isomers. The mixture was purified by SFC with the following conditions to separate the isomers: Instrument: Berger SFC; Column: LUX Cell-2 30×250 mm, 5-µm particles; Mobile Phase: 65% CO$_2$/35% MeOH; Flow Rate: 85 mL/min. Peak 1 RT: 2.3 min. Peak 2 RT: 4.1 min.
Peak 1: benzyl ((cis)-3-hydroxy-3-methylcyclobutyl)carbamate (173 mg, 48%). $^1$H NMR (400 MHz, CHLOROFORM-d) δ 7.42-7.27 (m, 5H), 5.19-5.03 (m, 3H), 3.85-3.69 (m, 1H), 2.65-2.55 (m, 1H), 2.54-2.43 (m, 2H), 2.11-1.92 (m, 2H), 1.41-1.31 (m, 3H)
Peak 2: benzyl ((trans)-3-hydroxy-3-methylcyclobutyl)carbamate (107 mg, 30%). $^1$H NMR (400 MHz, CHLOROFORM-d) δ 7.42-7.29 (m, 5H), 5.09 (s, 2H), 4.89 (br d, J=1.8 Hz, 1H), 4.32 (br d, J=7.0 Hz, 1H), 2.49 (br t, J=10.3 Hz, 2H), 2.02-1.90 (m, 2H), 1.69-1.64 (m, 1H), 1.41 (s, 3H)

191D: (cis)-3-amino-1-methylcyclobutan-1-ol

In a 100 mL round-bottomed flask was benzyl ((1s,3s)-3-hydroxy-3-methylcyclobutyl)carbamate (173 mg, 0.735 mmol) and Pd—C (156 mg, 0.074 mmol) in MeOH (20 mL) to give a suspension. The reaction was purged 3 times with vacuum and nitrogen then purged three times with vacuum and hydrogen, then stirred under a hydrogen balloon for 16 hour. The reaction was then filtered through celite and the filtrate was concentrated to give (cis)-3-amino-1-methylcyclobutan-1-ol (74 mg, 99%). HPLC RT (Method C): 1.00 min.

Example 191

(cis)-3-((2-Amino-7-(1H-pyrazol-5-yl)quinazolin-4-yl)amino)-1-methylcyclobutan-1-ol was prepared from (cis)-3-amino-1-methylcyclobutan-1-ol and 2-amino-7-(1-(tetrahydro-2H-pyran-2-yl)-1H-pyrazol-5-yl)quinazolin-4-ol according to the procedure described for Example 1.

Example 192: (trans)-3-((2-amino-7-(1H-pyrazol-5-yl)quinazolin-4-yl)amino)-1-methylcyclobutan-1-ol (trans)-3-((2-Amino-7-(1H-pyrazol-5-yl)quinazolin-4-yl)amino)-1-methylcyclobutan-1-ol was prepared from benzyl ((trans)-3-hydroxy-3-methylcyclobutyl)carbamate (Example 191C) according to the procedure describe in Example 191.

Example 198 and 199: racemic N4-((2,2-Difluorocyclopropyl)methyl)-7-(1H-pyrazol-3-yl)quinazoline-2,4-diamine and its Separation into Single, Unassigned Enantiomers Racemic N4-((2,2-Difluorocyclopropyl)methyl)-7-(1H-pyrazol-3-yl)quinazoline-2,4-diamine was prepared according to the procedure described in Example 14. The enantiomers were separated by chiral SFC. Chiral SFC conditions: Instrument: Waters 100 Prep SFC; Column: Chiral IC 21×250 mm, 5 µM; Mobile phase: 70% CO$_2$/30% MeOH with 0.1% DEA; Flow rate: 60 ml/min; Detector wavelength: 220 nm. Peak 1 (Example 198) RT: 11.38 min. Peak 2 (Example 199) RT: 12.91 min.
Analytical Chiral SFC conditions: Instrument: Shimadzu Nexera UC SFC; Column: Chiral IC, 150 mm×4.6 mm, 5-µm particles; Mobile Phase: 70% CO$_2$/30% MeOH w 0.1% diethylamine; Flow Rate: 2 mL/min. Example 198 (First eluting isomer): Peak 1 Chiral SFC RT: 4.9 min. Example 163 (Second eluting isomer): Peak 2 Chiral SFC RT: 5.5 min.

Example 200 and Example 201, 3-((2-amino-7-(1H-pyrazol-5-yl)quinazolin-4-yl)amino)butan-1-ol as single unassigned enantiomers, were prepared from the appropriate starting materials following the procedure described in Example 1, and purified via preparative chiral SFC with the following conditions to separate the enantiomers: Instrument: Waters 100 Prep SFC; Column: Chiral IC 250 mm×21 mm, 5-µm particles; Mobile Phase: 65% CO$_2$/35% MeOH w 0.1% diethylamine; Flow Rate: 60 mL/min. Peak 1 RT: 6.95 min. Peak 2 RT: 8.84 min.
Analytical Chiral SFC conditions: Instrument: Shimadzu Nexera UC SFC; Column: Chiral IC, 150 mm×4.6 mm, 5-µm particles; Mobile Phase: 65% CO$_2$/35% MeOH w 0.1% diethylamine; Flow Rate: 2 mL/min. Example 200 (First eluting isomer): Peak 1 Chiral SFC RT: 5.2 min. Example 201 (Second eluting isomer): Peak 2 Chiral SFC RT: 6.4 min.

Example 202 and Example 203. 3-((2-amino-7-(1H-pyrazol-5-yl)quinazolin-4-yl)amino)-2-methoxypropan-1-ol as single unassigned enantiomers, were prepared from the appropriate starting materials following the procedure described in Example 1, and purified via preparative chiral SFC with the following conditions to separate the enantiomers: Instrument: Waters 100 Prep SFC; Column: Chiral AD 250 mm×30 mm, 5-μm particles; Mobile Phase: 80% $CO_2$/20% MeOH w 0.1% diethylamine; Flow Rate: 60 mL/min. Peak 1 RT: 14.45 min. Peak 2 RT: 20.09 min.

Analytical Chiral SFC conditions: Instrument: Shimadzu Nexera UC SFC; Column: Chiral IC, 150 mm×4.6 mm, 5-μm particles; Mobile Phase: 80% $CO_2$/20%/MeOH w 0.1% diethylamine; Flow Rate: 2 mL/min. Example 202 (First eluting isomer): Peak 1 Chiral SFC RT: 4.7 min. Example 203 (Second eluting isomer): Peak 2 Chiral SFC RT: 6.4 min.

From the appropriate starting materials, Examples 26 to Example 110 were prepared according to the synthetic procedures described for Example 1; Examples 111 to Example 118 were prepared according to the synthetic procedures described for Example 2; Example 119 to Example 121 were prepared according to the synthetic procedures described for Example 14; Example 122 to Example 128 were prepared according to the synthetic procedures described for Example 15; Example 129 and Example 130 were prepared according to the synthetic procedures described for Example 18; Example 131 to Example 135 were prepared according to the synthetic procedures described for Example 20; Example 136 and Example 137 were prepared according to the synthetic procedures described for Example 21; Example 138 and Example 139 were prepared in the same manner as preparation of Example 23; Example 140 was prepared in the same manner as preparation of Example 1; Example 141 to Example 148 were prepared in the same manner as preparation of Example 1; Example 151 to Example 161 were prepared in the same manner as preparation of Example 1; Example 165 to Example 177 were prepared in the same manner as preparation of Example 1; Example 180 to Example 183 were prepared in the same manner as preparation of Example 1; Example 186 to Example 190 were prepared in the same manner as preparation of Example 1; Example 193 to Example 197 were prepared in the same manner as preparation of Example 14; Example 204 was prepared in the same manner as preparation of Example 1.

Biological data of compounds that were assayed using one or more of the above procedures. Unless otherwise indicated, the TLR7 agonist $EC_{50}$ and TLR8 agonist $EC_{50}$ of the below compounds were measured at values >100 μM.

| Ex No. | Structure | LC/MS $[M + H]^+$/ RT (Method)/ NLRP3 hIL1B $EC_{50}$ | $^1$H NMR (500 MHz, DMSO-$d_6$, unless otherwise indicated) |
|---|---|---|---|
| 1 | (R)-configured quinazoline with 7-(1H-pyrazol-3-yl), 2-NH$_2$, 4-NH-CH$_2$-CH(OH)-CH$_3$ | 285/ 1.09 min (A)/ 0.45 μM | δ 12.33 (s, 1H), 9.36 (br t, J = 5.3 Hz, 1H), 8.37 (d, J = 9.0 Hz, 1H), 8.25-7.56 (m, 3H), 6.90 (d, J = 2.1 Hz, 1H), 4.02 (br dd, J = 12.0, 6.6 Hz, 1H), 3.60-3.55 (m, 1H), 3.51-3.45 (m, 1H), 1.14 (d, J = 6.1 Hz, 3H) |
| 2 | Quinazoline with 7-(1H-pyrazol-3-yl), 2-NH$_2$, 4-NH-(1H-pyrazol-3-yl) | 293/ 0.95 min (C)/ 0.22 μM | δ 8.76-8.57 (m, 1H), 7.98-7.82 (m, 3H), 7.77 (br s, 1H), 7.08-6.97 (m, 1H), 6.93 (d, J = 2.0 Hz, 1H) |
| 3 | 6-Cl quinazoline with 7-(1H-pyrazol-3-yl), 2-NH$_2$, 4-NH-CH$_2$CH$_2$CH$_2$-OH | 319/ 1.07 min (B)/ 6.84 μM | δ 9.49-9.27 (m, 1H), 8.51 (s, 1H), 8.40-7.98 (m, 2H), 7.92 (br s, 2H), 6.91 (br s, 1H), 3.63 (q, J = 6.3 Hz, 2H), 3.57-3.43 (m, 2H), 1.83 (quin, J = 6.6 Hz, 2H) |

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 4 | (structure: 2-amino-7-(1H-pyrazol-5-yl)-4-(2-hydroxyethoxy)quinazoline) | 272/ 0.80 min (B)/ 6.54 μM; Both TLR7/ TLR8 agonist EC$_{50}$: <50% activity at 50 μM. | δ 7.92 (br d, J = 8.2 Hz, 1H), 7.82-7.74 (m, 1H), 7.73 (s, 1H), 7.62 (br d, J = 5.5 Hz, 1H), 6.84 (d, J = 1.5 Hz, 1H), 6.58 (br s, 2H), 4.45 (br t, J = 4.7 Hz, 2H), 3.85-3.77 (m, 2H) |
| 5 | (structure: pyrrolidinone-CH$_2$-NH-quinazoline, Enantiomer A) | 324.2/ 3.8 min (D)/ 13.04 μM | δ 7.98 (d, J = 8.5 Hz, 1H), 7.86 (br t, J = 5.0 Hz, 1H), 7.82-7.67 (m, 2H), 7.60 (s, 1H), 7.55-7.47 (m, 1H), 6.79 (d, J = 2.1 Hz, 1H), 6.05 (s, 2H), 3.94-3.82 (m, 1H), 2.26-2.17 (m, 1H), 2.16-2.05 (m, 2H), 1.85-1.75 (m, 1H) |
| 6 | (structure: pyrrolidinone-CH$_2$-NH-quinazoline, Enantiomer B) | 324.0/ 6.2 min (D)/ 2.11 μM | δ 7.98 (d, J = 8.5 Hz, 1H), 7.84 (br t, J = 5.0 Hz, 1H), 7.81-7.69 (m, 2H), 7.60 (s, 1H), 7.51 (br d, J = 5.2 Hz, 1H), 6.79 (d, J = 2.1 Hz, 1H), 6.03 (br s, 2H), 3.94-3.82 (m, 1H), 2.25-2.16 (m, 1H), 2.16-2.06 (m, 2H), 1.85-1.76 (m, 1H) |
| 7 | (structure: 2-amino-7-(1H-pyrazol-5-yl)-4-((1-methyl-1H-1,2,4-triazol-5-yl)methoxy)quinazoline) | 323.1/ 0.90 min (B)/ 4.46 μM | δ 7.95 (s, 1H), 7.88 (d, J = 8.4 Hz, 1H), 7.84-7.79 (m, 1H), 7.76 (s, 1H), 7.71-7.60 (m, 1H), 6.85 (d, J = 2.1 Hz, 2H), 5.67 (s, 2H), 4.00 (s, 3H) |

-continued

| Ex No. | Structure | LC/MS [M + H]+/ RT (Method)/ NLRP3 hIL1B EC50 | 1H NMR (500 MHz, DMSO-d6, unless otherwise indicated) |
|---|---|---|---|
| 8 | 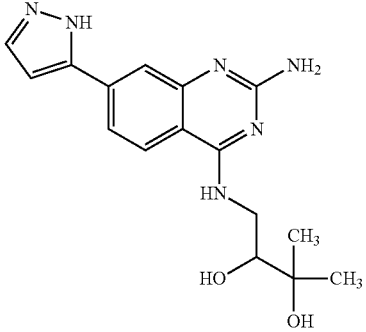<br>racemate | 329.0/<br>0.92 min (B)/<br>2.15 μM | δ 7.99 (d, J = 8.5 Hz, 1H), 7.91 (br s, 1H), 7.75 (br s, 1H), 7.63 (s, 1H), 7.60-7.48 (m, 1H), 6.87-6.75 (m, 1H), 6.24 (br s, 1H), 3.84-3.73 (m, 1H), 3.68-3.47 (m, 1H) (overlaps suppressed water peak), 3.39-3.29 (m, 1H), 1.15 (d, J = 18.3 Hz, 6H) |
| 9 | 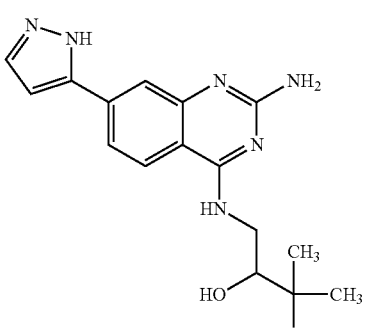<br>First eluting enantiomer | 329.3/<br>0.85 min (B)/<br>1.31 μM | δ 8.03-7.90 (m, 1H), 7.74 (br s, 2H), 7.60 (s, 1H), 7.54-7.45 (m, 1H), 6.79 (s, 1H), 6.06 (br s, 2H), 3.85-3.70 (m, 1H), 1.14 (br d, J = 19.8 Hz, 6H) |
| 10 | 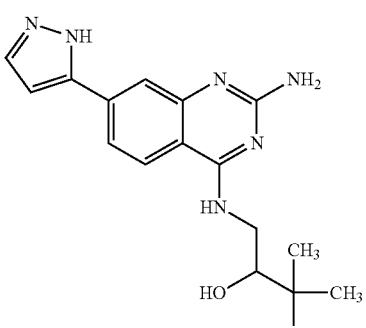<br>Second eluting enantiomer | 329.2/<br>0.93 min (B)/<br>1.86 μM | δ 7.99-7.94 (m, 1H), 7.81-7.68 (m, 2H), 7.60 (s, 1H), 7.53-7.45 (m, 1H), 6.79 (s, 1H), 6.04 (br s, 2H), 3.81-3.73 (m, 1H), 3.37-3.27 (m, 1H), 1.13 (br d, J = 18.6 Hz, 6H). One proton is not visible, likely due to overlap with suppressed water peak. |
| 11 | 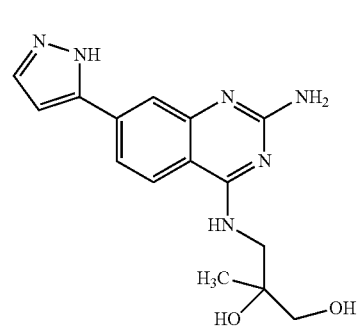<br>racemate | 315.0/<br>0.83 min (B)/<br>1.14 μM | δ 8.13 (br d, J = 8.5 Hz, 1H), 7.85-7.75 (m, 1H), 7.70 (br s, 1H), 7.67-7.57 (m, 1H), 6.84 (d, J = 2.1 Hz, 1H), 3.61-3.52 (m, 1H), 3.33-3.25 (m, 1H), 3.24-3.17 (m, 1H), 1.11 (s, 3H). One proton is not visible, likely due to overlap with suppressed water peak. |

-continued

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 12 | First eluting enantiomer | 327.1/ 0.94 min (B)/ 3.92 μM | δ 7.97 (d, J = 8.5 Hz, 1H), 7.82-7.67 (m, 1H), 7.60 (d, J = 1.5 Hz, 1H), 7.57-7.45 (m, 2H), 6.80 (d, J = 1.8 Hz, 1H), 6.10 (s, 2H), 4.42-4.27 (m, 1H), 3.93-3.85 (m, 1H), 3.79 (br dd, J = 10.5, 3.5 Hz, 1H), 3.68-3.57 (m, 1H), 3.14-3.05 (m, 1H), 3.03-2.96 (m, 1H), 2.25-2.14 (m, 1H), 1.62 (q, J = 11.2 Hz, 1H) |
| 13 | Second eluting enantiomer | 327.0/ 0.98 min (B)/ 1.18 μM | δ 7.98 (d, J = 8.2 Hz, 1H), 7.80-7.69 (m, 1H), 7.60 (d, J = 1.2 Hz, 1H), 7.55-7.46 (m, 2H), 6.80 (d, J = 2.1 Hz, 1H), 6.09 (br s, 2H), 4.40-4.28 (m, 1H), 3.91-3.85 (m, 1H), 3.82-3.76 (m, 1H), 3.67-3.58 (m, 1H), 3.08 (br t, J = 10.2 Hz, 1H), 3.03-2.97 (m, 1H), 2.20 (br d, J = 11.9 Hz, 1H), 1.67-1.55 (m, 1H) |
| 14 | 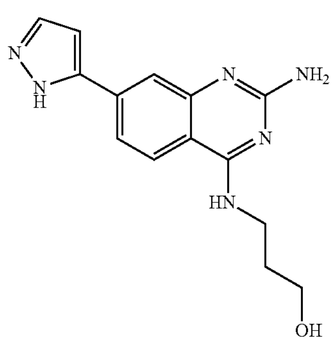 [SMILES: Nc1nc(NCCCO)c2ccc(-c3ccn[nH]3)cc2n1] | 285.2/ 0.90 min (B)/ 0.37 μM | δ 13.22 (br s, 1H), 9.29-9.24 (m, 1H), 8.24 (br d, J = 8.8 Hz, 1H), 8.13-7.92 (m, 1H), 7.91-7.82 (m, 3H), 6.88 (s, 1H), 4.64-4.60 (m, 1H), 3.63 (q, J = 6.5 Hz, 2H), 3.54-3.50 (m, 2H), 1.83 (quin, J = 6.7 Hz, 2H) |
| 15 | 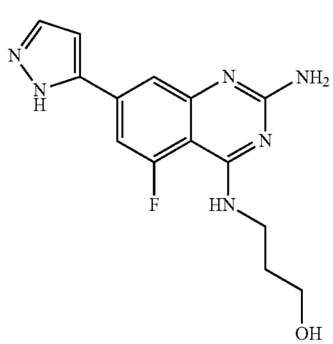 [SMILES: Nc1nc(NCCCO)c2c(F)cc(-c3ccn[nH]3)cc2n1] | 303.1/ 1.09 min (B)/ 0.24 μM | δ 13.30 (br s, 1H), 8.68-8.55 (m, 1H), 8.03-7.76 (m, 3H), 7.68 (br s, 1H), 7.64-7.54 (m, 1H), 6.95-6.86 (m, 1H), 4.88-4.78 (m, 1H), 3.70-3.63 (m, 2H), 3.59-3.54 (m, 2H), 1.81 (dt, J = 12.5, 6.2 Hz, 2H) |

| Ex No. | Structure | LC/MS [M + H]+/ RT (Method)/ NLRP3 hIL1B EC50 | 1H NMR (500 MHz, DMSO-d6, unless otherwise indicated) |
|---|---|---|---|
| 16 | racemate | 343.2/ 1.28 min (B)/ 0.78 μM | δ 7.87 (br s, 1H), 7.67 (br d, J = 6.1 Hz, 3H), 7.63 (s, 1H), 6.92 (s, 2H), 4.49-4.43 (m, 2H), 3.82 (br s, 1H), 1.96-1.89 (m, 1H), 1.80-1.73 (m, 1H), 1.69 (br d, J = 3.6 Hz, 4H), 1.52-1.43 (m, 1H), 1.38-1.28 (m, 1H) |
| 17 | racemate | 343.2/ 1.34 min (B)/ 0.95 μM | δ 7.80-7.74 (m, 1H), 7.44 (s, 1H), 7.24 (br d, J = 14.3 Hz, 1H), 6.85-6.83 (m, 1H), 6.64-6.50 (m, 1H), 6.27 (br s, 2H), 4.60-4.52 (m, 2H), 3.94 (br s, 1H), 1.87-1.79 (m, 2H), 1.76-1.70 (m, 2H), 1.54-1.45 (m, 4H) |
| 18 | 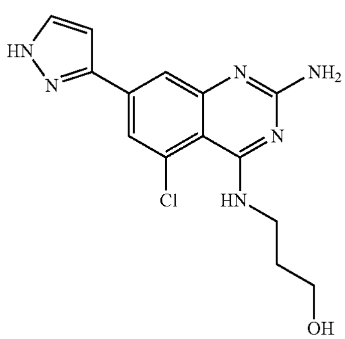 [SMILES: Nc1nc(NCCCO)c2c(Cl)cc(-c3cc[nH]n3)cc2n1] | 319.1/ 0.9 min (B)/ 0.65 μM | δ 13.28-13.19 (m, 1H), 8.57-8.47 (m, 1H), 7.87-7.82 (m, 1H), 7.74-7.68 (m, 2H), 7.31-7.19 (m, 1H), 6.89 (s, 2H), 4.91-4.73 (m, 1H), 3.67-3.63 (m, 4H), 1.81 (quin, J = 5.9 Hz, 2H) |
| 19 | 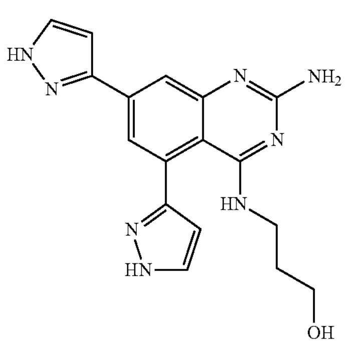 [SMILES: Nc1nc(NCCCO)c2c(-c3cc[nH]n3)cc(-c3cc[nH]n3)cc2n1] | 351.0/ 0.96 min (B)/ 9.86 μM | δ 13.45-13.38 (m, 1H), 13.17-13.09 (m, 1H), 8.06-7.98 (m, 1H), 7.86-7.79 (m, 2H), 7.75 (br s, 1H), 6.88 (s, 1H), 6.85 (br s, 1H), 6.60 (br s, 1H), 6.50-6.43 (m, 2H), 4.48 (br s, 1H), 3.63-3.50 (m, 4H), 1.59-1.54 (m, 2H) |

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 20 | (pyrazol-3-yl)-5-methoxy-quinazoline-2,4-diamine with N-(3-hydroxypropyl) | 303.1/ 1.09 min (B)/ 3.29 μM | δ 13.32-13.19 (m, 1H), 9.51-9.31 (m, 1H), 7.88 (br s, 1H), 8.08-7.67 (m, 1H), 7.42 (br s, 1H), 7.34 (s, 1H), 6.90 (br s, 1H), 5.00-4.93 (m, 1H), 4.06 (s, 3H), 3.70-3.65 (m, 2H), 3.60 (br d, J = 3.1 Hz, 2H), 1.84-1.77 (m, 2H) |
| 21 | (pyrazol-3-yl)-5-methyl-quinazoline-2,4-diamine with N-(3-hydroxypropyl) | 299.3/ 1.01 min (B)/ 0.65 μM | δ 7.79-7.68 (m, 1H), 7.50-7.44 (m, 1H), 7.34-7.30 (m, 1H), 6.94 (br s, 1H), 6.76 (br d, J = 1.9 Hz, 1H), 6.19-6.13 (m, 2H), 3.59-3.56 (m, J = 5.5 Hz, 4H), 2.76 (s, 3H), 1.83-1.78 (m, 2H) |
| 22 | (pyrazol-3-yl)-5-(dimethylamino)-quinazoline-2,4-diamine with N-(3-hydroxypropyl) | 328.1/ 1.08 min (B)/ 9.24 μM | δ 13.26-13.20 (m, 1H), 7.85 (br d, J = 1.4 Hz, 1H), 7.66 (s, 1H), 7.56 (br s, 1H), 6.89-6.87 (m, 1H), 4.90-4.79 (m, 1H), 3.67 (q, J = 6.2 Hz, 2H), 3.61-3.57 (m, 2H), 2.73 (s, 6H), 1.82 (quin, J = 6.3 Hz, 2H) |
| 23 | 7-(pyrazol-3-yl)-N4-((S)-tetrahydrofuran-3-yl)quinazoline-2,4-diamine | 297.3/ 0.93 min (B)/ 0.67 μM | δ 8.23-8.08 (m, 1H), 7.98-7.88 (m, 1H), 7.80-7.69 (m, 1H), 7.67-7.60 (m, 1H), 7.58-7.46 (m, 1H), 6.88-6.72 (m, 1H), 6.38-6.14 (m, 1H), 4.76-4.60 (m, 1H), 4.03-3.95 (m, 1H), 3.96-3.84 (m, 1H), 2.32-2.16 (m, 1H), 2.07-1.96 (m, 1H) |

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 24 | (2-amino-7-(1H-pyrazol-5-yl)-6-fluoroquinazolin-4-yl)-NH-(CH$_2$)$_3$-OH | 303.1/ 0.76 min (B)/ 1.68 μM | δ 8.07-7.89 (m, 2H), 7.88-7.66 (m, 2H), 6.67 (br d, J = 2.1 Hz, 1H), 6.28-6.08 (m, 1H), 3.69-3.64 (m, 2H), 3.56-3.48 (m, 2H), 1.85-1.72 (m, 2H). One methylene not visible, likely due to overlap with water/water suppression. |
| 25 | 2-amino-7-(1H-pyrazol-5-yl)-4-(trans-4-hydroxytetrahydrofuran-3-ylamino)quinazoline, racemate | 312.9/ 0.94 min (B)/ 0.72 μM | δ 9.26-9.14 (m, 1H), 8.47-8.33 (m, 1H), 7.95-7.78 (m, 3H), 6.95-6.82 (m, 1H), 4.60-4.48 (m, 1H), 4.47-4.39 (m, 1H), 4.16-4.08 (m, 1H), 4.05-3.97 (m, 1H), 3.82-3.74 (m, 1H) |
| 26 | 2-amino-7-(1H-pyrazol-5-yl)-4-(2,2-difluoro-2-(pyridin-2-yl)ethylamino)quinazoline | 368.1/ 1.07 min (B)/ 0.12 μM | δ 8.71 (d, J = 4.3 Hz, 1H), 8.06 (d, J = 8.5 Hz, 1H), 8.00-7.93 (m, 1H), 7.77-7.71 (m, 2H), 7.62 (d, J = 1.2 Hz, 1H), 7.56 (dd, J = 7.5, 5.0 Hz, 1H), 7.51 (br d, J = 8.2 Hz, 1H), 6.80 (d, J = 2.1 Hz, 1H), 6.12 (br s, 2H), 4.55-4.43 (m, 2H) |
| 27 | 2-amino-7-(1H-pyrazol-5-yl)-4-((1H-pyrazol-3-yl)methylamino)quinazoline | 307.1/ 1.17 min (A)/ 0.43 μM | δ 12.52 (br s, 1H), 9.86 (br t, J = 4.7 Hz, 1H), 8.33 (br d, J = 8.5 Hz, 1H), 8.11-7.73 (m, 4H), 7.64 (br s, 1H), 6.89 (s, 1H), 6.32 (s, 1H), 4.81 (br d, J = 5.0 Hz, 2H) |
| 28 | 2-amino-7-(1H-pyrazol-5-yl)-4-((thiazol-2-yl)methylamino)quinazoline | 323.9/ 0.98 min (B)/ 0.24 μM | δ 8.08 (br d, J = 8.5 Hz, 1H), 7.90-7.78 (m, 1H), 7.74 (br d, J = 3.4 Hz, 2H), 7.70-7.63 (m, 1H), 7.60 (d, J = 3.1 Hz, 1H), 6.83 (s, 1H), 6.77-6.61 (m, 1H), 5.02 (br d, J = 5.2 Hz, 2H) |

-continued

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 29 | 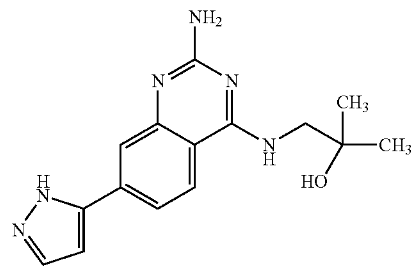 [SMILES: CC(C)(O)CNc1nc(N)nc2cc(-c3ccn[nH]3)ccc12] | 299.2/ 1.18 min (A)/ 0.39 μM | δ 12.47 (s, 1H), 9.19 (br t, J = 6.0 Hz, 1H), 8.46 (d, J = 8.9 Hz, 1H), 8.34-7.51 (m, 3H), 6.89 (d, J = 2.3 Hz, 1H), 3.63 (d, J = 6.0 Hz, 2H), 1.18 (s, 6H) |
| 30 | 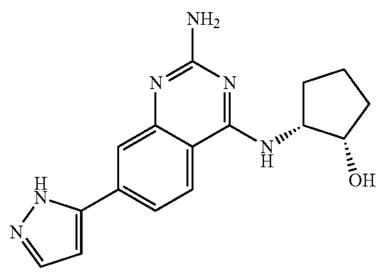 [SMILES: Nc1nc(N[C@@H]2CCC[C@@H]2O)c2ccc(-c3ccn[nH]3)cc2n1] | 311.1/ 1.36 min (A)/ 0.30 μM | δ 13.21 (s, 1H), 12.19 (br s, 1H), 8.77 (br d, J = 3.6 Hz, 1H), 8.46 (d, J = 8.4 Hz, 1H), 7.95-7.80 (m, 4H), 6.89 (s, 1H), 4.84 (d, J = 3.9 Hz, 1H), 4.44-4.34 (m, 1H), 4.30-4.24 (m, 1H), 2.04-1.90 (m, 2H), 1.87-1.77 (m, 2H), 1.73-1.63 (m, 1H), 1.60-1.47 (m, 1H) |
| 31 | 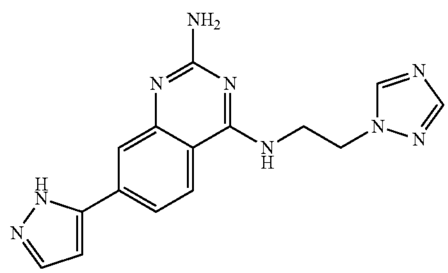 [SMILES: Nc1nc(NCCn2cncn2)c2ccc(-c3ccn[nH]3)cc2n1] | 322.2/ 0.85 min (B)/ 0.80 μM | δ 9.37 (br t, J = 5.2 Hz, 1H), 8.50 (s, 1H), 8.12 (br d, J = 8.8 Hz, 2H), 7.97 (s, 1H), 7.87-7.79 (m, 3H), 6.88 (d, J = 2.1 Hz, 1H), 4.53 (br t, J = 5.6 Hz, 2H), 3.95 (q, J = 5.6 Hz, 2H) |
| 32 | 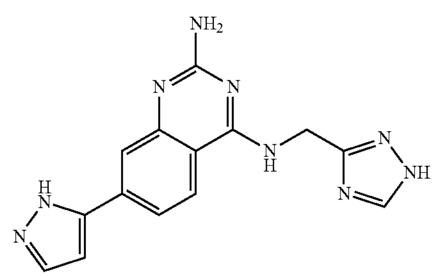 [SMILES: Nc1nc(NCc2nc[nH]n2)c2ccc(-c3ccn[nH]3)cc2n1] | 308.0/ 0.85 min (B)/ 0.64 μM | δ 10.03-9.81 (m, 1H), 8.44-8.23 (m, 2H), 7.88 (br t, J = 6.9 Hz, 3H), 6.91 (d, J = 2.1 Hz, 1H), 4.91 (d, J = 5.5 Hz, 2H) |
| 33 | racemate | 337.2/ 1.08 min (B)/ 5.39 μM | δ 8.13 (br d, J = 8.2 Hz, 1H), 7.81 (br d, J = 9.5 Hz, 1H), 7.73 (br d, J = 3.4 Hz, 1H), 7.61 (s, 1H), 7.51 (br s, 2H), 6.80 (d, J = 1.5 Hz, 1H), 6.24 (s, 1H), 6.07 (br s, 2H), 5.67-5.58 (m, 1H), 3.85 (br d, J = 5.5 Hz, 2H), 3.55-3.46 (m, 1H) |

-continued

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 34 | (racemate) | 337.1/ 0.68 min (B)/ 7.67 μM | δ 8.15 (br d, J = 8.5 Hz, 1H), 7.75 (br s, 1H), 7.65 (s, 1H), 7.57 (br d, J = 7.6 Hz, 1H), 6.93 (br s, 2H), 6.82 (d, J = 1.8 Hz, 1H), 6.43-6.34 (m, 1H), 5.55 (br d, J = 4.6 Hz, 1H), 4.03-3.95 (m, 1H), 3.93-3.86 (m, 1H), 3.47-3.39 (m, 1H) |
| 35 | (racemate) | 354.1/ 0.87 min (B)/ 5.53 μM | δ 8.23 (br d, J = 8.5 Hz, 1H), 7.76 (br d, J = 3.1 Hz, 2H), 7.68 (s, 1H), 7.65-7.53 (m, 2H), 6.83 (s, 1H), 6.45-6.29 (m, 1H), 5.90-5.79 (m, 1H), 4.13-4.04 (m, 1H), 4.03-3.93 (m, 1H), 3.46-3.30 (m, 1H) |
| 36 | 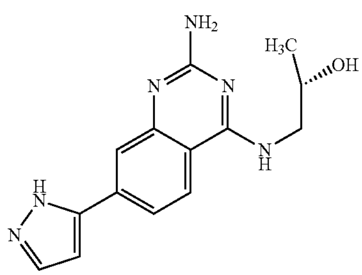 [SMILES: C[C@H](O)CNc1nc(N)nc2cc(-c3ccn[nH]3)ccc12] | 285.2/ 1.08 min (A)/ 0.71 μM | δ 12.47 (s, 1H), 9.40 (br t, J = 5.5 Hz, 1H), 8.40 (d, J = 9.0 Hz, 1H), 8.35-7.45 (m, 4H), 6.90 (d, J = 2.3 Hz, 1H), 4.10-3.94 (m, 1H), 3.65-3.52 (m, 2H), 3.52-3.40 (m, 1H), 1.14 (d, J = 6.2 Hz, 3H) |
| 37 | 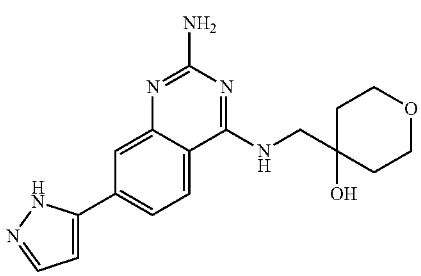 [SMILES: Nc1nc(NCC2(O)CCOCC2)c2ccc(-c3ccn[nH]3)cc2n1] | 341.2/ 1.11 min (A)/ 0.87 μM | δ 13.23 (br s, 1H), 12.33 (br s, 1H), 9.20 (br s, 1H), 8.43 (br d, J = 8.0 Hz, 1H), 8.03-7.76 (m, 4H), 6.89 (br s, 1H), 4.84 (br s, 1H), 3.75-3.57 (m, 6H), 1.70-1.58 (m, 2H), 1.48 (br d, J = 13.4 Hz, 2H) |
| 38 | 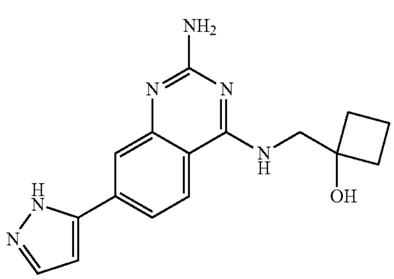 [SMILES: Nc1nc(NCC2(O)CCC2)c2ccc(-c3ccn[nH]3)cc2n1] | 311.1/ 1.29 min (A)/ 0.32 μM | δ 13.22 (br s, 1H), 12.26 (br s, 1H), 9.28-9.12 (m, 1H), 8.41 (br d, J = 7.9 Hz, 1H), 8.09-7.68 (m, 4H), 6.89 (br s, 1H), 5.36 (s, 1H), 3.80 (br d, J = 5.1 Hz, 2H), 2.10 (br s, 2H), 2.04-1.92 (m, 2H), 1.73-1.54 (m, 2H) |

-continued

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 39 | (structure: 2-amino-7-(1H-pyrazol-3-yl)quinazolin-4-yl with NH-CH$_2$-(1H-imidazol-2-yl)) | 307.1/ 0.72 min (A)/ 1.32 μM | δ 13.44-13.13 (m, 1H), 12.97-12.71 (m, 1H), 10.25 (br s, 1H), 8.55-8.23 (m, 2H), 8.07-7.80 (m, 4H), 7.63 (br s, 2H), 6.92 (br s, 1H), 5.03 (br s, 2H) |
| 40 | (structure: 2-amino-7-(1H-pyrazol-3-yl)quinazolin-4-yl with NH-CH$_2$-CH(OH)-CH$_2$-N(CH$_3$)$_2$) racemate | 328.2/ 0.75 min (A)/ 2.24 μM | δ 12.53 (br s, 1H), 9.69-9.51 (m, 2H), 8.40 (br d, J = 8.3 Hz, 1H), 8.22-7.80 (m, 4H), 6.90 (br s, 1H), 6.15-5.88 (m, 1H), 4.37-4.25 (m, 1H), 3.68-3.60 (m, 2H), 3.27-3.11 (m, 2H), 2.81 (br dd, J = 19.2, 4.2 Hz, 6H) |
| 41 | (structure: 2-amino-7-(1H-pyrazol-3-yl)quinazolin-4-yl with NH-CH$_2$-CH(OH)-CH$_2$-CF$_3$) racemate | 353.1/ 1.26 min (A)/ 0.76 μM | δ 12.33 (s, 1H), 9.38 (br t, J = 5.2 Hz, 1H), 8.33 (br d, J = 8.9 Hz, 1H), 7.87 (br d, J = 3.6 Hz, 4H), 6.89 (d, J = 2.2 Hz, 1H), 4.25-4.15 (m, 1H), 2.59-2.52 (m, 2H), 2.43-2.33 (m, 2H) |
| 42 | (structure: 2-amino-7-(1H-pyrazol-3-yl)quinazolin-4-yl with NH-CH$_2$-C*H(OH)-CF$_3$) | 299.2/ 1.25 min (A)/ 0.59 μM | δ 12.38 (s, 1H), 9.35 (br t, J = 4.6 Hz, 1H), 8.38 (br d, J = 9.0 Hz, 1H), 8.13-7.77 (m, 4H), 6.90 (d, J = 1.8 Hz, 1H), 3.77 (br dd, J = 7.3, 3.4 Hz, 1H), 3.67-3.61 (m, 1H), 3.51-3.42 (m, 1H), 1.58-1.45 (m, 1H), 1.38 (dquin, J = 14.2, 7.2 Hz, 1H), 0.95 (br t, J = 7.4 Hz, 3H) |
| 43 | (structure: 2-amino-7-(1H-pyrazol-3-yl)quinazolin-4-yl with NH-CH$_2$-(5-oxopyrrolidin-2-yl)) racemate | 324.3/ 1.13 min (A)/ 1.04 μM | δ 12.41 (br s, 1H), 9.41 (br t, J = 5.1 Hz, 1H), 8.31 (br d, J = 9.0 Hz, 1H), 8.14-7.80 (m, 5H), 6.90 (d, J = 2.2 Hz, 1H), 3.58-3.49 (m, 1H), 2.29-2.11 (m, 3H), 1.84-1.72 (m, 1H) |

-continued

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 44 | 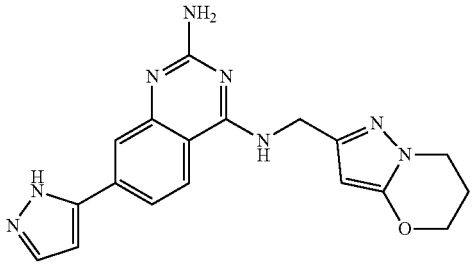 [SMILES: Nc1nc(NCc2cc3n(n2)CCCO3)c2ccc(-c3ccn[nH]3)cc2n1] | 363.2/ 1.04 min (B)/ 2.15 μM | δ 8.21 (br t, J = 5.5 Hz, 1H), 8.02 (d, J = 8.2 Hz, 1H), 7.73 (br s, 1H), 7.61 (s, 1H), 7.48 (br d, J = 8.5 Hz, 1H), 6.79 (d, J = 2.1 Hz, 1H), 6.17 (br s, 1H), 5.47 (s, 1H), 4.52 (d, J = 5.5 Hz, 2H), 4.24-4.18 (m, 2H), 4.00 (t, J = 6.3 Hz, 2H), 2.16-2.09 (m, 2H) |
| 45 | 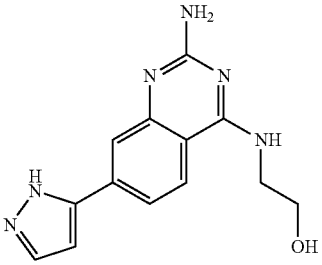 [SMILES: Nc1nc(NCCO)c2ccc(-c3ccn[nH]3)cc2n1] | 271.1/ 0.77 min (B)/ 0.45 μM | δ 8.29 (br d, J = 5.8 Hz, 1H), 8.09 (br d, J = 8.5 Hz, 1H), 7.77 (br s, 1H), 7.68 (br s, 1H), 7.60 (br s, 1H), 6.82 (br d, J = 1.8 Hz, 1H), 6.75-6.53 (m, 1H), 3.67-3.53 (m, 4H) |
| 46 | 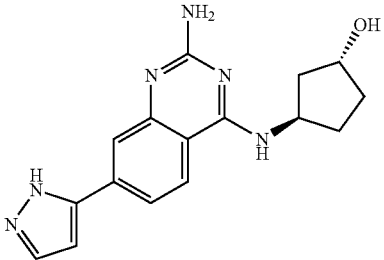 [SMILES: Nc1nc(N[C@@H]2CC[C@@H](O)C2)c2ccc(-c3ccn[nH]3)cc2n1] | 311.1/ 1.03 min (B)/ 0.21 μM | δ 8.17-8.13 (m, 1H), 7.83-7.74 (m, 1H), 7.72-7.65 (m, 1H), 7.65-7.56 (m, 1H), 6.82 (s, 1H), 4.85-4.77 (m, 1H), 4.28 (br s, 1H), 2.22-2.13 (m, 1H), 2.01-1.91 (m, 2H), 1.86-1.76 (m, 1H), 1.60-1.45 (m, 2H) |
| 47 | 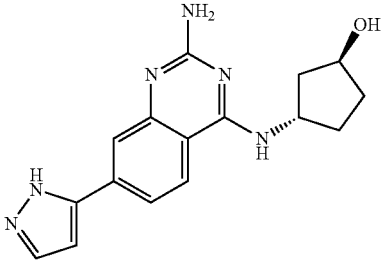 [SMILES: Nc1nc(N[C@H]2CC[C@H](O)C2)c2ccc(-c3ccn[nH]3)cc2n1] | 311.1/ 1.02 min (B)/ 0.55 μM; TLR7/TLR8 not tested. | δ 8.16 (br d, J = 8.5 Hz, 1H), 7.82-7.74 (m, 1H), 7.72-7.66 (m, 1H), 7.66-7.57 (m, 1H), 6.82 (br s, 1H), 4.87-4.77 (m, 1H), 4.28 (br s, 1H), 2.22 (s, 1H), 2.02-1.91 (m, 2H), 1.85-1.74 (m, 1H), 1.61-1.44 (m, 2H) |
| 48 | 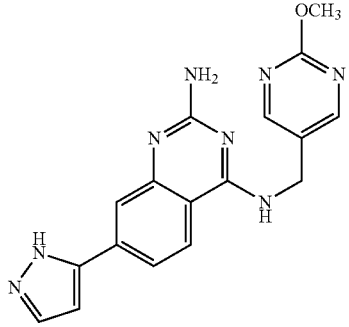 | 349.1/ 0.78 min (B)/ 2.92 μM | δ 8.73 (s, 2H), 8.10-8.05 (m, 1H), 7.88-7.67 (m, 3H), 6.84 (s, 1H), 4.62 (br d, J = 4.9 Hz, 2H), 3.89 (s, 3H) |

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 49 | (2-amino-7-(1H-pyrazol-5-yl)quinazolin-4-yl)-NH-CH$_2$-(pyrimidin-5-yl) | 319.1/ 1.16 min (B)/ 0.46 μM | δ 9.10 (s, 1H), 8.92 (s, 2H), 8.18 (br d, J = 8.2 Hz, 1H), 7.86 (br s, 3H), 6.88 (s, 1H), 4.77 (br d, J = 4.9 Hz, 2H) |
| 50 | (2-amino-7-(1H-pyrazol-5-yl)quinazolin-4-yl)-NH-CH$_2$-(pyrimidin-4-yl) | 319.1/ 0.73 min (B)/ 1.87 μM | δ 9.11 (s, 1H), 8.70 (d, J = 5.2 Hz, 1H), 8.55-8.45 (m, 1H), 8.10-8.02 (m, 1H), 7.64 (s, 1H), 7.44 (br d, J = 5.8 Hz, 1H), 6.81 (s, 1H), 6.08-5.96 (m, 2H), 4.78 (br d, J = 5.8 Hz, 2H) |
| 51 | (2-amino-7-(1H-pyrazol-5-yl)quinazolin-4-yl)-NH-CH$_2$-(pyrimidin-2-yl) | 319.3/ 0.92 min (B)/ 0.32 μM | δ 8.75 (d, J = 4.9 Hz, 2H), 8.14 (d, J = 8.5 Hz, 1H), 7.78 (br s, 1H), 7.70 (br s, 1H), 7.68-7.61 (m, 1H), 7.39 (t, J = 4.9 Hz, 1H), 6.84 (d, J = 1.8 Hz, 1H), 6.69-6.43 (m, 2H), 4.94 (br d, J = 5.6 Hz, 2H) |
| 52 | (2-amino-7-(1H-pyrazol-5-yl)quinazolin-4-yl)-NH-CH$_2$-(pyrazin-2-yl) | 319.2/ 0.93 min (B)/ 0.78 μM | δ 8.71 (s, 1H), 8.57 (s, 1H), 8.51 (d, J = 1.8 Hz, 1H), 8.05 (d, J = 8.5 Hz, 1H), 7.74 (br s, 1H), 7.64 (s, 1H), 7.56 (br d, J = 8.7 Hz, 1H), 6.81 (d, J = 2.1 Hz, 1H), 6.26 (br s, 2H), 4.82 (br d, J = 5.0 Hz, 2H) |
| 53 | (2-amino-7-(1H-pyrazol-5-yl)quinazolin-4-yl)-NH-(3-hydroxytetrahydro-2H-pyran-3-yl) | 327.1/ 1.06 min (B)/ 1.35 μM | δ 8.08 (d, J = 8.5 Hz, 1H), 7.75 (br s, 1H), 7.62 (s, 1H), 7.54 (br d, J = 7.3 Hz, 1H), 6.81 (d, J = 1.8 Hz, 1H), 6.22 (br s, 2H), 4.24-4.09 (m, 1H), 3.98-3.85 (m, 2H), 3.80 (td, J = 9.9, 4.9 Hz, 1H), 3.41-3.28 (m, 1H), 3.13-3.00 (m, 1H), 1.95 (br d, J = 12.8 Hz, 1H), 1.58-1.49 (m, 1H) |

-continued

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 54 | (structure: 2-amino-7-(1H-pyrazol-5-yl)quinazolin-4-yl linked via NH to a chiral CH(CH$_2$OH)CH$_2$-(1H-imidazol-4-yl) group) | 351.1/ 0.64 min (B)/ 4.01 μM | δ 8.09 (d, J = 8.4 Hz, 1H), 7.95 (s, 1H), 7.90-7.79 (m, 1H), 7.78-7.72 (m, 1H), 7.64 (s, 1H), 7.59-7.54 (m, 1H), 7.54-7.51 (m, 1H), 6.82 (s, 2H), 6.57-6.44 (m, 1H), 4.59-4.49 (m, 1H), 2.94-2.89 (m, 2H). Two protons are not visible, likely due to overlap with suppressed water peak. |
| 55 | (structure: 2-amino-7-(1H-pyrazol-5-yl)quinazolin-4-yl linked via NH to tetrahydro-2H-thiopyran 1,1-dioxide-4-yl) | 359.2/ 1.18 min (B)/ 19.7 μM | δ 8.07 (d, J = 8.5 Hz, 1H), 7.77-7.67 (m, 1H), 7.61 (s, 1H), 7.52 (br d, J = 8.5 Hz, 1H), 6.80 (d, J = 1.8 Hz, 1H), 6.13 (br s, 1H), 4.49-4.39 (m, 1H), 3.32-3.12 (m, 4H), 2.30-2.22 (m, 2H), 2.15 (q, J = 11.0 Hz, 2H) |
| 56 | (structure: 2-amino-7-(1H-pyrazol-5-yl)quinazolin-4-yl linked via NH to trans-2-(hydroxymethyl)cyclohexyl, racemate) | 339.2/ 1.13 min (B)/ μM | δ 8.98 (br d, J = 8.2 Hz, 1H), 8.30 (d, J = 8.5 Hz, 1H), 7.88-7.78 (m, 3H), 6.89 (d, J = 2.1 Hz, 1H), 4.24-4.12 (m, 1H), 3.44-3.37 (m, 1H), 3.35-3.27 (m, 1H), 1.96-1.87 (m, 2H), 1.81-1.67 (m, 3H), 1.50-1.38 (m, 1H), 1.30-1.10 (m, 3H) |
| 57 | (structure: 2-amino-7-(1H-pyrazol-5-yl)quinazolin-4-yl linked via NH to cis-2-(hydroxymethyl)cyclohexyl, racemate) | 339.2/ 1.08 min (B)/ 0.80 μM | δ 8.04 (d, J = 8.5 Hz, 1H), 7.77-7.71 (m, 1H), 7.61 (s, 1H), 7.52 (br d, J = 8.5 Hz, 1H), 7.39 (br d, J = 4.6 Hz, 1H), 6.80 (d, J = 1.8 Hz, 1H), 6.22 (br s, 1H), 4.48 (br d, J = 3.1 Hz, 1H), 3.56-3.47 (m, 1H), 3.41 (br dd, J = 10.8, 6.3 Hz, 1H), 2.01-1.93 (m, 1H), 1.83-1.58 (m, 4H), 1.56-1.28 (m, 4H) |
| 58 | (structure: 2-amino-7-(1H-pyrazol-5-yl)quinazolin-4-yl linked via NH to CH$_2$CH$_2$CN) | 280.1/ 0.99 min (B)/ 0.70 μM | δ 8.43-8.29 (m, 1H), 7.98 (br d, J = 8.4 Hz, 1H), 7.86-7.73 (m, 1H), 7.69-7.63 (m, 1H), 7.62-7.52 (m, 1H), 6.82 (d, J = 1.8 Hz, 1H), 6.45-6.26 (m, 1H), 3.73-3.66 (m, 2H), 2.93 (br t, J = 6.5 Hz, 2H) |

-continued

| Ex No. | Structure | LC/MS [M + H]+/ RT (Method)/ NLRP3 hIL1B EC50 | 1H NMR (500 MHz, DMSO-d6, unless otherwise indicated) |
|---|---|---|---|
| 59 | (structure: 2-amino-7-(1H-pyrazol-5-yl)quinazoline with 4-NH-CH2-CHF-C(OH)(CH3)2 side chain) | 331.2/ 1.00 min (B)/ 0.67 μM | δ 8.06-8.01 (m, 1H), 7.74 (br d, J = 0.9 Hz, 1H), 7.62 (d, J = 1.1 Hz, 1H), 7.52 (br d, J = 8.5 Hz, 1H), 6.81 (d, J = 2.1 Hz, 1H), 6.22 (br d, J = 4.2 Hz, 1H), 4.64-4.43 (m, 1H), 3.99-3.80 (m, 1H), 1.20 (br d, J = 9.0 Hz, 6H). One proton is not visible, likely due to overlap with suppressed water peak. |
| 60 | (structure: 2-amino-7-(1H-pyrazol-5-yl)quinazoline with 4-NH-CH2-pyridazinyl side chain) | 319.0/ 0.84 min (B)/ 3.49 μM | δ 9.27 (s, 1H), 9.13 (d, J = 5.2 Hz, 1H), 8.53-8.46 (m, 1H), 8.01 (br d, J = 8.2 Hz, 1H), 7.65-7.59 (m, 2H), 7.57-7.50 (m, 1H), 6.81 (d, J = 1.8 Hz, 1H), 6.09 (br d, J = 2.7 Hz, 2H), 4.72 (br d, J = 6.1 Hz, 2H) |
| 61 | (structure: 2-amino-7-(1H-pyrazol-5-yl)quinazoline with 4-NH-CH2-oxazolyl side chain) | 308.1/ 1.15 min (B)/ 0.22 μM | δ 8.14-7.99 (m, 2H), 7.80-7.70 (m, 1H), 7.66 (s, 1H), 7.59-7.50 (m, 1H), 7.15 (s, 1H), 6.82 (d, J = 1.9 Hz, 1H), 6.36-6.22 (m, 1H), 4.89-4.74 (m, 2H) |
| 62 | (structure: 2-amino-7-(1H-pyrazol-5-yl)quinazoline with 4-NH-CH(pyridin-3-yl)-CH2OH side chain) racemate | 348.1/ 0.74 min (B)/ 1.25 μM | δ 9.49 (br d, J = 7.5 Hz, 1H), 8.74 (s, 1H), 8.54 (br d, J = 4.4 Hz, 1H), 8.40 (br d, J = 8.3 Hz, 1H), 8.10-8.02 (m, 1H), 7.95-7.74 (m, 3H), 7.64-7.44 (m, 1H), 6.86 (d, J = 2.2 Hz, 1H), 5.58-5.39 (m, 1H), 3.94 (br dd, J = 11.1, 8.2 Hz, 1H), 3.86-3.77 (m, 1H) |
| 63 | (structure: 2-amino-7-(1H-pyrazol-5-yl)quinazoline with 4-NH-(hydroxymethyl)cyclopentyl side chain) | 325.2/ 1.10 min (B)/ 1.75 μM | δ 8.12-8.03 (m, 1H), 7.83-7.72 (m, 1H), 7.69-7.63 (m, 1H), 7.61-7.52 (m, 1H), 6.81 (s, 1H), 4.65-4.50 (m, 1H), 2.20-2.04 (m, 2H), 1.98-1.92 (m, 1H), 1.73-1.57 (m, 2H), 1.57-1.45 (m, 1H), 1.37-1.26 (m, 1H). Two protons are not visible in NMR, likely due to overlap with suppressed water peak. |

-continued

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 64 | 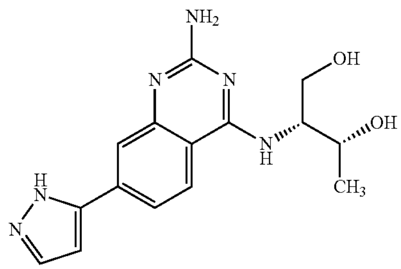 [SMILES: C[C@@H](O)[C@@H](CO)Nc1nc(N)nc2cc(-c3ccn[nH]3)ccc12] | 315.3/ 0.85 min (B)/ 3.73 μM | δ 8.72 (br d, J = 8.3 Hz, 1H), 8.49-8.40 (m, 1H), 7.85 (br d, J = 8.1 Hz, 3H), 6.89 (d, J = 2.3 Hz, 1H), 4.50-4.34 (m, 1H), 4.04-3.93 (m, 1H), 3.71 (br dd, J = 11.1, 4.8 Hz, 1H), 3.67-3.60 (m, 1H), 1.11 (d, J = 6.3 Hz, 3H) |
| 65 | 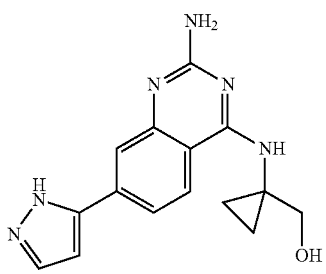 [SMILES: Nc1nc(NC2(CO)CC2)c2ccc(-c3ccn[nH]3)cc2n1] | 297.0/ 0.92 min (B)/ 0.25 μM | δ 8.14 (s, 1H), 8.02 (d, J = 8.5 Hz, 1H), 7.77-7.67 (m, 1H), 7.60 (s, 1H), 7.49 (br d, J = 7.6 Hz, 1H), 6.79 (d, J = 1.8 Hz, 1H), 6.10 (br s, 1H), 3.75-3.67 (m, 2H), 0.88-0.75 (m, 4H) |
| 66 | 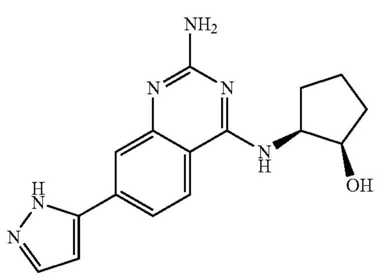 [SMILES: Nc1nc(N[C@H]2CCC[C@H]2O)c2ccc(-c3ccn[nH]3)cc2n1] | 311.1/ 1.25 min (B)/ 0.74 μM | δ 8.11 (d, J = 8.9 Hz, 1H), 7.74 (br s, 1H), 7.64 (s, 1H), 7.60-7.49 (m, 2H), 6.81 (d, J = 1.8 Hz, 1H), 6.51-6.38 (m, 1H), 4.37-4.26 (m, 1H), 4.19 (br s, 1H), 1.97-1.89 (m, 1H), 1.84-1.73 (m, 3H), 1.68-1.58 (m, 1H), 1.55-1.45 (m, 1H) |
| 67 | 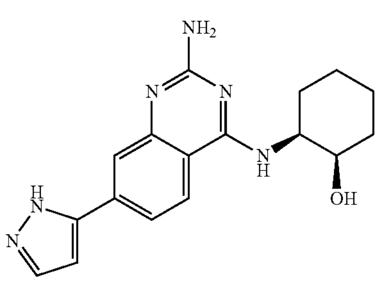 [SMILES: Nc1nc(N[C@H]2CCCC[C@H]2O)c2ccc(-c3ccn[nH]3)cc2n1] | 325.1/ 1.37 min (B)/ 2.26 μM | δ 8.14 (br d, J = 8.8 Hz, 1H), 7.76 (br s, 1H), 7.64 (s, 1H), 7.59-7.50 (m, 1H), 7.42-7.30 (m, 1H), 6.81 (d, J = 1.5 Hz, 1H), 6.54-6.31 (m, 1H), 4.25-4.13 (m, 1H), 3.99 (br s, 1H), 1.86-1.75 (m, 2H), 1.73-1.66 (m, 1H), 1.60 (br d, J = 12.2 Hz, 2H), 1.52-1.43 (m, 1H), 1.40-1.28 (m, 2H) |
| 68 | 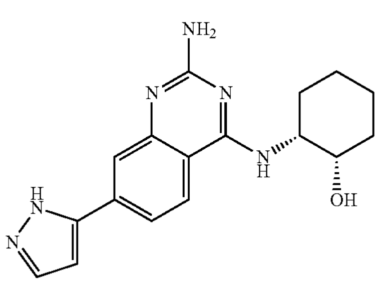 [SMILES: Nc1nc(N[C@@H]2CCCC[C@@H]2O)c2ccc(-c3ccn[nH]3)cc2n1] | 325.2/ 0.98 min (B)/ 1.10 μM | δ 8.13 (d, J = 8.5 Hz, 1H), 7.75 (br s, 1H), 7.64 (s, 1H), 7.58 (br d, J = 8.5 Hz, 1H), 7.50-7.42 (m, 1H), 6.82 (d, J = 1.5 Hz, 1H), 6.56 (br s, 1H), 4.24-4.11 (m, 1H), 3.98 (br s, 1H), 1.85-1.73 (m, 2H), 1.72-1.64 (m, 1H), 1.61-1.42 (m, 3H), 1.39-1.24 (m, 2H) |

-continued

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 69 | (structure) | 301.0/ 0.92 min (B)/ 1.86 μM | δ 9.13 (br d, J = 1.8 Hz, 1H), 8.21 (d, J = 8.5 Hz, 1H), 7.87-7.76 (m, 3H), 6.87 (s, 1H), 3.85-3.74 (m, 2H), 3.57-3.48 (m, 1H), 3.45-3.36 (m, 2H) |
| 70 | (structure) | 301.2/ 0.83 min (B)/ 0.80 μM | δ 8.07-7.98 (m, 2H), 7.75 (br d, J = 1.1 Hz, 1H), 7.63 (s, 1H), 7.58-7.49 (m, 1H), 6.81 (d, J = 2.1 Hz, 1H), 6.42 -6.25 (m, 2H), 3.83-3.75 (m, 1H), 3.72-3.63 (m, 2H), 3.49-3.35 (m, 2H) |
| 71 | (structure) | 308.2/ 0.98 min (B)/ 0.64 μM | δ 9.88 (br s, 1H), 8.91-8.84 (m, 1H), 8.27-8.20 (m, 1H),7.88 (br s, 3H), 6.90 (s, 1H), 6.73-6.65 (m, 1H), 4.88 (br d, J = 5.5 Hz, 2H) |
| 72 | (structure) racemate | 315.1/ 0.94 min (B)/ 0.53 μM | δ 9.27 (br s, 1H), 8.36-8.25 (m, 1H), 7.92-7.79 (m, 3H), 6.89 (s, 1H), 4.01 (br s, 1H), 3.67 (dt, J = 13.3, 4.8 Hz, 1H), 3.59-3.48 (m, 1H), 3.44-3.24 (m, 5H) (peaks distorted due to overlap with suppressed water peak). |
| 73 | (structure) | 313.2/ 0.90 min (B)/ 0.23 μM | δ 8.03 (d, J = 8.5 Hz, 1H), 7.88 (br s, 1H), 7.75 (br s, 1H), 7.62 (s, 1H), 7.53 (br d, J = 8.5 Hz, 1H), 6.80 (s, 1H), 6.27 (br s, 2H), 3.12 (s, 2H), 0.89 (s, 6H). Two protons are not visible, likely due to overlap with suppressed water peak. |

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 74 | 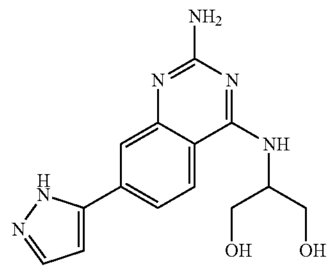 [SMILES: Nc1nc(NC(CO)CO)c2ccc(-c3ccn[nH]3)cc2n1] | 301.2/ 0.56 min (B)/ 0.78 μM | δ 8.23 (br d, J = 8.2 Hz, 1H), 7.84-7.77 (m, 1H), 7.76-7.71 (m, 1H), 7.71-7.63 (m, 1H), 6.84 (s, 1H), 4.47-4.34 (m, 1H), 3.70-3.56 (m, 2H). Two protons are not visible, likely due to overlap with suppressed water peak. |
| 75 | 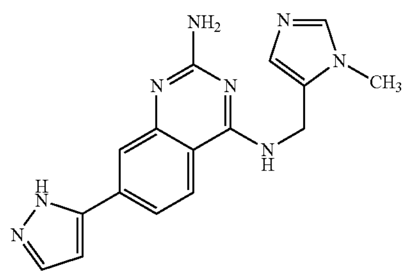 [SMILES: Cn1cncc1CNc1nc(N)nc2cc(-c3ccn[nH]3)ccc12] | 321.2/ 0.91 min (B)/ 5.52 μM | δ 8.28-8.18 (m, 1H), 8.03 (br d, J = 8.4 Hz, 1H), 7.73 (br s, 1H), 7.61 (d, J = 1.2 Hz 1H), 7.54 (s, 1H), 7.52-7.45 (m, 1H), 6.94 (s, 1H), 6.80 (d, J = 2.1 Hz, 1H), 6.26 (br s, 1H), 4.65 (br d, J = 4.5 Hz, 2H), 3.65 (s, 3H) |
| 76 | 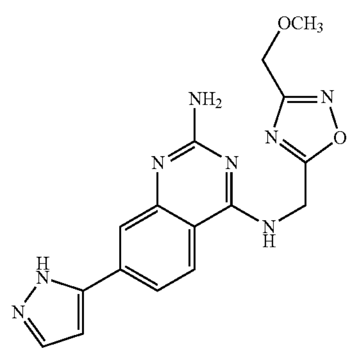 [SMILES: COCc1noc(CNc2nc(N)nc3cc(-c4ccn[nH]4)ccc23)n1] | 353.3/ 0.99 min (B)/ 0.76 μM | δ 8.23 (br d, J = 8.9 Hz, 1H), 7.93-7.79 (m, 3H), 6.91-6.87 (m, 1H), 5.08 (br s, 2H), 4.51 (s, 2H), 3.30 (s, 3H) |
| 77 | racemate | 339.3/ 1.16 min (B)/ 0.65 μM | δ 9.20 (br s, 1H), 8.25 (br d, J = 8.5 Hz, 1H), 7.91-7.77 (m, 3H), 6.88 (d, J = 1.2 Hz, 1H), 3.82 (br s, 1H), 3.61-3.32 (m, 2H) (overlaps suppressed water peak), 1.85 (br d, J = 6.4 Hz, 1H), 1.72-1.53 (m, 3H), 1.45-1.31 (m, 4H), 1.25-1.13 (m, 1H) |
| 78 | 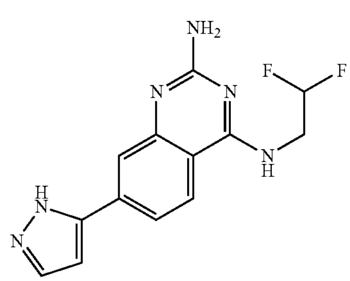 [SMILES: Nc1nc(NCC(F)F)c2ccc(-c3ccn[nH]3)cc2n1] | 291.2/ 1.02 min (B)/ 0.63 μM | δ 8.03-7.95 (m, 1H), 7.77-7.69 (m, 1H), 7.64-7.58 (m, 1H), 7.56-7.45 (m, 1H), 6.83-6.77 (m, 1H), 6.41-6.14 (m, 3H), 3.93-3.79 (m, 2H) |

-continued

| Ex No. | Structure | LC/MS [M + H]+/ RT (Method)/ NLRP3 hIL1B EC50 | 1H NMR (500 MHz, DMSO-d6, unless otherwise indicated) |
|---|---|---|---|
| 79 | 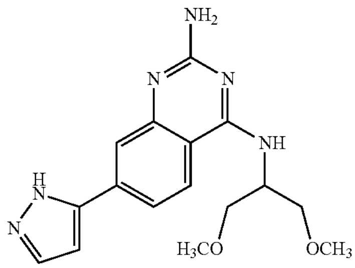 [SMILES: COCC(COC)Nc1nc(N)nc2cc(-c3ccn[nH]3)ccc12] | 329.2/ 0.89 min (B)/ 1.20 μM TLR7 Agonist EC50 value >20 μM ≤100 μM | δ 8.25 (br d, J = 8.2 Hz, 1H), 7.87-7.67 (m, 3H), 6.85 (br d, J = 1.5 Hz, 1H), 4.79 (br d, J = 6.1 Hz, 1H), 3.61-3.50 (m, 1H), 3.28 (s, 4H). 5 protons from sidechain are not visible, likely due to overlap with suppressed water peak. |
| 80 | 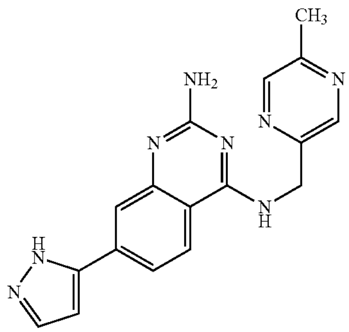 [SMILES: Cc1cnc(CNc2nc(N)nc3cc(-c4ccn[nH]4)ccc23)cn1] | 333.2/ 1.04 min (B)/ 0.71 μM | δ 9.98 (br t, J = 5.5 Hz, 1H), 8.68 (d, J + 1.6 Hz, 1H), 8.51 (s, 1H), 8.29 (br d, J = 7.7 Hz, 1H), 7.89 (br s, 3H), 6.90 (d, J = 2.0 Hz, 1H), 4.88 (br d, J = 5.5 Hz, 2H), 2.49 (s, 3H) |
| 81 | 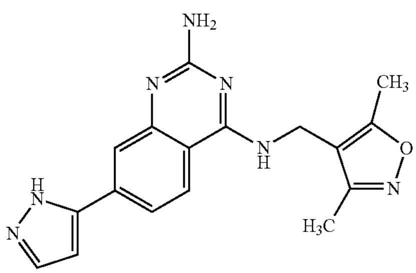 [SMILES: Cc1noc(C)c1CNc1nc(N)nc2cc(-c3ccn[nH]3)ccc12] | 336.3/ 1.10 min (B)/ 1.20 μM | δ 8.16 (br s, 1H), 8.01 (d, J = 8.2 Hz, 1H), 7.73 (br s, 1H), 7.61 (s, 1H), 7.50 (br d, J = 8.2 Hz, 1H), 6.79 (d, J = 1.2 Hz, 1H), 6.14 (br s, 2H), 4.42 (br d, J = 4.9 Hz, 2H), 2.43 (s, 3H), 2.23 (s, 3H) |
| 82 | racemate | 375.2/ 1.11 min (B)/ 3.65 μM | δ 9.65 (br d, J = 7.6 Hz, 1H), 8.77 (br s, 1H), 8.51 (br s, 1H), 8.33 (d, J = 8.5 Hz, 1H), 8.01 (br d, J = 7.3 Hz, 1H), 7.89-7.86 (m, 1H), 7.86-7.81 (m, 2H), 7.53 (br s, 1H), 7.48 (br dd, J = 6.7, 5.8 Hz, 1H), 6.95 (br s, 1H), 6.88 (s, 1H), 5.87 (q, J = 7.4 Hz, 1H), 3.00-2.88 (m, 2H) |
| 83 | 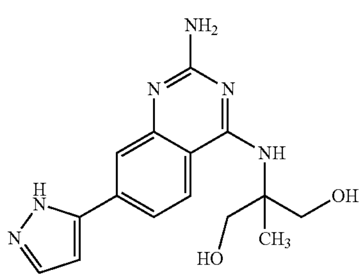 [SMILES: CC(CO)(CO)Nc1nc(N)nc2cc(-c3ccn[nH]3)ccc12] | 314.9/ 0.90 min (B)/ 2.41 μM | δ 8.32 (br d, J = 8.5 Hz, 1H), 7.86-7.76 (m, 3H), 7.72 (s, 1H), 6.88 (d, J = 1.8 Hz, 1H), 3.84-3.74 (m, 4H), 1.42 (s, 3H) |

| Ex No. | Structure | LC/MS [M + H]+/ RT (Method)/ NLRP3 hIL1B EC50 | 1H NMR (500 MHz, DMSO-d6, unless otherwise indicated) |
|---|---|---|---|
| 84 | 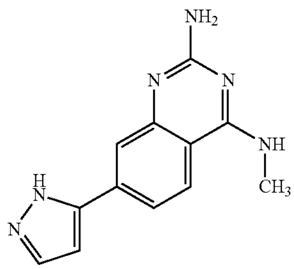 [SMILES: CNc1nc(N)nc2cc(-c3ccn[nH]3)ccc12] | 240.1/ 0.97 min (B)/ 0.28 µM | δ 9.39 (br d, J = 4.0 Hz, 1H), 8.18 (br d, J = 8.4 Hz, 1H), 7.91-7.80 (m, 3H), 6.88 (d, J = 2.2 Hz, 1H), 3.06 (d, J = 4.5 Hz, 3H) |
| 85 | 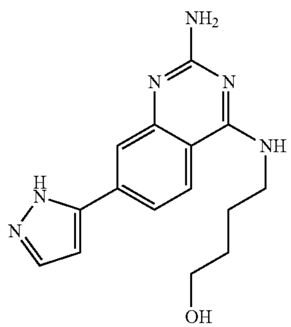 [SMILES: Nc1nc(NCCCCO)c2ccc(-c3ccn[nH]3)cc2n1] | 299.2/ 0.94 min (B)/ 0.23 µM | δ 8.02 (br d, J = 8.2 Hz, 1H), 7.94 (br s, 1H), 7.74 (br s, 1H), 7.62 (s, 1H), 7.55-7.46 (m, 1H), 6.80 (s, 1H), 6.26 (br s, 2H), 1.72-1.60 (m, 2H), 1.54-1.45 (m, 2H). Four protons are not visible, likely due to overlap with suppressed water peak. |
| 86 | 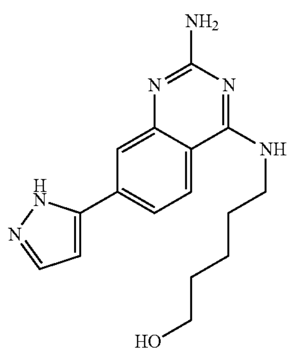 [SMILES: Nc1nc(NCCCCCO)c2ccc(-c3ccn[nH]3)cc2n1] | 313.3/ 1.03 min (B)/ 0.22 µM | δ 8.17-8.07 (m, 1H), 8.04 (d, J = 8.6 Hz, 1H), 7.75 (br s, 1H), 7.64 (s, 1H), 7.55 (br d, J = 8.3 Hz, 1H), 6.85-6.77 (m, 1H), 6.54-6.40 (m, 1H), 3.40 (t, J = 6.5 Hz, 1H), 1.66-1.58 (m, 2H), 1.53-1.43 (m, 2H), 1.40-1.29 (m, 2H). Three protons are not visible, likely due to overlap with suppressed water peak. |
| 87 | 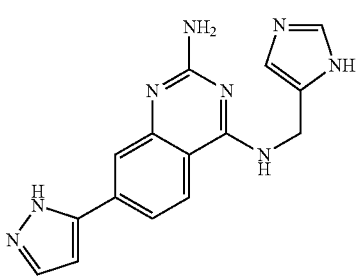 [SMILES: Nc1nc(NCc2cnc[nH]2)c2ccc(-c3ccn[nH]3)cc2n1] | 306.9/ 0.81 min (B)/ 1.63 µM | δ 8.69 (br s, 1H), 8.23-8.17 (m, 1H), 7.86 (br d, J = 7.3 Hz, 3H), 7.71-7.64 (m, 1H), 7.55 (br s, 1H), 6.89 (d, J = 2.0 Hz, 1H), 4.78 (br d, J = 4.8 Hz, 2H) |
| 88 | 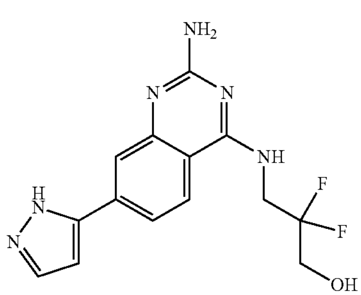 [SMILES: Nc1nc(NCC(F)(F)CO)c2ccc(-c3ccn[nH]3)cc2n1] | 321.0/ 0.76 (B)/ 0.22 µM | δ 8.27-8.18 (m, 1H), 7.85-7.64 (m, 3H), 6.86 (br d, J = 1.8 Hz, 1H), 4.16-4.03 (m, 2H), 3.78-3.61 (m, 2H) |

-continued

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 89 | 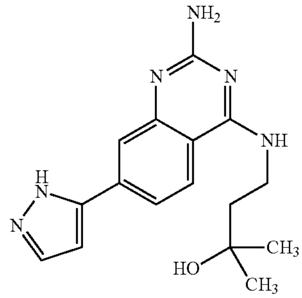 [SMILES: CC(C)(O)CCNc1nc(N)nc2cc(-c3ccn[nH]3)ccc12] | 313.2/ 0.80 min (B)/ 0.46 μM | δ 8.90-8.62 (m, 1H), 8.07 (br d, J = 8.2 Hz, 1H), 7.84-7.65 (m, 3H), 7.31-7.05 (m, 1H), 6.84 (d, J = 1.8 Hz, 1H), 3.90-3.53 (m, 2H), 1.79-1.67 (m, 2H), 1.16 (s, 6H) |
| 90 | 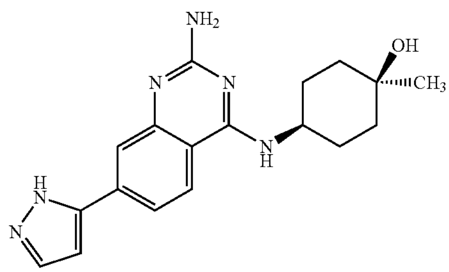 [SMILES: C[C@]1(O)CC[C@@H](Nc2nc(N)nc3cc(-c4ccn[nH]4)ccc23)CC1] | 338.9/ 1.03 min (B)/ 0.83 μM | δ 8.13 (d, J = 8.5 Hz, 1H), 7.74 (br s, 1H), 7.67 (br d, J = 6.1 Hz, 1H), 7.60 (s, 1H), 7.50 (br d, J = 8.5 Hz, 1H), 6.79 (d, J = 2.1 Hz, 1H), 6.22 (br s, 1H), 4.19-4.00 (m, 1H), 1.87-1.74 (m, 2H), 1.69-1.55 (m, 4H), 1.43-1.30 (m, 2H), 1.14 (s, 3H) |
| 91 | 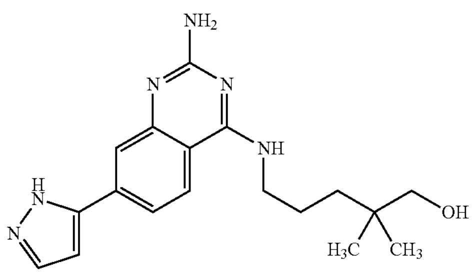 [SMILES: CC(C)(CO)CCCNc1nc(N)nc2cc(-c3ccn[nH]3)ccc12] | 341.2/ 1.00 min (B)/ 1.30 μM | δ 9.32-9.24 (m, 1H), 8.26 (br d, J = 8.6 Hz, 1H), 7.91-7.79 (m, 3H), 6.88 (s, 1H), 3.55 (q, J = 6.4 Hz, 1H), 3.10 (br d, J = 5.1 Hz, 2H), 1.65-1.57 (m, 2H), 1.31-1.19 (m, 2H), 0.80 (s, 6H). One proton is not visible, likely due to overlap with suppressed water peak. |
| 92 | 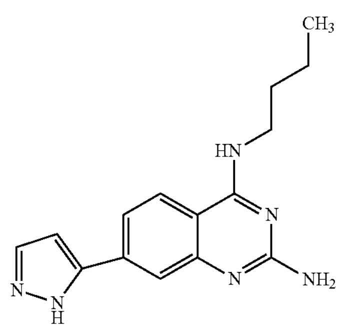 [SMILES: CCCCNc1nc(N)nc2cc(-c3ccn[nH]3)ccc12] | 283.1/ 0.63 min (C)/ 0.20 μM TLR7 Agonist EC$_{50}$value >1 μM ≤μM | $^1$H NMR (400 MHz, METHANOL-d$_4$) δ 8.12 (d, J = 8.6 Hz, 1H), 7.91-7.73 (m, 3H), 6.86 (d, J = 2.3 Hz, 1H), 3.71 (t, J = 7.3 Hz, 2H), 1.75 (t, J = 7.2 Hz, 2H), 1.57-1.39 (m, 2H), 1.02 (t, J = 7.4 Hz, 3H) |
| 93 | 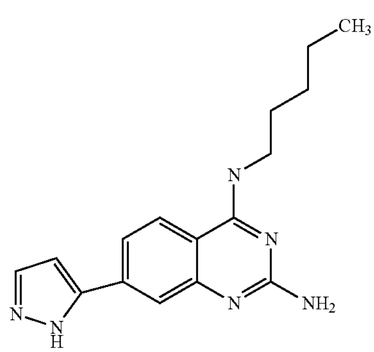 [SMILES: CCCCCNc1nc(N)nc2cc(-c3ccn[nH]3)ccc12] | 297.3/ 1.66 min (B)/ 0.27 μM; TLR7 Agonist EC$_{50}$ value >1 μM ≤20 μM | δ 8.03 (d, J = 8.5 Hz, 1H), 7.95 (br s, 1H), 7.75 (br s, 1H), 7.63 (s, 1H), 7.53 (br d, J = 8.2 Hz, 1H), 6.81 (d, J = 1.8 Hz, 1H), 6.29 (br s, 2H), 2.55 (s, 2H), 1.64 (br t, J = 6.7 Hz, 2H), 1.42-1.27 (m, 4H), 0.89 (br t, J = 6.4 Hz, 3H) |

-continued

| Ex No. | Structure | LC/MS [M + H]+/ RT (Method)/ NLRP3 hIL1B EC50 | 1H NMR (500 MHz, DMSO-d6, unless otherwise indicated) |
|---|---|---|---|
| 94 | (structure) | 299.2/ 0.85 min (B)/ 0.18 μM | δ 8.11-8.10 (m, 1H), 8.03 (br d, J = 8.5 Hz, 2H), 7.76 (br s, 1H), 7.64 (s, 1H), 7.54 (br d, J = 7.0 Hz, 1H), 6.81 (d, J = 1.8 Hz, 1H), 6.37 (br s, 2H), 3.53 (br d, J = 5.8 Hz, 2H), 3.26 (s, 2H), 1.97-1.82 (m, 5H) |
| 95 | (structure) | 299.2/ 1.40 min (B)/ 0.63 μM | δ 7.70 (br s, 1H), 7.64 (d, J = 8.2 Hz, 1H), 7.45-7.31 (m, 2H), 6.70 (d, J = 1.5 Hz, 1H), 4.02 (t, J = 6.6 Hz, 2H), 1.76-1.62 (m, 2H), 1.51-1.34 (m, 2H), 0.92 (t, J = 7.5 Hz, 3H) |
| 96 | (structure) racemic | 327.3/ 1.20 min (B)/ 0.69 μM; TLR7 Agonist EC50 value >1 μM ≤20 μM | δ 8.07 (d, J = 8.5 Hz, 1H), 7.74 (br s, 1H), 7.61 (s, 1H), 7.53 (br t, J = 8.5 Hz, 2H), 6.80 (d, J = 2.1 Hz, 1H), 6.15 (br s, 2H), 4.50-4.39 (m, 1H), 3.45 (br t, J = 6.4 Hz, 2H), 1.82-1.68 (m, 2H), 1.63-1.49 (m, 2H), 1.39-1.24 (m, 2H), 0.88 (t, J = 7.3 Hz, 3H) |
| 97 | (structure) homochiral | 327.2/ 1.03 min (B)/ 0.71 μM; TLR7 Agonist EC50 value >1 μM ≤20 μM | δ 8.07 (d, J = 8.5 Hz, 1H), 7.74 (br s, 1H), 7.61 (s, 1H), 7.53 (br t, J = 8.5 Hz, 2H), 6.80 (d, J = 2.1 Hz, 1H), 6.15 (br s, 2H), 4.50-4.39 (m, 1H), 3.45 (br t, J = 6.4 Hz, 2H), 1.82-1.68 (m, 2H), 1.63-1.49 (m, 2H), 1.39-1.24 (m, 2H), 0.88 (t, J = 7.3 Hz, 3H) |

-continued

| Ex No. | Structure | LC/MS [M + H]+/ RT (Method)/ NLRP3 hIL1B EC50 | 1H NMR (500 MHz, DMSO-d6, unless otherwise indicated) |
|---|---|---|---|
| 98 | 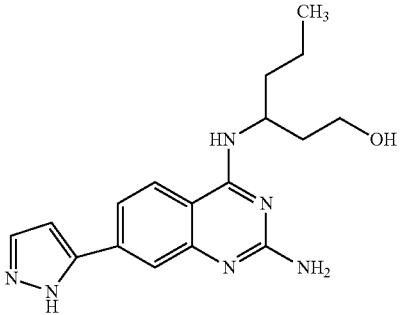 homochiral | 327.2/ 1.03 min (B)/ 0.86 μM | δ 8.07 (d, J = 8.5 Hz, 1H), 7.74 (br s, 1H), 7.61 (s, 1H), 7.53 (br t, J = 8.5 Hz, 2H), 6.80 (d, J = 2.1 Hz, 1H), 6.15 (br s, 2H), 4.50-4.39 (m, 1H), 3.45 (br t, J = 6.4 Hz, 2H), 1.82-1.68 (m, 2H), 1.63-1.49 (m, 2H), 1.39-1.24 (m, 2H), 0.88 (t, J = 7.3 Hz, 3H) |
| 99 | 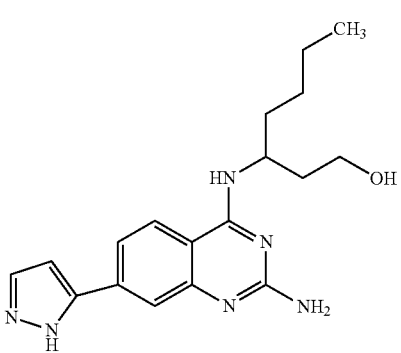 racemic | 341.3/ 1.29 min (B)/ 0.74 μM; TLR7 Agonist EC50 value >1 μM ≤20 μM | δ 8.09 (d, J = 8.5 Hz, 1H), 7.75 (br s, 1H), 7.62 (s, 1H), 7.59-7.47 (m, 2H), 6.80 (d, J = 1.5 Hz, 1H), 6.26 (br s, 2H), 4.51-4.36 (m, 1H), 3.55-3.35 (m, 2H), 1.82-1.66 (m, 2H), 1.61 (br s, 2H), 1.29 (br d, J = 5.5 Hz, 4H), 0.85 (br s, 3H) |
| 100 | 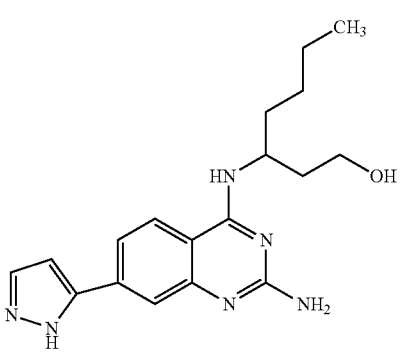 homochiral | 341.1/ 1.30 min (B)/ 0.45 μM; TLR7 Agonist EC50 value >1 μM ≤20 μM | δ 8.09 (d, J = 8.5 Hz, 1H), 7.75 (br s, 1H), 7.62 (s, 1H), 7.59-7.47 (m, 2H), 6.80 (d, J = 1.5 Hz, 1H), 6.26 (br s, 2H), 4.51-4.36 (m, 1H), 3.55-3.35 (m, 2H), 1.82-1.66 (m, 2H), 1.61 (br s, 2H), 1.29 (br d, J = 5.5 Hz, 4H), 0.85 (br s, 3H) |
| 101 | 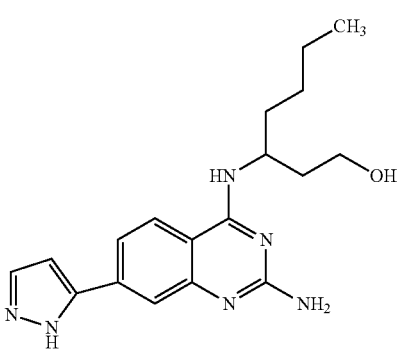 homochiral | 341.3/ 1.30 min (B)/ 0.83 μM | δ 8.09 (d, J = 8.5 Hz, 1H), 7.75 (br s, 1H), 7.62 (s, 1H), 7.59-7.47 (m, 2H), 6.80 (d, J = 1.5 Hz, 1H), 6.26 (br s, 2H), 4.51-4.36 (m, 1H), 3.55-3.35 (m, 2H), 1.82-1.66 (m, 2H), 1.61 (br s, 2H), 1.29 (br d, J = 5.5 Hz, 4H), 0.85 (br s, 3H) |

-continued

| Ex No. | Structure | LC/MS [M + H]+/ RT (Method)/ NLRP3 hIL1B EC50 | 1H NMR (500 MHz, DMSO-d6, unless otherwise indicated) |
|---|---|---|---|
| 102 | 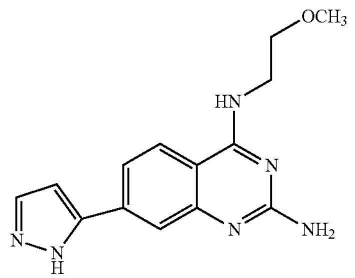 [SMILES: COCCNc1nc(N)nc2cc(-c3ccn[nH]3)ccc12] | 285.3/ 1.02 min (B)/ 0.21 μM | δ 8.25 (br d, J = 8.5 Hz, 1H), 7.85 (br d, J = 7.3 Hz, 3H), 6.89 (s, 1H), 3.84-3.70 (m, 2H), 3.55 (br s, 2H), 3.29 (s, 3H), |
| 103 | 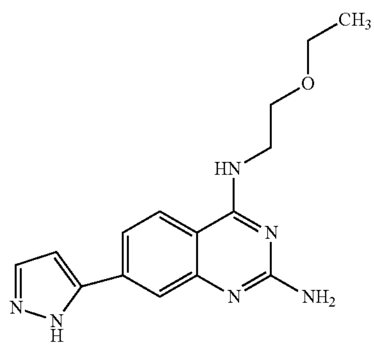 [SMILES: CCOCCNc1nc(N)nc2cc(-c3ccn[nH]3)ccc12] | 298.9/ 1.12 min (B)/ 0.37 μM | 1NMR (400 MHz, METHANOL-d4) δ 8.04 (d, J = 9.0 Hz, 1H), 7.75 (br s, 3H), 6.83 (d, J = 2.2 Hz, 1H), 3.90-3.81 (m, 2H), 3.77-3.69 (m, 2H), 3.60 (q, J = 7.0 Hz, 2H), , 1.21 (m, 3H) |
| 104 | 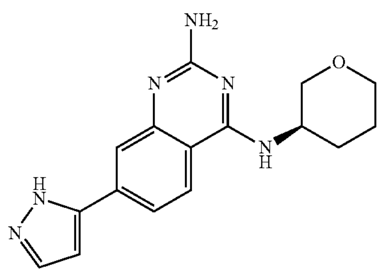 [SMILES: Nc1nc(N[C@@H]2CCCOC2)c2ccc(-c3ccn[nH]3)cc2n1] | 310.9/ 1.05 min (B)/ 0.39 μM | δ 8.28-8.09 (m, 1H), 7.96-7.84 (m, 1H), 7.80-7.60 (m, 2H), 6.87-6.78 (m, 1H), 4.41-4.20 (m, 1H), 3.40-3.27 (m, 1H), 3.27-3.17 (m, 1H), 2.94-2.83 (m, 1H), 2.78-2.67 (m, 1H), 2.12-1.93 (m, 1H), 1.80-1.64 (m, 1H), 1.63-1.34 (m, 2H) |
| 105 | 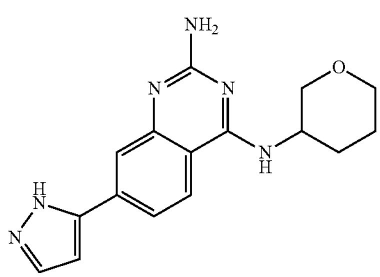 [SMILES: Nc1nc(NC2CCCOC2)c2ccc(-c3ccn[nH]3)cc2n1] | 311.3/ 0.95 min (B)/ 1.98 μM | δ 8.07 (d, J = 8.6 Hz, 1H), 7.67-7.59 (m, 1H), 6.81 (d, J = 2.0 Hz, 1H), 6.16 (br s, 2H), 3.94 (br dd, J = 11.4, 2.7 Hz, 2H), 3.23 (s, 1H), 1.93-1.85 (m, 4H), 1.66 (br d, J = 7.9 Hz, 2H) |
| 106 | 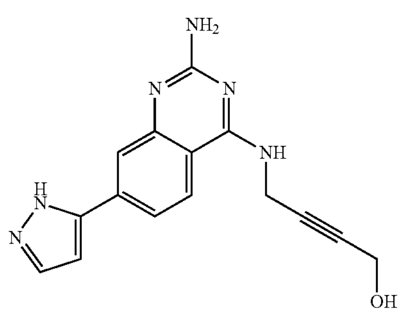 [SMILES: Nc1nc(NCC#CCO)c2ccc(-c3ccn[nH]3)cc2n1] | 295.2/ 0.65 min (B)/ 0.50 μM | δ 9.85-9.68 (m, 1H), 8.27-8.19 (m, 1H), 7.94-7.82 (m, 4H), 6.98-6.85 (m, 1H), 4.50-4.41 (m, 2H), 4.14 -4.07 (m, 2H). Three protons not visible , likely due to overlap with water/water suppression. |

-continued

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 107 | (racemate) | 325.2/ 1.01 min (B)/ 0.67 μM | δ 8.11-8.04 (m, 1H), 7.83-7.77 (m, 1H), 7.77-7.70 (m, 1H), 7.64-7.58 (m, 1H), 7.57-7.45 (m, 1H), 6.87-6.74 (m, 1H), 6.33-6.20 (m, 1H), 4.90-4.78 (m, 1H), 2.30-2.16 (m, 1H), 2.08-2.00 (m, 1H), 1.81-1.72 (m, 1H), 1.68-1.50 (m, 5H), 1.30 (s, 3H), −3.59−3.62 (m, 1H) |
| 108 | (racemate) | 325.2/ 1.05 min (B)/ 4.17 μM | δ 8.12-8.06 (m, 1H), 7.86-7.71 (m, 1H), 7.71-7.64 (m, 1H), 7.64-7.53 (m, 1H), 6.85-6.79 (m, 1H), 4.65-4.55 (m, 1H), 2.47-2.38 (m, 2H), 2.11-2.03 (m, 2H), 1.84-1.75 (m, 2H), 1.70-1.62 (m, 2H), 1.61-1.46 (m, 4H), 1.28 (s, 2H) |
| 109 | (racemate) | 327.3/ 0.84 min (B)/ 1.95 μM | δ 9.10-9.01 (m, 1H), 8.34-8.25 (m, 1H), 7.85-7.81 (m, 2H), 7.81-7.78 (m, 1H), 6.94-6.84 (m, 1H), 4.87-4.74 (m, 1H), 2.50-2.44 (m, 1H), 2.42-2.36 (m, 1H), 2.12-2.02 (m, 1H), 2.01-1.91 (m, 1H), 1.68-1.59 (m, 2H), 1.59-1.46 (m, 4H). Two protons not visible, likely due to overlap with water/water suppression. |
| 110 | (racemate) | 327.1/ 0.95 min (B)/ 0.64 μM | δ 8.11-8.01 (m, 1H), 7.82-7.70 (m, 1H), 7.62 (d, J = 1.5 Hz, 1H), 7.56-7.44 (m, 1H), 7.18-7.07 (m, 1H), 6.84-6.79 (m, 1H), 6.10-6.03 (m, 1H), 4.77-4.68 (m, 1H), 2.21-1.95 (m, 3H), 1.83-1.65 (m, 2H), 1.64-1.52 (m, 1H), 1.49-1.24 (m, 2H). Two protons not visible, likely due to overlap with water/water suppression. |

-continued

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 111 | 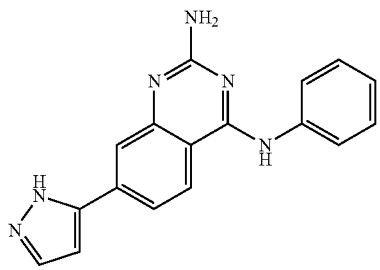 [SMILES: Nc1nc(Nc2ccccc2)c2ccc(-c3ccn[nH]3)cc2n1] | 303.1/ 1.59 min (A)/ 0.40 μM | δ 12.79 (br s, 1H), 10.71 (br s, 1H), 8.62 (br d, J = 8.7 Hz, 1H), 8.43-7.62 (m, 7H), 7.48 (br t, J = 7.6 Hz, 2H), 7.36-7.25 (m, 1H), 6.94 (s, 1H) |
| 112 | 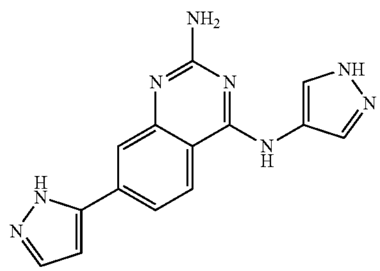 [SMILES: Nc1nc(Nc2cn[nH]c2)c2ccc(-c3ccn[nH]3)cc2n1] | 293.1/ 0.72 mm (B)/ 0.24 μM | δ 8.19 (br d, J = 9.2 Hz, 1H), 8.16-8.01 (m, 1H), 7.85-7.70 (m, 1H), 7.65 (s, 1H), 7.61-7.50 (m, 1H), 6.82 (s, 1H), 6.44-6.27 (m, 2H) |
| 113 | 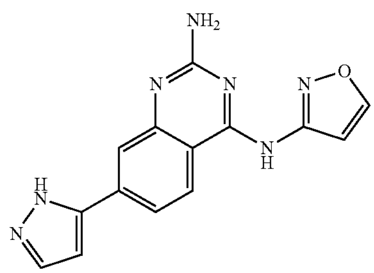 [SMILES: Nc1nc(Nc2ccon2)c2ccc(-c3ccn[nH]3)cc2n1] | 294.2/ 1.00 min (B)/ 2.23 μM | δ 8.86 (d, J = 1.2 Hz, 1H), 8.43 (d, J = 8.5 Hz, 1H), 7.89-7.78 (m, 1H), 7.75 (br s, 1H), 7.70-7.60 (m, 1H), 7.54 (s, 1H), 6.87 (d, J = 1.8 Hz, 1H), 6.83-6.68 (m, 1H) |
| 114 | 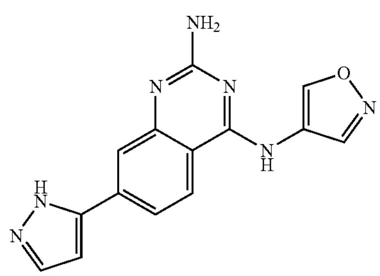 [SMILES: Nc1nc(Nc2cnoc2)c2ccc(-c3ccn[nH]3)cc2n1] | 293.9/ 1.01 min (B)/ 0.37 μM | δ 9.75 (s, 1H), 8.83 (s, 1H), 15 (d, J = 8.3 Hz, 1H), 7.91-7.77 (m, 1H), 7.72 (s, 1H), 7.69-7.61 (m, 1H), 6.86 (d, J = 2.1 Hz, 1H), 6.78-6.62 (m, 2H) |
| 115 | 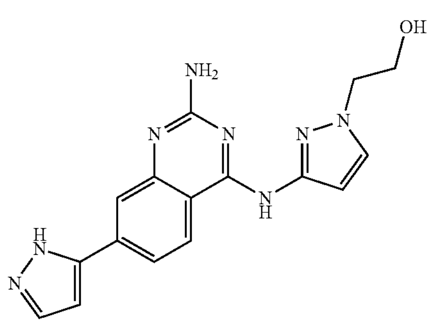 [SMILES: Nc1nc(Nc2ccn(CCO)n2)c2ccc(-c3ccn[nH]3)cc2n1] | 337.0/ 1.30 min (A)/ 18.02 μM | δ 12.61 (br s, 1H), 11.45 (br s, 1H), 8.77-8.62 (m, 1H), 8.06-7.68 (m, 5H), 7.09 (br s, 1H), 6.93 (br s, 1H), 4.15 (br s, 2H), 3.78 (br s, 2H) |

| Ex No. | Structure | LC/MS [M + H]+/ RT (Method)/ NLRP3 hIL1B EC50 | 1H NMR (500 MHz, DMSO-d6, unless otherwise indicated) |
|---|---|---|---|
| 116 | (structure) | 337.1/ 1.02 min (B)/ 0.50 μM | δ 8.39-8.23 (m, 1H), 7.90-7.76 (m, 1H), 7.66 (br s, 1H), 7.61-7.48 (m, 1H), 6.83 (d, J = 1.9 Hz, 1H), 6.56-6.24 (m, 2H), 3.71-3.63 (m, 2H), 2.73 (br t, J = 6.9 Hz, 2H) |
| 117 | (structure) racemate | 327.3/ 0.83 min (B)/ 1.56 μM | δ 9.13 (br d, J = 7.1 Hz, 1H), 8.31 (br d, J = 8.4 Hz, 1H), 7.95 (d, J = 8.2 Hz, 1H), 7.87-7.75 (m, 3H), 7.71-7.64 (m, 2H), 6.90 (d, J = 2.3 Hz, 1H), 6.84 (d, J = 2.2 Hz, 1H), 4.45-4.30 (m, 2H), 4.25-4.20 (m, 1H), 2.47-2.40 (m, 1H), 1.94-1.84 (m, 1H), 1.81-1.69 (m, 1H), 1.60-1.49 (m, 1H) |
| 118 | (structure) racemate | 327/ 0.57 min (B)/ 0.98 μM | δ 9.10-9.01 (m, 1H), 8.33 (br d, J = 8.4 Hz, 1H), 7.97 (dd, J = 8.2, 2.3 Hz, 1H), 7.89-7.77 (m, 2H), 7.76-7.65 (m, 2H), 6.91 (br s, 1H), 6.87-6.78 (m, 1H), 4.79 (s, 1H), 4.23-4.07 (m, 1H), 2.42-2.28 (m, 1H), 2.01-1.91 (m, 1H), 1.90-1.79 (m, 1H), 1.53-1.41 (m, 1H) |
| 119 | (structure) | 332.2/ 0.94 min (B)/ 0.49 μM | δ 8.54-8.48 (m, 1H), 8.08 (br s, 1H), 8.00-7.93 (m, 1H), 7.77-7.68 (m, 2H), 7.62 (s, 1H), 7.54-7.48 (m, 1H), 7.33 (br d, J = 7.7 Hz, 1H), 7.23 (br dd, J = 6.7, 5.1 Hz, 1H), 6.80 (d, J = 1.4 Hz, 1H), 6.30 (br s, 2H), 3.85-3.80 (m, 2H), 3.12 (br t, J = 7.6 Hz, 2H). |
| 120 | (structure) | 311.3/ 1.01 min (B)/ 0.68 μM | δ 13.29-13.22 (m, 1H), 8.08 (d, J = 8.8 Hz, 1H), 7.95-7.76 (br s, 2H), 7.90 (br s, 2H), 7.82-7.78 (m, 1H), 6.90-6.86 (m, 1H), 4.17-4.12 (m, 4H), 3.91 (br s, 2H), 3.76-3.73 (m, 2H), 2.07 (br d, J = 5.0 Hz, 2H) |

-continued

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 121 | 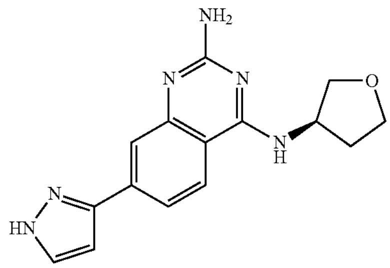 [SMILES: Nc1nc(N[C@@H]2CCOC2)c2ccc(-c3cc[nH]n3)cc2n1] | 297.0/ 0.93 min (B)/ 1.85 μM | δ 13.28-13.21 (m, 1H), 9.20-9.15 (m, 1H), 8.39 (br d, J = 8.5 Hz, 1H), 8.21-7.95 (m, 2H), 7.86 (br s, 3H), 6.89 (s, 1H), 4.83-4.76 (m, 1H), 4.02-3.93 (m, 2H), 3.79-3.73 (m, 2H), 2.28 (dt, J = 13.5, 6.8 Hz, 1H), 2.16-2.05 (m, 1H) |
| 122 | 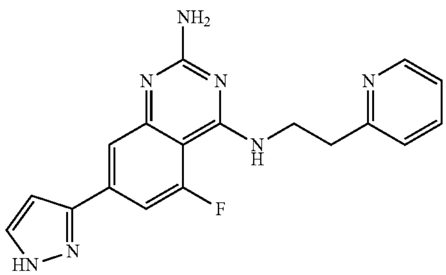 [SMILES: Nc1nc(NCCc2ccccn2)c2c(F)cc(-c3cc[nH]n3)cc2n1] | 349.9/ 1.20 min (B)/ 1.11 μM | δ 13.36-13.31 (m, 1H), 8.97 (s, 1H), 8.51 (br d, J = 3.7 Hz, 1H), 7.92-7.86 (m, 1H), 7.76 (td, J = 7.5, 1.6 Hz, 1H), 7.69 (br s, 1H), 7.67-7.63 (m, 1H), 7.37 (d, J = 7.7 Hz, 1H), 7.30 (br d, J = 1.8 Hz, 1H), 6.92 (s, 1H), 3.96 (br d, J = 5.7 Hz, 2H), 3.14 (br t, J = 7.4 Hz, 2H). |
| 123 | 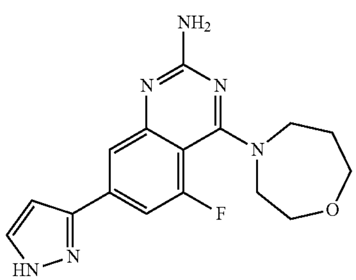 [SMILES: Nc1nc(N2CCCOCC2)c2c(F)cc(-c3cc[nH]n3)cc2n1] | 329.2/ 1.02 min (B)/ 2.86 μM | δ 13.26-13.01 (m, 1H), 7.81-7.74 (m, 1H), 7.50 (s, 1H), 7.26 (br d, J = 12.9 Hz, 1H), 6.86-6.82 (m, 1H), 6.52-6.45 (m, 2H), 1.97-1.92 (m, 2H). 8 protons from 1,4-oxazepan ring are not visible, likely due to overlap with water/water suppression. |
| 124 | 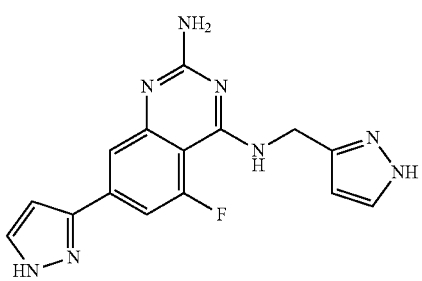 | 325.1/ 0.84 min (B)/ 0.60 μM | δ 7.78-7.73 (m, 1H), 7.68-7.62 (m, 1H), 7.56-7.54 (m, 1H), 7.45 (s, 1H), 7.23 (br d, J = 2.9 Hz, 1H), 6.84-6.82 (m, 1H), 6.44-6.38 (m, 2H), 6.26-6.23 (m, 1H), 4.67 (br d, J = 5.3 Hz, 2H).. |
| 125 | 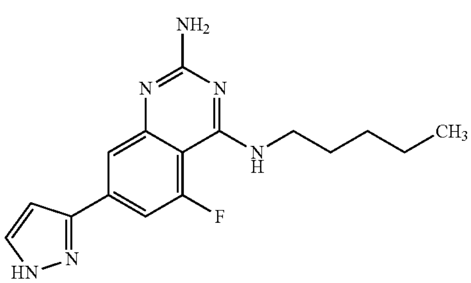 [SMILES: CCCCCNc1nc(N)nc2cc(-c3cc[nH]n3)cc(F)c12] | 315.2/ 1.59 min (B)/ 0.71 μM; TLR7 Agonist EC$_{50}$value >1 μM ≤20 μM | δ 13.13-13.08 (m, 1H), 7.86-7.79 (m, 1H), 7.46 (br s, 1H), 7.41-7.32 (m, 1H), 7.31-7.23 (m, 1H), 6.84 (s, 1H), 6.53-6.41 (m, 2H), 1.67-1.58 (m, 2H), 1.36-1.28 (m, 4H), 0.90-0.86 (m, 3H). 2 aliphatic protons are not visible, likely due to overlap with water/water suppression. |

-continued

| Ex No. | Structure | LC/MS [M + H]⁺/ RT (Method)/ NLRP3 hIL1B EC$_{50}$ | ¹H NMR (500 MHz, DMSO-d$_6$, unless otherwise indicated) |
|---|---|---|---|
| 126 | 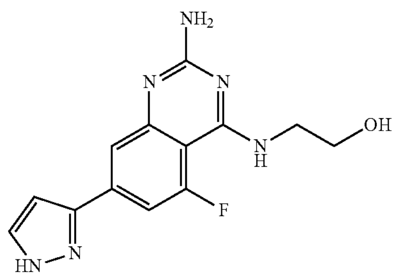 [SMILES: Nc1nc(NCCO)c2c(F)cc(-c3cc[nH]n3)cc2n1] | 289.1/ 0.79 min (B)/ 0.76 μM | δ 7.79-7.74 (m, 1H), 7.45 (s, 1H), 7.25 (br d, J = 13.5 Hz, 1H), 7.20-7.12 (m, 1H), 6.84 (d, J = 1.7 Hz, 1H), 6.29 (br s, 2H). 4 aliphatic protons are not visible, likely due to overlap with water/water suppression. |
| 127 | 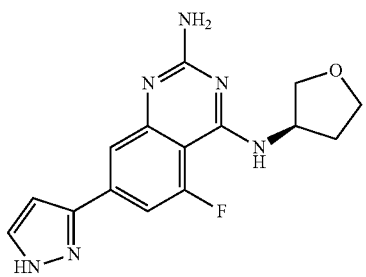 [SMILES: Nc1nc(N[C@@H]2CCOC2)c2c(F)cc(-c3cc[nH]n3)cc2n1] | 315.2/ 1.12 min (B)/ 1.22 μM | δ 7.77-7.73 (m, 1H), 7.46-7.43 (m, 1H), 7.29-7.23 (m, 1H), 6.93-6.88 (m, 1H), 6.84-6.82 (m, 1H), 6.31 (br s, 2H), 4.69-4.64 (m, 1H), 3.95 (dd, J = 8.8, 6.1 Hz, 2H), 3.89-3.84 (m, 2H), 2.30-2.22 (m, 1H), 2.00-1.93 (m, 1H) |
| 128 | 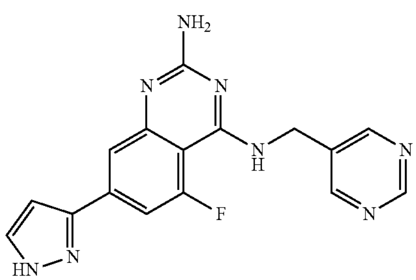 [SMILES: Nc1nc(NCc2cncnc2)c2c(F)cc(-c3cc[nH]n3)cc2n1] | 337.0/ 1.00 min (B)/ 0.83 μM | δ 13.37-13.28 (m, 1H), 9.28-9.20 (m, 1H), 9.11-9.08 (m, 1H), 8.96 (s, 1H), 7.88 (br s, 1H), 7.72-7.70 (m, 1H), 7.70-7.66 (m, 1H), 6.92 (d, J = 1.9 Hz, 1H), 4.76 (br d, J = 5.5 Hz, 2H) |
| 129 | 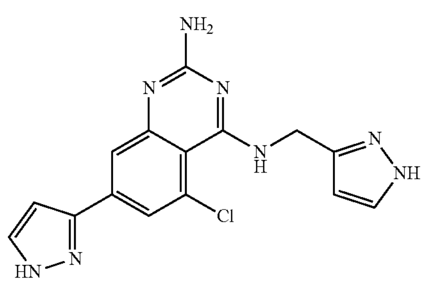 [SMILES: Nc1nc(NCc2cc[nH]n2)c2c(Cl)cc(-c3cc[nH]n3)cc2n1] | 341.2/ 1.07 min (B)/ 0.37 μM | δ 8.15 (br s, 1H), 7.80-7.74 (m, 1H), 7.61 (br s, 1H), 7.58 (s, 1H), 7.55 (s, 1H), 6.86 (d, J = 1.7 Hz, 1H), 6.41 (br s, 2H), 6.30-6.27 (m, 1H), 4.69 (br d, J = 4.7 Hz, 2H) |
| 130 | 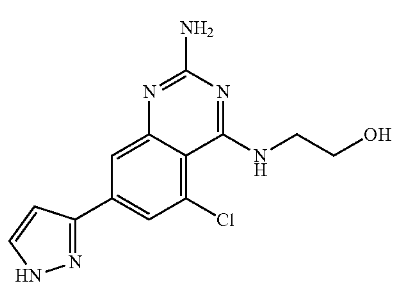 [SMILES: Nc1nc(NCCO)c2c(Cl)cc(-c3cc[nH]n3)cc2n1] | 306.1/ 0.89 min (B)/ 1.08 μM | δ 13.33-12.93 (m, 1H), 7.88-7.84 (m, 1H), 7.81-7.75 (m, 1H), 7.57 (d, J = 0.8 Hz 1H), 7.55 (s, 1H), 6.87-6.85 (m, 1H), 6.35 (br s, 2H), 5.10-4.93 (m, 1H), 3.67-3.63 (m, 2H), 3.60-3.57 (m, 2H) |

-continued

| Ex No. | Structure | LC/MS [M + H]+/ RT (Method)/ NLRP3 hIL1B EC50 | 1H NMR (500 MHz, DMSO-d6, unless otherwise indicated) |
|---|---|---|---|
| 131 | 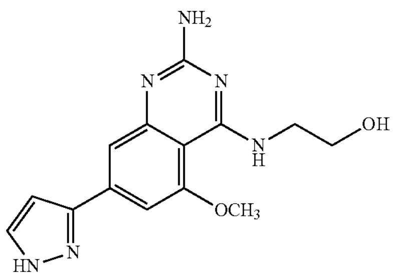 [SMILES: COc1cc(-c2cc[nH]n2)cc2nc(N)nc(NCCO)c12] | 301.2/ 0.84 min (B)/ 5.61 μM | δ 13.30-13.22 (m, 1H), 9.08-9.05 (m, 1H), 8.07-7.71 (m, 3H), 7.47-7.40 (m, 1H), 7.36 (s, 1H), 6.91 (s, 1H), 5.11-5.03 (m, 1H), 4.09 (s, 3H), 3.66 (br s, 4H) |
| 132 | 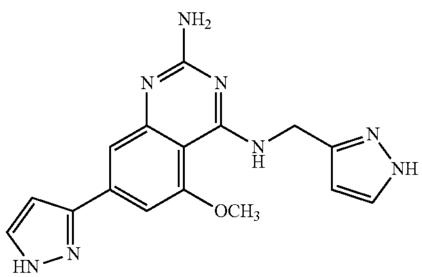 [SMILES: COc1cc(-c2cc[nH]n2)cc2nc(N)nc(NCc3cc[nH]n3)c12] | 336.9/ 1.22 min (B)/ 2.18 μM | δ 8.50-8.37 (m, 1H), 7.81-7.71 (m, 1H), 7.63-7.57 (m, 1H), 7.31-7.21 (m, 1H), 7.10-7.02 (m, 1H), 6.82 (d, J = 1.4 Hz, 1H), 6.42-6.28 (m, 2H), 6.27-6.18 (m, 1H), 4.67 (br d, J = 5.2 Hz, 2H), 4.00 (s, 3H) |
| 133 | 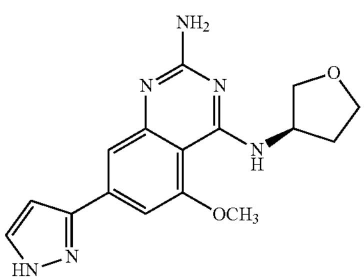 [SMILES: COc1cc(-c2cc[nH]n2)cc2nc(N)nc(N[C@@H]3CCOC3)c12] | 337.3/ 1.01 min (B)/ 0.65 μM | δ 13.31-13.21 (m, 1H), 8.70 (br d, J = 6.6 Hz, 1H), 8.20-7.69 (m, 4H), 7.49-7.43 (m, 1H), 7.37 (s, 1H), 6.92 (s, 1H), 4.79-4.70 (m, 1H), 4.11 (s, 3H), 3.97-3.90 (m, 2H), 3.80-3.71 (m, 2H), 2.36-2.28 (m, 1H), 2.09-1.99 (m, 1H) |
| 134 | 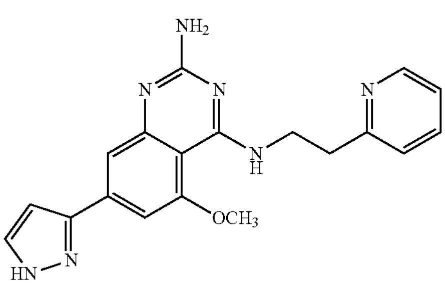 [SMILES: COc1cc(-c2cc[nH]n2)cc2nc(N)nc(NCCc3ccccn3)c12] | 362.3/ 1.20 min (B)/ 1.74 μM | δ 12.56-12.54 (m, 1H), 9.35 (br t, J = 5.5 Hz, 1H), 8.65 (d, J = 4.9 Hz, 1H), 7.95 (br t, J = 7.3 Hz, 1H), 7.87 (d, J = 1.8 Hz, 1H), 8.16-7.71 (m, 2H), 7.54 (br d, J = 7.9 Hz, 1H), 7.47-7.43 (m, 1H), 7.42 (s, 1H), 7.34 (s, 1H), 6.91 (d, J = 2.3 Hz, 1H), 4.06 (s, 3H), 3.98 (q, J = 6.5 Hz, 2H), 3.20 (br t, J = 6.6 Hz, 2H) |
| 135 | 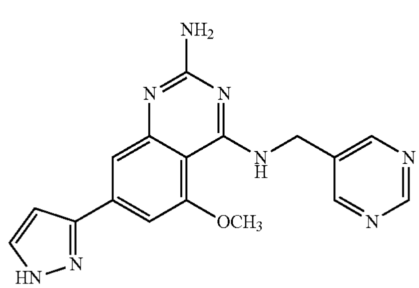 [SMILES: COc1cc(-c2cc[nH]n2)cc2nc(N)nc(NCc3cncnc3)c12] | 349.2/ 0.98 min (B)/ 1.44 μM | δ 13.30-13.24 (m, 1H), 12.68-12.40 (m, 4H), 9.62 (br d, J = 5.8 Hz, 1H), 9.09 (s, 1H), 8.94 (s, 1H), 7.87 (br s, 1H), 7.45-7.40 (m, 1H), 7.36 (br s, 1H), 6.91 (br s, 1H), 4.78 (br d, J = 5.9 Hz, 2H), 4.10 (s, 3H) |

-continued

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 136 | 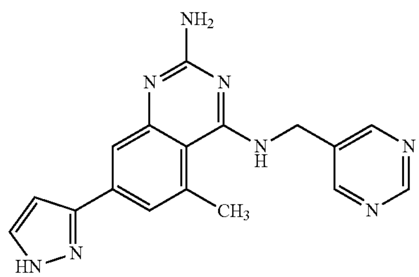 [SMILES: Cc1cc(-c2cc[nH]n2)cc2nc(N)nc(NCc3cncnc3)c12] | 333.2/ 0.97 min (B)/ 1.06 μM | δ 9.10-9.08 (m, 1H), 8.97 (s, 2H), 7.85 (br s, 1H), 7.81 (br s, 1H), 7.69 (br s, 1H), 6.85 (d, J = 2.2 Hz, 1H), 6.83 (d, J = 2.1 Hz, 1H), 4.79 (br d, J = 5.7 Hz, 2H), 2.88-2.86 (m, 3H). |
| 137 | 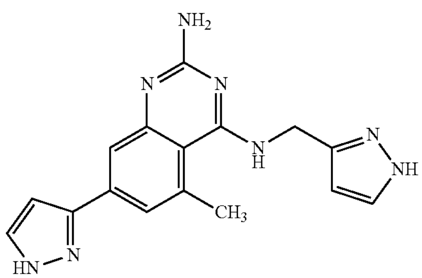 [SMILES: Cc1cc(-c2cc[nH]n2)cc2nc(N)nc(NCc3cc[nH]n3)c12] | 321.2/ 0.80 min (B)/ 0.17 μM | δ 13.27-13.16 (m, 1H), 8.20-8.13 (m, 1H), 7.82-7.79 (m, 1H), 7.65-7.60 (m, 3H), 6.84 (d, J = 2.2 Hz, 1H), 6.32-6.30 (m, 1H), 4.80-4.79 (m, 2H), 2.83 (s, 3H) |
| 138 | 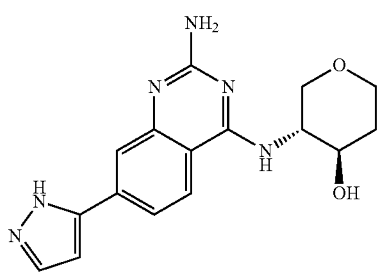 [SMILES: Nc1nc(N[C@@H]2COCC[C@H]2O)c2ccc(-c3ccn[nH]3)cc2n1] | 327.2/ 0.47 min (C)/ 2.14 μM | (400 MHz, METHANOL-d$_4$) δ 8.29-8.17 (m, 1H), 7.92-7.85 (m, 1H), 7.84-7.76 (m, 2H), 6.92-6.82 (m, 1H), 4.53-4.38 (m, 1H), 4.16-4.07 (m, 1H), 4.06-3.92 (m, 2H), 3.59-3.47 (m, 1H), 2.18-2.05 (m, 1H), 1.83-1.62 (m, 2H) |
| 139 | 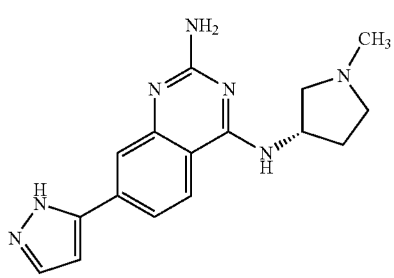 [SMILES: CN1CC[C@H](Nc2nc(N)nc3cc(-c4ccn[nH]4)ccc23)C1] | 310.1/ 0.61 min (B)/ 1.77 μM | δ 8.38-8.27 (m, 1H), 7.95-7.84 (m, 1H), 7.84-7.76 (m, 2H), 6.94-6.86 (m, 1H), 4.85-4.73 (m, 1H), 3.33-3.26 (s, 3H), 2.95-2.85 (m, 2H), 2.73-2.60 (m, 2H), 2.57-2.53 (m, 2H) |
| 140 | 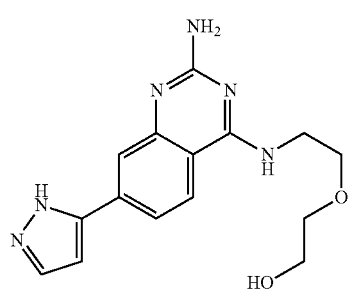 [SMILES: Nc1nc(NCCOCCO)c2ccc(-c3ccn[nH]3)cc2n1] | 315.1/ 0.70 min (B)/ 1.02 μM | δ 9.26 (br d, J = 1.2 Hz, 1H), 8.22 (d, J = 8.9 Hz, 1H), 7.94-7.75 (m, 3H), 6.87 (d, J = 1.8 Hz, 1H), 3.78-3.72 (m, 1H), 3.69-3.64 (m, 1H), 3.53-3.45 (m, 1H). Five protons from sidechain are not visible, likely due to overlap with suppressed water peak and/or low integration. |

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 141 | (racemate) quinazoline with 2-NH$_2$, 4-NH-cyclopentyl bearing OCH$_3$ and OH, 7-(1H-pyrazol-5-yl) | 341.0/ 0.84 min (B)/ 3.65 μM | δ 8.08 (d, J = 8.9 Hz, 1H), 7.76-7.70 (m, 1H), 7.61 (s, 1H), 7.54-7.48 (m, 1H), 6.83-6.77 (m, 1H), 6.25-6.12 (m, 2H), 4.75 (dq, J = 16.1, 7.9 Hz, 1H), 4.07 (br d, J = 2.4 Hz, 1H), 3.28 (s, 3H), 1.96-1.88 (m, 2H), 1.56-1.45 (m, 2H). One proton is not visible, likely due to overlap with suppressed water peak. |
| 142 | 2-amino-4-(pyridazin-3-ylmethylamino)-7-(1H-pyrazol-5-yl)quinazoline | 318.9/ 0.91 min (B)/ 0.51 μM | δ 9.14-9.09 (m, 1H), 8.62-8.58 (m, 1H), 8.05 (d, J = 8.5 Hz, 1H), 7.77-7.71 (m, 1H), 7.70-7.66 (m, 1H), 7.65-7.59 (m, 2H), 7.56-7.49 (m, 1H), 6.81 (d, J = 2.1 Hz, 1H), 6.09 (br s, 2H), 4.98 (br d, J = 5.2 Hz, 2H) |
| 143 | 2-amino-4-[(4,6-dimethyl-2-oxo-1,2-dihydropyridin-3-yl)methylamino]-7-(1H-pyrazol-5-yl)quinazoline | 362.1/ 0.88 min (B)/ 1.23 μM; TLR7 activity not tested. | δ 8.03 (d, J = 8.5 Hz, 1H), 7.73 (br s, 2H), 7.61 (s, 1H), 7.46 (br d, J = 7.6 Hz, 1H), 6.79 (d, J = 2.1 Hz, 1H), 6.22 (br s, 1H), 5.90 (s, 1H), 4.48 (d, J = 4.3 Hz, 2H), 2.26-2.17 (m, 3H), 2.15-2.08 (m, 3H) |
| 144 | 2-amino-4-(pyridin-3-ylmethylamino)-7-(1H-pyrazol-5-yl)quinazoline | 318.1/ 1.05 min (B)/ 0.09 μM | δ 9.93 (br t, J = 5.8 Hz, 1H), 8.76 (s, 1H), 8.58 (br d, J = 4.3 Hz, 1H), 8.24 (d, J = 8.9 Hz, 1H), 8.05 (br d, J = 7.9 Hz, 1H), 7.90-7.83 (m, 3H), 7.55 (dd, J = 7.6, 5.2 Hz, 1H), 6.88 (d, J = 2.1 Hz, 1H), 4.84 (br d, J = 5.5 Hz, 2H) |
| 145 | 2-amino-4-[(1-methyl-1H-pyrazol-3-yl)methylamino]-7-(1H-pyrazol-5-yl)quinazoline | 321.0/ 0.81 min (B)/ 0.41 μM | δ 9.76 (br t, J = 5.3 Hz, 1H), 8.28 (br d, J = 8.5 Hz, 1H), 7.92-7.80 (m, 3H), 7.62 (d, J = 2.0 Hz, 1H), 6.88 (d, J = 2.1 Hz, 1H), 6.28 (d, J = 2.1 Hz, 1H), 4.75 (d, J = 5.7 Hz, 2H), 3.79 (s, 3H) |

-continued

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 146 | 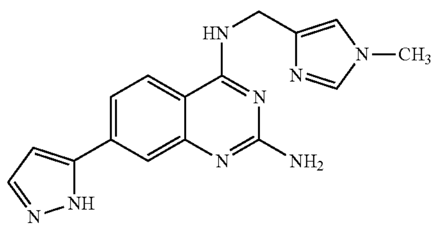 [SMILES: Cn1cnc(CNc2nc(N)nc3cc(-c4ccn[nH]4)ccc23)c1] | 321.3/ 0.69 min (B)/ 8.48 μM | δ 8.18 (br d, J = 8.2 Hz, 1H), 7.89-7.64 (m, 3H), 7.52 (br s, 1H), 7.09 (br s, 1H), 6.84 (s, 1H), 4.61 (br s, 2H), 3.60 (s, 2H). CH$_3$peak integrates to less than 3H, possibly due to overlap with suppressed water peak. |
| 147 | 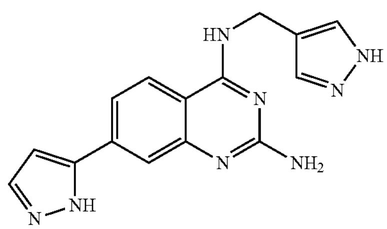 [SMILES: Nc1nc(NCc2cn[nH]c2)c2ccc(-c3ccn[nH]3)cc2n1] | 307.3/ 0.72 min (B)/ 0.26 μM | δ 9.67 (br d, J = 4.0 Hz, 1H), 8.25-8.18 (m, 1H), 7.90-7.80 (m, 3H), 7.70-7.51 (m, 1H), 6.87 (s, 1H), 4.63 (br d, J = 5.2 Hz, 2H) |
| 148 | 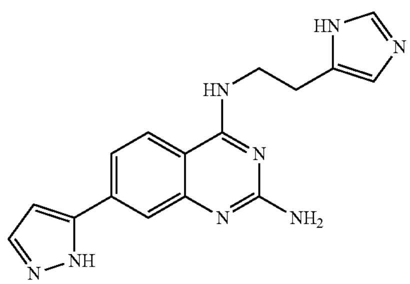 [SMILES: Nc1nc(NCCc2cnc[nH]2)c2ccc(-c3ccn[nH]3)cc2n1] | 321.1/ 0.73 min (B)/ 0.51 μM | δ 8.20 (br d, J = 7.9 Hz, 1H), 7.98 (br s, 1H), 7.91-7.79 (m, 3H), 7.06 (s, 1H), 6.88 (d, J = 1.8 Hz, 1H), 3.81 (br d, J = 5.3 Hz, 2H), 2.96 (br t, J = 7.1 Hz, 2H) |
| 149 | First eluting enantiomer | 351.2/ 1.03 min (B)/ 4.42 μM | δ 8.07-7.93 (m, 2H), 7.83-7.67 (m, 1H), 7.61 (s, 1H), 7.53-7.45 (m, 1H), 7.09 (s, 1H), 6.88-6.72 (m, 2H), 6.14 (br s, 1H), 5.04 (br dd, J = 8.1, 4.4 Hz, 1H), 4.04 (dt, J = 13.2, 5.3 Hz, 1H), 3.79 (ddd, J = 13.8, 8.2, 5.2 Hz, 1H), 3.69 (s, 3H) |
| 150 | Second eluting enantiomer | 351.2/ 1.03 min (B)/ 2.45 μM | δ 8.04-7.95 (m, 2H), 7.79-7.70 (m, 1H), 7.61 (s, 1H), 7.50 (br d, J = 6.7 Hz, 1H), 7.09 (s, 1H), 6.82-6.78 (m, 2H), 6.15 (br s, 1H), 5.04 (br dd, J = 7.6, 4.6 Hz, 1H), 4.08-3.99 (m, 1H), 3.83-3.75 (m, 1H), 3.69 (s, 3H) |

-continued

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 151 | 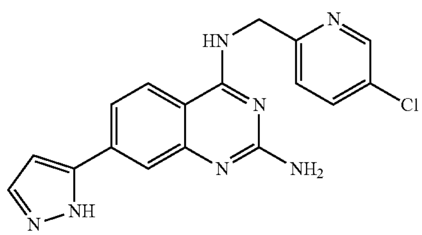 [SMILES: Nc1nc(NCc2ccc(Cl)cn2)c2ccc(-c3ccn[nH]3)cc2n1] | 352.2/ 1.08 min (B)/ 0.65 μM | δ 8.62-8.54 (m, 1H), 8.07 (d, J = 8.5 Hz, 1H), 7.89-7.81 (m, 1H), 7.78-7.70 (m, 1H), 7.67-7.61 (m, 1H), 7.57-7.49 (m, 1H), 7.41 (d, J = 8.5 Hz, 1H), 6.81 (d, J = 2.1 Hz, 1H), 6.25-6.10 (m, 1H). Two protons are not visible in NMR, likely due to overlap with suppressed water peak. |
| 153 | 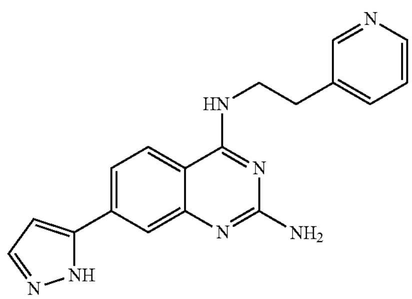 [SMILES: Nc1nc(NCCc2cccnc2)c2ccc(-c3ccn[nH]3)cc2n1] | 332.3/ 1.11 min (B)/ 0.42 μM | δ 9.44 (br t, J = 5.5 Hz, 1H), 8.69 (s, 1H), 8.60 (br d, J = 4.6 Hz, 1H), 8.18 (d, J = 8.5 Hz, 1H), 8.09 (br d, J = 8.2 Hz, 1H), 7.88-7.80 (m, 2H), 7.63 (dd, J = 7.6, 5.2 Hz, 1H), 6.87 (d, J = 2.1 Hz, 1H), 3.88-3.81 (m, 2H), 3.10 (br t, J = 7.0 Hz, 2H) |
| 154 | 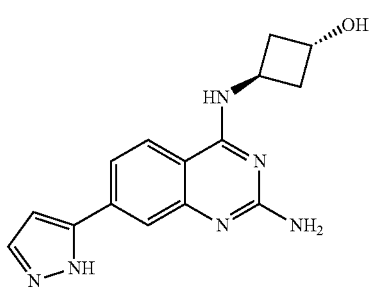 [SMILES: Nc1nc(N[C@H]2C[C@H](O)C2)c2ccc(-c3ccn[nH]3)cc2n1] | 297.3/ 0.96 min (B)/ 0.16 μM | δ 9.35-9.28 (m, 1H), 8.34 (br d, J = 8.4 Hz, 1H), 7.89-7.78 (m, 3H), 6.88 (d, J = 2.3 Hz, 1H), 4.85-4.73 (m, 1H), 4.43-4.33 (m, 1H), 2.46-2.38 (m, 2H), 2.30-2.20 (m, 2H) |
| 155 | 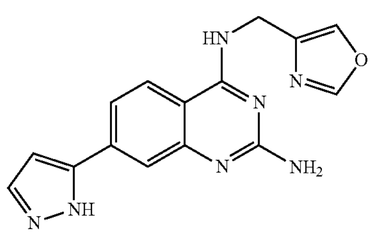 [SMILES: Nc1nc(NCc2cocn2)c2ccc(-c3ccn[nH]3)cc2n1] | 308.0/ 0.75 min (B)/ 0.49 μM | δ 9.79 (br t, J = 4.9 Hz, 1H), 8.32 (dd, J = 3.0, 1.7 Hz, 1H), 8.26-8.20 (m, 1H), 8.13 (dd, J = 2.8, 1.6 Hz, 1H), 7.84 (br d, J = 6.2 Hz, 3H), 6.88 (d, J = 2.2 Hz, 1H), 4.67 (br d, J = 5.5 Hz, 2H) |
| 156 | 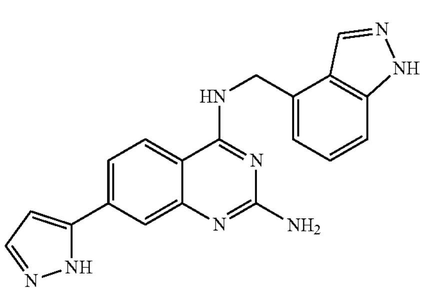 [SMILES: Nc1nc(NCc2cccc3[nH]ncc23)c2ccc(-c3ccn[nH]3)cc2n1] | 357.3/ 1.24 min (B)/ 0.44 μM | δ 9.82 (br s, 1H), 8.32 (br d, J = 8.7 Hz, 1H), 8.15 (s, 1H), 7.90 (br d, J = 9.0 Hz, 2H), 7.72 (d, J = 8.1 Hz, 1H), 7.30 (br d, J = 6.9 Hz, 1H), 7.10 (t, J = 7.6 Hz, 1H), 6.90 (d, J = 1.9 Hz, 1H), 5.12 (br d, J = 5.3 Hz, 2H) |

-continued

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 157 | 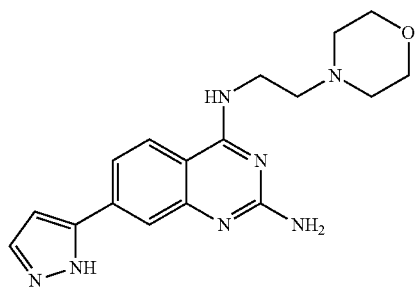 [SMILES: Nc1nc(NCCN2CCOCC2)c2ccc(-c3ccn[nH]3)cc2n1] | 340.1/ 1.04 min (B)/ 1.32 μM | δ 9.53 (br s, 1H), 8.19-8.12 (m, 1H), 7.91-7.81 (m, 3H), 6.93-6.85 (m, 1H), 3.92 (br d, J = 5.0 Hz, 2H), 3.68-3.56 (m, 1H), 3.43 (br s, 1H). 8 protons from sidechain are not visible, likely due to overlap with suppressed water peak and/or low integration. |
| 158 | 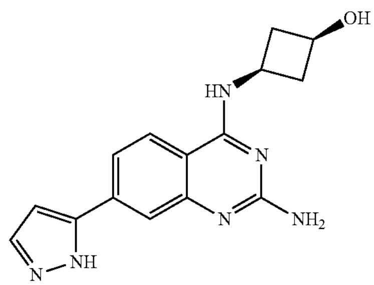 [SMILES: Nc1nc(N[C@H]2C[C@@H](O)C2)c2ccc(-c3ccn[nH]3)cc2n1] | 297.3/ 1.01 min (B)/ 1.59 μM | δ 9.32 (br d, J = 6.6 Hz, 1H), 8.36 (br d, J = 8.7 Hz, 1H), 7.94-7.81 (m, 3H), 6.88 (d, J = 1.8 Hz, 1H), 4.27-4.16 (m, 1H), 4.00-3.87 (m, 1H), 2.75-2.63 (m, 2H), 2.08 (qd, J = 8.6, 2.9 Hz, 2H) |
| 159 | 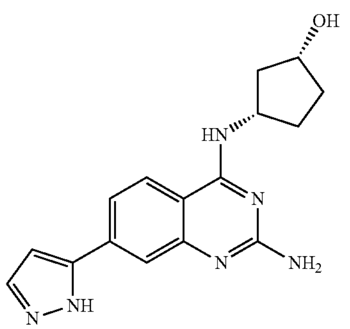 [SMILES: Nc1nc(N[C@H]2CC[C@@H](O)C2)c2ccc(-c3ccn[nH]3)cc2n1] | 311.3/ 0.77 min (B)/ 0.43 μM | δ 8.04 (d, J = 8.6 Hz, 1H), 7.80-7.72 (m, 1H), 7.71-7.64 (m, 1H), 7.60 (d, J = 1.2 Hz, 1H), 7.53-7.46 (m, 1H), 6.80 (d, J = 2.1 Hz, 1H), 6.16 (br s, 1H), 4.56-4.45 (m, 1H), 4.19-4.10 (m, 1H), 2.32-2.22 (m, 1H), 2.04-1.93 (m, 1H), 1.85-1.71 (m, 2H), 1.69-1.52 (m, 2H) |
| 160 | 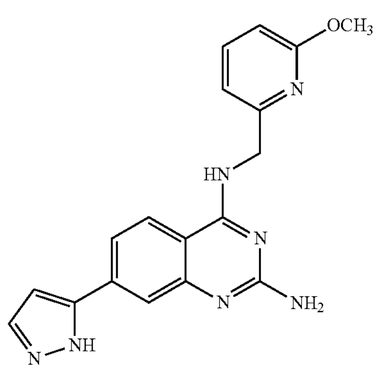 [SMILES: COc1cccc(CNc2nc(N)nc3cc(-c4ccn[nH]4)ccc23)n1] | 348.3/ 1.27 min (B)/ 0.65 μM | δ 8.24 (br d, J = 8.3 Hz, 1H), 7.89-7.72 (m, 3H), 7.65 (t, J = 7.8 Hz, 1H), 6.93 (d, J = 7.3 Hz, 1H), 6.87 (d, J = 1.9 Hz, 1H), 6.70 (d, J = 8.2 Hz, 1H), 4.80 (br d, J = 5.3 Hz, 2H), 3.81 (s, 3H) |
| 161 | 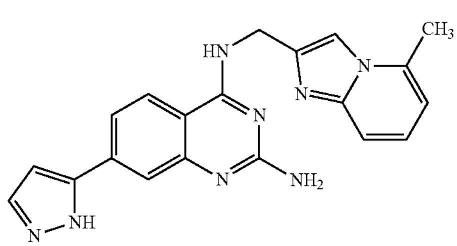 [SMILES: Cc1cccc2nc(CNc3nc(N)nc4cc(-c5ccn[nH]5)ccc34)cn12] | 371.3/ 1.01 min (B)/ 2.00 μM | δ 8.30 (br d, J = 8.2 Hz, 1H), 8.23 (s, 1H), 7.93-7.85 (m, 3H), 7.76-7.66 (m, 2H), 7.22 (br s, 5.5 Hz, 1H), 6.90 (d, J = 2.1 Hz, 1H), 5.02 (br d, J = 5.5 Hz, 2H), 2.70 (s, 3H) |

-continued

| Ex No. | Structure | LC/MS [M + H]+/ RT (Method)/ NLRP3 hIL1B EC50 | 1H NMR (500 MHz, DMSO-d6, unless otherwise indicated) |
|---|---|---|---|
| 162 | Relative stereochemistry; first eluting enantiomer | 344.2/ 1.25 min (B)/ 0.24 μM | δ 8.51 (d, J = 1.2 Hz, 1H), 8.40 (d, J = 4.0 Hz, 1H), 8.01 (d, J = 8.5 Hz, 1H), 7.80-7.70 (m, 1H), 7.65-7.59 (m, 2H), 7.56-7.48 (m, 1H), 7.33 (dd, J = 7.9, 4.9 Hz, 1H), 6.81 (d, J = 2.1 Hz, 1H), 6.05 (br s, 2H), 3.28 (br d, J = 4.0 Hz, 1H), 2.22-2.16 (m, 1H), 1.48 (dt, J = 9.6, 5.0 Hz, 1H), 1.42-1.35 (m, 1H) |
| 163 | Relative stereochemistry; second eluting enantiomer | 344.0/ 1.25 min (B)/ 0.65 μM | δ 8.51 (s, 1H), 8.40 (d, J = 4.6 Hz, 1H), 8.01 (d, J = 8.8 Hz, 1H), 7.79-7.69 (m, 1H), 7.66-7.59 (m, 2H), 7.55-7.48 (m, 1H), 7.33 (dd, J = 7.6, 4.9 Hz, 1H), 6.81 (d, J = 2.1 Hz, 1H), 6.00 (br s, 2H), 3.31-3.24 (m, 1H), 2.19 (ddd, J = 9.3, 6.3, 3.4 Hz, 1H), 1.48 (dt, J = 9.7, 5.1 Hz, 1H), 1.42-1.34 (m, 1H) |
| 164 | 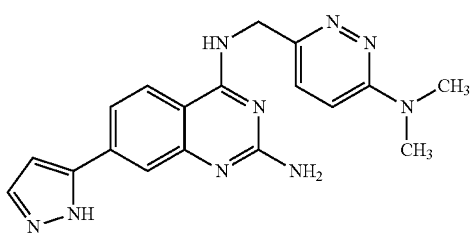 [SMILES: CN(C)c1ccc(CNc2nc(N)nc3cc(-c4ccn[nH]4)ccc23)nn1] | 362.3/ 1.08 min (B)/ 1.24 μM | δ 9.93 (br t, J = 6.0 Hz, 1H), 8.27 (d, J = 9.2 Hz, 1H), 7.91-7.82 (m, 3H), 7.65 (d, J = 9.8 Hz, 1H), 7.37-7.29 (m, 1H), 6.89 (d, J = 2.1 Hz, 1H), 4.89 (d, J = 5.5 Hz, 2H), 3.11 (s, 6H) |
| 165 | 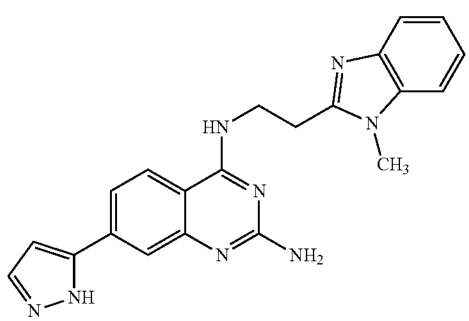 [SMILES: Cn1c(CCNc2nc(N)nc3cc(-c4ccn[nH]4)ccc23)nc2ccccc21] | 385.2/ 1.27 min (B)/ 4.12 μM; TLR8 activity <50% at 62.5 μM. | δ 8.69-8.54 (m, 1H), 8.01 (br d, J = 8.2 Hz, 1H), 7.82-7.75 (m, 1H), 7.73-7.67 (m, 1H), 7.65-7.59 (m, 1H), 7.57-7.53 (m, 1H), 7.52-7.47 (m, 1H), 7.28-7.12 (m, 2H), 6.86-6.80 (m, 1H), 6.79-6.65 (m, 1H), 4.00-3.91 (m, 2H), 3.80-3.74 (m, 3H), 3.31-3.22 (m, 2H) |

-continued

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 166 | 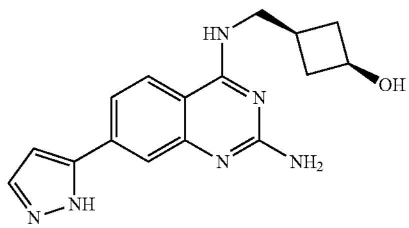 [SMILES: Nc1nc(NC[C@H]2C[C@@H](O)C2)c2ccc(-c3ccn[nH]3)cc2n1] | 311.2/ 1.06 min (B)/ 0.81 μM | δ 8.72-8.49 (m, 1H), 8.19-8.07 (m, 1H), 7.92-7.60 (m, 3H), 7.20-6.91 (m, 1H), 6.83 (s, 1H), 4.02-3.86 (m, 1H), 3.61-3.48 (m, 1H), 2.36-2.21 (m, 2H), 2.17-2.02 (m, 1H), 1.66-1.49 (m, 2H). One proton is not visible due to overlap with suppressed water peak or low integration. |
| 167 | 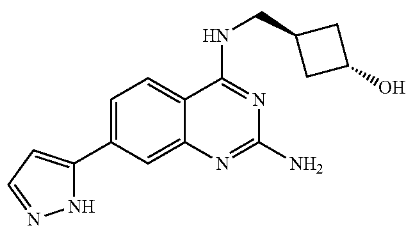 [SMILES: Nc1nc(NC[C@H]2C[C@H](O)C2)c2ccc(-c3ccn[nH]3)cc2n1] | 311.3/ 0.98 min (B)/ 1.24 μM | δ 8.98-8.77 (m, 1H), 8.17 (br d, J = 8.4 Hz, 1H), 7.92-7.67 (m, 3H), 7.50-7.22 (m, 1H), 6.85 (d, J = 1.8 Hz, 1H), 4.35-4.20 (m, 1H), 3.68-3.44 (m, 2H), 2.14-2.03 (m, 2H), 1.98-1.90 (m, 2H)/ One proton is not visible, likely due to overlap with with DMSO peak. |
| 168 | 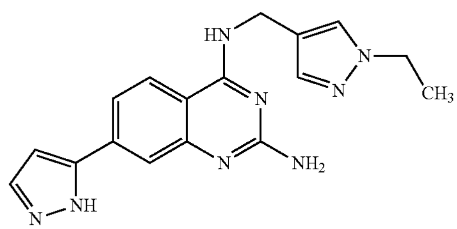 [SMILES: CCn1cc(CNc2nc(N)nc3cc(-c4ccn[nH]4)ccc23)cn1] | 335.3/ 1.05 min (B)/ 1.28 μM | δ 8.08 (d, J = 8.5 Hz, 1H), 7.82-7.75 (m, 1H), 7.75-7.73 (m, 1H), 7.72-7.68 (m, 1H), 7.65-7.59 (m, 1H), 7.47 (s, 1H), 6.82 (d, J = 2.1 Hz, 1H), 4.59-4.48 (m, 2H), 4.07 (q, J = 7.3 Hz, 2H), 1.33 (t, J = 7.2 Hz, 3H) |
| 169 | 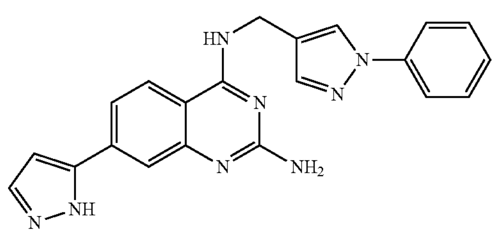 [SMILES: Nc1nc(NCc2cnn(-c3ccccc3)c2)c2ccc(-c3ccn[nH]3)cc2n1] | 383.2/ 1.36 min (B)/ 0.73 μM | δ 9.78 (br t, J = 5.2 Hz, 1H), 8.54 (s, 1H), 8.24 (d, J = 8.2 Hz, 1H), 7.90-7.74 (m, 3H), 7.81-7.74 (m, 3H), 7.48 (t, J = 7.9 Hz, 2H), 7.32-7.25 (m, 1H), 6.88 (d, J = 2.1 Hz, 1H), 4.69 (d, J = 5.5 Hz, 2H) |
| 170 | 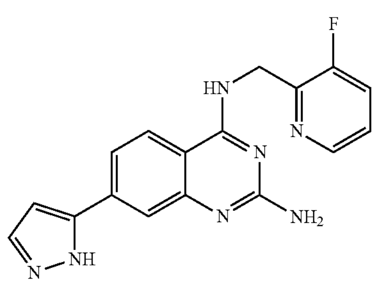 [SMILES: Nc1nc(NCc2ncccc2F)c2ccc(-c3ccn[nH]3)cc2n1] | 336.2/ 1.17 min (B)/ 0.20 μM; TLR7/8 activity not tested. | δ 8.37 (br d, J = 4.3 Hz, 1H), 8.13 (d, J = 8.5 Hz, 1H), 7.87-7.76 (m, 1H), 7.74-7.67 (m, 2H), 7.66-7.55 (m, 1H), 7.41 (dt, J = 8.4, 4.3 Hz, 1H), 6.83 (d, J = 1.8 Hz, 1H), 6.60-6.43 (m, 1H), 4.93 (br d, J = 4.6 Hz, 2H) |
| 171 | 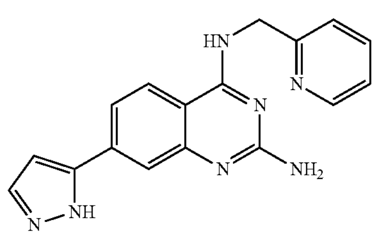 [SMILES: Nc1nc(NCc2ccccn2)c2ccc(-c3ccn[nH]3)cc2n1] | 318.0/ 113 min (B)/ 0.27 μM; TLR7/8 activity not tested. | δ 8.53 (d, J = 4.6 Hz, 1H), 8.16 (d, J = 8.5 Hz, 1H), 7.83-7.77 (m, 1H), 7.74 (dt, J = 9.2, 7.6 Hz, 2H), 7.68-7.57 (m, 1H), 7.38 (d, J = 7.9 Hz, 1H), 7.30-7.23 (m, 1H), 6.84 (d, J = 1.8 Hz, 1H), 4.85 (br d, J = 5.8 Hz, 2H) |

| Ex No. | Structure | LC/MS [M + H]⁺/ RT (Method)/ NLRP3 hIL1B EC$_{50}$ | ¹H NMR (500 MHz, DMSO-d$_6$, unless otherwise indicated) |
|---|---|---|---|
| 172 | 7-(1H-pyrazol-5-yl)-N4-((1-(2-methoxyethyl)pyrrolidin-2-yl)methyl)quinazoline-2,4-diamine | 368.1/ 1.02 min (B)/ 2.60 μM | δ 8.02 (br d, J = 8.4 Hz, 1H), 7.83-7.73 (m, 1H), 7.71-7.66 (m, 1H), 7.65-7.58 (m, 1H), 6.82 (s, 1H), 3.65-3.58 (m, 1H), 3.27-3.22 (m, 3H), 3.20-3.09 (m, 2H), 2.67-2.28 (m, 6H overlaps DMSO), 1.93-1.82 (m, 1H), 1.77-1.58 (m, 3H) |
| 173 | N4-(3-methoxycyclobutyl)-7-(1H-pyrazol-5-yl)quinazoline-2,4-diamine | 311.1/ 1.13 min (B)/ 0.14 μM | δ 8.23-8.16 (m, 1H), 8.12 (d, J = 8.5 Hz, 1H), 7.76 (br s, 1H), 7.66-7.63 (m, 1H), 7.57 (br d, J = 7.9 Hz, 1H), 6.81 (d, J = 2.1 Hz, 1H), 6.58-6.46 (m, 1H), 4.80-4.70 (m, 1H), 4.06-3.98 (m, 1H), 3.18 (s, 3H), 2.33 (dd, J = 7.3, 5.2 Hz, 4H) |
| 174 | N4-(isothiazol-4-ylmethyl)-7-(1H-pyrazol-5-yl)quinazoline-2,4-diamine | 324.3/ 1.07 min (B)/ 0.18 μM | δ 9.05 (d, J = 1.8 Hz, 1H), 8.42 (br t, J = 6.0 Hz, 1H), 8.05 (d, J = 8.5 Hz, 1H), 7.74 (br d, J = 1.2 Hz, 1H), 7.62 (s, 1H), 7.55-7.46 (m, 2H), 6.80 (d, J = 2.1 Hz, 1H), 6.12 (s, 2H), 4.85 (d, J = 5.5 Hz, 2H) |
| 175 | 7-(1H-pyrazol-5-yl)-N4-(thiazol-5-ylmethyl)quinazoline-2,4-diamine | 324.0/ 1.06 min (B)/ 0.73 μM | δ 9.99-9.94 (m, 1H), 9.02 (s, 1H), 8.20 (br d, J = 8.5 Hz, 1H), 8.00 (s, 1H), 7.93-7.82 (m, 3H), 6.88 (d, J = 1.8 Hz, 1H), 4.99 (br d, J = 5.5 Hz, 2H) |
| 176 | N4-(3-(hydroxymethyl)cyclobutyl)-7-(1H-pyrazol-5-yl)quinazoline-2,4-diamine | 311.1/ 1.04 min (B)/ 0.09 μM | δ 8.08 (d, J = 8.5 Hz, 1H), 7.93 (br d, J = 7.0 Hz, 1H), 7.77-7.69 (m, 1H), 7.59 (s, 1H), 7.50 (br d, J = 7.9 Hz, 1H), 6.79 (d, J = 2.1 Hz, 1H), 6.09 (br s, 2H), 4.78-4.64 (m, 1H), 2.37-2.25 (m, 1H), 2.24-2.09 (m, 4H) Two protons are not visible in NMR, likely due to overlap with suppressed water peak |

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 177 | *[cyclobutyl-HN substituted 7-(1H-pyrazol-5-yl)quinazolin-2-amine]* | 281.3/ 1.17 min (B)/ 0.16 μM | δ 8.07 (d, J = 8.5 Hz, 1H), 7.97 (br d, J = 7.0 Hz, 1H), 7.78-7.71 (m, 1H), 7.60 (s, 1H), 7.51 (br d, J = 8.2 Hz, 1H), 6.80 (d, J = 2.1 Hz, 1H), 6.14 (br s, 2H), 4.76-4.63 (m, 1H), 2.30 (q, J = 8.1 Hz, 2H), 2.18-2.04 (m, 2H), 1.79-1.61 (m, 2H) |
| 178 | *[Rel trans-4-hydroxycyclohexyl-HN substituted 7-(1H-pyrazol-5-yl)quinazolin-2-amine]* Relative stereochemistry; first eluting enantiomer | 325.1/ 1.07 min (B)/ 0.66 μM | δ 8.03 (br d, J = 8.2 Hz, 1H), 7.85-7.75 (m, 1H), 7.62-7.58 (m, 1H), 7.57-7.53 (m, 1H), 7.52-7.45 (m, 1H), 6.80 (d, J = 2.1 Hz, 1H), 6.04-5.96 (m, 2H), 4.25-4.14 (m, 1H), 3.71-3.49 (m, 1H), 2.14-2.05 (m, 1H), 1.88-1.81 (m, 2H), 1.78-1.70 (m, 1H), 1.40-1.21 (m, 3H), 1.18-1.04 (m, 1H) |
| 179 | *[Rel trans-4-hydroxycyclohexyl-HN substituted 7-(1H-pyrazol-5-yl)quinazolin-2-amine]* Relative stereochemistry; second eluting enantiomer | 325.3/ 0.99 min (B)/ 0.27 μM | δ 8.08-7.98 (m, 1H), 7.83-7.71 (m, 1H), 7.62-7.53 (m, 2H), 7.52-7.40 (m, 1H), 6.79 (d, J = 2.0 Hz, 1H), 6.01 (br s, 2H), 4.28-4.07 (m, 1H), 3.63-3.55 (m, 1H), 2.14-2.02 (m, 1H), 1.87-1.77 (m, 2H), 1.75-1.66 (m, 1H), 1.38-1.20 (m, 3H), 1.17-1.01 (m, 1H) |
| 180 | *[tert-butyl-HN substituted 7-(1H-pyrazol-5-yl)quinazolin-2-amine]* | 282/ 1.23 min (B)/ 0.71 μM | δ 8.15-8.09 (m, 1H), 7.80-7.70 (m, 1H), 7.64-7.58 (m, 1H), 7.55-7.45 (m, 1H), 7.07-6.96 (m, 1H), 6.85-6.76 (m, 1H), 6.36-6.22 (m, 2H), 1.59-1.49 (m, 9H) |

-continued

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 181 | 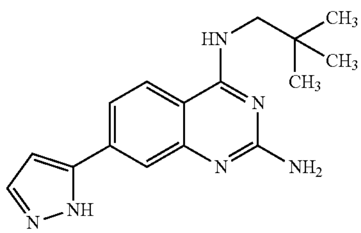 [SMILES: CC(C)(C)CNc1nc(N)nc2cc(-c3ccn[nH]3)ccc12] | 297/ 1.32 min (B)/ 0.18 µM | δ 8.18-8.09 (m, 1H), 7.82-7.71 (m, 2H), 7.67-7.60 (m, 1H), 7.58-7.49 (m, 1H), 6.86-6.76 (m, 1H), 6.37-6.24 (m, 1H), 0.96 (s, 9H) (1 methylene missing due to water supression) |
| 182 | 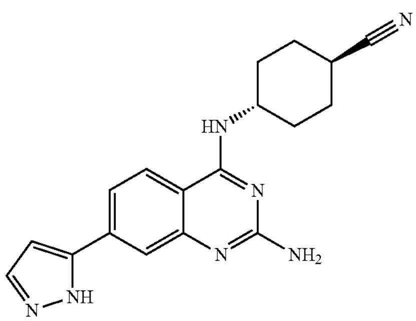 [SMILES: N#C[C@H]1CC[C@H](Nc2nc(N)nc3cc(-c4ccn[nH]4)ccc23)CC1] | 334/ 1.21 min (B)/ 0.13 µM | δ 9.06-8.88 (m, 1H), 8.40-8.25 (m, 1H), 7.95-7.79 (m, 3H), 6.95-6.82 (m, 1H), 4.32-4.17 (m, 1H), 3.78-3.45 (m, 2H), 2.82-2.69 (m, 1H), 2.23-2.10 (m, 2H), 2.04-1.92 (m, 2H), 1.70-1.43 (m, 4H) |
| 183 | 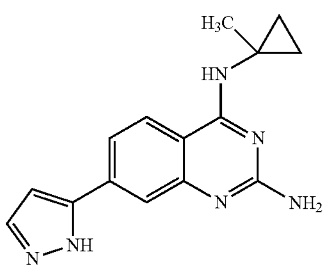 [SMILES: CC1(Nc2nc(N)nc3cc(-c4ccn[nH]4)ccc23)CC1] | 281/ 1.14 min (B)/ 0.53 µM | δ 8.40-8.21 (m, 1H), 8.09-7.98 (m, 1H), 7.83-7.73 (m, 1H), 7.70-7.61 (m, 1H), 7.59-7.48 (m, 1H), 6.87-6.76 (m, 1H), 6.57-6.32 (m, 1H), 1.54-1.44 (m, 3H), 0.90-0.80 (m, 3H), 0.76-0.65 (m, 2H) |
| 184 Relative stereochemistry; First eluting enatiomer | | 320/ 1.1 min (B)/ | δ 8.07-8.00 (m, 1H), 7.80-7.72 (m, 1H), 7.69-7.63 (m, 1H), 7.63-7.58 (m, 1H), 7.54-7.47 (m, 1H), 6.87-6.70 (m, 1H), 6.17-5.95 (m, 2H), 4.78-4.59 (m, 1H), 3.32-3.21 (m, 1H), 2.30-2.05 (m, 4H), 1.89-1.67 (m, 3H) |

-continued

| Ex No. | Structure | LC/MS [M + H]+/ RT (Method)/ NLRP3 hIL1B EC50 | 1H NMR (500 MHz, DMSO-d6, unless otherwise indicated) |
|---|---|---|---|
| 185 | *Relative stereochemistry; Second eluting enatiomer* | 320/ 1.15 min (B)/ 0.17 μM | δ 9.14-9.04 (m, 1H), 8.39-8.29 (m, 1H), 7.95-7.80 (m, 3H), 6.93-6.85 (m, 1H), 4.88-4.69 (m, 1H), 2.38-2.12 (m, 4H), 1.94-1.75 (m, 2H) (1 methine missing due to water supression) |
| 186 | 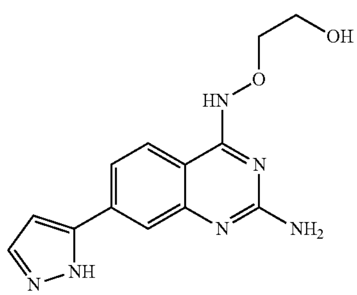 [SMILES: Nc1nc(NOCCO)c2ccc(-c3ccn[nH]3)cc2n1] | 287/ 1.01 min (B)/ 3.00 μM | 7.90-7.76 (m, 2H), 7.74-7.60 (m, 2H), 6.84-6.73 (m, 1H), 4.24-4.10 (m, 2H), 3.79-3.67 (m, 2H), 3.60-3.43 (m, 2H) (1 methylene missing due to water supression) |
| 187 | 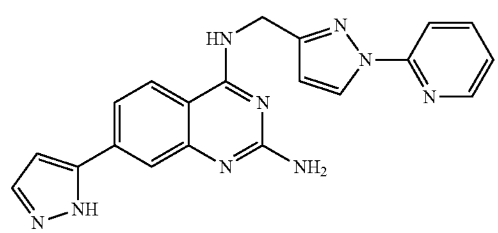 [SMILES: Nc1nc(NCc2ccn(-c3ccccn3)n2)c2ccc(-c3ccn[nH]3)cc2n1] | 384/ 1.24 min (B)/ 0.23 μM | δ 8.63-8.50 (m, 2H), 8.50-8.41 (m, 1H), 8.13-8.04 (m, 1H), 8.02-7.94 (m, 1H), 7.89 (d, J = 8.2 Hz, 1H), 7.76 (br s, 1H), 7.71-7.62 (m, 1H), 7.63-7.48 (m, 1H), 7.34 (dd, J = 6.9, 5.3 Hz, 2H), 6.82 (d, J = 2.1 Hz, 1H), 6.59 (d, J = 2.4 Hz, 1H), 6.35 (br s, 2H), 4.80 (br d, J = 5.4 Hz, 2H) |
| 188 | 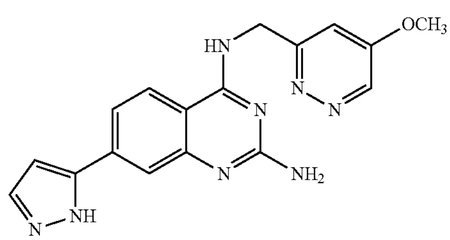 [SMILES: COc1cnnc(CNc2nc(N)nc3cc(-c4ccn[nH]4)ccc23)c1] | 349/ 0.97 min (B)/ 8.32 μM | δ 8.97-8.88 (m, 1H), 8.22-8.11 (m, 1H), 7.84-7.71 (m, 2H), 7.71-7.61 (m, 1H), 7.41-7.29 (m, 1H), 6.90-6.82 (m, 1H), 5.08-4.89 (m, 2H), 3.96-3.82 (m, 3H) |
| 189 | 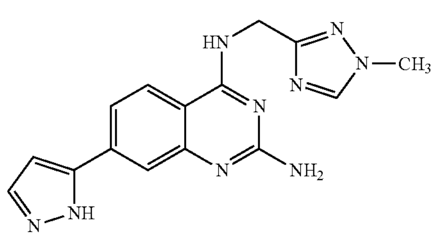 | 322/ 0.92 min (B)/ 1.41 μM | δ 8.44-8.34 (m, 1H), 8.17-8.07 (m, 1H), 7.86-7.74 (m, 1H), 7.73-7.67 (m, 1H), 7.66-7.53 (m, 1H), 6.89-6.78 (m, 1H), 6.71-6.50 (m, 1H), 4.84-4.74 (m, 2H), 3.87-3.73 (m, 3H) |

-continued

| Ex No. | Structure | LC/MS [M + H]+/ RT (Method)/ NLRP3 hIL1B EC50 | 1H NMR (500 MHz, DMSO-d6, unless otherwise indicated) |
|---|---|---|---|
| 190 | 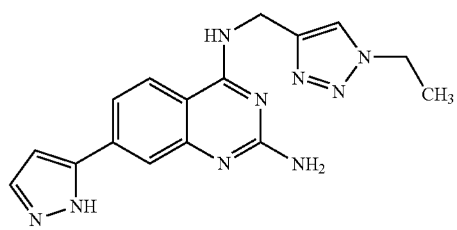 [SMILES: CCn1cc(CNc2nc(N)nc3cc(-c4ccn[nH]4)ccc23)nn1] | 336/ 0.97 min (B)/ 4.89 μM | δ 8.44-8.34 (m, 1H), 8.17-8.07 (m, 1H), 7.86-7.74 (m, 1H), 7.73-7.67 (m, 1H), 7.66-7.53 (m, 1H), 6.89-6.78 (m, 1H), 6.71-6.50 (m, 1H), 4.84-4.74 (m, 2H), 3.87-3.73 (m, 3H), 3.57 (br s, 4H) |
| 191 | 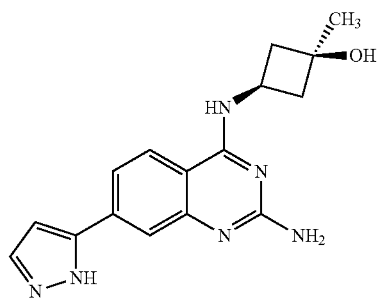 [SMILES: C[C@]1(O)C[C@@H](Nc2nc(N)nc3cc(-c4ccn[nH]4)ccc23)C1] | 311/ 1.05 min (B)/ 0.46 μM | δ 9.28-8.98 (m, 1H), 8.42-8.25 (m, 1H), 7.96-7.78 (m, 3H), 6.95-6.82 (m, 1H), 4.36-4.18 (m, 1H), 2.55-2.53 (m, 4H), 2.49-2.37 (m, 2H), 2.31-2.20 (m, 2H), 1.37-1.23 (m, 3H) |
| 192 | 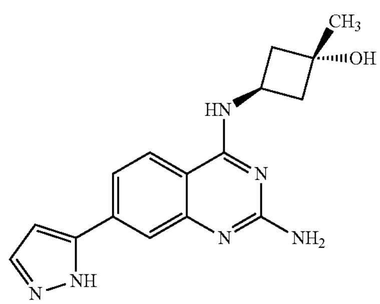 [SMILES: C[C@]1(O)C[C@H](Nc2nc(N)nc3cc(-c4ccn[nH]4)ccc23)C1] | 311/ 1.02 min (B)/ 0.37 μM | δ 9.37-9.24 (m, 1H), 8.42-8.29 (m, 1H), 7.95-7.79 (m, 3H), 6.94-6.85 (m, 1H), 4.95-4.81 (m, 1H), 2.44-2.35 (m, 2H), 2.26-2.18 (m, 2H), 1.41-1.23 (m, 3H) (2 methylene under solvent residual peak) |
| 193 | 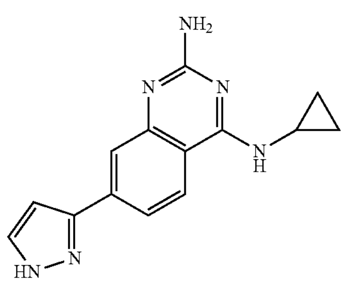 [SMILES: Nc1nc(NC2CC2)c2ccc(-c3cc[nH]n3)cc2n1] | 267/ 0.8 min (B)/ 0.10 μM | δ 8.01 (d, J = 8.5 Hz, 1H), 7.75 (br s, 1H), 7.64 (s, 1H), 7.59-7.48 (m, 1H), 6.80 (d, J = 2.4 Hz, 1H), 6.43 (br s, 2H), 3.07-3.00 (m, 1H), 0.80-0.74 (m, 2H), 0.69-0.64 (m, 2H) |
| 194 | 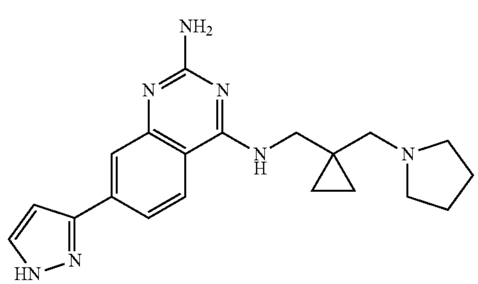 [SMILES: Nc1nc(NCC2(CN3CCCC3)CC2)c2ccc(-c3cc[nH]n3)cc2n1] | 364/ 1.06 min (B)/ 0.21 μM | δ 9.46-9.32 (m, 1H), 8.31 (br d, J = 8.9 Hz, 1H), 8.26-8.02 (m, 2H), 7.94-7.81 (m, 3H), 6.90 (d, J = 2.4 Hz, 1H), 3.74-3.60 (m, 2H), 3.58-3.33 (m, 1H), 3.25-3.04 (m, 3H), 2.08-1.89 (m, 4H), 1.70-1.44 (m, 1H), 0.92-0.82 (m, 2H), 0.77-0.69 (m, 2H) |

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 195 | (quinazoline with 2-NH$_2$, 7-pyrazolyl, 4-NH-CH$_2$-cyclopropyl-CH$_2$-morpholine) | 380/ 1.29 min (B)/ 0.30 μM | δ 9.31-9.17 (m, 1H), 8.39-8.27 (m, 1H), 8.23-7.98 (m, 2H), 7.98-7.81 (m, 3H), 6.89 (d, J = 2.1 Hz, 1H), 3.68 (br d, J = 2.4 Hz, 2H), 3.42-2.80 (m, 2H), 2.43-2.32 (m, 1H), 1.73-1.44 (m, 1H), 1.16 (t, J = 7.3 Hz, 1H), 0.88-0.28 (m, 4H). Protons missing due to either overlap with suppressed water peak or low integration. |
| 196 | (quinazoline with 2-NH$_2$, 7-pyrazolyl, 4-NH-CH$_2$-cyclopropyl-CH$_2$-OCH$_3$) | 325/ 1.21 min (E)/ 0.23 μM | δ 9.25-9.14 (m, 1H), 8.36-8.29 (m, 1H), 7.98-7.74 (m, 4H), 6.88 (d, J = 2.2 Hz, 1H), 3.67-3.62 (m, 2H), 3.26 (s, 2H), 3.22 (s, 3H), 0.74-0.58 (m, 2H), 0.53-0.42 (m, 2H) |
| 197 | (quinazoline with 2-NH$_2$, 7-pyrazolyl, 4-NH-CH$_2$-cyclopropyl-OH) | 297/ 1.02 min (B)/ 0.31 μM | δ 9.39-9.28 (m, 1H), 8.38 (br d, J = 8.5 Hz, 1H), 7.93-7.80 (m, 3H), 6.89 (d, J = 2.1 Hz, 1H), 3.90 (s, 1H), 3.78-3.69 (m, 2H), 3.17 (s, 1H), 0.76-0.58 (m, 4H) |
| 198 | (quinazoline with 2-NH$_2$, 7-pyrazolyl, 4-NH-CH$_2$-(2,2-difluorocyclopropyl)) Enantiomer 1 | 317/ 1.03 min (B)/ 0.07 μM | δ 8.19-8.10 (m, 1H), 8.00 (d, J = 8.8 Hz, 1H), 7.84-7.70 (m, 1H), 7.62 (s, 1H), 7.57-7.48 (m, 1H), 6.80 (d, J = 2.1 Hz, 1H), 6.19 (br s, 2H), 3.65-3.47 (m, 1H), 2.28-2.13 (m, 1H), 1.67-1.55 (m, 1H), 1.45-1.34 (m, 1H) |
| 199 | (quinazoline with 2-NH$_2$, 7-pyrazolyl, 4-NH-CH$_2$-(2,2-difluorocyclopropyl)) Enantiomer 2 | 317/ 1.03 min (B)/ 0.08 μM | δ 8.08 (br t, J = 5.3 Hz, 1H), 7.99 (br d, J = 8.2 Hz, 1H), 7.85-7.67 (m, 1H), 7.62 (s, 1H), 7.56-7.46 (m, 1H), 6.80 (d, J = 2.1 Hz, 1H), 6.13 (br s, 2H), 3.67-3.41 (m, 1H), 2.28-2.13 (m, 1H), 1.67-1.54 (m, 1H), 1.45-1.33 (m, 1H) |

-continued

| Ex No. | Structure | LC/MS [M + H]+/ RT (Method)/ NLRP3 hIL1B EC50 | 1H NMR (500 MHz, DMSO-d6, unless otherwise indicated) |
|---|---|---|---|
| 200 | 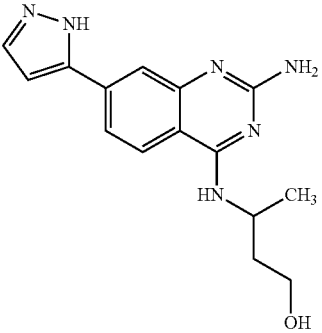<br>Single, unassigned enantiomer | 299/<br>1.02 min (A)/<br>0.86 μM | δ 8.13 (br d, J = 8.5 Hz, 1H), 7.92-7.76 (m, 1H), 7.68 (br s, 1H), 7.64-7.47 (m, 1H), 6.85 (br d, J = 1.2 Hz, 1H), 6.70-6.34 (m, 2H), 4.65-4.45 (m, 1H), 3.93 (s, 1H), 3.52 (br s, 1H), 1.84 (dt, J = 13.5, 6.8 Hz, 1H), 1.76 (br dd, J = 13.1, 6.4 Hz, 2H), 1.26 (br d, J = 6.4 Hz, 3H) |
| 201 | 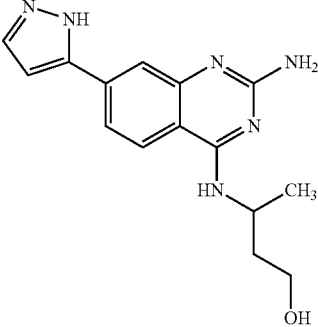<br>Single, unassigned enantiomer | 299/<br>1.02 min (A)/<br>0.07 μM | δ 8.12 (br d, J = 8.2 Hz, 1H), 7.98-7.75 (m, 2H), 7.67 (br s, 1H), 7.60 (td, J = 5.3, 2.3 Hz, 1H), 6.93-6.80 (m, 1H), 6.72-6.24 (m, 2H), 4.63-4.44 (m, 1H), 3.92 (s, 1H), 3.50 (br t, J = 4.9 Hz, 1H), 1.89-1.80 (m, 1H), 1.75 (dq, J = 13.4, 6.5 Hz, 1H), 1.25 (br d, J = 6.7 Hz, 3H) |
| 202 | 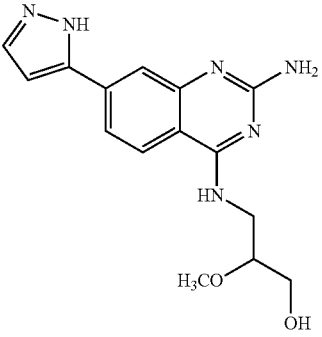<br>Single, unassigned enantiomer | 315/<br>1.04 min (A)/<br>0.88 μM | δ 8.01 (br d, J = 8.5 Hz, 1H), 7.75 (br s, 1H), 7.64 (s, 1H), 7.55 (br d, J = 8.2 Hz, 1H), 6.82 (d, J = 1.8 Hz, 1H), 6.20 (br s, 1H), 3.87-3.70 (m, 1H), 3.88-3.40 (m, 4H), 3.37 (s, 2H) |
| 203 | 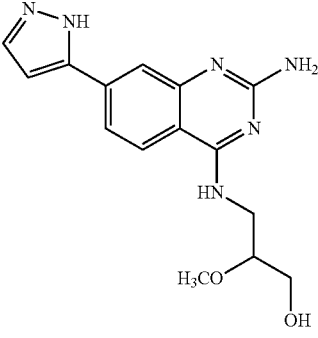<br>Single, unassigned enantiomer | 315/<br>1.03 min (A)/<br>0.45 μM | δ 8.02 (br d, J = 8.5 Hz, 1H), 7.92 (br s, 1H), 7.76 (br s, 1H), 7.63 (s, 1H), 7.57-7.47 (m, 1H), 6.82 (d, J = 1.8 Hz, 1H), 6.12 (br s, 1H), 3.62 (br s, 5H), 3.38 (s, 3H) |

| Ex No. | Structure | LC/MS [M + H]+/ RT (Method)/ NLRP3 hIL1B EC$_{50}$ | $^1$H NMR (500 MHz, DMSO-d$_6$, unless otherwise indicated) |
|---|---|---|---|
| 204 | 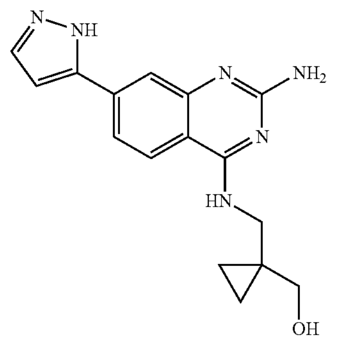 [SMILES: Nc1nc(NCC2(CO)CC2)c2ccc(-c3ccn[nH]3)cc2n1] | 311/ 1.07 min (A)/ 0.18 μM | δ 8.22-8.09 (m, 1H), 8.06 (d, J = 8.5 Hz, 1H), 7.76 (br s, 1H), 7.66 (s, 1H), 7.58 (br d, J = 7.2 Hz, 1H), 6.82 (d, J = 2.2 Hz, 1H), 6.50 (br dd, J = 10.2, 6.8 Hz, 2H), 3.33 (s, 2H), 0.61-0.49 (m, 2H), 0.45-0.33 (m, 2H) Two protons are not visible, likely due to overlap with suppressed water peak. |

A number of embodiments of the invention have been described. Nevertheless, it will be understood that various modifications may be made without departing from the spirit and scope of the invention. Accordingly, other embodiments are within the scope of the following claims.

What is claimed is:

1. A compound of Formula (II):

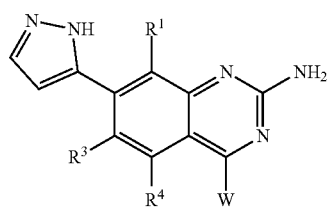

or a stereoisomer, a tautomer, or a pharmaceutically acceptable salt thereof, wherein:

W is independently selected from: -Y-R$^6$, —O—R$^{6a}$, —NH—R$^{6a}$, —O—Y—R$^6$, —NH—Y—R$^6$, R$^{6b}$, and

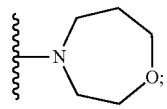 [SMILES: *N1CCCOCC1]

Y is independently C$_{1-8}$ alkylene or C$_{2-6}$ alkynylene, each of which is substituted with 0 to 3 R$^e$; wherein C$_{1-8}$ alkylene is optionally interrupted by one O;

R$^1$ is H;

R$^3$ is independently selected from: H, F and Cl;

R$^4$ is independently selected from: H, F, Cl, CH$_3$, OCH$_3$, N(CH$_3$)$_2$, and pyrazolyl;

R$^6$ is independently selected from: H, OH, C$_{1-6}$ alkoxy, CN, N(C$_{1-4}$ alkyl)$_2$, C$_{1-6}$ haloalkyl, and R$^{6a}$;

R$^{6a}$ is independently selected from: phenyl substituted with 0 to 3 R$^d$; heteroaryl selected from oxazolyl, isoxazolyl, thiazolyl, imidazolyl, N—C$_{1-4}$ alkyl-imidazolyl, pyrazolyl, N—C$_{1-4}$ alkyl-pyrazolyl, N—CH$_2$CH$_2$OH-pyrazolyl, oxadiazolyl, triazolyl, N—C$_{1-4}$ alkyl-triazolyl, pyridyl, pyrimidinyl, pyrazinyl, and pyridazinyl, wherein the heteroaryl is substituted with 0 to 3 R$^d$, C$_{3-6}$ cycloalkyl substituted with 0 to 3 R$^g$; heterocyclyl selected from

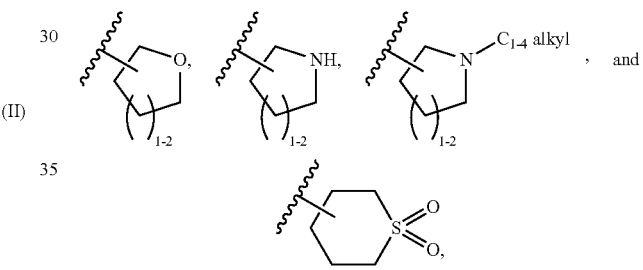

wherein the heterocyclyl is substituted with 0 to 3 R$^g$; and

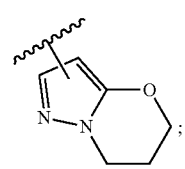

R$^{6b}$ is independently selected from: C$_{1-6}$ alkoxy, C$_{1-4}$ haloalkoxy, N(C$_{1-4}$ alkyl)$_2$, C$_{1-6}$ haloalkyl, cyano, phenyl substituted with 0 to 4 R$^d$; heteroaryl including from 5 to 10 ring atoms, wherein from 1 to 4 ring atoms are each independently selected from N, N(R$^f$), O, and S, wherein the heteroaryl is substituted with 0 to 4 R$^d$; C$_{3-10}$ cycloalkyl substituted with 0 to 4 R$^g$;

R$^d$ is independently selected from: halogen, cyano, OH, —(CH$_2$)$_{1-4}$OH, C$_{1-4}$ alkoxy, C$_{1-4}$ haloalkyl, N(C$_{1-4}$ alkyl)$_2$, and C$_{1-4}$ alkyl substituted with 0 to 2 C$_{1-4}$ alkoxy; and R$^g$ is independently oxo or R$^d$.

2. The compound of claim 1, wherein:

W is independently selected from: —Y—R$^6$, —NH—R$^{6a}$, —NH—Y—R$^6$, R$^{6b}$, and

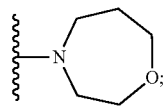

Y is independently C$_{1-6}$ alkylene or C$_{2-4}$ alkynylene, each of which is substituted with 0 to 3 R$^e$; wherein C$_{1-6}$ alkylene is optionally interrupted by one O;

R$^4$ is independently selected from: H, F, Cl, CH$_3$ and OCH$_3$;

R$^{6a}$ is independently selected from: phenyl substituted with 0 to 3 R$^d$; heteroaryl selected from oxazolyl, isoxazolyl, thiazolyl, imidazolyl, pyrazolyl, oxadiazolyl, triazolyl, pyridyl, pyrimidinyl, pyrazinyl, and pyridazinyl, wherein the heteroaryl is substituted with 0 to 3 R$^d$; C$_{3-6}$ cycloalkyl substituted with 0 to 3 R$^g$; heterocyclyl selected from

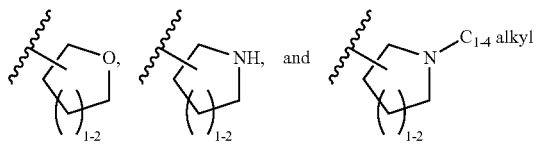

wherein the heterocyclyl is substituted with 0 to 3 R$^g$; and

R$^e$ is independently selected from: F, OH and C$_{1-4}$ alkyl.

3. The compound of claim 2, wherein:

W is independently —NH—R$^{6a}$ or —NH—Y—R$^6$;

Y is independently C$_{1-4}$ alkylene substituted with 0 to 3 R$^e$;

R$^1$ is H;

R$^3$ is H;

R$^4$ is H;

R$^{6a}$ is independently selected from: heteroaryl selected from oxazolyl, isoxazolyl, thiazolyl, imidazolyl, pyrazolyl, pyridyl, pyrimidinyl, pyrazinyl, and pyridazinyl; C$_{3-6}$ cycloalkyl substituted with 1 OH; and

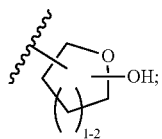

R$^6$ is OH; and

R$^e$ is independently OH or C$_{1-4}$ alkyl.

4. The compound of claim 3, wherein:

W is independently selected from: —NH(CH$_2$)$_{2-4}$OH, —NHCH$_2$CH(CH$_3$) OH, —NHCH$_2$CH(CH$_2$CH$_3$) OH, —NHCH$_2$C(CH$_3$)$_2$OH, —NH(CH$_2$)$_2$C(CH$_3$)$_2$OH, —NHCH$_2$C(CH$_3$)$_2$CH$_2$OH,

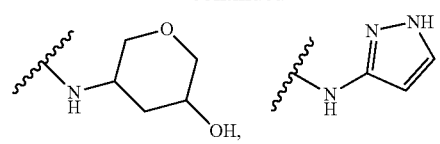

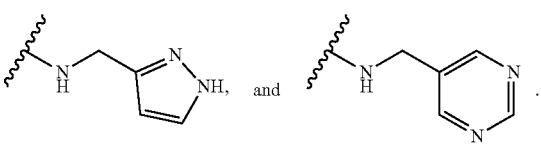

5. A compound selected from

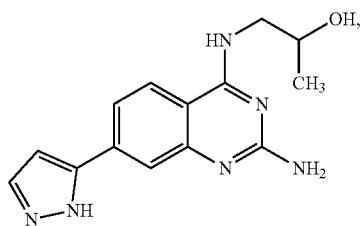

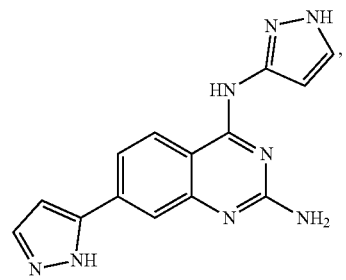

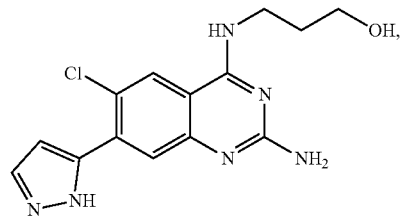

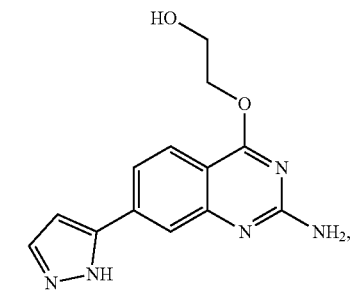

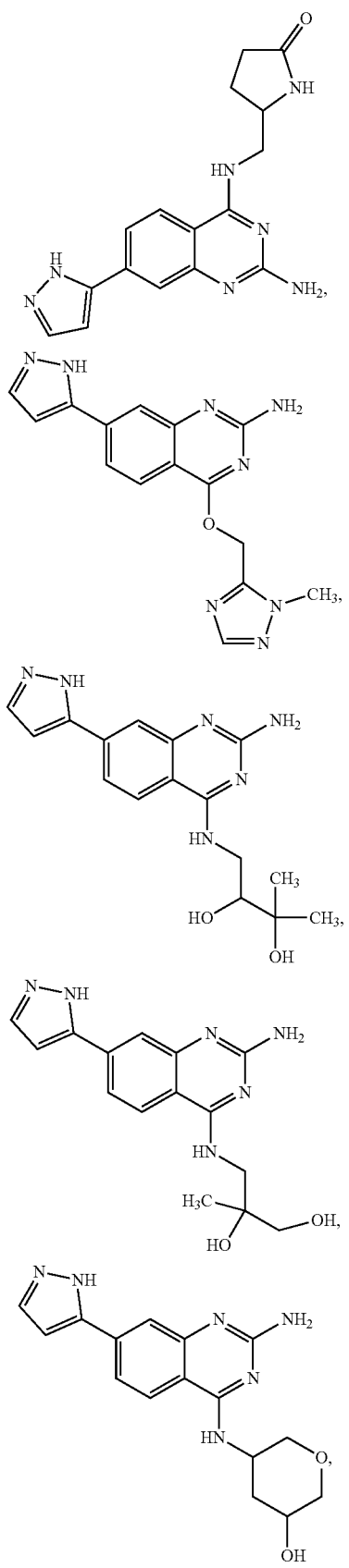
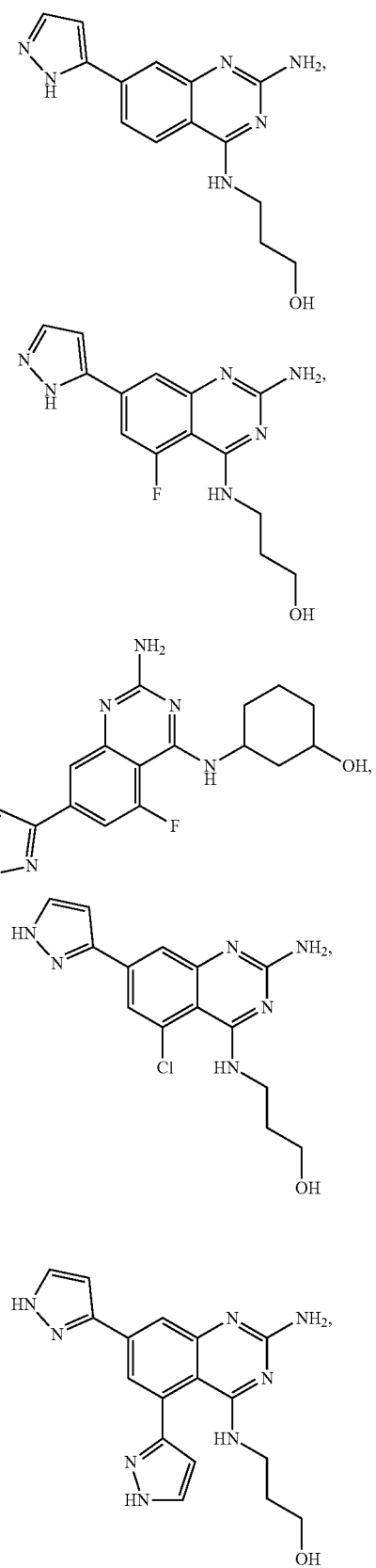

-continued
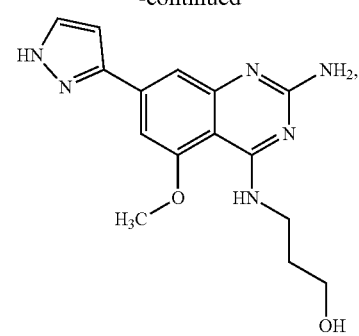
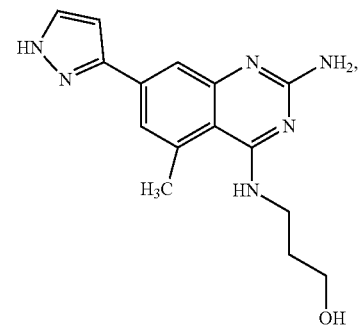
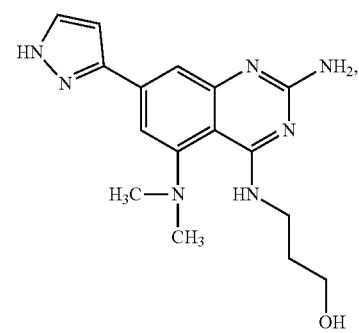
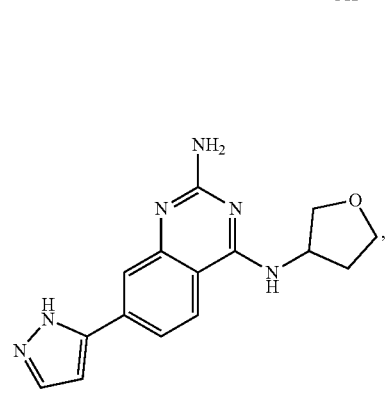
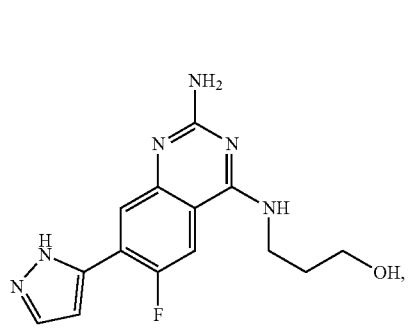
-continued
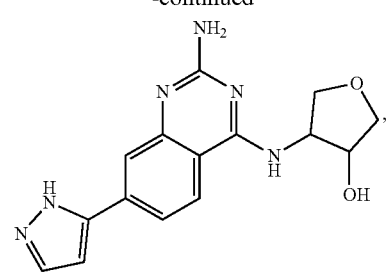
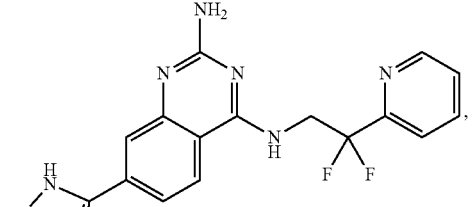
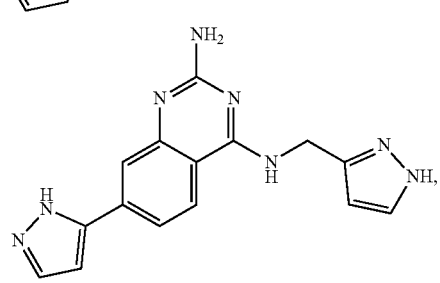
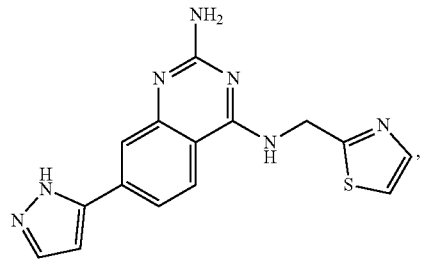
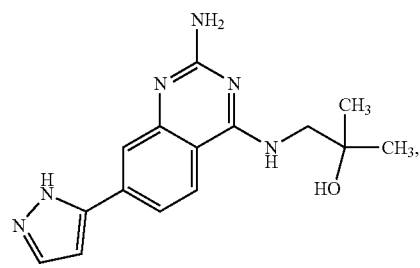
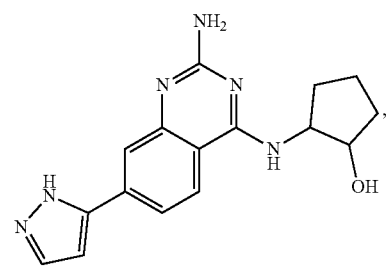

-continued
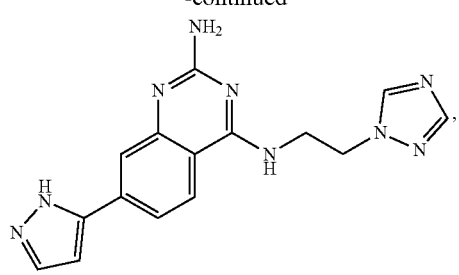
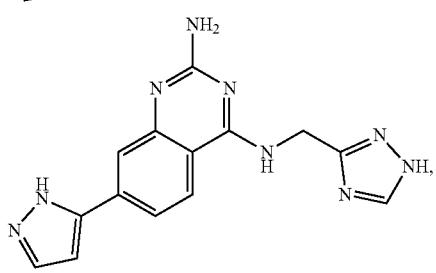
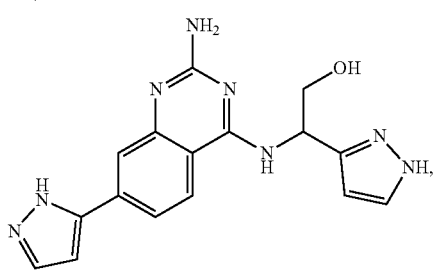
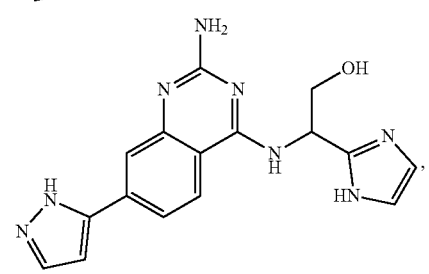
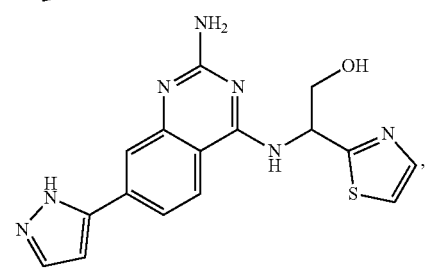
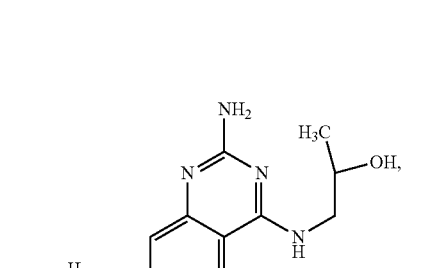
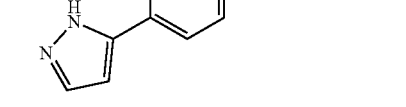
-continued
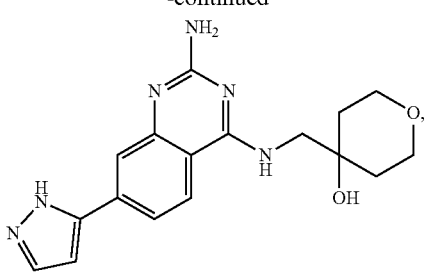
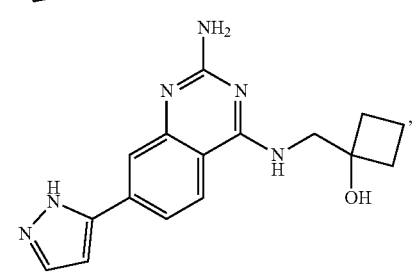
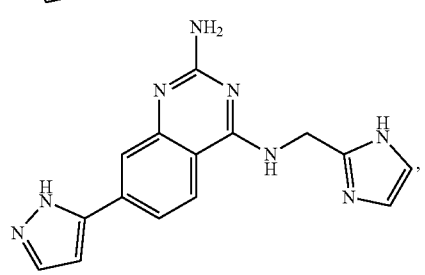
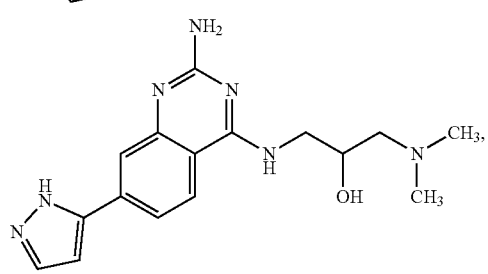
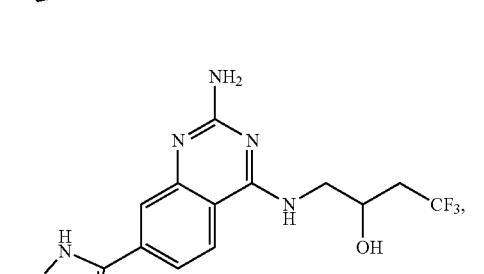
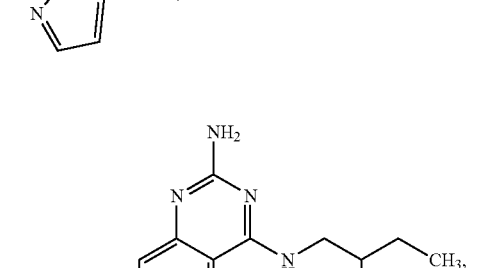
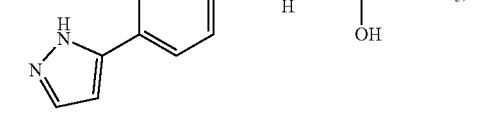

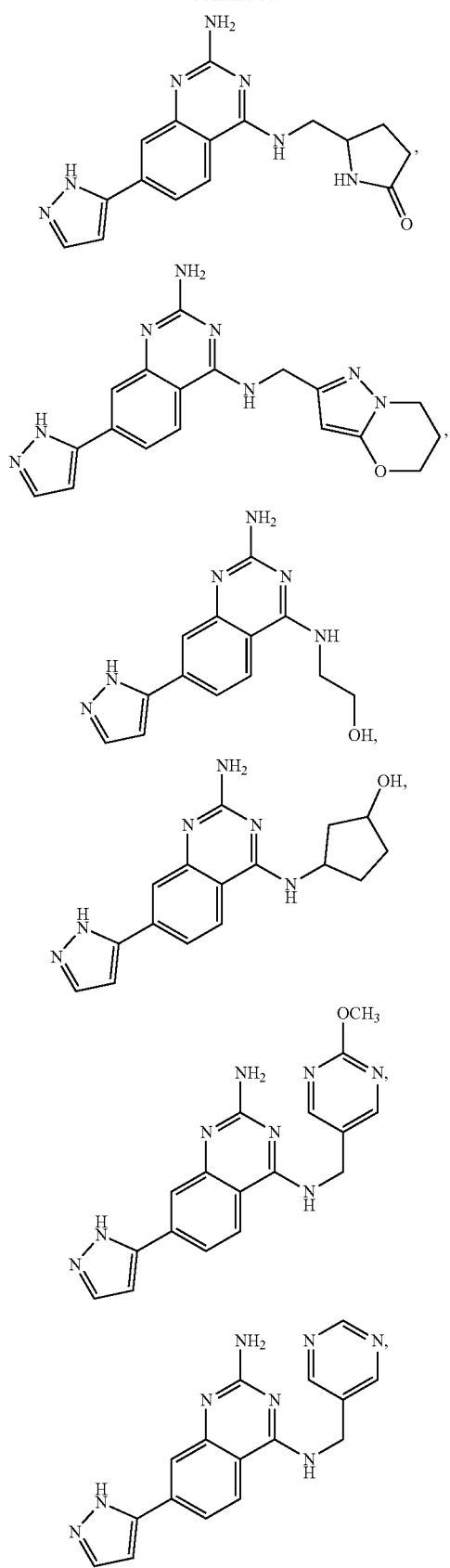
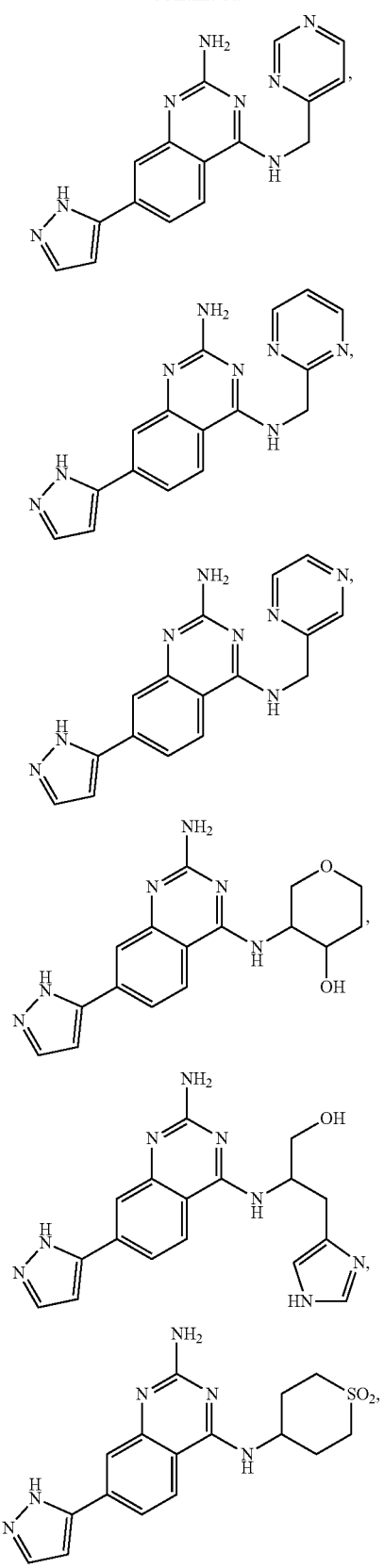

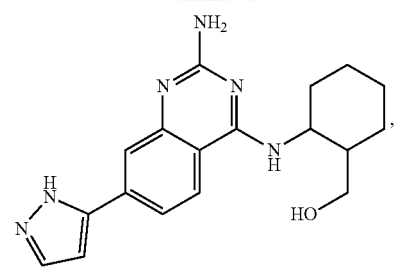
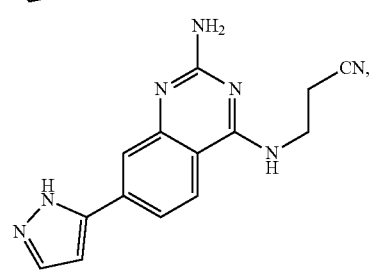
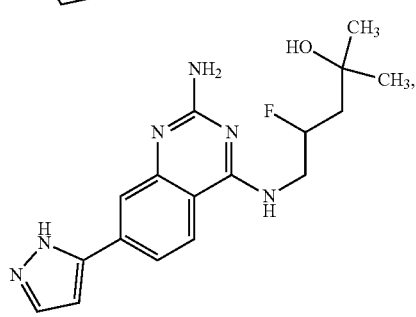
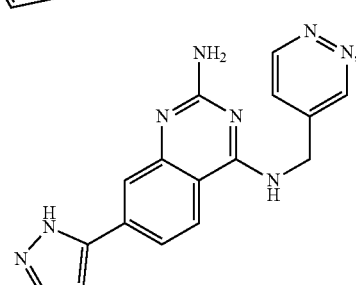
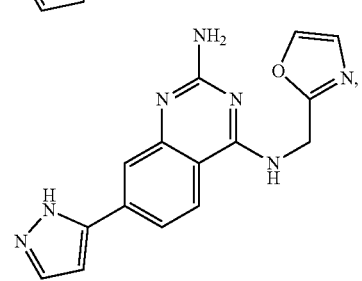
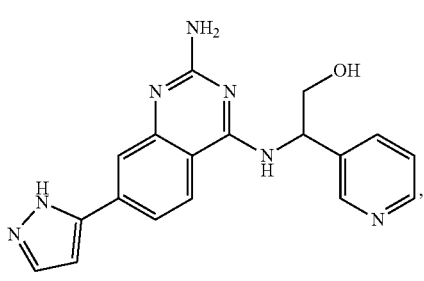
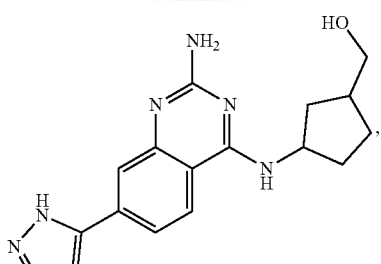
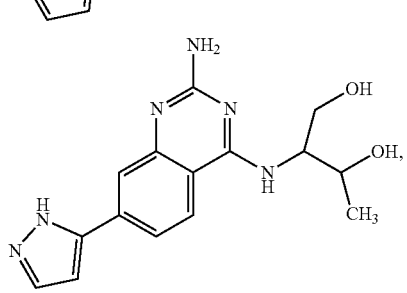
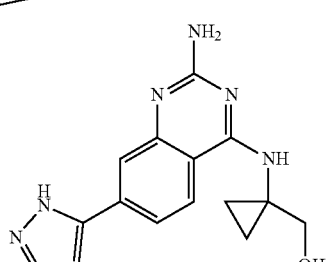
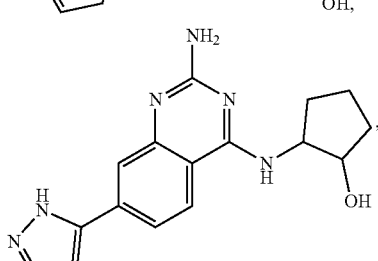
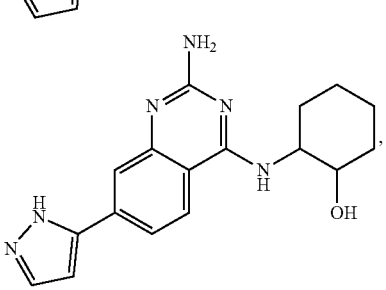
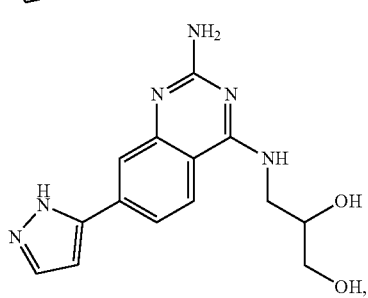

177
-continued
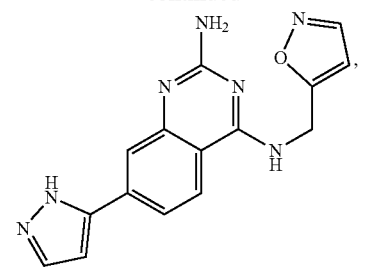
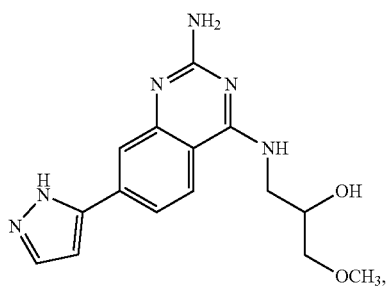
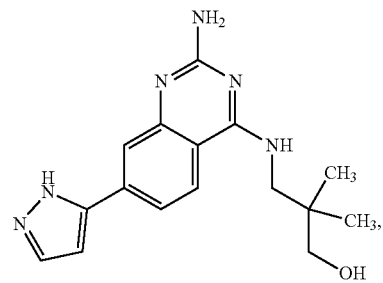
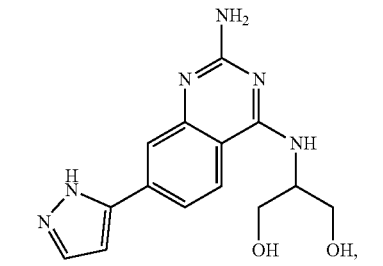
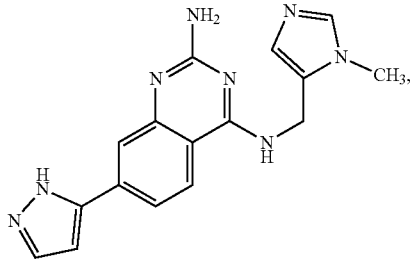
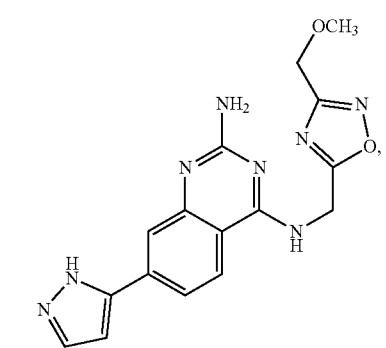
178
-continued
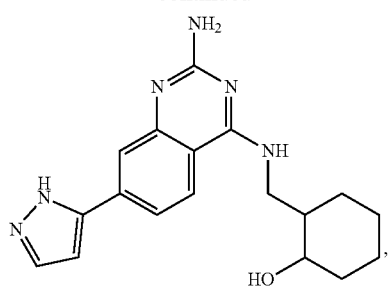
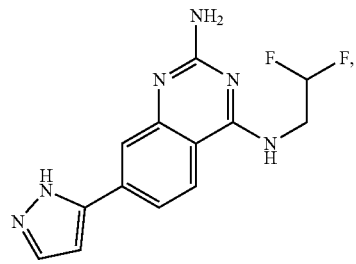
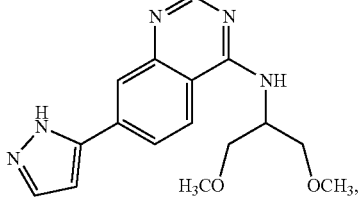
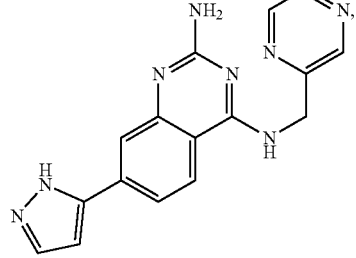
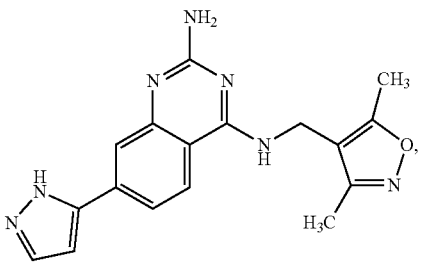
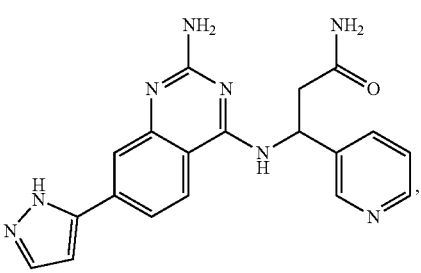

-continued
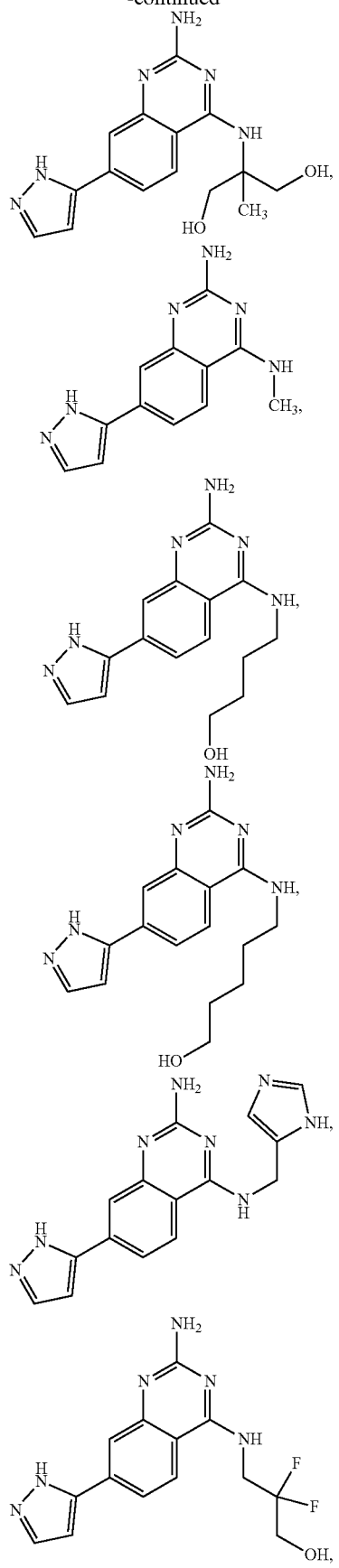
-continued
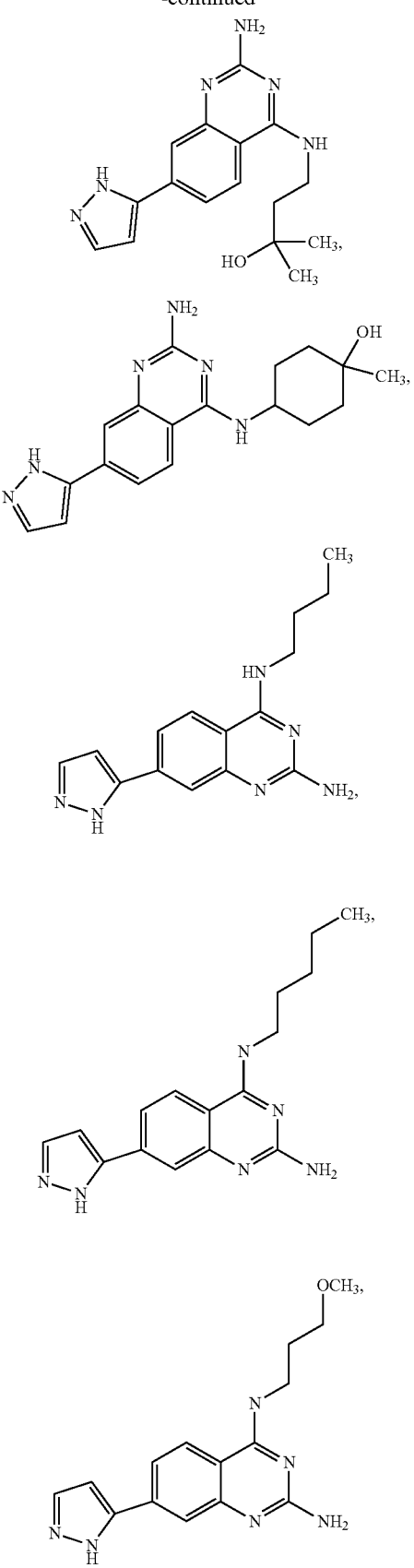

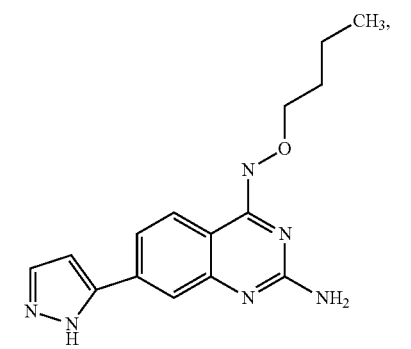
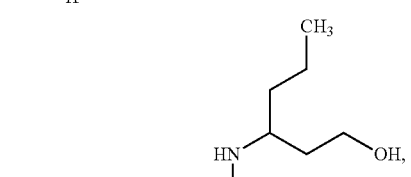
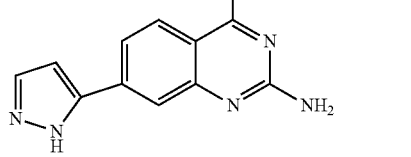
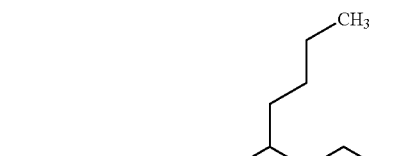
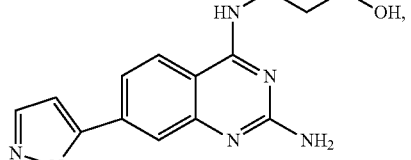
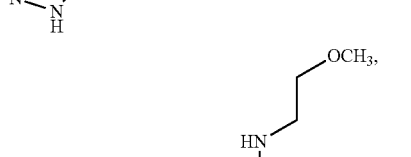
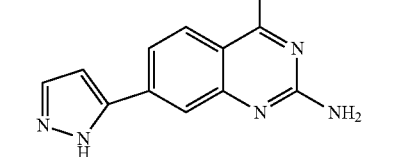
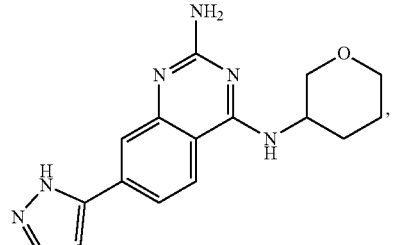
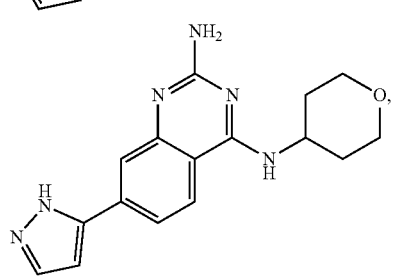
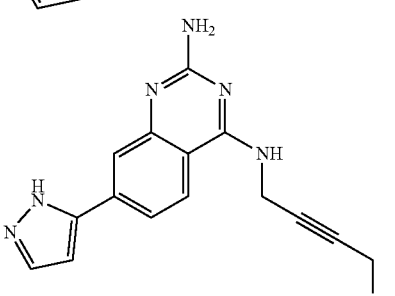
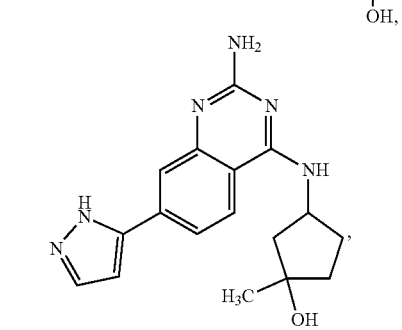
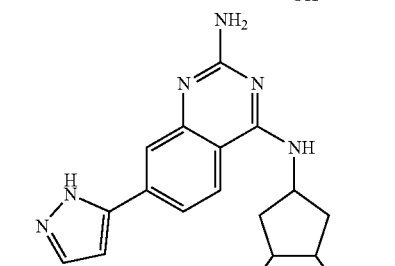
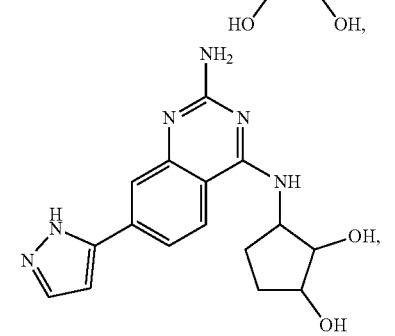

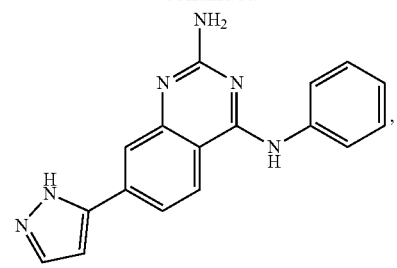
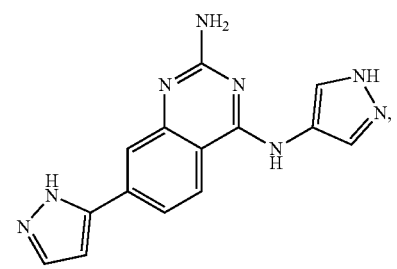
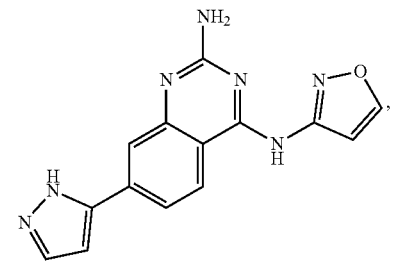
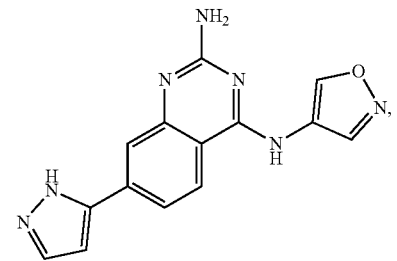
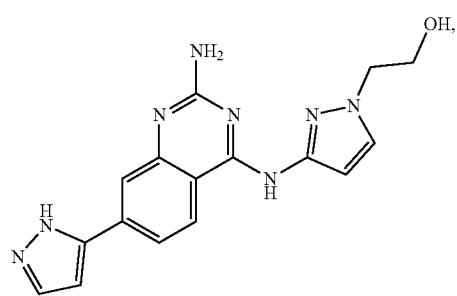
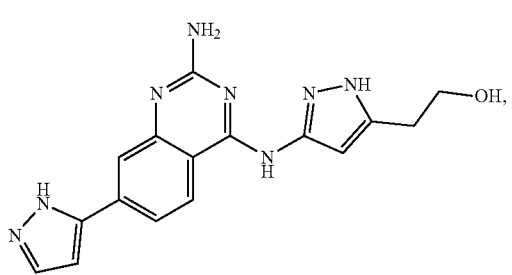
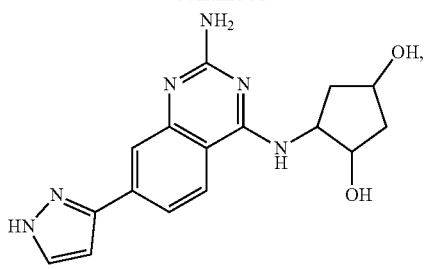
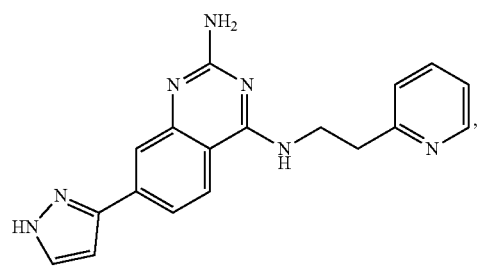
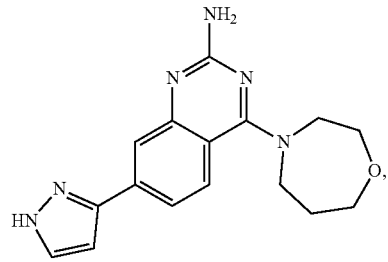
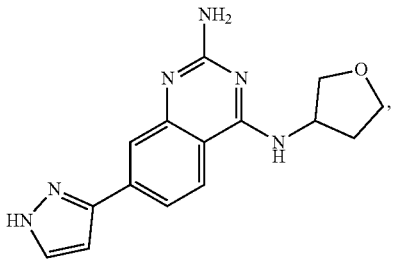
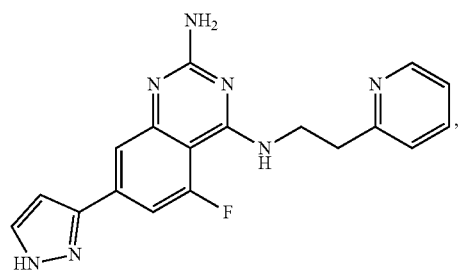
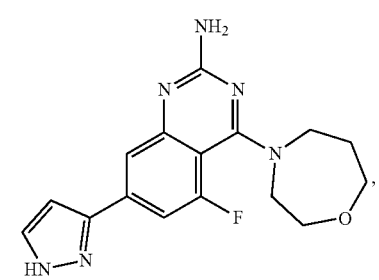

-continued
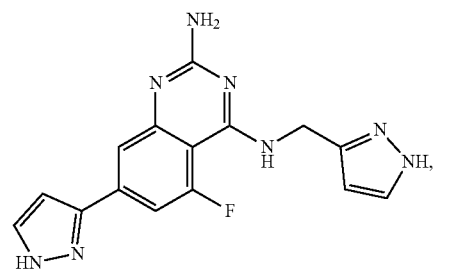
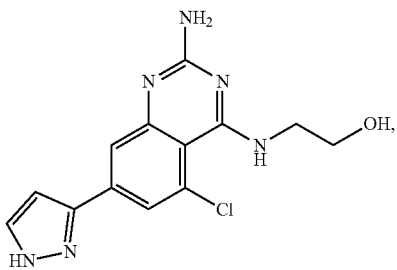
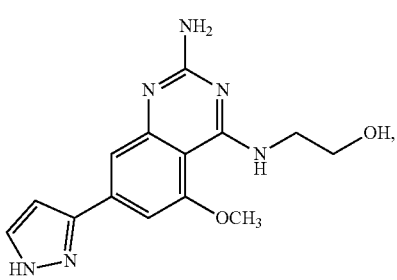
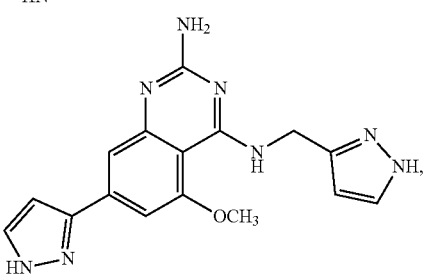
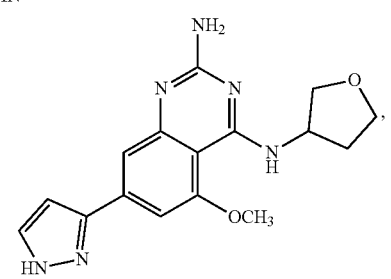
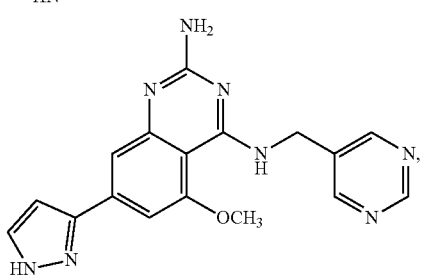
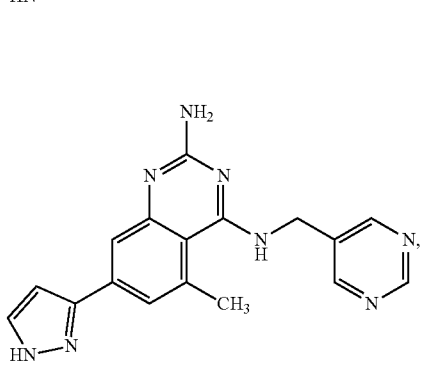

-continued
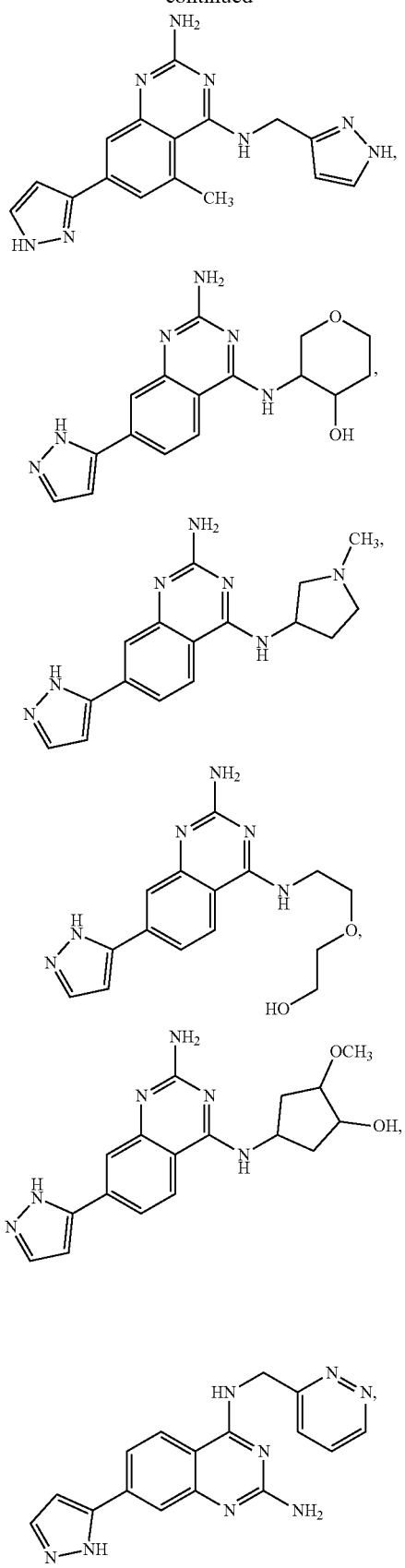
-continued
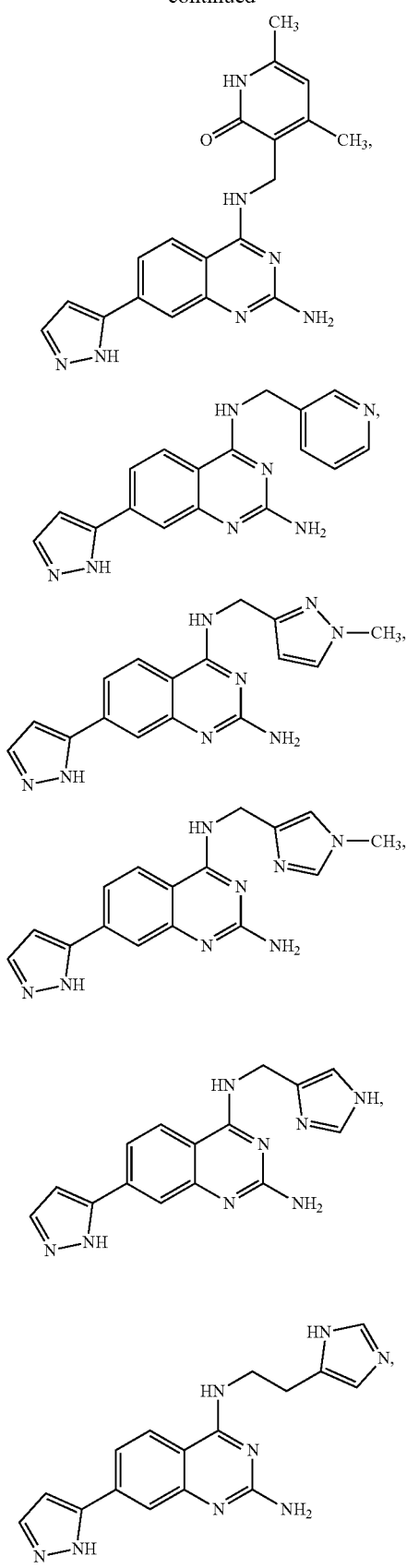

-continued
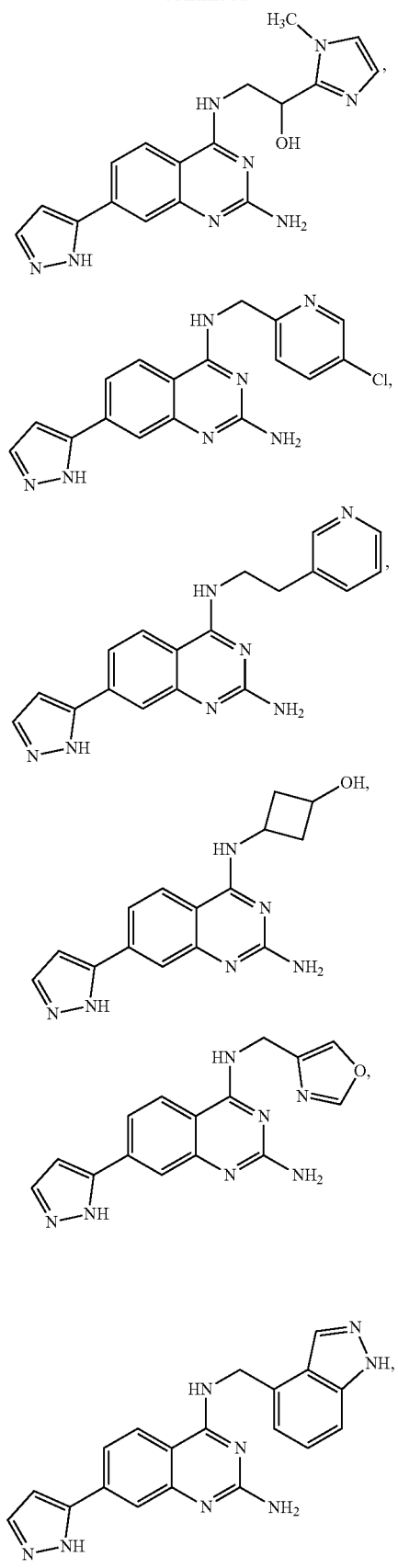
-continued
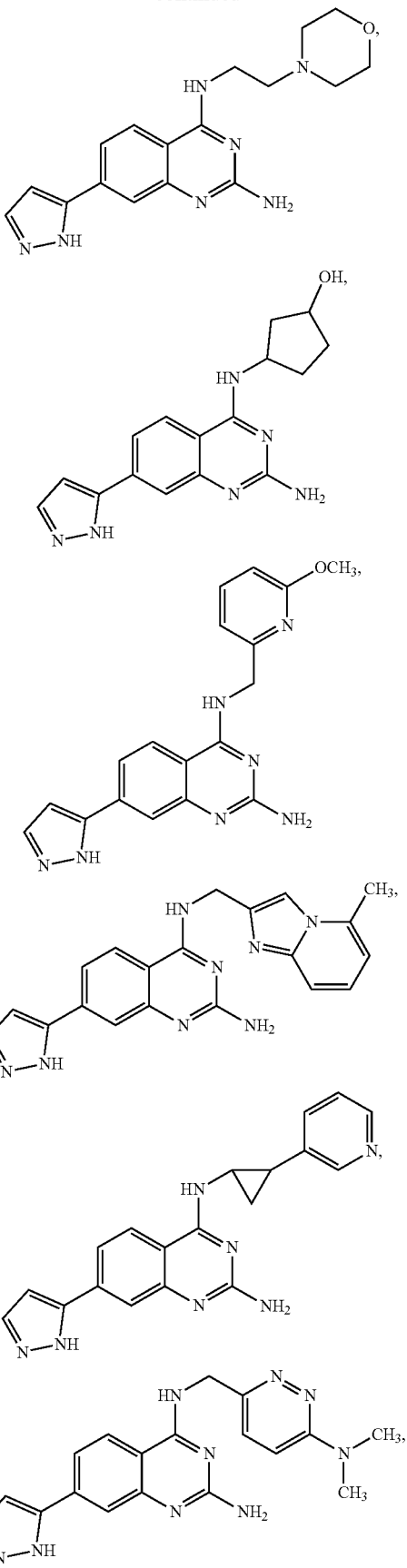

-continued
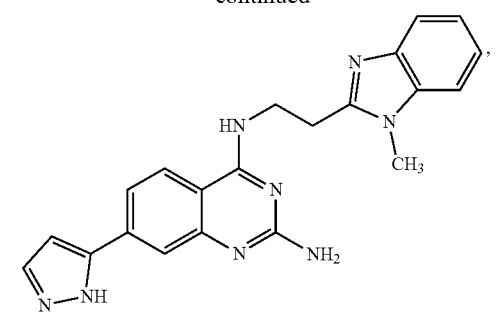
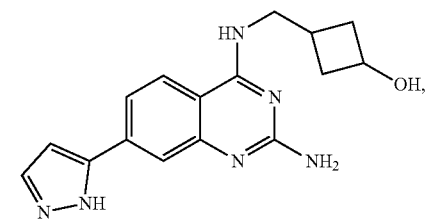
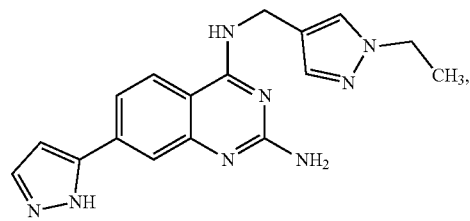
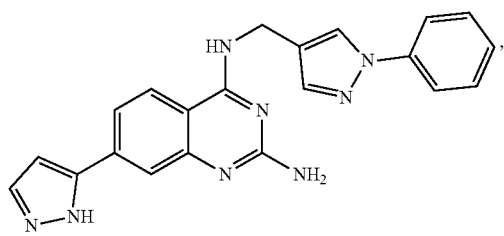
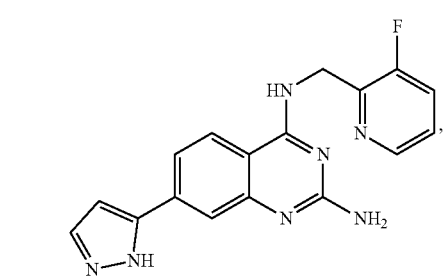
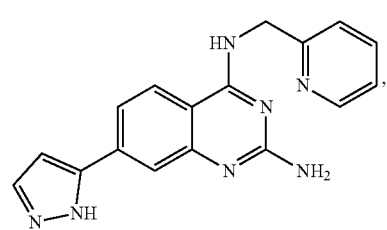
-continued
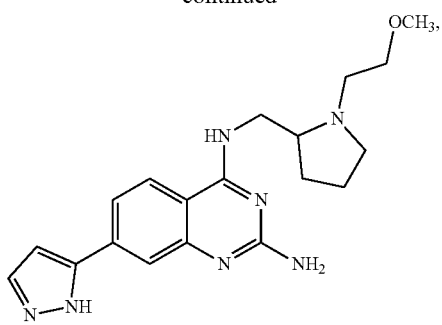
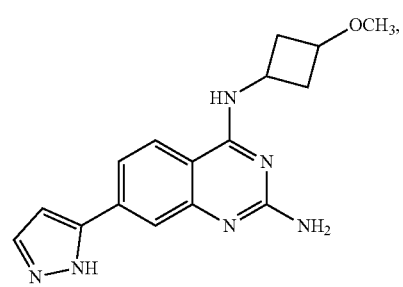
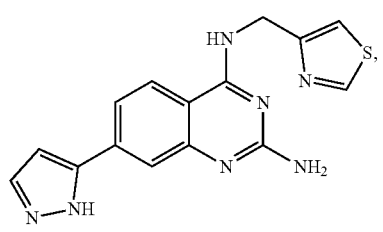
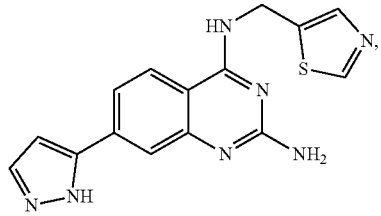
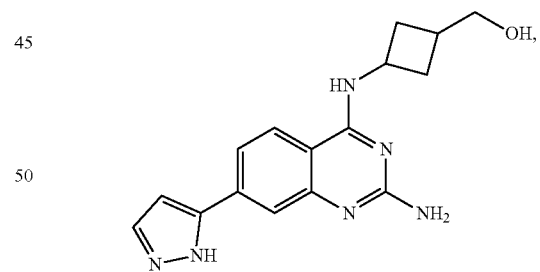
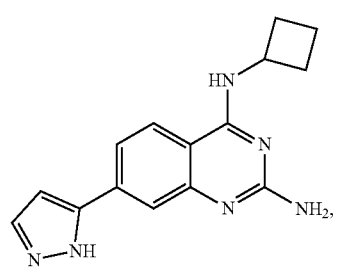

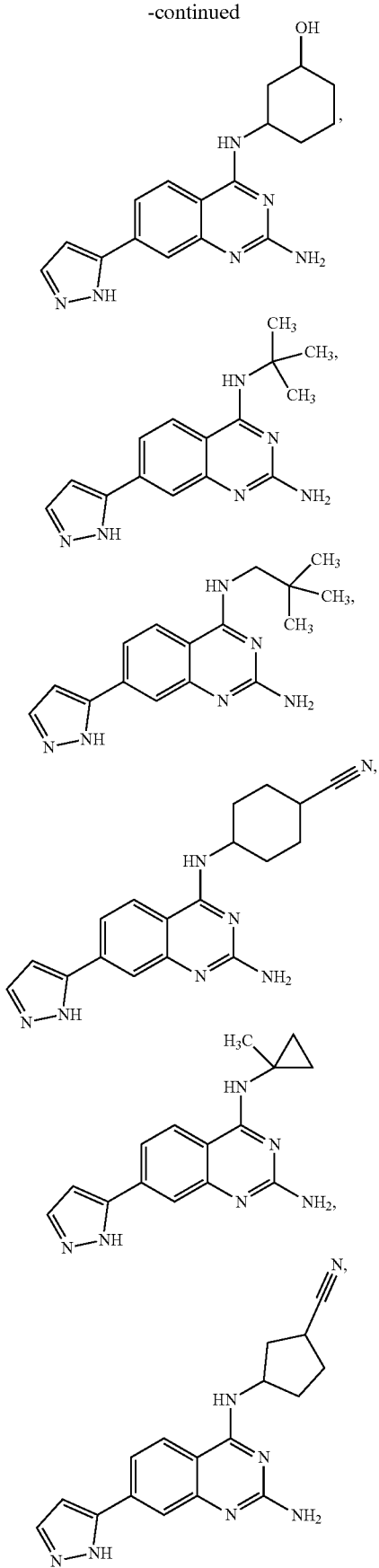
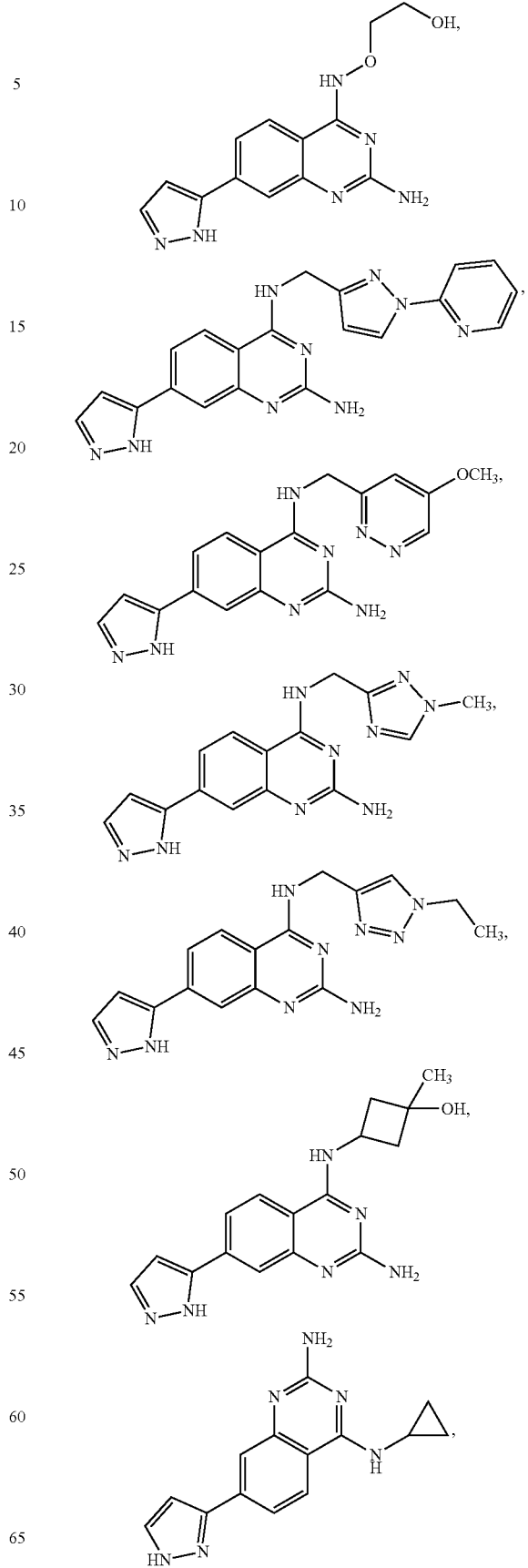

195
-continued

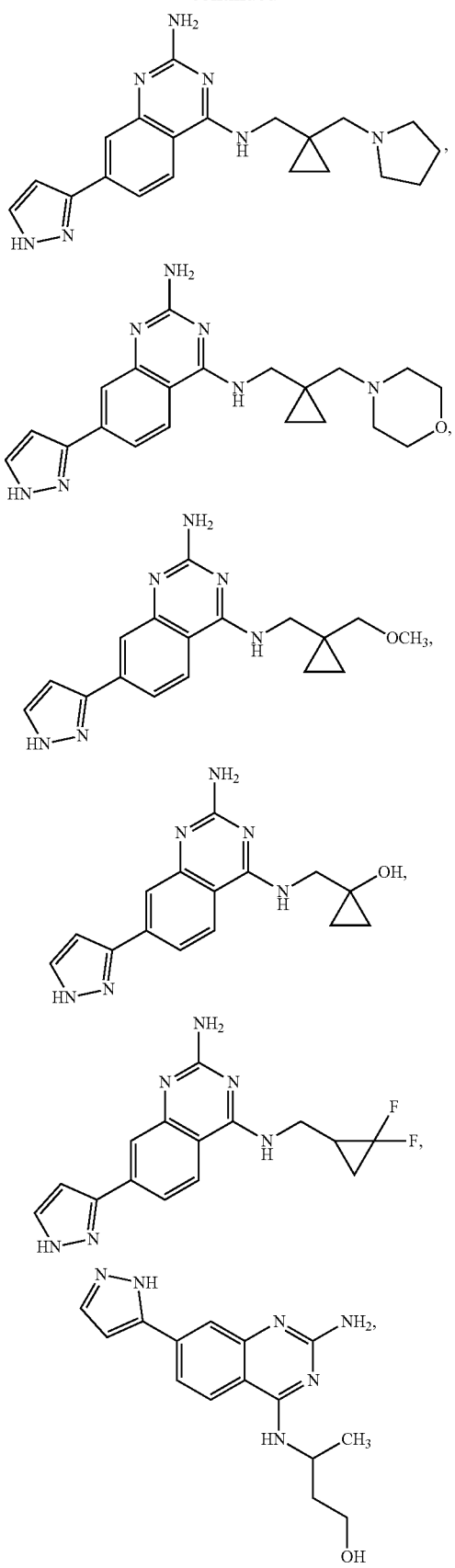

196
-continued

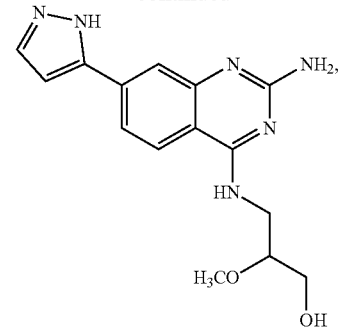

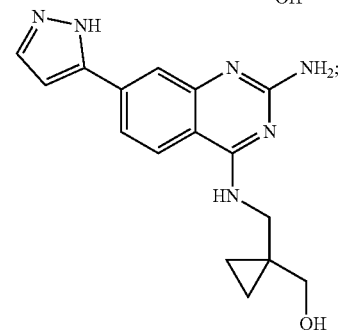

or a stereoisomer, a tautomer, or a pharmaceutically acceptable salt thereof.

6. A pharmaceutical composition comprising a compound or a pharmaceutically acceptable salt thereof as claimed in claim 1 and one or more pharmaceutically acceptable excipients.

7. A pharmaceutical composition comprising a compound or a pharmaceutically acceptable salt thereof as claimed in claim 2 and one or more pharmaceutically acceptable excipients.

8. A pharmaceutical composition comprising a compound or a pharmaceutically acceptable salt thereof as claimed in claim 3 and one or more pharmaceutically acceptable excipients.

9. A pharmaceutical composition comprising a compound or a pharmaceutically acceptable salt thereof as claimed in claim 4 and one or more pharmaceutically acceptable excipients.

10. A pharmaceutical composition comprising a compound or a pharmaceutically acceptable salt thereof as claimed in claim 5 and one or more pharmaceutically acceptable excipients.

11. A method of treating cancer, comprising administering to a subject in need of such treatment an effective amount of a compound or a pharmaceutically acceptable salt thereof as claimed in claim 1.

12. The method of claim 11, wherein the cancer is selected from acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

13. The method of claim 11, wherein the cancer is selected from breast cancer, colon cancer, rectal cancer, colorectal cancer, pancreatic cancer, and prostate cancer.

14. The method of claim 11, wherein the cancer is selected from hormone receptor positive breast cancer, microsatellite stable colon or rectal cancer, pancreatic cancer and prostate cancer.

15. The method of claim 11, wherein the compound is administered in combination with one or more additional cancer therapies.

16. The method of claim 15, wherein the one or more additional cancer therapies comprise surgery, radiotherapy, chemotherapy, toxin therapy, immunotherapy, cryotherapy or gene therapy, or a combination thereof.

17. The method of claim 15, wherein the additional cancer therapy comprises one or more agents selected from nivolumab, pembrolizumab, PDR001, MEDI-0680, cemiplimab, JS001, BGB-A317, INCSHR1210, TSR-042, GLS-010, AM-0001, STI-1110, AGEN2034, MGD013, IBI308, BMS-936559, atezolizumab, durvalumab, avelumab, STI-1014, CX-072, LY3300054, CK-301, urelumab, PF-05082566, MEDI6469, TRX518, varlilumab, CP-870893, BMS-986016, MGA271, lirilumab, IPH2201, emactuzumab, INCB024360, galunisertib, ulocuplumab, BKT140, Bavituximab, CC-90002, bevacizumab, MNRP1685A, ipilimumab, MK-1308, AGEN-1884, and tremelimumab.

18. The method of claim 15, wherein the additional cancer therapy comprises one or more agents selected from nivolumab, ipilimumab, pembrolizumab, atezolizumab, durvalumab and avelumab.

* * * * *